(12) United States Patent
Cox et al.

(10) Patent No.: US 12,378,233 B2
(45) Date of Patent: Aug. 5, 2025

(54) IMMUNOMODULATING AZALIDES

(71) Applicant: Zoetis Services LLC, Parsippany, NJ (US)

(72) Inventors: Mark R. Cox, Kalamazoo, MI (US); Richard Andrew Ewin, Kalamazoo, MI (US); Tomasz Respondek, Kalamazoo, MI (US); Imelda Hot, Sherman Oaks, CA (US); Todd M. Maddux, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 353 days.

(21) Appl. No.: 17/929,777

(22) Filed: Sep. 6, 2022

(65) Prior Publication Data

US 2023/0129040 A1    Apr. 27, 2023

Related U.S. Application Data

(60) Provisional application No. 63/241,126, filed on Sep. 7, 2021.

(51) Int. Cl.

| | |
|---|---|
| C07D 413/12 | (2006.01) |
| A61K 31/7052 | (2006.01) |
| A61P 11/00 | (2006.01) |
| A61P 29/00 | (2006.01) |
| A61P 37/02 | (2006.01) |
| C07D 413/14 | (2006.01) |

(52) U.S. Cl.
CPC ......... *C07D 413/12* (2013.01); *C07D 413/14* (2013.01)

(58) Field of Classification Search
CPC    C07D 413/12; C07D 413/14; A61K 31/7052; C07H 17/08; A61P 11/00; A61P 29/00; A61P 37/02
See application file for complete search history.

(56) References Cited

U.S. PATENT DOCUMENTS

| | | |
|---|---|---|
| 5,985,844 A | 11/1999 | Heck et al. |
| 2002/0019353 A1 | 2/2002 | Canning et al. |
| 2006/0166904 A1 | 7/2006 | Napoletano et al. |
| 2007/0167381 A1 | 7/2007 | Mereu et al. |
| 2016/0031925 A1 | 2/2016 | Gardarsson et al. |
| 2018/0354981 A1 | 12/2018 | Gardarsson et al. |
| 2020/0017522 A1 | 1/2020 | Fajdetic et al. |
| 2021/0290591 A1 | 9/2021 | Cox et al. |
| 2023/0129438 A1 | 4/2023 | Zook et al. |
| 2023/0136177 A1 | 5/2023 | Ewin et al. |
| 2023/0137567 A1 | 5/2023 | Maddux et al. |

FOREIGN PATENT DOCUMENTS

| | | | |
|---|---|---|---|
| WO | 2009/023196 A1 | 2/2009 | |
| WO | WO-2011116312 A1 * | 9/2011 | ....... A61K 47/48038 |

OTHER PUBLICATIONS

Alaa El-Gindy, et al., "Drug Formulations and Clinical Methods Optimization and Validation of a Stability-Indicating RP-HPLC Method for Determination of Azithromycin and Its Related Compounds," Journal of AOAC International, vol. 94, No. 2, 2011, pp. 513-522.

* cited by examiner

*Primary Examiner* — Joseph K McKane
*Assistant Examiner* — Sagar Patel
(74) *Attorney, Agent, or Firm* — Paul M. Misiak

(57) ABSTRACT

Defined herein are immunomodulating Formula (1) compounds, wherein R, $R^0$, $R^1$, $R^2$

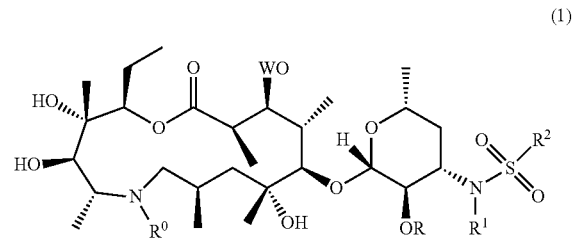

(1)

and W are as defined herein, stereoisomers thereof, and pharmaceutically acceptable salts thereof; and compositions comprising said compounds. The invention also includes methods for treating or preventing an inflammatory and/or immunological disease or disorder in an animal by administering a therapeutically effective amount of a Formula (1) compound, stereoisomer thereof, or pharmaceutically acceptable salt thereof; or use of said Formula (1) compound to prepare a medicament for treating or preventing an inflammatory and/or immunological disease or disorder in an animal.

11 Claims, 4 Drawing Sheets

FIGURE 1. Mechanism of an Immunomodulator in Context of BRD Progression
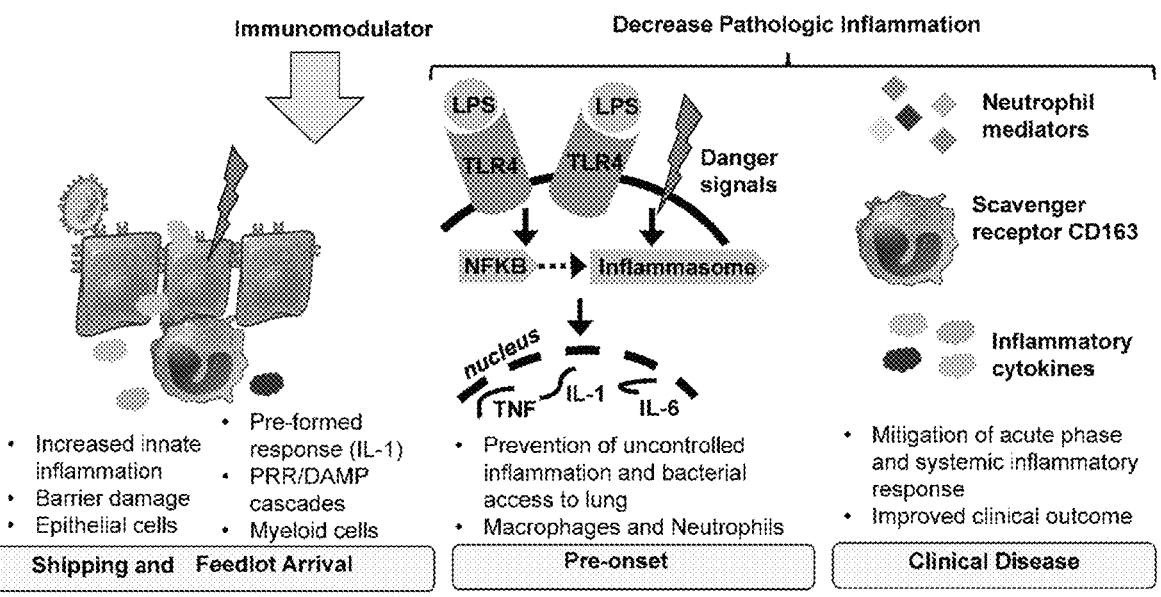

FIGURE 2. Clinical and Genomics Temporal Data Summary
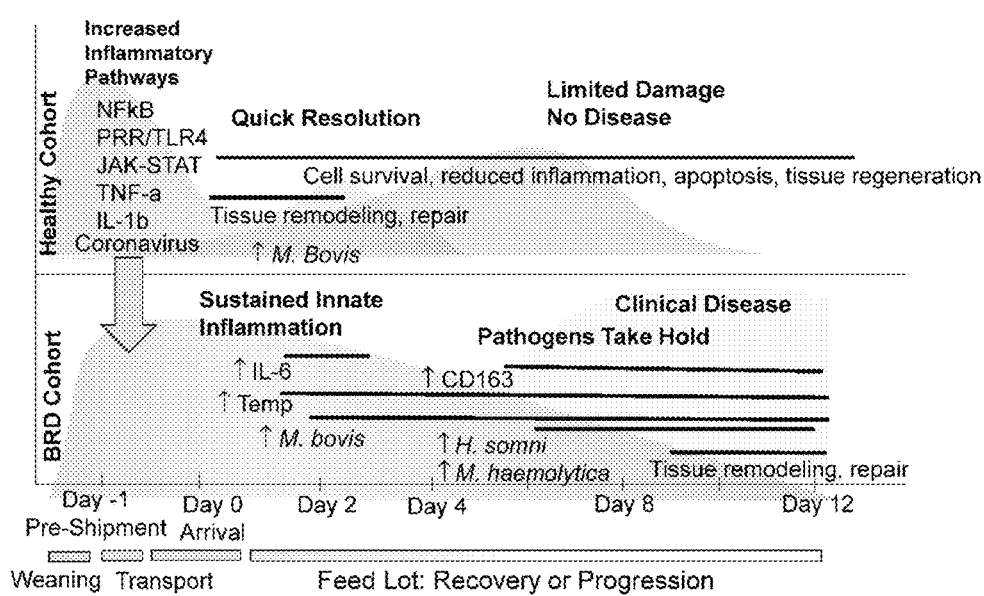

FIGURE 3. Plasma Cytokine (IL-6, IL-8, IL-10 and IFN-γ) Levels upon Arrival to the Feedlot for Calves at Risk for BRD
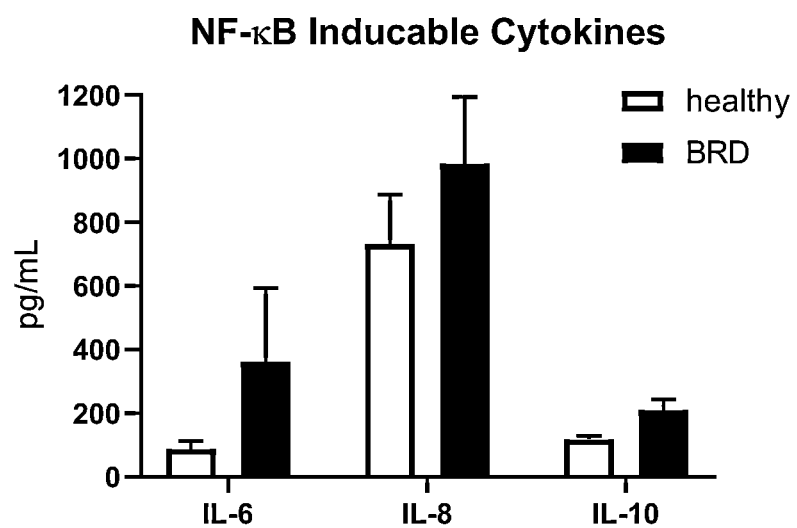
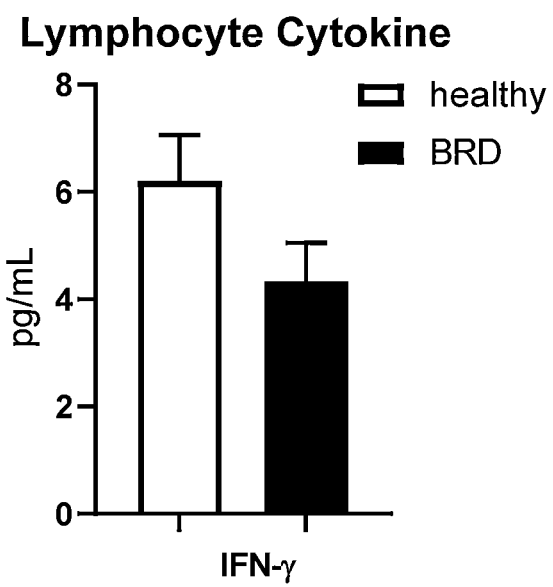

FIGURE 4. Biomarker Evaluation for M9 Intratracheal Lung Challenge; IL-6 (A) and CD163 Biomarker (B) Results
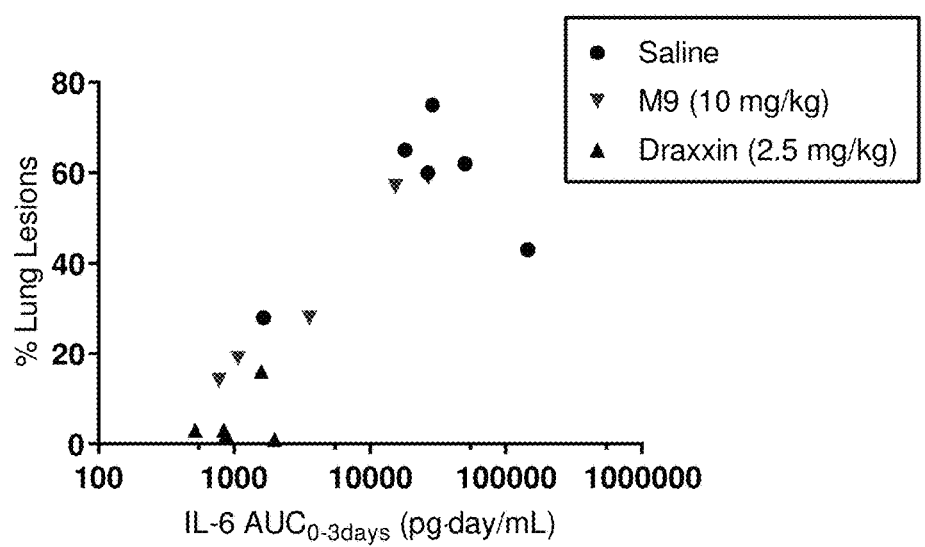
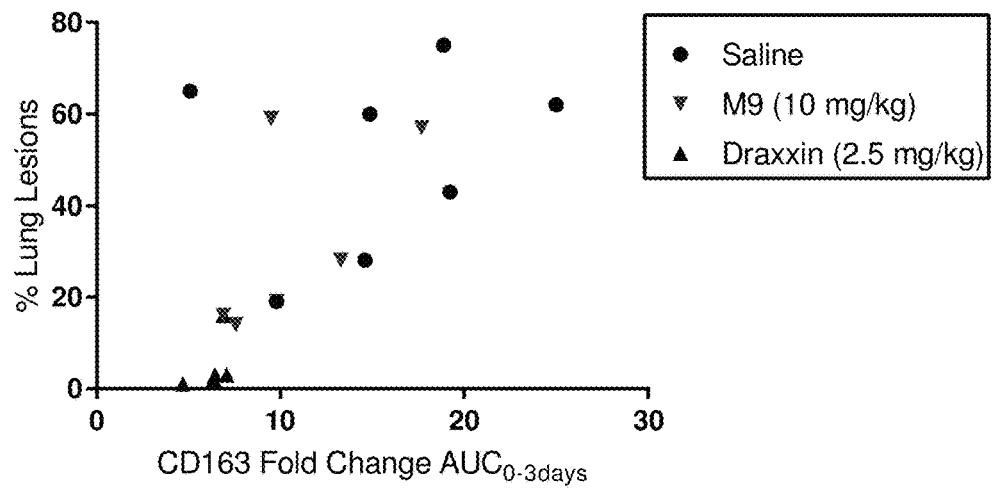

IMMUNOMODULATING AZALIDES

Defined herein are anti-inflammatory and immune-modulating compounds; non-antibacterial, anti-inflammatory and immune-modulating compounds; stereoisomers thereof, and pharmaceutically acceptable salts thereof. The invention includes the respective 13-membered macrolide ring compounds that are in equilibrium with the 15-membered macrolide ring compounds. The invention also includes pharmaceutical compositions comprising a compound of the invention and methods for treating an inflammatory and/or immunological disease or disorder in an animal. The compounds of the invention are azalides.

BACKGROUND OF THE INVENTION

Macrolides are antibacterial compounds that consist of a large macrocyclic lactone ring containing 12 to 16 atoms, which are attached, via glycosidic bonds, to at least one or two deoxy sugars. Azalides are a class of macrolide wherein the lactone ring contains a nitrogen atom. Draxxin® is a semi-synthetic macrolide (azalide) antibiotic that is sold as a ready to use sterile parenteral preparation containing tulathromycin. The preparation consists of an equilibrated mixture of two isomeric forms of tulathromycin in a 9:1 (Tula-A:Tula-B) ratio. Tula-A is a 15-membered lactone ring structure wherein Tula-B is a 13-membered lactone ring structure. Equilibrium is pH and time dependent. Tulathromycin is marketed for bovine respiratory disease (BRD) and swine respiratory disease (SRD) under the tradename, Draxxin®.

Macrolides are known for inhibiting protein synthesis in bacteria (Gram positive and Gram negative) by reversibly binding to the P site of the 50S unit of the ribosome. Macrolides tend to be bacteriostatic and may be bactericidal against some pathogens. Their activity against the Gram-negative pathogens of BRD and ability to concentrate in lung tissue make them an excellent therapeutic. They are the first-line treatment against BRD and are also used to treat respiratory infections in humans.

Known macrolide antibiotics include, for example, erythromycin, tilmicosin, azithromycin, clarithromycin, gamithromycin, fidaxomicin, roxithromycin, tulathromycin and others. In addition, some macrolides have been shown to have anti-inflammatory and immune-modulating properties. For example, azithromycin, a broad-spectrum antibiotic, suppresses interleukin 12p40 expression in lipopolysaccharide (LPS) and interferon-gamma stimulated macrophages and attenuates LPS induced induction of CXCL8 (IL-8) and GM-CSF from primary bronchial epithelial cells; and in epithelial cells, interactions with phospholipids and Erk1/2, are followed by down-regulation of transcription factors AP-1, NFκB, inflammatory cytokines and mucin release following LPS stimulation. US2016-0031925 describes certain azithromycin analogues that are immune-modulating but have been modified to reduce or eliminate the antibiotic effect. Clarithromycin has an immunomodulatory effect on ERJ-mediated inflammation induced by *Pseudomonas aeruginosa* flagellin. Erythromycin inhibits interleukin-6 and interleukin-8 expression and promotes apoptosis of activated human neutrophils in vitro. Tilmicosin modulates COX-2 and iNOS gene expression and production of cytokines in LPS-stimulated macrophages and monocytes. Roxithromycin down-regulates Th2 chemokine production by keratinocytes and chemokine receptor expression on Th2 cells. Tulathromycin promotes apoptosis and down-regulates pro-inflammatory mediators like leukotriene B4 and CXCL8; and induces production of anti-inflammatory and pro-resolving lipid lipoxin A4. Research findings demonstrate that these antibacterial macrolides modulate certain excessive immune responses which in turn cascade into certain anti-inflammatory benefits.

Inflammation and pro-inflammatory mediators negatively affect production in the food animal industry by reducing growth, feed and water intake, reproduction, milk production, and metabolic health. Increased clinical use of macrolide antibiotics is linked with an increase in pneumococcal macrolide resistance and resistance in BRD pathogens. Recent concerns by global governmental agencies and the general public relative to use of antibiotics in food producing animals (e.g., cattle and swine) has been thought to lead to cross resistance to human pathogens. Bovine respiratory disease (BRD) remains a major problem in modern day cattle production and judicious management is vitally important for both animal welfare and human food safety. In fact, *Mannheimia haemolytica* is a principal bacterium isolated from respiratory disease in feedlot cattle and is a significant component of enzootic pneumonia in neonatal calves. One of the hallmarks of BRD is a heightened inflammatory response in the host that promotes progression to the full BRD complex. Inhibiting or reversing the inflammation in the host has the ability to prevent or control the development of BRD in cattle and other inflammatory diseases or disorders in animals. Therefore, there is an unmet desire to develop a new anti-inflammatory and immune-modulating agent that lacks the antibacterial effects of the known macrolides. The compounds of the invention have been shown to be non-antibacterial in multiple bacterial species and possess upwards of 5-20 times greater immune-modulating activity at lower dosages than current macrolides (e.g., azithromycin, erythromycin and tulathromycin). Therefore, the compounds can be used to control or prevent the onset of a bacterial infection or viral infection which is enabled by an inflammatory and/or immune response due to a stressful event or other environmental factor(s) thereby preventing or mitigating the pathobiological cascade from advancing to the full disease complex. A number of other non-antibiotic immune-modulating azalide analogs have been developed and recently published as WO2021/183758, WO2021/183754, WO2021/183759 and WO2021/183762. The compounds of the invention presented herein are non-antibiotic, anti-inflammatory and immune-modulating macrolides for the reduction of an inflammatory state in animals with the potential for reducing the use of antibiotics in animals.

SUMMARY OF THE INVENTION

In one aspect of the invention, is an anti-inflammatory and immune-modulating Formula (1) compound; or a non-antibacterial, anti-inflammatory and immune-modulating Formula (1) compound;

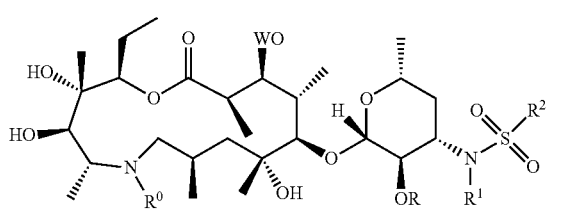

(1)

wherein W is H or a Formula (A) compound

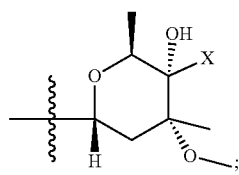

wherein X is $R^a$, —$(CH_2)_mNR^5R^6$, —$(CH_2)_mOR^7$, —$(CH_2)_mSR^7$, —$(CH_2)_mN^3$, —$(CH_2)_mCN$ or —$(CH_2)_mX'$;

X' is F, Cl, I or Br;

R is H, phenyl, naphthyl, a 5- or 6-member monocyclic heteroaryl ring or a 9- or 11-membered fused heteroaryl ring, and wherein each of the heteroaryl rings contains at least one heteroatom selected from N, O and S; and wherein the phenyl $(R^9)_n$; and wherein each of the heteroaryl rings contains at least one heteroatom selected from N, O and S; and wherein the phenyl, naphthyl and heteroaryl rings are each substituted with $(R^9)_n$;

$R^a$, $R^0$ and $R^1$ are each independently H or $C_1$-$C_6$alkyl;

or $R^1$ is benzyl substituted with $(R^9)_n$;

or $R^1$ is —$CH_2$Het wherein Het is a 5- or 6-membered heteroaryl ring containing at least one heteroatom selected from N, O and S; and wherein the heteroaryl ring is substituted with $(R^9)_n$;

or $R^1$ is $C_3$-$C_6$cycloalkyl substituted with $(R^9)_n$;

$R^b$ is H, $C_1$-$C_4$alkyl, $C_1$-$C_4$haloalkyl, $C_0$-$C_3$alkylphenyl, $C_0$-$C_3$alkylC$_3$-$C_6$cycloalkyl, $C_0$-$C_3$alkylheterocycle, $C_0$-$C_3$alkylheteroaryl; wherein the heterocycle is a 5- or 6-membered saturated or partially saturated monocyclic ring; the heteroaryl is a 5- or 6-membered monocyclic ring; and wherein the heterocycle and heteroaryl rings each contain at least one heteroatom selected from N, O and S; and wherein the cycloalkyl, phenyl, heterocycle and heteroaryl rings are each substituted with $(R^9)_n$;

$R^c$ is $C_1$-$C_4$alkyl;

$R^2$ is H, $C_1$-$C_6$alkyl, —$R^cOR^b$, $C_1$-$C_6$haloalkyl, $C_0$-$C_3$alkylC$_3$-$C_6$cycloalkyl, —$R^cNR^aR^b$, —$NR^aR^cS(O)_pR^8$, —$NR^aR^cC(O)NR^aR^c$, $R^cCN$, —$R^cS(O)_pR^8$, —$NR^aR^b$, —$NR^bR^b$, $C_0$-$C_3$alkylaryl, $C_0$-$C_3$alkylheterocycle that is a 5- or 6-membered saturated or partially saturated heterocycle ring; $C_0$-$C_3$alkylheteroaryl wherein the heteroaryl is a 5- or 6-membered heteroaryl ring; and wherein the heterocycle and heteroaryl rings each contain at least one heteroatom selected from N, O and S; and wherein the cycloalkyl, aryl, heterocyclic and heteroaryl rings are each substituted with $(R^9)_n$ and wherein each ring is optionally fused with Y;

or R and $R^2$ join to form a bond to form the fused di-oxo-oxathiazole ring that is

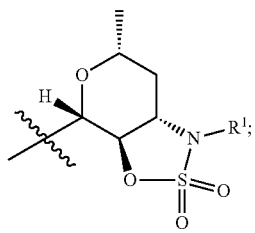

$R^5$ and $R^6$ are each independently selected from H; $C_1$-$C_6$alkyl optionally substituted with hydroxy; $C_1$-$C_6$alkoxy, cyano, $C_1$-$C_6$haloalkyl, $C_1$-$C_6$haloalkoxy, —$C(O)R^8$, —$C(O)NR^aR^8$, —$C(O)R^cNR^aR^b$, —$C(O)OR^cR^8$, —$C(O)ONR^aR^b$, —$R^cN$-$R^aC(O)R^8$, —$R^cC(O)R^b$, —$R^cC(O)OH$, —$R^cC(O)NR^aR^b$, —$R^cNR^aC(O)H$, —$R^cS(O)_pR^8$, —$R^cNR^aR^b$, —$R^cOR^b$, —$S(O)_pR^8$, —$S(O)_pR^8NR^aR^b$, —$R^cS(O)_pNR^aR^b$ or —$R^cNR^aS(O)_pR^8$; or $C_0$-$C_4$alkylaryl, $C_0$-$C_4$alkylC$_3$-$C_6$cycloalkyl, $C_0$-$C_4$alkylheterocycle and $C_0$-$C_4$alkylheteroaryl; wherein the heterocycle and heteroaryl rings are a 5- or 6-membered monocyclic ring or a 9- or 10-membered fused ring, each containing at least one heteroatom selected from the group consisting of N, O and S; and wherein the aryl, cycloalkyl, heterocycle and heteroaryl rings are each substituted with $(R^9)_n$;

or $R^5$ and $R^6$ taken together with the nitrogen atom to which they are attached form Ring B, a 4- to 8-membered heterocyclic ring or a 5-membered heteroaryl ring, each optionally containing at least one additional heteroatom selected from N, O and S; and wherein each ring is substituted with $(R^9)_n$; and wherein each ring is optionally fused with Y;

$R^7$ is H, $C_1$-$C_6$alkyl, phenyl, —$R^cNR^aR^b$, —$R^cOR^b$, —$R^cS(O)_pR^a$, —$R^cNR^aC(O)R^b$, —$R^cC(O)NR^aR^b$, —$R^cNR^aC(O)NR^aR^b$ or —$R^cNR^aC(O)OR^b$; $R^8$ is $C_1$-$C_6$alkyl, $C_1$-$C_6$haloalkyl, $C_0$-$C_4$alkylC$_3$-$C_6$cycloalkyl, —$NR^aR^b$, phenyl, a 5- or 6-membered heterocyclic ring or heteroaryl ring each containing at least one heteroatom selected from N, O and S; and wherein the cycloalkyl, phenyl, heterocycle and heteroaryl rings are each substituted with $(R^9)_n$ independently selected from the group consisting of methyl, ethyl, isopropyl, methoxy, F, Cl, Br, I, oxo, cyano, —$NH_2$, —$N(CH_3)_2$, —$CF_3$, —$CHF_2$ and —$OCHF2$;

$R^9$ is independently selected from the group consisting of $C_1$-$C_6$alkyl optionally substituted with hydroxy; $C_1$-$C_6$alkoxy, $C_0$-$C_4$alkylC$_3$-$C_6$cycloalkyl, halo, oxo, nitro, hydroxy, —$R^cOR^b$, cyano, —$NR^aR^b$, $C_1$-$C_6$haloalkyl, $C_1$-$C_6$haloalkoxy, —$S(O)_pR^8$, —$SF_5$, phenyl; a 5- or 6-membered heterocyclic or heteroaryl ring each containing at least one heteroatom selected from the group consisting of N, O and S; and wherein the phenyl, heterocyclic and heteroaryl rings are further optionally substituted with F, Cl, cyano or —$CF_3$;

Y is cyclopentyl, cyclohexyl, phenyl, pyridinyl, pyrimidyl, pyrazolyl, thiophenyl, thiazolyl, triazolyl, isothiazolyl, pyrrolyl, oxazolyl, oxadiazolyl, imidazolyl, furanyl or tetrahydrothiophenyl, each optionally substituted with methyl, F, Cl, cyano, oxo or —$CF_3$; m is the integer 1, 2, or 3;

n is the integer 0, 1, 2 or 3; and when n is 2 or 3 then each $R^9$ substituent can be the same or different;

p is the integer 0, 1, or 2;

stereoisomers thereof, or pharmaceutically acceptable salts thereof.

In another aspect, is a composition comprising a Formula (1) compound, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1) compound, stereoisomer thereof, or pharmaceutically acceptable salt thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNFα and IL-6 in the animal.

In another aspect, is the use of a Formula (1) compound, stereoisomer thereof, or a pharmaceutically acceptable salt thereof; to prepare a medicament for treating or preventing an inflammatory response in an animal wherein the inflammatory response is due to a bacterial, viral, or fungal infection, stress, and/or an environmental factor. In another aspect of the use, the use of the medicament for treating or and preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNFα and IL-6 in the animal.

In another aspect of the invention, $R^a$ and $R^b$ are each independently H, methyl, ethyl, propyl, isopropyl, isobutyl, n-butyl or t-butyl. In another aspect, $R^a$ and $R^b$ are each independently H, methyl, ethyl, propyl or isopropyl. In another aspect, $R^a$ and $R^b$ are each independently H, methyl, ethyl or propyl. In another aspect, $R^a$ and $R^b$ are each independently H or methyl.

In another aspect of the invention, $R^c$ is methyl, ethyl, propyl, isopropyl, n-butyl, or t-butyl. In another aspect of the invention, $R^c$ is methyl, ethyl, propyl, isopropyl, or t-butyl. In another aspect of the invention, $R^c$ is methyl, ethyl, propyl, or isopropyl. In another aspect of the invention, $R^c$ is methyl, ethyl or propyl. In another aspect, $R^c$ is methyl. In another aspect, $R^c$ is ethyl. In another aspect, $R^c$ is propyl.

In another aspect, X' is F, Cl, or Br. In another aspect, X' is F or Cl. In another aspect, X' is F. In another aspect, X' is Cl.

In another aspect of the invention, $R^0$ and $R^1$ are each independently H, methyl, ethyl, propyl, isopropyl, isobutyl, n-butyl or t-butyl; or $R^1$ is benzyl, cyclopentyl, cyclohexyl, —CH$_2$pyridinyl, —CH$_2$pyrimidinyl, —CH$_2$pyridazinyl, —CH$_2$pyrazinyl, —CH$_2$pyrrolyl, —CH$_2$furanyl, —CH$_2$thiophenyl, —CH$_2$pyrazolyl, —CH$_2$imidazolyl, —CH$_2$-triazolyl, —CH$_2$tetrazolyl, —CH$_2$oxazolyl, —CH$_2$isoxazolyl, —CH$_2$thiazolyl, —CH$_2$isothiazolyl or —CH$_2$oxadiazolyl, each substituted with $(R^9)_n$ independently selected from methyl, ethyl, isopropyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, $R^0$ and $R^1$ are each independently H, methyl, ethyl, propyl, isopropyl or isobutyl; or $R^1$ is benzyl, cyclopentyl, cyclohexyl, —CH$_2$pyridinyl, —CH$_2$pyrimidinyl, —CH$_2$pyrazolyl, —CH$_2$imidazolyl, —CH$_2$-triazolyl, —CH$_2$tetrazolyl, —CH$_2$oxazolyl, —CH$_2$isoxazolyl, —CH$_2$thiazolyl, —CH$_2$isothiazolyl or —CH$_2$oxadiazolyl, each substituted with $(R^9)_n$ independently selected from methyl, ethyl, isopropyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, $R^0$ is H, methyl, ethyl or propyl; and $R^1$ is methyl, ethyl, propyl or isobutyl; or $R^1$ is benzyl, cyclopentyl, cyclohexyl, —CH$_2$pyridinyl, —CH$_2$pyrimidinyl, —CH$_2$pyrazolyl, —CH$_2$thiazolyl or —CH$_2$imidazolyl, each substituted with $(R^9)_n$ independently selected from methyl, ethyl, isopropyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, $R^0$ is H, methyl, ethyl or propyl; and $R^1$ is methyl, ethyl, propyl or isobutyl; or $R^1$ is cyclohexyl, benzyl, —CH$_2$pyridinyl or —CH$_2$thiazolyl; each substituted with $(R^9)_n$ independently selected from methyl, ethyl, isopropyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, $R^0$ is H or methyl; and $R^1$ is methyl, propyl or isobutyl. In another aspect, $R^0$ is H or methyl and $R^1$ is methyl.

In another aspect of the invention, R is H; or phenyl, naphthyl, pyrrolyl, furanyl, thiophenyl, pyrazolyl, imidazolyl, isoxazolyl, oxazolyl, isothiazolyl, thiazolyl, triazolyl, tetrazolyl, pyridinyl, pyrimidinyl, pyridazinyl, pyrazinyl, quinolinyl, isoquinolinyl, benzofuranyl, benzothiophenyl, indolyl, benzimidazolyl or indazolyl, each substituted with $(R^9)_n$. In another aspect, R is H; or phenyl, pyrrolyl, furanyl, thiophenyl, pyrazolyl, imidazolyl, isoxazolyl, oxazolyl, isothiazolyl, thiazolyl, triazolyl, tetrazolyl, pyridinyl, pyrimidinyl, quinolinyl, isoquinolinyl, benzofuranyl, indolyl, benzimidazolyl or indazolyl, each substituted with $(R^9)_n$. In another aspect, R is H; or phenyl, pyrrolyl, pyrazolyl, imidazolyl, thiazolyl, triazolyl, thiophenyl, pyridinyl, pyrimidinyl, quinolinyl, isoquinolinyl, indolyl, benzimidazolyl or indazolyl, each substituted with $(R^9)_n$. In another aspect, R is H; or phenyl, pyrrolyl, pyrazolyl, imidazolyl, thiazolyl, triazolyl, thiophenyl, pyridinyl, pyrimidinyl, quinolinyl, isoquinolinyl, indolyl, benzimidazolyl or indazolyl, each substituted with $(R^9)_n$ independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, R is H; or phenyl, pyrazolyl, imidazolyl, thiazolyl, thiophenyl, pyridinyl or pyrimidinyl, each substituted with $(R^9)_n$ independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, R is H; or phenyl substituted with $(R^9)_n$ independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In another aspect, R is H; or phenyl substituted with $(R^9)_n$ independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$.

In another aspect of the invention, $R^2$ is H, C$_1$-C$_6$alkyl, —CH$_2$CN, —R$^c$OR$^b$, —R$^c$S(O)$_p$R$^a$, C$_1$-C$_6$haloalkyl, C$_0$-C$_3$alkylC$_3$-C$_6$cycloalkyl, —R$^c$NR$^a$R$^b$, —NR$^a$R$^b$, pyrrolyl, —CH$_2$pyrrolyl, —CH$_2$CH$_2$pyrrolyl, tetrahydrofuranyl, —CH$_2$tetrahydrofuranyl, —CH$_2$CH$_2$tetrahydrofuranyl, tetrahydrothiophenyl, —CH$_2$tetrahydrothiphenyl, —CH$_2$CH$_2$tetrahydrothioiphenyl, tetrahydropyranyl, —CH$_2$tetrahydropyranyl, —CH$_2$CH$_2$tetrahydropyranyl, tetrahydrothiopyranyl, —CH$_2$tetrahydrothiopyranyl, —CH$_2$CH$_2$tetrahydrothiopyranyl, pyrrolidinyl, —CH$_2$pyrrolidinyl, —CH$_2$CH$_2$pyrrolidinyl, piperidinyl, —CH₂piperidinyl, —CH₂CH₂piperidinyl, piperazinyl, —CH₂piperazinyl, —CH₂CH₂piperazinyl, morpholinyl, —CH₂morpholinyl, —CH₂CH₂morpholinyl, furanyl, —CH₂furanyl, —CH₂CH₂furanyl, thiophenyl, —CH₂thiophenyl, —CH₂CH₂thiophenyl, pyrazolyl, —CH₂pyrazolyl, —CH₂CH₂pyrazolyl, imidazolyl, —CH₂imidazolyl, —CH₂CH₂imidazolyl, isoxazolyl, —CH₂isoxazolyl, —CH₂CH₂isoxazolyl, oxazolyl, —CH₂oxazolyl, —CH₂CH₂oxazolyl, isothiazolyl, —CH₂isothioazolyl, —CH₂CH₂isothiazolyl, thiazolyl, —CH₂thiazolyl, —CH₂CH₂thiazolyl, triazolyl, —CH₂triazolyl, —CH₂CH₂traizolyl, oxadiazolyl, —CH₂oxadiazolyl, —CH₂CH₂oxadiazolyl, thiadiazolyl, —CH₂thiadiazolyl, —CH₂CH₂thiadiazolyl, tetrazolyl, —CH₂tetrazolyl, —CH₂CH₂tetrazolyl, phenyl, —CH₂phenyl (benzyl), —CH₂CH₂phenyl, pyridinyl, —CH₂pyridinyl, —CH₂CH₂pyridinyl, pyrimidinyl, —CH₂pyrimidinyl, —CH₂CH₂pyrimidinyl, pyridazinyl, —CH₂pyridazinyl, —CH₂CH₂pyridazinyl, pyrazinyl, —CH₂pyrazinyl or —CH₂CH₂pyrazinyl; and wherein the cycloalkyl, phenyl, heterocyclic and heteroaryl rings are each substituted with $(R^9)_n$, and wherein each ring is optionally fused with Y. In another aspect, $R^2$ is H, $C_1$-$C_6$alkyl, —CH₂OCH₃, —(CH₂)₂OCH₃, —CH₂CN, —CH₂F, —CHF₂, —CH₂CF₃, —CF₃, —CH₂S(O)₂CH₃, cyclopropyl, —CH₂cyclopropyl, cyclobutyl, —CH₂cyclobutyl, cyclopentyl, —CH₂cyclopentyl, cyclohexyl, —CH₂cyclohexyl, —R$^c$NR$^a$R$^b$, —NR$^a$R$^b$, pyrrolyl, —CH₂pyrrolyl, tetrahydrofuranyl, —CH₂tetrahydrofuranyl, tetrahydrothiophenyl, —CH₂tetrahydrothiphenyl, tetrahydropyranyl, —CH₂tetrahydropyranyl, tetrahydrothiopyranyl, —CH₂tetrahydro-thiopyranyl, pyrrolidinyl, —CH₂pyrrolidinyl, piperidinyl, —CH₂piperidinyl, piperazinyl, —CH₂piperazinyl, morpholinyl, —CH₂morpholinyl, furanyl, —CH₂furanyl, thiophenyl, —CH₂thiophenyl, pyrazolyl, —CH₂pyrazolyl, imidazolyl, —CH₂imidazolyl, isoxazolyl, —CH₂isoxazolyl, oxazolyl, —CH₂oxazolyl, isothiazolyl, —CH₂isothioazolyl, thiazolyl, —CH₂thiazolyl, triazolyl, —CH₂triazolyl, oxadiazolyl, —CH₂oxadiazolyl, thiadiazolyl, —CH₂thiadiazolyl, tetrazolyl, —CH₂tetrazolyl, phenyl, —CH₂phenyl (benzyl), pyridinyl, —CH₂pyridinyl, pyrimidinyl, —CH₂pyrimidinyl, pyridazinyl, —CH₂pyridazinyl, pyrazinyl or —CH₂pyrazinyl; and wherein the cycloalkyl, phenyl, heterocyclic and heteroaryl rings are each substituted with $(R^9)_n$ and wherein each ring is optionally fused with Y which is cyclopentyl, cyclohexyl, thiophenyl or phenyl. In another aspect, $R^2$ is H, $C_1$-$C_6$alkyl, —CH₂OCH₃, —(CH₂)₂OCH₃, —CH₂F, —CH₂CF₃, —CF₃, —CHF₂, —CH₂CF₃, —CF₃, —CH₂S(O)₂CH₃, cyclopropyl, —CH₂cyclopropyl, cyclobutyl, —CH₂cyclobutyl, cyclopentyl, —CH₂cyclopentyl, cyclohexyl, —CH₂cyclohexyl, —R$^c$NR$^a$R$^b$, —NR$^a$R$^b$, pyrrolyl, tetrahydrofuranyl, tetrahydrothiophenyl, tetrahydropyranyl, tetrahydrothiopyranyl, pyrrolidinyl, piperidinyl, piperazinyl, morpholinyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, phenyl, pyridinyl, pyrimidinyl, pyridazinyl or pyrazinyl; and wherein the cycloalkyl, phenyl, heterocyclic and heteroaryl rings are each substituted with $(R^9)_n$ and wherein each ring is optionally fused with Y which is cyclopentyl, cyclohexyl, thiophenyl or phenyl. In another aspect, $R^2$ is H, $C_1$-$C_6$alkyl, —CH₂OCH₃, —(CH₂)₂OCH₃, —CH₂F, —CH₂CF₃, —CF₃, —CH₂S(O)₂CH₃, —CH₂CN, —NHR$^b$, —NCH₂R$^b$, cyclopropyl, —CH₂cyclopropyl, cyclobutyl, cyclopentyl, cyclohexyl, tetrahydrothiophenyl, pyrrolidinyl, tetrahydropyranyl, piperidinyl, piperazinyl, morpholinyl, phenyl, pyrrolyl, furanyl, thiophenyl, pyrazolyl, imidazolyl, isoxazolyl, oxazolyl, isothiazolyl, thiazolyl, triazolyl, tetrazolyl, pyridinyl, pyrimidinyl, pyridazinyl or pyrazinyl; and wherein the cycloalkyl, phenyl, heterocyclic and heteroaryl rings are each substituted with $(R^9)_n$ and wherein each ring is optionally fused with Y which is cyclopentyl, cyclohexyl, thiophenyl or phenyl. In another aspect, $R^2$ is H, $C_1$-$C_6$alkyl, —CH₂OCH₃, —(CH₂)₂OCH₃, —CH₂CN, —CH₂CF₃, —CF₃, —CH₂S(O)₂CH₃, —NHR$^b$ or —NCH₂R$^b$ wherein R$^b$ is methyl, cyclohexyl, phenyl or pyridinyl and wherein the phenyl and pyridinyl rings are optionally substituted with F, Cl, cyano or —CF₃; or $R^2$ is cyclopropyl, —CH₂cyclopropyl, cyclohexyl, furanyl, piperidinyl, piperazinyl, pyrrolodinyl, morpholinyl, phenyl, thiophenyl, pyrazolyl, imidazolyl, isoxazolyl, thiazolyl, triazolyl, pyridinyl, pyrimidinyl; and when fused with Y is benzofuranyl, 6,7-dihydro-5H-pyrrolo[1,2-a]imidazolyl, benzo[b]thiophenyl, dihydroimidazo[1,2a]pyridinyl, tetrahydroisoquinolinyl, or isoindolinyl; and wherein the cycloalkyl, phenyl, heterocyclic and heteroaryl rings are each substituted with $(R^9)_n$ independently selected from the group consisting of methyl, ethyl, propyl, isopropyl, butyl, n-butyl, t-butyl, methoxy, F, Cl, Br, I, oxo, cyano, —NH₂, —N(CH₃)₂, —CF₃, —CHF₂, —OCHF₂, —S(O)₂NH₂, —SCH₃, —S(O)CH₃ and —S(O)₂CH₃; or $R^2$ is phenyl or pyridinyl each substituted with morpholine. In another aspect, $R^2$ is H, methyl, ethyl, propyl, isopropyl, butyl, isobutyl, n-butyl, —CH₂OCH₃, —(CH₂)₂OCH₃, —CH₂CF₃, —CF₃, —CH₂S(O)₂CH₃, —NHR$^b$ or —NCH₂R$^b$ wherein R$^b$ is methyl, cyclohexyl, phenyl or pyridinyl and wherein the phenyl and pyridinyl rings are optionally substituted with F, Cl, cyano or —CF₃; or $R^2$ is cyclopropyl, —CH₂cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl; and wherein the cycloalkyl, phenyl, heterocyclic and heteroaryl rings are each substituted with $(R^9)_n$ independently selected from the group consisting of methyl, ethyl, propyl, isopropyl, butyl, n-butyl, t-butyl, methoxy, F, Cl, Br, I, oxo, cyano, —NH₂, —N(CH₃)₂, —CF₃, —CHF₂, —OCHF₂, —S(O)₂NH₂, —SCH₃, —S(O)CH₃ and —S(O)₂CH₃; or $R^2$ is phenyl or pyridinyl each substituted with morpholine. In another aspect, $R^2$ is H, methyl, ethyl, propyl, isopropyl, butyl, isobutyl, n-butyl, —CH₂OCH₃, —(CH₂)₂OCH₃, —CH₂CF₃, —CF₃, —CH₂S(O)₂CH₃, —NHR$^b$ or —NCH₂R$^b$ wherein R$^b$ is methyl, cyclohexyl, phenyl or pyridinyl and wherein the phenyl and pyridinyl rings are optionally substituted with F, Cl, cyano or —CF₃; or $R^2$ is cyclopropyl, —CH₂cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl; and wherein the cycloalkyl, phenyl, heterocyclic and heteroaryl rings are each substituted with $(R^9)_n$ independently selected from the group consisting of methyl, ethyl, propyl, isopropyl, butyl, n-butyl, t-butyl, methoxy, F, Cl, Br, I, oxo, cyano, —NH₂, —N(CH₃)₂, —CF₃, —CHF₂, —OCHF₂, —S(O)₂NH₂, —SCH₃, —S(O)CH₃ and —S(O)₂CH₃; or $R^2$ is phenyl or pyridinyl each substituted with morpholine.

In another aspect of the invention, R and $R^2$ join to form a bond to form the di-oxo-oxathiazolyl ring,

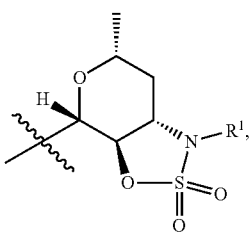

wherein $R^1$ is as defined herein. In another aspect, R and $R^2$ join to form a bond to form the di-oxo-oxathiazolyl ring wherein $R^1$ is H, methyl, phenyl or benzyl wherein the phenyl moiety is substituted with $(R^9)_n$. In another aspect, R and $R^2$ join to form a bond to form the di-oxo-oxathiazolyl ring wherein $R^1$ is H, methyl, phenyl or benzyl wherein the phenyl moiety is substituted with $(R^9)_n$ independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$. In another aspect, R and $R^2$ join to form a bond to form the di-oxo-oxathiazolyl ring wherein $R^1$ is H, methyl, phenyl or benzyl wherein the phenyl moiety is substituted with $(R^9)_n$ independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$. In another aspect, R and $R^2$ join to form a bond to form the di-oxo-oxathiazolyl ring wherein $R^1$ is H, methyl, phenyl or benzyl wherein the phenyl moiety is substituted with $(R^9)_n$ independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$.

In another aspect of the invention, $R^5$ and $R^6$ are each independently H; $C_1$-$C_6$alkyl optionally substituted with hydroxy; $C_1$-$C_6$alkoxy, cyano, $C_1$-$C_6$haloalkyl, $C_1$-$C_6$haloalkoxy, —C(O)$R^8$, —C(O)NR$^a$R$^8$, —C(O)R$^c$NR$^a$R$^b$, —C(O)OR$^c$R$^8$, —C(O)ONR$^a$R$^b$, —R$^c$NR$^a$C(O)R$^8$, —R$^c$C(O)OH, —R$^c$C(O)NR$^a$R$^b$, —R$^c$NR$^a$C(O)H, —R$^c$S(O)$_p$R$^8$, —R$^c$NR$^a$R$^b$, —R$^c$OR$^b$, —S(O)$_p$R$^8$, —S(O)$_p$R$^8$NR$^a$R$^b$, —R$^c$S(O)$_p$NR$^a$R$^b$, —R$^c$NR$^a$S(O)$_p$R$^8$; $C_0$-$C_4$alkylphenyl, $C_0$-$C_4$alkylC$_3$-$C_6$cycloalkyl, $C_0$-$C_4$alkylheterocycle, $C_0$-$C_4$alkylheteroaryl, wherein the heterocycle and heteroaryl rings are each 5-6 membered monocyclic rings and wherein each heterocycle and heteroaryl ring each contain at least one heteroatom selected from the group consisting of N, O and S; and wherein the phenyl, cycloalkyl ring, heterocycle ring and heteroaryl ring are each substituted with $(R^9)_n$. In another aspect, $R^5$ and $R^6$ are each independently H; $C_1$-$C_6$alkyl optionally substituted with hydroxy; $C_1$-$C_6$alkoxy, cyano, $C_1$-$C_6$haloalkyl, $C_1$-$C_6$haloalkoxy, —C(O)$R^8$, —C(O)NR$^a$R$^8$, —C(O)R$^c$NR$^a$R$^b$, —C(O)OR$^c$R$^8$, —C(O)ONR$^a$R$^b$, —R$^c$NR$^a$C(O)R$^8$, —R$^c$C(O)OH, —R$^c$C(O)NR$^a$R$^b$, —R$^c$NR$^a$C(O)H, —R$^c$S(O)$_p$R$^8$, —R$^c$NR$^a$R$^b$, —R$^c$OR$^b$, —S(O)$_p$R$^8$, —S(O)$_p$R$^8$NR$^a$R$^b$, —R$^c$S(O)$_p$NR$^a$R$^b$, —R$^c$NR$^a$S(O)$_p$R$^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, $C_1$-$C_2$alkylcyclopentyl, $C_1$-$C_2$alkylcyclohexyl, tetrahydrofuranyl, tetrahydropyranyl, oxazolidinyl, pyrrolidinyl, piperidinyl, piperazinyl, morpholinyl, $C_1$-$C_2$alkyltetrahydrofuranyl, $C_1$-$C_2$alkyloxazolidinyl, $C_1$-$C_2$alkyltetrahydropyranyl, $C_1$-$C_2$alkylpyrrolidinyl, $C_1$-$C_2$alkylpiperidinyl, $C_1$-$C_2$alkylpiperazinyl, $C_1$-$C_2$morpholinyl; pyrazolyl, imidazolyl, triazolyl, tetrazolyl, oxazolyl, pyridinyl, pyridazinyl, pyrimidinyl, pyrazinyl, $C_1$-$C_2$alkylpyrazolyl, $C_1$-$C_2$alkylimidazolyl, $C_1$-$C_2$alkyltriazolyl, $C_1$-$C_2$alkyltetrazolyl, $C_1$-$C_2$alkyloxazolyl, $C_1$-$C_2$alkylpyridinyl, $C_1$-$C_2$alkylpyridazinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$. In another aspect, $R^5$ and $R^6$ are each independently H; $C_1$-$C_6$alkyl optionally substituted with hydroxy; $C_1$-$C_6$alkoxy, cyano, $C_1$-$C_6$haloalkyl, $C_1$-$C_6$haloalkoxy, —C(O)$R^8$, —C(O)NR$^a$R$^8$, —C(O)R$^c$NR$^a$R$^b$, —C(O)ONR$^a$R$^b$, —R$^c$NR$^a$C(O)R$^8$, —R$^c$C(O)NR$^a$R$^b$, —R$^c$NR$^a$C(O)H, —R$^c$S(O)$_p$R$^8$, —R$^c$NR$^a$R$^b$, S(O)$_p$R$^8$, —S(O)$_p$R$^8$NR$^a$R$^b$, —R$^c$S(O)$_p$NR$^a$R$^b$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydrofuranyl, tetrahydropyranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydrofuran, $C_1$-$C_2$tetrahydropyran, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$ independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$. In another aspect, $R^5$ and $R^6$ are each independently H; $C_1$-$C_6$alkyl optionally substituted with hydroxy; $C_1$-$C_6$alkoxy, $C_1$-$C_6$haloalkyl, $C_1$-$C_6$haloalkoxy, —C(O)$R^8$, —C(O)NR$^a$R$^8$, —C(O)R$^c$NR$^a$R$^b$, —R$^c$S(O)$_p$R$^8$, —R$^c$NR$^a$R$^b$, —R$^c$OR$^b$, —S(O)$_p$R$^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$piperadinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$ independently selected from the group methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$. In another aspect, $R^5$ and $R^6$ are each independently H; $C_1$-$C_6$alkyl optionally substituted with hydroxy; $C_1$-$C_6$alkoxy, $C_1$-$C_6$haloalkyl, —OCF$_3$, —C(O)NR$^a$R$^8$, —R$^c$S(O)$_p$R$^8$, —R$^c$NR$^a$R$^b$, —R$^c$OR$^b$, —S(O)$_p$R$^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$ independently selected from methyl, ethyl, isopropyl, methoxy, ethoxy, F, Cl, Br, I, oxo, hydroxy, cyano, nitro, —$NH_2$, —$NHCH_3$, —$N(CH_3)_2$, —$CF_3$, —$CHF_2$, —$CH_2F$, —$OCF_3$, —$OCHF_2$, —$S(O)_2NH_2$, —$SCH_3$, —$S(O)CH_3$ and —$S(O)_2CH_3$. In another aspect, $R^5$ is H, $C_1$-$C_6$alkyl, morpholinyl, piperadinyl, —$CH_2$morpholinyl, —$CH_2$piperadinyl, —$(CH_2)_2$morpholinyl or $(CH_2)_2$piperadinyl. In another aspect, $R^5$ is H, methyl, ethyl, propyl, isopropyl, —$CH_2$morpholinyl, —$CH_2$piperadinyl, —$(CH_2)_2$morpholinyl or $(CH_2)_2$piperadinyl. In another aspect, $R^5$ is H, methyl, ethyl, propyl or isopropyl. In another aspect, $R^6$ is H; $C_1$-$C_6$alkyl optionally substituted with hydroxy; $C_1$-$C_6$alkoxy, $C_1$-$C_6$haloalkyl, —$OCF_3$, —$C(O)NR^aR^8$, —$R^cS(O)_pR^8$, —$R^cNR^aR^b$, —$R^cOR^b$, —$S(O)_pR^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$. In another aspect, $R^6$ is H, methyl, ethyl, propyl, isopropyl, butyl, isobutyl, t-butyl, methoxy, ethoxy, —$CH_2CF_3$, —$CF_3$, —$OCF_3$; —$C(O)NR^aR^8$ wherein $R^a$ is H or methyl and $R^8$ is H, methyl, cyclopropyl, phenyl optionally substituted with F, Cl or —$CF_3$; —$(CH_2)S(O)_2R^8$ wherein $R^8$ is methyl or phenyl; —$CH_2NR^aR^b$ or —$(CH_2)_2NR^aR^b$ wherein $R^a$ and $R^b$ are each independently H or methyl; —$(CH_2)_2OCH_3$, —$(CH_2)_3OCH_3$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, pyrrolidinyl, piperidinyl, piperazinyl, morpholinyl, tetrahydropyranyl, tetrahydrofuranyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$.

In another aspect of the invention, $R^5$ and $R^6$ taken together with the nitrogen atom to which they are attached form Ring B, a 4-8 membered heterocyclic or a 5-membered heteroaryl ring, each optionally containing at least one additional heteroatom selected from N, O and S; and wherein each ring is substituted with $(R^9)_n$; and wherein each ring is further optionally fused with Y which is phenyl, pyridinyl, pyrimidyl, pyrazolyl, thiophenyl, thiazolyl or triazolyl. In another aspect, $R^5$ and $R^6$ taken together with the nitrogen atom to which they are attached form Ring B, a 4-8 membered heterocyclic ring or a 5-membered heteroaryl ring, each optionally containing at least one additional heteroatom selected from N, O and S; and wherein each ring is substituted with $(R^9)_n$; and wherein each ring is further optionally fused with Y which is phenyl, pyridinyl or pyrimidyl. In another aspect, $R^5$ and $R^6$ taken together with the nitrogen atom to which they are attached form Ring B which is azetidinyl, pyrrolyl, pyrazolyl, imidazolyl, triazolyl, tetrazolyl, pyrrolidinyl, piperidinyl, piperazinyl, morpholinyl, or thiomorpholinyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and wherein each ring is further optionally fused with Y which is phenyl or pyridinyl. In another aspect, $R^5$ and $R^6$ taken together with the nitrogen atom to which they are attached form Ring B which is pyrrolyl, pyrazolyl, imidazolyl, triazolyl, tetrazolyl, pyrrolidinyl, piperidinyl, piperazinyl, morpholinyl or thiomorpholinyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and wherein each ring is further optionally fused with Y which is phenyl. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and wherein each ring is further optionally fused with Y which is phenyl. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; or when fused with Y which is phenyl, Ring B is indolinyl, isoindolinyl, tetrahydroquinolinyl, tetrahydroisoquinolinyl or dihydrobenzooxazinyl. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$.

In another aspect of the invention, $R^7$ is H, $C_1$-$C_6$alkyl, phenyl, —$(CH_2)_mNH_2$, —$(CH_2)_mNHCH_3$, —$(CH_2)_mN(CH_3)_2$, —$(CH_2)_mC(O)H$, —$(CH_2)_mC(O)CH_3$, —$(CH_2)_mS(O)_pCH_3$, —$(CH_2)_mNHC(O)CH_3$, —$(CH_2)_mNHC(O)NHCH_3$, —$(CH_2)_mNHC(O)N(CH_3)_2$ or —$(CH_2)_mNHC(O)CH_3$; wherein m is the integer 1, 2, or 3. In another aspect, $R^7$ is H, $C_1$-$C_6$alkyl, phenyl, —$(CH_2)_mNH_2$, —$(CH_2)_mNHCH_3$, —$(CH_2)_mN(CH_3)_2$, —$(CH_2)_mC(O)CH_3$, —$(CH_2)_mS(O)_pCH_3$ or —$(CH_2)_mNHC(O)CH_3$; wherein m is the integer 1 or 2. In another aspect, $R^7$ is H, $C_1$-$C_6$alkyl, phenyl, —$(CH_2)NH_2$, —$(CH_2)NHCH_3$, —$(CH_2)N(CH_3)_2$, —$(CH_2)C(O)CH_3$, —$(CH_2)S(O)_pCH_3$ or —$(CH_2)NHC(O)CH_3$. In another aspect, $R^7$ is H, methyl, ethyl, propyl, isopropyl, t-butyl, —(CH$_2$)$_m$NH$_2$, —(CH$_2$)NHCH$_3$, —(CH$_2$)N(CH$_3$)$_2$, —(CH$_2$)C(O)CH$_3$, —(CH$_2$)S(O)$_p$CH$_3$ or —(CH$_2$)NHC(O)CH$_3$. In another aspect, R$^7$ is H, methyl, ethyl, propyl, isopropyl, t-butyl, —CH$_2$NH$_2$, —CH$_2$NHCH$_3$ or —CH$_2$N(CH$_3$)$_2$. In another aspect, R$^7$ is H, methyl, ethyl, propyl, isopropyl or —CH$_2$N(CH$_3$)$_2$. In another aspect, R$^7$ is H, methyl, ethyl or propyl.

In another aspect of the invention, R$^8$ is C$_1$-C$_6$alkyl, C$_1$-C$_6$haloalkyl, —NR$^a$R$^b$; or C$_0$-C$_4$alkylC$_3$-C$_6$cycloalkyl, phenyl, pyrrolyl, pyrazolyl, pyridinyl or pyrimidinyl, each substituted with (R$^9$)$_n$ independently selected from the group consisting of methyl, ethyl, isopropyl, methoxy, F, Cl, Br, I, oxo, cyano, —NH$_2$, —N(CH$_3$)$_2$, —CF$_3$, —CHF$_2$ and —OCHF$_2$. In another aspect, R$^8$ is methyl, ethyl, propyl; or cyclopropyl, C$_1$alkylcyclopropyl, phenyl or pyridinyl, each substituted with (R$^9$)$_n$ independently selected from the group consisting of methyl, ethyl, isopropyl, methoxy, F, Cl, Br, I, oxo, cyano, —NH$_2$, —N(CH$_3$)$_2$, —CF$_3$, —CHF$_2$ and —OCHF$_2$. In another aspect, R$^8$ is methyl, ethyl; or cyclopropyl or phenyl each optionally substituted with one or two substituents independently selected from the group consisting of methyl, methoxy, F, Cl, Br, oxo, cyano and —CF$_3$.

In another aspect of the invention, each R$^9$ is independently selected from the group consisting of C$_1$-C$_6$alkyl, C$_1$-C$_6$alkoxy, halo, oxo, hydroxy, —CH$_2$OH, nitro, cyano, —NR$^a$R$^b$, C$_1$-C$_6$haloalkyl, C$_1$-C$_6$haloalkoxy, —S(O)$_p$R$^8$; or phenyl, tetrahydrofuranyl, tetrahydrothiophenyl, pyrrolidinyl, tetrahydropyranyl, tetrahydrothiopyranyl, piperidinyl, morpholinyl, piperazinyl, pyrrolyl, furanyl thiophenyl, pyrazolyl, imidazolyl, isoxazolyl, oxazolyl, isothiazolyl, thiazolyl, triazolyl, oxadiazolyl, thiadiazolyl, pyridinyl, pyridazinyl, pyrimidinyl and pyrazinyl, each of which is further optionally substituted with fluoro, chloro, cyano or —CF$_3$. In yet another aspect, each R$^9$ is independently selected from the group consisting of C$_1$-C$_6$alkyl, C$_1$-C$_6$alkoxy, halo, oxo, hydroxy, —CH$_2$OH, nitro, cyano, —NR$^a$R$^b$, C$_1$-C$_6$haloalkyl, C$_1$-C$_6$haloalkoxy, —S(O)$_p$R$^8$; or phenyl, tetrahydrofuranyl, pyrrolidinyl, tetrahydropyranyl, piperidinyl, morpholinyl, piperazinyl, pyrrolyl, furanyl, thiophenyl pyrazolyl, imidazolyl, isoxazolyl, pyridinyl, pyrimidinyl and pyrazinyl, each optionally substituted with fluoro, chloro, cyano or —CF$_3$. In yet another aspect, each R$^9$ is independently selected from the group consisting of C$_1$-C$_6$alkyl, C$_1$-C$_6$alkoxy, halo, oxo, hydroxy, —CH$_2$OH, nitro, cyano, —NR$^a$R$^b$, C$_1$-C$_6$haloalkyl, C$_1$-C$_6$haloalkoxy, —S(O)$_p$R$^8$; or phenyl, piperidinyl, morpholinyl, piperazinyl and pyridinyl, each optionally substituted with fluoro, chloro, cyano or —CF$_3$. In yet another aspect, R$^9$ is independently selected from the group consisting of C$_1$-C$_6$alkyl, C$_1$-C$_6$alkoxy, halo, oxo, hydroxy, —CH$_2$OH, cyano, nitro, —NH$_2$, —NHCH$_3$, —N(CH$_3$)$_2$, —N(CH$_2$CH$_3$)$_2$, —CHF$_2$, —CF$_3$, —CH$_2$F, —OCHF$_2$, —OCF$_3$, —S(O)$_2$NH$_2$, —SCH$_3$, —S(O)CH$_3$, —S(O)$_2$CH$_3$; or phenyl, piperidinyl, morpholinyl, piperazinyl and pyridinyl, each optionally substituted with fluoro, chloro, cyano or —CF$_3$. In yet another aspect, R$^9$ is independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$; or phenyl, piperidinyl, morpholinyl, piperazinyl and pyridinyl, each optionally substituted with fluoro, chloro, cyano or —CF$_3$. In yet another aspect, R$^9$ is independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In yet another aspect, each R$^9$ is independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$. In yet another aspect, each R$^9$ is independently selected from the group consisting of methyl, methoxy, F, Cl, Br, I, oxo, cyano, —NHCH$_3$, —N(CH$_3$)$_2$, and —CF$_3$.

In another aspect of the invention, X is R$^a$, —(CH$_2$)$_m$NR$^5$R$^6$, —(CH$_2$)$_m$OR$^7$, —(CH$_2$)$_m$SR$^7$, —(CH$_2$)$_m$N$_3$, —(CH$_2$)$_m$CN or —(CH$_2$)$_m$X'; wherein m is the integer 1 or 2. In another aspect, X is R$^a$. In another aspect, X is —CH$_2$NR$^5$R$^6$. In another aspect, X is —CH$_2$OR$^7$. In another aspect, X is —CH$_2$SR$^7$. In another aspect, X is —CH$_2$N$_3$. In another aspect, X is —CH$_2$CN. In another aspect, X is —CH$_2$X'.

In another aspect of the invention, Y is cyclopentyl, cyclohexyl, phenyl, pyridinyl, pyrimidyl, pyrazolyl, thiophenyl, thiazolyl, triazolyl, isothiazolyl, pyrrolyl, imidazolyl or tetrahydrothiophene, each optionally substituted with methyl, F, Cl, cyano, oxo or —CF$_3$. In another aspect, Y is cyclopentyl, cyclohexyl, phenyl, pyridinyl, thiophenyl, thiazolyl, isothiazolyl, pyrrolyl, imidazolyl or tetrahydrothiophene, each optionally substituted with methyl, F, Cl, cyano, oxo or —CF$_3$. In another aspect, Y is cyclopentyl, cyclohexyl, phenyl, pyridinyl, thiophenyl, thiazolyl or tetrahydrothiophene, each optionally substituted with methyl, F, Cl, cyano, oxo or —CF$_3$. In another aspect, Y is cyclopentyl, phenyl or thiophenyl, each optionally substituted with methyl, F, Cl, cyano, oxo or —CF$_3$. In another aspect, Y is cyclopentyl, phenyl or thiophenyl. In another aspect, when Y is fused with a 5- or 6-membered heterocyclic or heteroaryl ring, the fused moiety is selected from benzofuranyl, 6,7-dihydro-5H-pyrrolo[1,2-a]imidazolyl, thieno[3,2 b]pyridinyl, 3,4-dihydroisoquinolinyl, isoindolinyl and imidazo[1,2α]pyridinyl.

In another aspect of the invention, p is the integer 0. In another aspect, p is the integer 1. In another aspect, p is the integer 2. In another aspect of the invention, n is the integer 0, 1 or 2. In yet another aspect, n is the integer 0 or 1. In yet another aspect, n is the integer 0. In yet another aspect, n is the integer 1. In yet another aspect, n is the integer 2.

In another aspect, is a Formula (1) compound wherein W is Formula (A) that is a

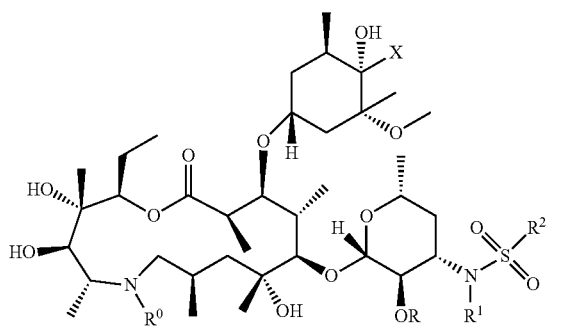

(1A)

Formula (1A) compound, wherein R, R$^0$, R$^1$, R$^2$ and X are as defined herein, stereoisomers thereof, and pharmaceutically acceptable salts thereof. In another aspect, is a Formula (1A) compound wherein R$^0$ is H, methyl, ethyl or propyl; and R is H, phenyl or a 5- or 6-membered heteroaryl ring containing at least one heteroatom selected from N, O and S; and wherein the phenyl and heteroaryl ring is substituted with $(R^9)_n$; $R^1$ is $C_1$-$C_6$alkyl or cyclohexyl; or $R^1$ is benzyl, —$CH_2$pyridinyl or —$CH_2$thiazolyl, each of which is substituted with $(R^9)_n$ independently selected from methyl, fluoro, chloro, methoxy, cyano and —$CF_3$; $R^2$, n and X are as defined herein; or R and $R^2$ join to form a bond to form the di-oxo-oxathiazolyl ring, stereoisomers thereof, and pharmaceutically acceptable salts thereof. In another aspect, is a Formula (1A) compound wherein $R^0$ is H, methyl, ethyl or propyl; and R is H or phenyl, pyridinyl or thiophenyl, each substituted with $(R^9)_n$; $R^1$ is $C_1$-$C_6$alkyl or cyclohexyl; or $R^1$ is benzyl, —$CH_2$pyridinyl or —$CH_2$thiazolyl, each of which is substituted with $(R^9)_n$ independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; $R^2$, n and X are as defined herein; stereoisomers thereof, and pharmaceutically acceptable salts thereof.

In another aspect, is a composition comprising a Formula (1A) compound, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1A) compound, stereoisomer thereof, or pharmaceutically acceptable salt thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNFα and IL-6 in the animal.

In another aspect, is the use of a Formula (1A) compound, stereoisomer thereof, or a pharmaceutically acceptable salt thereof; to prepare a medicament for treating or preventing an inflammatory response in an animal wherein the inflammatory response is due to a bacterial, viral, or fungal infection, stress, and/or an environmental factor. In another aspect of the use, the use of the medicament for treating or and preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNFα and IL-6 in the animal.

In another aspect of the invention, Formula (A) is selected from the group consisting of: Formula (A0), Formula (A1), Formula (A2), Formula (A3), Formula (A4), Formula (A5) or Formula (A6)

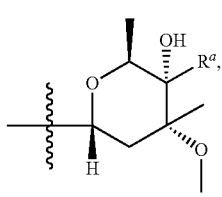
(A0)

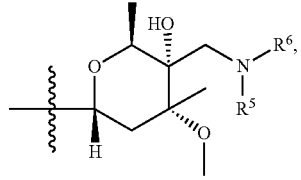
(A1)

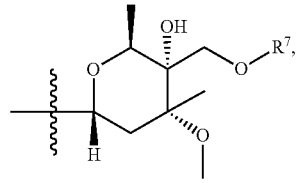
(A2)

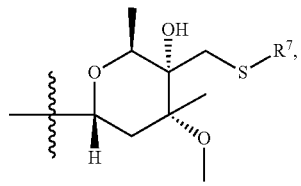
(A3)

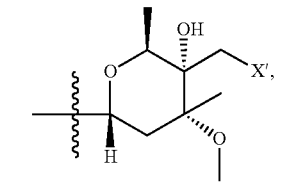
(A4)

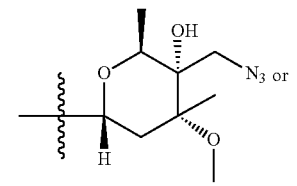
(A5)

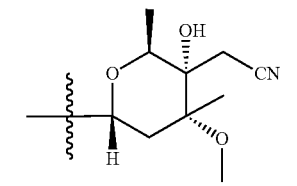
(A6)

stereoisomers thereof, and pharmaceutically acceptable salts thereof. In another aspect, Formula (A) compound is Formula (A0). In another aspect, Formula (A) is Formula (A1). In another aspect, Formula (A) is Formula (A2). In another aspect, Formula (A) is Formula (A3) compound. In another aspect, Formula (A) is Formula (A4). In another aspect, Formula (A) is Formula (A5). In another aspect, Formula (A) is Formula (A6). In another aspect, the preferred Formula (A) is Formula (A1).

In another aspect of the invention, is a Formula (1) compound wherein W is H that is a Formula (1.1) compound, wherein $R^0$, R, $R^1$ and $R^2$ are as defined herein, (1.1)

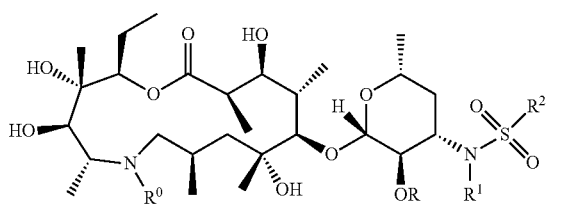

stereoisomers thereof, and pharmaceutically acceptable salts thereof. In another aspect, is a Formula (1.1) compound wherein $R^0$ is H, methyl ethyl or propyl; and R, $R^1$ and $R^2$ are as defined herein, stereoisomers thereof, and pharmaceutically acceptable salts thereof. In another aspect, is a Formula (1.1) compound, wherein R is H or phenyl substituted with $(R^9)_n$; $R^0$ is H, methyl, ethyl or propyl; $R^1$ is methyl, ethyl, propyl, isopropyl, isobutyl or cyclohexyl; or $R^1$ is benzyl, —$CH_2$pyridinyl or —$CH_2$thiazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; $R^2$ and n are as defined herein, stereoisomers thereof, and pharmaceutically acceptable salts thereof. In another aspect, is a Formula (1.1) compound, wherein R is H or phenyl substituted with $(R^9)_n$; $R^0$ is H, methyl, ethyl or propyl; $R^1$ is methyl, ethyl, propyl or cyclohexyl; or $R^1$ is benzyl, —$CH_2$pyridinyl or —$CH_2$thiazolyl, each substituted with $(R^9)_n$; $R^2$ is cyclopropyl, cyclopentyl, cyclohexyl, 6,7-dihydro-5H-pyrrolo[1,2-a]imidazolyl; or $R^2$ is phenyl, thiophenyl, benzofuranyl, thiazolyl, imidazolyl, pyridinyl or —NHPhenyl, each substituted with $(R^9)_n$; or $R^2$ is phenyl or pyridinyl each substituted with morpholine; and wherein each $R^9$ is independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$, —$S(O)_2CH_3$ and morpholine; and wherein n is as defined herein, stereoisomers thereof, and pharmaceutically acceptable salts thereof. In another aspect, is a Formula (1.1) compound, wherein R is H or phenyl substituted with $(R^9)_n$; $R^0$ is H or methyl; $R^1$ is methyl; $R^2$ is cyclopropyl, cyclohexyl, 6,7-dihydro-5H-pyrrolo[1,2-a]imidazolyl; or $R^2$ is phenyl, thiophenyl, benzofuranyl, thiazolyl, imidazolyl, pyridinyl or —NHPhenyl, each substituted with $(R^9)_n$; or $R^2$ is phenyl or pyridinyl each substituted with morpholine; and wherein each $R^9$ is independently selected from methyl, ethyl, isopropyl, methoxy, F, Cl, Br, I, oxo, —$NO_2$, cyano, —$NH_2$, —$N(CH_3)_2$, —$CF_3$, —$CHF_2$, —$OCHF_2$, —$S(O)_2NH_2$, —$SCH_3$, —$S(O)CH_3$, and —$S(O)_2CH_3$; or $R^2$ is phenyl or pyridinyl each substituted with morpholine; and wherein n is the integer 0, 1 or 2, stereoisomers thereof, and pharmaceutically acceptable salts thereof. In another aspect, is a Formula (1.1) compound, wherein R is H or phenyl substituted with $(R^9)_n$; $R^0$ is H or methyl; $R^1$ is methyl; $R^2$ is phenyl substituted with $(R^9)_n$; and wherein each $R^9$ is independently selected from methyl, methoxy, F, Cl, Br, cyano, and —$CF_3$; and wherein n is the integer 0, 1 or 2, stereoisomers thereof, and pharmaceutically acceptable salts thereof. In another aspect, is a Formula (1.1) compound that is a Table A compound, stereoisomers thereof, and pharmaceutically acceptable salts thereof. In another aspect, is a non-antibacterial Formula (1.1) compound Table A compound, stereoisomers thereof, and pharmaceutically acceptable salts thereof. In another aspect, is a Formula (1) compound that is a Formula (1.1) compound that is Example A-9, stereoisomers thereof, and pharmaceutically acceptable salts thereof.

In another aspect, is a composition comprising a Formula (1.1) compound; stereoisomer thereof, or a pharmaceutically acceptable salt thereof. In another aspect, is a composition comprising a non-antibacterial Formula (1.1) compound; stereoisomer thereof, or a pharmaceutically acceptable salt thereof. In another aspect, is a composition comprising a Formula (1.1) Table A compound, stereoisomer thereof, or a pharmaceutically acceptable salt thereof. In another aspect, is a composition comprising a non-antibacterial Formula (1.1) Table A compound, stereoisomer thereof, or a pharmaceutically acceptable salt thereof. In another aspect, is a composition comprising a non-antibacterial Formula (1.1) Table A compound, that is Example A-9, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1.1) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1.1) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1.1) Table A compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1.1) Table A compound that is Example A-9, stereoisomer thereof, or a pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (1.1) compound; stereoisomer thereof, or a pharmaceutically acceptable salt thereof, to prepare a medicament for treating or preventing an inflammatory response in an animal. In another aspect, is the use of a non-antibacterial Formula (1.1) compound;

stereoisomer thereof, or a pharmaceutically acceptable salt thereof, to prepare a medicament for treating or preventing an inflammatory response in an animal. In another aspect, is the use of a non-antibacterial Formula (1.1) Table A compound; stereoisomer thereof, or a pharmaceutically acceptable salt thereof, to prepare a medicament for treating or preventing an inflammatory response in an animal. In another aspect, is the use of a non-antibacterial Formula (1.1) Table A compound that is Example A-9, stereoisomer thereof, or a pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention is a Formula (1) compound wherein W is Formula (A) and Formula (A) is Formula (A0) wherein $R^a$ is H that is a Formula (1-A0)

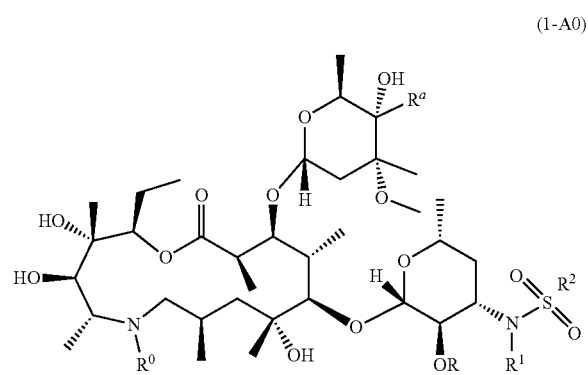

(1-A0)

compound, wherein R, $R^a$, $R^0$, $R^1$ and $R^2$ are as defined herein, stereoisomers thereof, and pharmaceutically acceptable salts thereof. In another aspect, is a Formula (1-A0) compound wherein $R^a$ is H, methyl or ethyl; $R^0$ is H, methyl, ethyl or propyl; and R, $R^1$ and $R^2$ are as defined herein, stereoisomers thereof, and pharmaceutically acceptable salts thereof. In another aspect, is a Formula (1-A0) compound wherein $R^a$ is H or methyl; $R^0$ is H, methyl, ethyl or propyl; and R, $R^1$ and $R^2$ are as defined herein, stereoisomers thereof, and pharmaceutically acceptable salts thereof. In another aspect, is a Formula (1-A0) compound wherein $R^a$ is H; $R^0$ is H, methyl, ethyl or propyl; and R, $R^1$ and $R^2$ are as defined herein, stereoisomers thereof, and pharmaceutically acceptable salts thereof. In another aspect, is a Formula (1-A0) compound wherein $R^a$ is H; $R^0$ is H, methyl, ethyl or propyl; $R^1$ is $C_1$-$C_6$alkyl or cyclohexyl; or $R^1$ is benzyl, —$CH_2$pyridinyl or —$CH_2$thiazolyl, each substituted with $(R^9)_n$; R is H, or R is phenyl, thiophenyl or pyridinyl, each substituted with $(R^9)_n$; and wherein $R^2$, $R^9$ and n are as defined herein; or R and $R^2$ join to form a bond to form the di-oxo-oxathiazolyl ring; stereoisomers thereof, and pharmaceutically acceptable salts thereof. In another aspect, is a Formula (1-A0) compound wherein $R^a$ is H; $R^0$ is H, methyl, ethyl or propyl; $R^1$ is $C_1$-$C_6$alkyl or cyclohexyl; or $R^1$ is benzyl, —$CH_2$pyridinyl or —$CH_2$thiazolyl, each substituted with $(R^9)_n$; R is H, or R is phenyl, thiophenyl or pyridinyl, each substituted with $(R^9)_n$; and wherein $R^2$ is as defined herein; and wherein each $R^9$ is independently selected from halo, methyl, ethyl, isopropyl, methoxy, —$CF_3$, cyano, nitro, oxo, amino, —$N(CH_3)_2$, —$S(O)CH_3$, —$S(O)_2CH_3$, —$SCH_3$ and —$S(O)_2NH_2$; and n is the integer 0, 1 or 2; or R and $R^2$ join to form a bond to form the di-oxo-oxathiazolyl ring; stereoisomers thereof, and pharmaceutically acceptable salts thereof. In another aspect, is a Formula (1-A0) compound wherein $R^a$ is H; $R^0$ is H, methyl, ethyl or propyl; $R^1$ is $C_1$-$C_6$alkyl or cyclohexyl; or $R^1$ is benzyl, —$CH_2$pyridinyl or —$CH_2$thiazolyl, each substituted with $(R^9)_n$; R is H, or R is phenyl, thiophenyl or pyridinyl, each substituted with $(R^9)_n$; $R^2$ is phenyl, thiophenyl, benzofuranyl, thiazolyl, imidazolyl, pyridinyl or —NHPhenyl, each substituted with $(R^9)_n$; or $R^2$ is phenyl or pyridinyl each substituted with morpholine; and wherein each $R^9$ is independently selected from methyl, ethyl, isopropyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2, stereoisomers thereof, and pharmaceutically acceptable salts thereof. In another aspect, is a Formula (1-A0) compound wherein $R^a$ and $R^0$ are both H; $R^1$ is methyl; R is H, or R is phenyl, thiophenyl or pyridinyl, each substituted with $(R^9)_n$; $R^2$ is phenyl, thiophenyl, benzofuranyl, thiazolyl, imidazolyl, pyridinyl or —NHPhenyl, each substituted with $(R^9)_n$; or $R^2$ is phenyl or pyridinyl each substituted with morpholine; and wherein each $R^9$ is independently selected from halo, methyl, ethyl, isopropyl, methoxy, —$CF_3$, cyano, nitro, oxo, amino, —$N(CH_3)_2$, —$S(O)CH_3$, —$S(O)_2CH_3$, —$SCH_3$ and —$S(O)_2NH_2$; and n is the integer 0, 1 or 2; stereoisomers thereof, and pharmaceutically acceptable salts thereof.

In another aspect, is a composition comprising a Formula (1-A0) compound; stereoisomer thereof, or a pharmaceutically acceptable salt thereof. In another aspect, is a composition comprising a non-antibacterial Formula (1-A0) compound; stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A0) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A0) compound; stereoisomer thereof, or a pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (1-A0) compound; stereoisomer thereof, or a pharmaceutically acceptable salt thereof, to prepare a medicament for treating or preventing an inflammatory response in an animal. In another aspect, is the use of a non-antibacterial Formula (1-A0) compound; stereoisomer thereof, or a pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound wherein W is Formula (A) and Formula (A) is Formula (A1) that is a Formula (1-A1) compound,

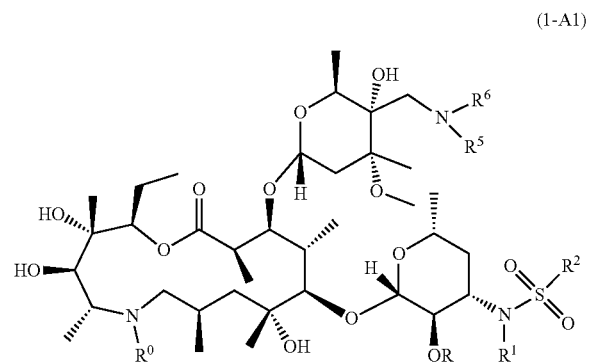

(1-A1)

wherein R, $R^0$, $R^1$, $R^2$, $R^5$ and $R^6$ are as defined herein, stereoisomers thereof, and pharmaceutically acceptable salts thereof. In another aspect, is a Formula (1-A1) compound wherein $R^0$ is H, methyl, ethyl or propyl; and R, $R^1$, $R^2$, $R^5$ and $R^6$ are as defined herein, stereoisomers thereof, and pharmaceutically acceptable salts thereof. In another aspect, is a Formula (1-A1) compound wherein $R^0$ is H, methyl, ethyl or propyl; R is H, or phenyl, pyridinyl or thiophenyl, each substituted with $(R^9)_n$; $R^1$ is $C_1$-$C_6$alkyl, cyclohexyl; or $R^1$ is or benzyl, —$CH_2$pyridinyl or —$CH_2$thiazolyl, each substituted with $(R^9)_n$; $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$, —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; $R^5$ and $R^6$ are each independently H; $C_1$-$C_6$alkyl optionally substituted with hydroxy; $C_1$-$C_6$alkoxy, $C_1$-$C_6$haloalkyl, —$OCF_3$, —$C(O)NR^aR^8$, —$R^cS(O)_pR^8$, —$R^cNR^aR^b$, —$R^cOR^b$ or —$S(O)_pR^8$; or $C_0$-$C_3$alkylphenyl, $C_0$-$C_3$alkyl$C_3$-$C_6$cycloalkyl, $C_0$-$C_3$alkyloxazolidinyl, $C_0$-$C_3$alkylpyrrolidinyl, $C_0$-$C_3$alkylpiperidinyl, $C_0$-$C_3$alkylpiperazinyl, $C_0$-$C_3$alkylmorpholinyl, $C_0$-$C_3$alkyl-tetrahydropyranyl, $C_0$-$C_3$alkyltetrahydrofuranyl, $C_0$-$C_3$alkylpyrazolyl, $C_0$-$C_3$alkylimidazolyl, $C_0$-$C_3$alkylpyridinyl, $C_0$-$C_3$alkylpyrimidinyl, $C_0$-$C_3$alkylpyridazinyl, $C_0$-$C_3$alkylthiazolyl or $C_0$-$C_3$alkylpyrazinyl, each substituted with $(R^9)_n$; or $R^5$ and $R^6$ taken together with the nitrogen atom to which they are attached form Ring B which is azetidinyl, pyrrolyl, pyrazolyl, pyrrolidinyl, piperidinyl, piperazinyl, morpholinyl, imidazolyl, azathianyl, tetrazolyl, triazolyl, 3,4-dihydroisoquinolinyl or thiomorpholinyl, each substituted with $(R^9)_n$ or Ring B is indolinyl, isoindolinyl, tetrahydroquinolinyl, dihydrobenzooxazinyl or dihydrobenzothiazinyl optionally substituted with at least one oxo; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is as defined herein; stereoisomers thereof, and pharmaceutically acceptable salts thereof. In another aspect, is a Formula (1-A1) compound wherein $R^0$ is H, methyl, ethyl or propyl; R is H, or phenyl, pyridinyl or thiophenyl, each substituted with $(R^9)_n$; $R^1$ is methyl; or $R^1$ is benzyl, —$CH_2$pyridinyl or —$CH_2$thiazolyl, each substituted with $(R^9)_n$; $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$, —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; $R^5$ is H or $C_1$-$C_6$alkyl; and $R^6$ is H; $C_1$-$C_6$alkyl optionally substituted with hydroxy; $C_1$-$C_6$alkoxy, $C_1$-$C_6$haloalkyl, —$OCF_3$, —$C(O)NR^aR^8$, —$R^cS(O)_pR^8$, —$R^cNR^aR^b$, —$R^cOR^b$ or —$S(O)_pR^8$; or $C_0$-$C_3$alkylphenyl, $C_0$-$C_3$alkyl$C_3$-$C_6$cycloalkyl, $C_0$-$C_3$alkylpyrrolidinyl, $C_0$-$C_3$alkylpiperidinyl, $C_0$-$C_3$alkyl-piperazinyl, $C_0$-$C_3$alkylmorpholinyl, $C_0$-$C_3$alkyltetrahydropyranyl, pyrazolyl, imidazolyl, pyridazinyl, $C_0$-$C_3$alkylpyridinyl or $C_0$-$C_3$alkylthiazolyl, each substituted with $(R^9)_n$; or $R^5$ and $R^6$ taken together with the nitrogen atom to which they are attached form Ring B is azetidinyl, pyrazolyl, pyrrolidinyl, piperidinyl, piperazinyl, morpholinyl, imidazolyl, azathianyl or tetrazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof. In another aspect, is a Formula (1-A1) compound wherein $R^0$ is H; R is H, phenyl, pyridinyl or thiophenyl, each substituted with $(R^9)_n$; $R^1$ is methyl; $R^2$H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$, —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; $R^5$ is H or $C_1$-$C_6$alkyl; and $R^6$ is H; $C_1$-$C_6$alkyl, methoxy, ethoxy, $C_1$-$C_6$haloalkyl, —$OCF_3$, —$CH_2OCF_3$, —$(CH_2)_2OCF_3$, —$CH_2CN$, —$R^cS(O)_pCH_3$; —$R^cS(O)_pNR^aR^b$; —$R^cS(O)_p$Phenyl, —$R^cNR^aR^b$, $R^cOR^b$, —$R^cNHC(O)CH_3$; wherein $R^a$ and $R^b$ are each independently H, methyl and ethyl; or $R^6$ is or $C_0$-$C_3$alkylphenyl, $C_0$-$C_3$alkyl$C_3$-$C_6$cycloalkyl, $C_0$-$C_3$alkylpyrrolidinyl, $C_0$-$C_3$alkylpiperidinyl, piperazinyl, morpholinyl, $C_0$-$C_3$alkyltetrahydropyranyl, pyrazolyl, imidazolyl, pyridazinyl, $C_0$-$C_3$alkylpyridinyl or $C_0$-$C_3$alkylthiazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof. In another aspect, is a Formula (1-A1) compound wherein $R^0$ is H; R is H, phenyl substituted with $(R^9)_n$; $R^1$ is methyl; $R^2$ is imidazole optionally substituted with methyl; phenyl, —$NHR^b$, —$NCH_2R^b$ wherein $R^b$ is cyclohexyl or phenyl each optionally substituted with F, Cl, cyano or —$CF_3$; or $R^2$ is phenyl substituted with $(R^9)_n$ or $R^2$ is imidazolyl optionally substituted with methyl; $R^5$ is H; and $R^6$ is propyl; and wherein each $R^9$ is independently selected from the group consisting of methyl, methoxy, F, Cl, cyano and —$CF_3$; and n is the integer 0, 1 or 2; stereoisomers thereof, and pharmaceutically acceptable salts thereof. In another aspect, is a Formula (1-A1) Table B compound, stereoisomers thereof, and pharmaceutically acceptable salts thereof. In another aspect, is a non-antibacterial Formula (1-A1) Table B compound, stereoisomers thereof, and pharmaceutically acceptable salts thereof. In another aspect, is a Formula (1-A1) Table B compound that is selected from the group consisting of Example B-26, B-41, B-48, B-49, B-50, B-58, B-60, B-107, B-113 or B-148, stereoisomers thereof, and pharmaceutically acceptable salts thereof.

In another aspect, is a composition comprising a Formula (1-A1) compound; stereoisomer thereof, or a pharmaceutically acceptable salt thereof. In another aspect, is a composition comprising a non-antibacterial Formula (1-A1) compound; stereoisomer thereof, or a pharmaceutically acceptable salt thereof. In another aspect, is a composition comprising a Formula (1-A1) Table B compound, stereoisomer thereof, or a pharmaceutically acceptable salt thereof. In another aspect, is a composition comprising a non-antibacterial Formula (1-A1) Table B compound, stereoisomer thereof, or a pharmaceutically acceptable salt thereof. In another aspect, is a composition comprising a non-antibacterial Formula (1-A1) Table B compound selected from the group consisting of B-26, B-41, B-48, B-49, B-50, B-58, B-60, B-107, B-113 or B-148, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A1) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1) Table B compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1) Table B compound selected from the group consisting of B-26, B-41, B-48, B-49, B-50, B-58, B-60, B-107, B-113 or B-148, stereoisomer thereof, or pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (1-A1) compound; stereoisomer thereof, or a pharmaceutically acceptable salt thereof, to prepare a medicament for treating or preventing an inflammatory response in an animal. In another aspect, is the use of a non-antibacterial Formula (1-A1) compound; stereoisomer thereof, or a pharmaceutically acceptable salt thereof, to prepare a medicament for treating or preventing an inflammatory response in an animal. In another aspect, is the use of a non-antibacterial Formula (1-A1) Table B compound; stereoisomer thereof, or a pharmaceutically acceptable salt thereof, to prepare a medicament for treating or preventing an inflammatory response in an animal. In another aspect, is the use of a non-antibacterial Formula (1-A1) Table B compound selected from the group consisting of B-26, B-41, B-48, B-49, B-50, B-58, B-60, B-107, B-113 or B-148, stereoisomer thereof, or pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention is a Formula (1-A1) compound wherein $R^5$ and $R^6$ with the nitrogen atom they share join together to form Ring B that is substituted with $(R^9)_n$, that is a Formula (1-A1a) compound,

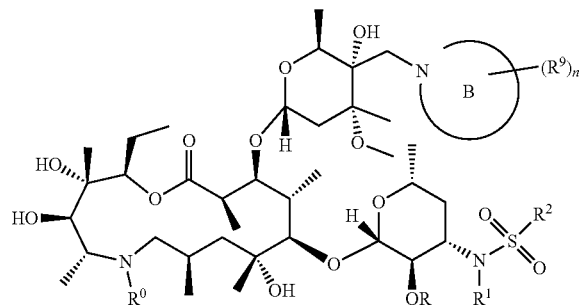

(1-A1a)

wherein R, $R^0$, $R^1$, $R^2$, $R^9$, Ring B and n are as defined herein, stereoisomers thereof, and pharmaceutically acceptable salts thereof. In another aspect, is a Formula (1-A1a) compound wherein $R^0$ is H, methyl ethyl or propyl; and R, $R^1$, $R^2$, Ring B, $R^9$ and n are as defined herein, stereoisomers thereof, and pharmaceutically acceptable salts thereof.

In another aspect, is a Formula (1-A1a) compound wherein $R^0$ is H, methyl, ethyl or propyl; R is H, or phenyl, pyridinyl or thiophenyl, each substituted with $(R^9)_n$; $R^1$ is $C_1$-$C_6$alkyl or cyclohexyl; or $R^1$ is benzyl, —$CH_2$pyridinyl or —$CH_2$thiazolyl, each substituted with $(R^9)_n$; $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$, —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; Ring B is azetidinyl, pyrrolyl, pyrazolyl, pyrrolidinyl, piperidinyl, piperazinyl, morpholinyl, imidazolyl, azathianyl, tetrazolyl, triazolyl, 3,4-dihydroisoquinolinyl or thiomorpholinyl, each substituted with $(R^9)_n$; or Ring B, when fused with Y, is indolinyl, isoindolinyl, tetrahydroquinolinyl, dihydrobenzooxazinyl or dihydrobenzothiazinyl; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is as defined herein; stereoisomers thereof, and pharmaceutically acceptable salts thereof. In another aspect, is a Formula (1-A1a) compound wherein $R^0$ is H, methyl, ethyl or propyl; R is H, or phenyl, pyridinyl or thiophenyl, each substituted with $(R^9)_n$; $R^1$ is methyl; or $R^1$ is benzyl, —$CH_2$pyridinyl or —$CH_2$thiazolyl, each substituted with $(R^9)_n$; $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$, —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; Ring B is azetidinyl, pyrazolyl, pyrrolidinyl, piperidinyl, piperazinyl, morpholinyl, imidazolyl, azathianyl or tetrazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, —$NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof. In another aspect, is a Formula (1-A1a) compound wherein $R^0$ is H; R is H, phenyl or piperidinyl each substituted with $(R^9)_n$; $R^1$ is methyl; $R^2$ is —NHphenyl or phenyl each substituted $(R^9)_n$; Ring B is piperidine; and wherein each $R^9$ is independently selected from the group consisting of methyl, methoxy, F, Cl, Br, cyano, —$NH_2$, —$N(CH_3)_2$ and —$CF_3$; and n is the integer 0, 1 or 2; stereoisomers thereof, and pharmaceutically acceptable salts thereof. In another aspect, is a Formula (1-A1a) Table C compound, stereoisomers thereof, and pharmaceutically acceptable salts thereof. In another aspect, is a non-antibacterial Formula (1-A1a) Table C compound, stereoisomers thereof, and pharmaceutically acceptable salts thereof. In another aspect, is a non-antibacterial Formula (1-A1a) Table C compound that is Example C-4 or C-11, stereoisomers thereof, and pharmaceutically acceptable salts thereof.

In another aspect, is a composition comprising a Formula (1-A1a) compound; stereoisomer thereof, or a pharmaceutically acceptable salt thereof. In another aspect, is a composition comprising a non-antibacterial Formula (1-A1a) compound; stereoisomer thereof, or a pharmaceutically acceptable salt thereof. In another aspect, is a composition comprising a Formula (1-A1a) Table C compound, stereoisomer thereof, or a pharmaceutically acceptable salt thereof. In another aspect, is a composition comprising a non-antibacterial Formula (1-A1a) Table C compound, stereoisomer thereof, or a pharmaceutically acceptable salt thereof. In another aspect, is a composition comprising a non-antibacterial Formula (1-A1a) Table C compound that is Example C-4 or C-11, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A1a) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1a) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1a) Table C compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A1a) Table C compound that is Example C-4 or C-11; stereoisomer thereof, or a pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (1-A1a) compound; stereoisomer thereof, or a pharmaceutically acceptable salt thereof, to prepare a medicament for treating or preventing an inflammatory response in an animal. In another aspect, is the use of a non-antibacterial Formula (1-A1a) compound; stereoisomer thereof, or a pharmaceutically acceptable salt thereof, to prepare a medicament for treating or preventing an inflammatory response in an animal. In another aspect, is the use of a non-antibacterial Formula (1-A1a) Table C compound; stereoisomer thereof, or a pharmaceutically acceptable salt thereof, to prepare a medicament for treating or preventing an inflammatory response in an animal. In another aspect, is the use of a non-antibacterial Formula (1-A1a) Table C compound that is Example C-4 or C-11; stereoisomer thereof, or a pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a compound selected from the group consisting of: N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-methoxyphenoxy)-6-methyltetrahydro-2H-pyran-4-yl)-N-methylbenzenesulfonamide (A-9); N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,4-dimethylbenzenesulfonamide (B-26); (2R,3S,4R,5R,8R,10R,11R,12S,13S,14R)-11-[(2S,3R,4S,6R)-4-[[(4-chlorophenyl)methyl-methylsulfamoyl]-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one (B-41); (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(phenylsulfamoyl)amino]oxan-2-yl]oxy-3,5,8,10,12,14-hexamethyl-15-oxo-1-oxa-6-azacyclopentadecane (B-48); (2R,3S,4R,5R,8R,10R,11R,12S,13S,14R)-11-[(2S,3R,4S,6R)-4-[[cyclohexyl(methyl)sulfamoyl]-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one (B-49); (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane (B-50); 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((3-(piperidin-1-yl)propyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (B-58); 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (B-60); N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,1-dimethylimidazole-2-sulfonamide (B-107); (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[methyl-[4-(trifluoromethyl)phenyl]sulfamoyl]amino]oxan-2-yl]oxy-3,5,8,10,12,14-hexamethyl-1-oxa-6-azacyclopentadecan-15-one (B-113); N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-(4-methoxybenzyl)benzenesulfonamide (B-148); 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (C-4); and (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane (C-11), stereoisomers thereof, and pharmaceutically acceptable salts.

In another aspect, is a compound selected from the group consisting of (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane (B-50); N-[(2S,3R,4S,6R)-2-[[(2R,3S, 4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10, 12,14-hexamethyl-15-oxo-1-oxa-6-azacyclopentadec-11-yl] oxy]-3-(4-fluorophenoxy)-6-methyloxan-4-yl]-N,1-dimethylimidazole-2-sulfonamide (B-107); (2R,3S,4R,5R, 8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[methyl-[4-(trifluoromethyl) phenyl]sulfamoyl]amino]oxan-2-yl]oxy-3,5,8,10,12,14-hexamethyl-1-oxa-6-azacyclopentadecan-15-one (B-113); and 4-chloro-N-((2S,3R,4S,6R)-2-(((2R,3S,4R,5R,8R,10R, 11R,12S,13S,14R)-2-ethyl-3,4,10-trihydroxy-13-(((2R,4R, 5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl) oxy)-3-hydroxy-6-methyltetrahydro-2H-pyran-4-yl)-N-methylbenzenesulfonamide (C-4), stereoisomers thereof, and pharmaceutically acceptable salts.

In another aspect, is the compound (2R,3S,4R,5R,8R, 10R,11R,12S,13S,14R)-2-ethyl-3,4,10-trihydroxy-13-[(2R, 4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[[4-(trifluoromethyl)phenyl] sulfamoyl]amino]oxan-2-yl]oxy-3,5,8,10,12,14-hexamethyl-15-oxo-1-oxa-6-azacyclopentadecane (B-50), stereoisomers thereof, and pharmaceutically acceptable salts thereof.

In another aspect, is the compound N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,1-dimethylimidazole-2-sulfonamide (B-107), stereoisomers thereof, and pharmaceutically acceptable salts thereof.

In another aspect, is the compound (2R,3S,4R,5R,8R, 10R,11R,12S,13S,14R)-2-ethyl-3,4,10-trihydroxy-13-[(2R, 4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[methyl-[4-(trifluoromethyl) phenyl]sulfamoyl]amino]oxan-2-yl]oxy-3,5,8,10,12,14-hexamethyl-1-oxa-6-azacyclopentadecan-15-one (B-113), stereoisomers thereof, and pharmaceutically acceptable salts thereof.

In another aspect, is the compound 4-chloro-N-((2S,3R, 4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (C-4), stereoisomers thereof, and pharmaceutically acceptable salts thereof.

In another aspect, is a composition comprising an exemplified compound selected from the group consisting of A-9, B-26, B-41, B-48, B-49, B-50, B-58, B-60, B-107, B-113, B-148, C-4 and C-11, stereoisomer thereof, or pharmaceutically acceptable salt thereof. In another aspect, is a composition comprising an exemplified compound selected from the group consisting of B-50, B-107, B-113 and C-4, stereoisomer thereof, or pharmaceutically acceptable salt thereof. In another aspect, is a composition comprising Example B-50, stereoisomer thereof, or pharmaceutically acceptable salt thereof. In another aspect, is a composition comprising Example B-107, stereoisomer thereof, or pharmaceutically acceptable salt thereof. In another aspect, is a composition comprising Example B-113, stereoisomer thereof, or pharmaceutically acceptable salt thereof. In another aspect, is a composition comprising Example C-4, stereoisomer thereof, or pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of an exemplified compound selected from the group consisting A-9, B-26, B-41, B-48, B-49, B-50, B-58, B-60, B-107, B-113, B-148, C-4 and C-11, stereoisomer thereof, or pharmaceutically acceptable salt thereof. In another aspect, is a method of treating or preventing an inflammatory response in an animal by administering to said animal in need thereof, a therapeutically effective amount of an exemplified compound selected from the group consisting of B-50, B-107, B-113, and C-4, stereoisomer thereof, or pharmaceutically acceptable salt thereof. In another aspect, is a method of treating or preventing an inflammatory response in an animal by administering to said animal in need thereof, a therapeutically effective amount of Example B-50, stereoisomer thereof, or pharmaceutically acceptable salt thereof. In another aspect, is a method of treating or preventing an inflammatory response in an animal by administering to said animal in need thereof, a therapeutically effective amount of Example B-107, stereoisomer thereof, or pharmaceutically acceptable salt thereof. In another aspect, is a method of treating or preventing an inflammatory response in an animal by administering to said animal in need thereof, a therapeutically effective amount of Example B-113, stereoisomer thereof, or pharmaceutically acceptable salt thereof. In another aspect, is a method of treating or preventing an inflammatory response in an animal by administering to said animal in need thereof, a therapeutically effective amount of Example C-4, stereoisomer thereof, or pharmaceutically acceptable salt thereof. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of an exemplified compound selected from the group consisting of A-9, B-26, B-41, B-48, B-49, B-50, B-58, B-60, B-107, B-113, B-148, C-4 and C-11, stereoisomer thereof, or pharmaceutically acceptable salt thereof, to prepare a medicament for the prevention or treatment of an inflammatory response in an animal. In another aspect, is the use of an exemplified compound selected from the group consisting of B-50, B-107, B-113 and C-4, stereoisomer thereof, or pharmaceutically acceptable salt thereof, to prepare a medicament for the prevention or treatment of an inflammatory response in an animal. In another aspect, is the use of Example B-50, stereoisomer thereof, or pharmaceutically acceptable salt thereof, to prepare a medicament for the prevention or treatment of an inflammatory response in an animal. In another aspect, is the use of Example B-107, stereoisomer thereof, or pharmaceutically acceptable salt thereof, to prepare a medicament for the prevention or treatment of an inflammatory response in an animal. In another aspect, is the use of Example B-113, stereoisomer thereof, or pharmaceutically acceptable salt thereof, to prepare a medicament for the prevention or treatment of an inflammatory response in an animal. In another aspect, is the use of Example C-4, stereoisomer thereof, or pharmaceutically acceptable salt thereof, to prepare a medicament for the prevention or treatment of an inflammatory response in an animal. In another aspect, the use of the medicament for use in the treatment or prevention of an inflammatory response in the animal prevents or mitigates the progression of a respiratory disease or disorder in the animal. In another aspect of the use, the animal is livestock; and wherein the respiratory disease or disorder is bovine respiratory disease or swine respiratory disease. In another aspect of the use, IL-6 and TNF-α are down regulated in the animal.

In another aspect of the invention, is a Formula (1) compound wherein W is Formula (A) and Formula (A) is Formula (A2) that is a Formula (1-A2) compound,

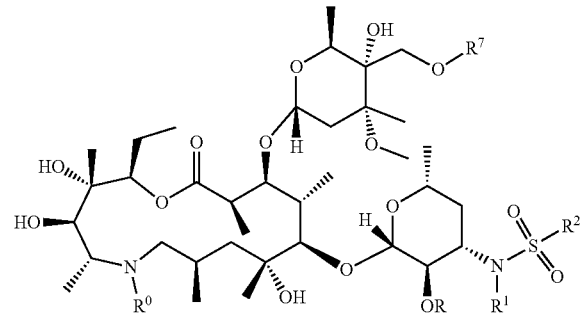

(1-A2)

wherein R, $R^0$, $R^1$, $R^2$ and $R^7$ are as defined herein, stereoisomers thereof, and pharmaceutically acceptable salts thereof. In another aspect, is a Formula (1-A2) compound wherein $R^0$ is H, methyl, ethyl or propyl; and R, $R^1$, $R^2$ and $R^7$ are as defined herein, stereoisomers thereof, and pharmaceutically acceptable salts thereof. In another aspect, is a Formula (1-A2) compound wherein $R^0$ is H or methyl; $R^1$ is methyl; R is H or phenyl optionally substituted with $(R^9)_n$; $R^2$ is H, methyl, ethyl, propyl, isopropyl, butyl, isobutyl, n-butyl, —CH$_2$OCH$_3$, —(CH$_2$)$_2$OCH$_3$, —CH$_2$CF$_3$, —CF$_3$, —NHR$^b$ or —NCH$_2$R$^b$ wherein R$^b$ is methyl, cyclohexyl, phenyl or pyridinyl and wherein the phenyl and pyridinyl rings are optionally substituted with F, Cl, cyano or —CF$_3$; or $R^2$ is cyclopropyl, —CH$_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; and wherein each $R^9$ is independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$; and n is the integer 0, 1 or 2, stereoisomers thereof, and pharmaceutically acceptable salts thereof.

In another aspect of the invention, is a Formula (1) compound wherein W is Formula (A) and Formula (A) is Formula (A3) that is a Formula (1-A3) compound,

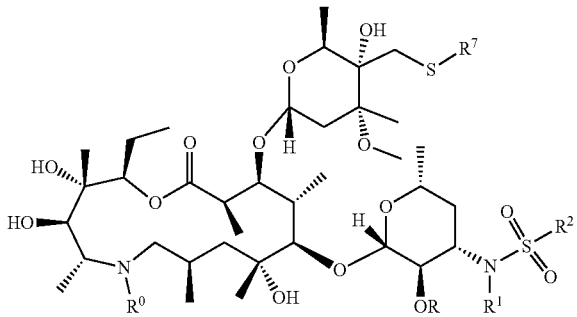

(1-A3)

wherein R, $R^0$, $R^1$, $R^2$ and $R^7$ are as defined herein, stereoisomers thereof, and pharmaceutically acceptable salts thereof. In another aspect, is a Formula (1-A3) compound wherein $R^0$ is H, methyl, ethyl or propyl; and R, $R^1$, $R^2$ and $R^7$ are as defined herein, stereoisomers thereof, and pharmaceutically acceptable salts thereof. In another aspect, is a Formula (1-A3) compound wherein $R^0$ is H or methyl; $R^1$ is methyl; R is H or phenyl optionally substituted with $(R^9)_n$; $R^2$ is H, methyl, ethyl, propyl, isopropyl, butyl, isobutyl, n-butyl, —CH$_2$OCH$_3$, —(CH$_2$)$_2$OCH$_3$, —CH$_2$CF$_3$, —CF$_3$, —NHR$^b$ or —NCH$_2$R$^b$ wherein R$^b$ is methyl, cyclohexyl, phenyl or pyridinyl and wherein the phenyl and pyridinyl rings are optionally substituted with F, Cl, cyano or —CF$_3$; or $R^2$ is cyclopropyl, —CH$_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; and wherein each $R^9$ is independently selected from the group consisting of methyl, ethyl, propyl, isopropyl, butyl, n-butyl, t-butyl, methoxy, F, Cl, Br, I, oxo, cyano, —NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$; an n is the integer 0, 1 or 2; and $R^7$ is H, methyl, ethyl, propyl, isopropyl, t-butyl, —CH$_2$NH$_2$, —CH$_2$NHCH$_3$ or —CH$_2$N(CH$_3$)$_2$; stereoisomers thereof, and pharmaceutically acceptable salts thereof. In another aspect, is a non-antibacterial Formula (1-A3) compound that is 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((phenylthio)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (Ex #. A3-1; [M+H]$^+$=1018; i.e., $R^0$ is H, $R^1$ is methyl, $R^2$ is 4-chlorophenyl and $R^7$ is phenyl); stereoisomers thereof, and pharmaceutically acceptable salts thereof.

In another aspect of the invention, is a Formula (1) compound wherein W is Formula (A) and Formula (A) is Formula (A4) that is a Formula (1-A4) compound, (1-A4)

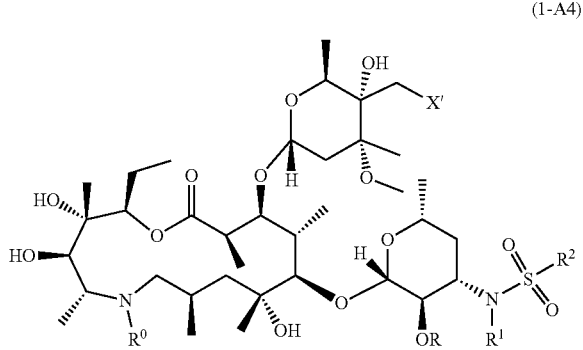

wherein R, $R^0$, $R^1$, $R^2$ and X' are as defined herein, stereoisomers thereof, and pharmaceutically acceptable salts thereof. In another aspect, is a Formula (1-A4) compound wherein $R^0$ is H, methyl, ethyl or propyl; and R, $R^1$, $R^2$ and X' are as defined herein, stereoisomers thereof, and pharmaceutically acceptable salts thereof. In another aspect, is a Formula (1-A4) compound wherein $R^0$ is H or methyl; $R^1$ is methyl; R is H or phenyl optionally substituted with $(R^9)_n$; X is F or Cl; and $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$ or —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2, stereoisomers thereof, and pharmaceutically acceptable salts thereof. In another aspect, is a non-antibacterial Formula (1-A4) compound that is 4-chloro-N-((2S,3R,4S,6R)-2-(((2R,3S,4R,5R,8R,10R,11R,12S,13S,14R)-13-(((2R,4R,5S,6S)-5-(chloromethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (Ex #. A4-1; $[M+H]^+$=944; i.e., $R^0$ is H, $R^1$ is methyl, $R^2$ is 4-chlorophenyl and X is chloro)), stereoisomers thereof, and pharmaceutically acceptable salts thereof.

In another aspect of the invention, is a Formula (1) compound wherein W is Formula (A) and Formula (A) is Formula (A5) that is a Formula (1-A5) compound, (1-A5)

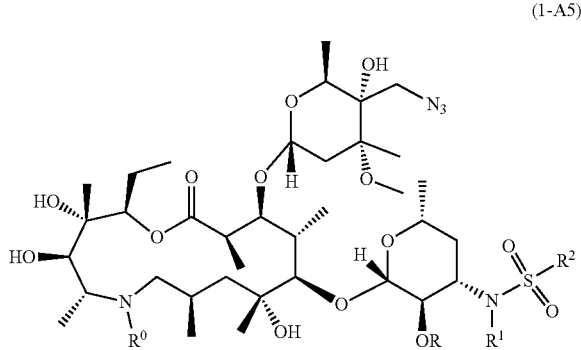

wherein R, $R^0$, $R^1$ and $R^2$ are as defined herein, stereoisomers thereof, and pharmaceutically acceptable salts thereof. In another aspect, is a Formula (1-A5) compound wherein $R^0$ is H, methyl, ethyl or propyl; and R, $R^1$ and $R^2$ are as defined herein, stereoisomers thereof, and pharmaceutically acceptable salts thereof. In another aspect, is a Formula (1-A5) compound wherein $R^0$ is H or methyl; $R^1$ is methyl; R is H or phenyl optionally substituted with $(R^9)_n$, and $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$ or —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2, stereoisomers thereof, and pharmaceutically acceptable salts thereof.

In another aspect of the invention, is a Formula (1) compound wherein W is Formula A and Formula (A) is Formula (A6) that is a Formula (1-A6) compound, (1-A6)

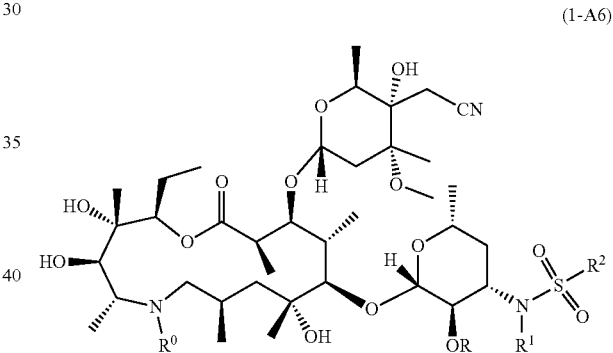

Wherein R, $R^0$, $R^1$ and $R^2$ are as defined herein, stereoisomers thereof, and pharmaceutically acceptable salts thereof. In another aspect, is a Formula (1-A6) compound wherein $R^0$ is H, methyl, ethyl or propyl; and R, $R^1$ and $R^2$ are as defined herein; or R and $R^2$ join to form a bond to form the di-oxo-oxathiazolyl ring; stereoisomers thereof, and pharmaceutically acceptable salts thereof. In another aspect, is a Formula (1-A6) compound wherein $R^0$ is H or methyl; $R^1$ is methyl; R is H or phenyl optionally substituted with $(R^9)_n$, and $R^2$ is H, methyl, ethyl, propyl, isopropyl, butyl, isobutyl, n-butyl, —$CH_2OCH_3$, —$(CH_2)_2OCH_3$, —$CH_2CF_3$, —$CF_3$, —$NHR^b$ or —$NCH_2R^b$ wherein $R^b$ is methyl, cyclohexyl, phenyl or pyridinyl and wherein the phenyl and pyridinyl rings are optionally substituted with F, Cl, cyano or —$CF_3$; or $R^2$ is cyclopropyl, —$CH_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$; or $R^2$ is phenyl or pyridinyl each substituted with morpholine; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —S(O)$_2$CH$_3$; and n is the integer 0, 1 or 2, stereoisomers thereof, and pharmaceutically acceptable salts thereof. In another aspect, is a non-antibacterial Formula (1-A6) compound that is 4-chloro-N-((2S,3R,4S,6R)-2-(((2R,3S,4R,5R,8R,10R,11R,12S,13S,14R)-13-(((2R,4R,5S,6S)-5-(cyanomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide (Ex #. A6-1; [M+H]$^+$ 935; i.e., R$^0$ is H, R$^1$ is methyl and R$^2$ is 4-chlorophenyl); stereoisomers thereof, and pharmaceutically acceptable salts thereof.

In another aspect, is a composition comprising a Formula (1-A0), (1-A2), (1-A3), (1-A4), (1-A5) or (1-A6) compound; stereoisomer thereof, or a pharmaceutically acceptable salt thereof. In another aspect, is a composition comprising a non-antibacterial Formula (1-A0), (1-A2), (1-A3), (1-A4), (1-A5) or (1-A6) compound; stereoisomer thereof, or a pharmaceutically acceptable salt thereof. In another aspect, is a composition comprising a non-antibacterial Formula (1-A3) compound that is Example A3-1; a non-antibacterial Formula (1-A4) compound that is Example (A4-1) or a non-antibacterial Formula (1-A6) compound that is Example (A6-1), stereoisomer thereof, or pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A0), (1-A2), (1-A3), (1-A4), (1-A5) or (1-A6) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A0), (1-A2), (1-A3), (1-A4), (1-A5) or (1-A6) compound; stereoisomer thereof, or a pharmaceutically acceptable salt thereof. In another aspect, is a method of treating or preventing an inflammatory response in an animal by administering to said animal in need thereof, a therapeutically effective amount of a non-antibacterial Formula (1-A3) compound that is Example A3-1; or a non-antibacterial Formula (1-A4) compound that is Example (A4-1) or a non-antibacterial Formula (1-A6) compound that is Example (A6-1), stereoisomer thereof, or pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (1-A0), (1-A2), (1-A3), (1-A4), (1-A5) or (1-A6) compound; stereoisomer thereof, or a pharmaceutically acceptable salt thereof, to prepare a medicament for treating or preventing an inflammatory response in an animal. In another aspect, is the use of a non-antibacterial Formula (1-A0), (1-A2), (1-A3), (1-A4), (1-A5) or (1-A6) compound; stereoisomer thereof, or a pharmaceutically acceptable salt thereof, to prepare a medicament for treating or preventing an inflammatory response in an animal. In another aspect, is the use of a non-antibacterial Formula (1-A3) compound that is Example A3-1; a non-antibacterial Formula (1-A4) compound that is Example (A4-1) or a non-antibacterial Formula (1-A6) compound that is Example (A6-1), stereoisomer thereof, or pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound wherein R and R$^2$ join to form a bond to form the 2-di-oxo-oxathiazolyl ring that is a Formula (2) compound, wherein W, R$^0$ and R$^1$ are as defined herein, stereoisomers thereof, or (2)

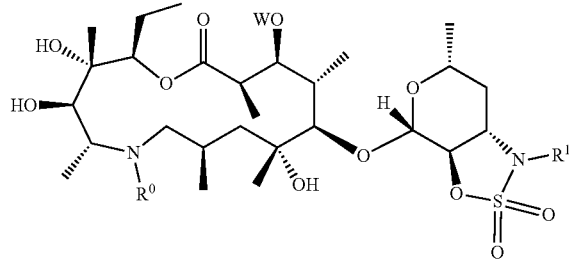

pharmaceutically acceptable salts thereof. In another aspect, is a Formula (2) compound, wherein R$^0$ is H, methyl, ethyl or propyl; and W and R$^1$ are as defined herein, stereoisomers thereof, and pharmaceutically acceptable salts thereof. In another aspect, is a Formula (2) compound, wherein R$^0$ is H; and W and R$^1$ are as defined herein, stereoisomers thereof, and pharmaceutically acceptable salts thereof.

In another aspect of the invention, is a Formula (2) compound, wherein W is H that is a Formula (2.1) compound wherein R$^0$ and R$^1$ are as described herein, (2.1)

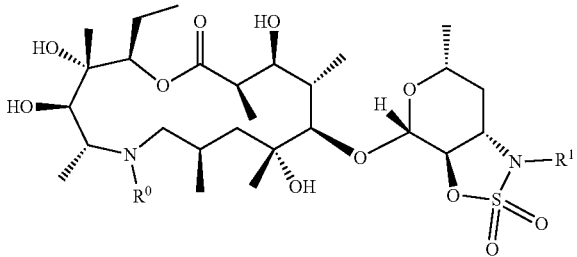

stereoisomers thereof, and pharmaceutically acceptable salts thereof. In another aspect, is a Formula (2.1) compound, wherein R$^0$ is H, methyl, ethyl or propyl; and R$^1$ is as described herein, stereoisomers thereof, and pharmaceutically acceptable salts thereof. In another aspect, is a Formula (2.1) compound, wherein $R^0$ is H; and $R^1$ is as described herein, stereoisomers thereof, and pharmaceutically acceptable salts thereof. In another aspect, is a Formula (2.1) compound, wherein $R^0$ is H or methyl; $R^1$ is $C_1$-$C_6$alkyl; or $R^1$ is benzyl, —$CH_2$pyridinyl or —$CH_2$thiazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof.

In another aspect of the invention, is a Formula (2) compound, wherein W is Formula (A) wherein X is $R^a$ and $R^a$ is H that is a Formula (2-A0) compound wherein $R^0$ and $R^1$ are as described herein, stereoisomers thereof, and pharmaceutically acceptable (2-A0)

salts thereof. In another aspect, is a Formula (2-A0) compound, wherein $R^a$ is H; $R^0$ is H, methyl, ethyl or propyl; and $R^1$ is as described herein, stereoisomers thereof, and pharmaceutically acceptable salts thereof. In another aspect, is a Formula (2-A0) compound, wherein $R^a$ is H; $R^0$ is H or methyl; $R^1$ is $C_1$-$C_6$alkyl; or $R^1$ is benzyl, —$CH_2$pyridinyl or —$CH_2$thiazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof.

In another aspect of the invention, is a Formula (2) compound, wherein W is Formula (A) wherein X is —$(CH_2)_mNR^5R^6$ and m is the integer 1 that is a Formula (2-A1)

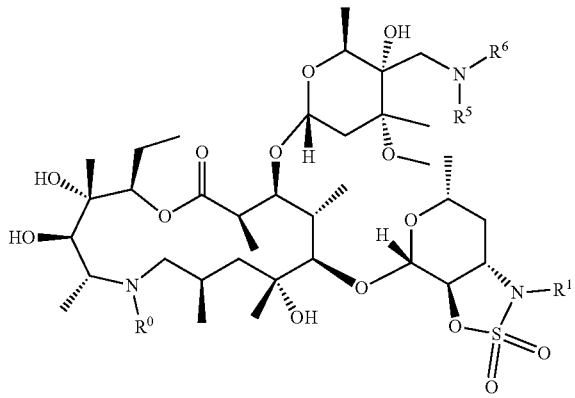

(2-A1)

compound, wherein $R^0$, $R^1$, $R^5$ and $R^6$ are as described herein, stereoisomers thereof, and pharmaceutically acceptable salts thereof. In another aspect, is a Formula (2-A1) compound, wherein $R^0$ is H, methyl, ethyl or propyl; and $R^1$, $R^5$ and $R^6$ are as described herein, stereoisomers thereof, and pharmaceutically acceptable salts thereof. In another aspect, is a Formula (2-A1) compound, wherein $R^0$ is H or propyl; $R^5$ is H and $R^6$ is propyl; and $R^1$ is $C_1$-$C_6$alkyl or cyclohexyl; or $R^1$ is benzyl, —$CH_2$pyridinyl or —$CH_2$thiazolyl, each substituted with $(R^9)_n$; or $R^5$ and $R^6$ taken together with the nitrogen atom to which they are attached form Ring B, which is piperidinyl or piperazinyl each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2; stereoisomers thereof, and pharmaceutically acceptable salts thereof. In another aspect, is a Formula (2-A1) compound, wherein $R^0$ is H or propyl; $R^5$ is H and $R^6$ is propyl; and $R^1$ is methyl or benzyl optionally substituted with $(R^9)_n$; or $R^5$ and $R^6$ taken together with the nitrogen atom to which they are attached form piperidine; and wherein each $R^9$ is independently selected from the group consisting of methyl, methoxy, F, Cl, cyano, and —$CF_3$; and n is the integer 0, 1 or 2; stereoisomers thereof, and pharmaceutically acceptable salts thereof. In another aspect, is a Formula (2-A1) Table D compound, stereoisomers thereof, and pharmaceutically acceptable salts thereof.

In another aspect, is a composition comprising a Formula (2-A1) compound or a Formula (2-A1) Table D compound, stereoisomer thereof, or a pharmaceutically acceptable salt thereof. In another aspect, the composition further comprises a pharmaceutically acceptable carrier. In another aspect, is a method of treating or preventing an inflammatory response in an animal by administering to said animal in need thereof, a therapeutically effective amount of a Formula (2-A1) compound or a Formula (2-A1) Table D compound, stereoisomer thereof, or a pharmaceutically acceptable salt thereof.

In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a Formula (2-A1) compound or a Formula (2-A1) Table D compound, stereoisomer thereof, or a pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (2) compound, wherein W is Formula (A) wherein X is —(CH$_2$)$_m$OR$^7$ or X is —(CH$_2$)$_m$SR$^7$; and m is the integer 1 that is a Formula (2-A2) or Formula (2-A3) compound, wherein R$^0$, R$^1$ and R$^7$ are as described herein, stereoisomers thereof, or pharmaceutically acceptable salts thereof, respectively. In another aspect, is a Formula (2-A2) or Formula (2-A3) compound, wherein R$^0$ is H, methyl, ethyl or propyl; and R$^1$ and R$^7$ are as described herein, stereoisomers thereof, and pharmaceutically acceptable salts thereof. In another aspect, is a Formula (2-A2) or Formula (2-A3) compound, wherein R$^0$ is H, methyl, ethyl or propyl; R$^1$ is C$_1$-C$_6$alkyl or cyclohexyl; or R$^1$ is benzyl, —CH$_2$pyridinyl or —CH$_2$thiazolyl, each substituted with (R$^9$)$_n$; R$^7$ is H, methyl, ethyl, propyl, isopropyl, t-butyl, —CH$_2$NH$_2$, —CH$_2$NHCH$_3$ or —CH$_2$N(CH$_3$)$_2$; and wherein each R$^9$ is independently selected from the group consisting of methyl, ethyl, propyl, isopropyl, butyl, n-butyl, t-butyl, methoxy, F, Cl, Br, I, oxo, cyano, NH$_2$, —N(CH$_3$)$_2$, —CF$_3$, —CHF$_2$, —OCHF$_2$, —S(O)$_2$NH$_2$, —SCH$_3$, —S(O)CH$_3$ and —S(O)$_2$CH$_3$; and n is the integer 0, 1 or 2, stereoisomers thereof, and pharmaceutically acceptable salts thereof. In another aspect, is a Formula (2-A2) or Formula (2-A3) compound, wherein R$^0$ is H; R$^1$ is methyl; and R$^7$ is H, methyl, ethyl or propyl, stereoisomers thereof, and pharmaceutically acceptable salts thereof.

In another aspect of the invention, is a Formula (2) compound, wherein W is Formula (A) wherein X is —(CH$_2$)$_m$X' or X is —(CH$_2$)$_m$N$_3$, or X is —(CH$_2$)$_m$CN; and m is the integer 1 that is a Formula (2-A4), Formula (2-A5) or Formula (2-A6) compound, wherein R$^0$, R$^1$ (2-A2)

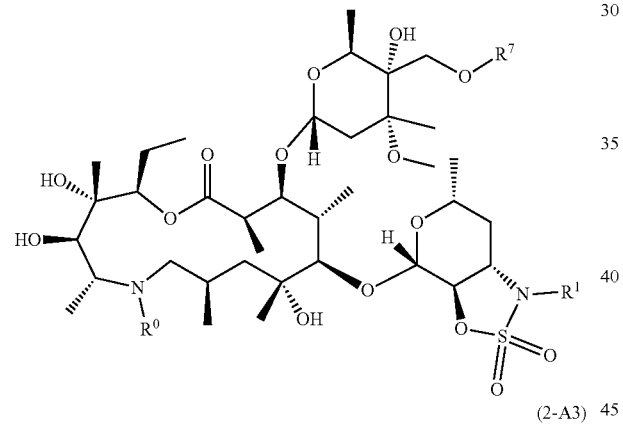

(2-A3)

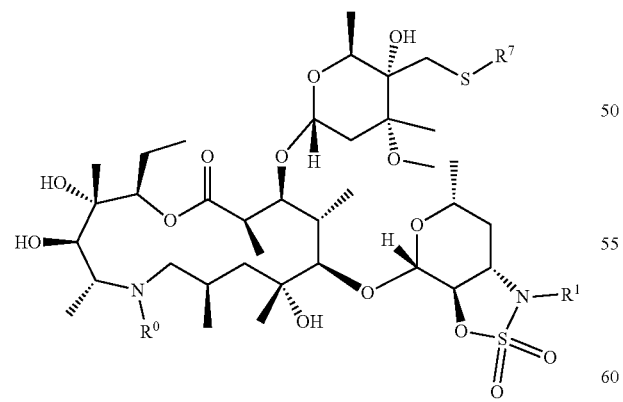

(2-A4)

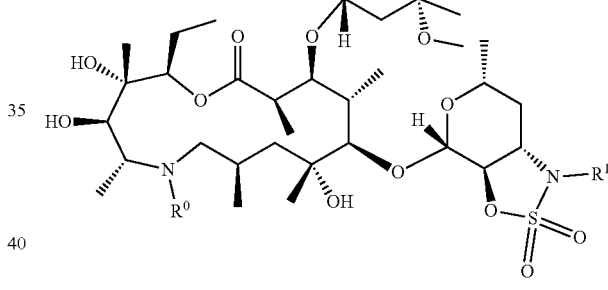

(2-A5)

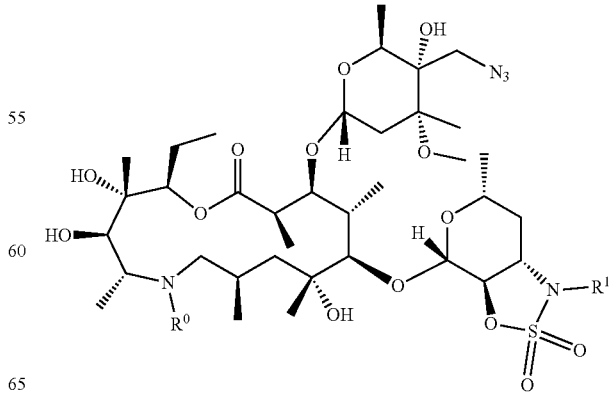

-continued (2-A6)

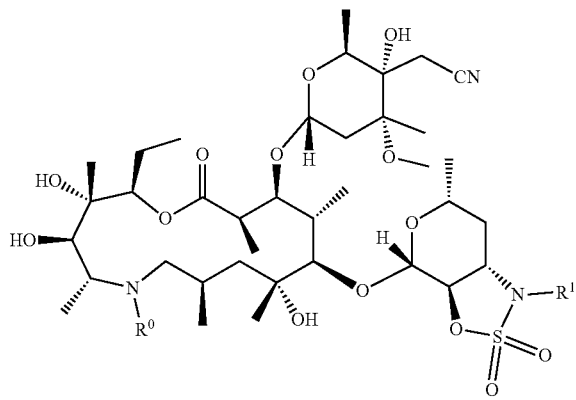

and X' are as described herein, stereoisomers thereof, or pharmaceutically acceptable salts thereof, respectively. In another aspect, is a Formula (2-A4), Formula (2-A5) or Formula (2-A6) compound, wherein $R^0$ is H, methyl, ethyl or propyl; X is fluoro or chloro; and $R^1$ is as described herein, stereoisomers thereof, and pharmaceutically acceptable salts thereof. In another aspect, is a Formula (2-A4), Formula (2-A5) or Formula (2-A6) compound, wherein $R^0$ is H, methyl, ethyl or propyl; X is fluoro or chloro; and $R^1$ is $C_1$-$C_6$alkyl or cyclohexyl; or $R^1$ is benzyl, —$CH_2$pyridinyl or —$CH_2$thiazolyl, each substituted with $(R^9)_n$; and wherein each $R^9$ is independently selected from the group consisting of methyl, ethyl, propyl, isopropyl, butyl, n-butyl, t-butyl, methoxy, F, Cl, Br, I, oxo, cyano, $NH_2$, —$N(CH_3)_2$, —$CF_3$, —$CHF_2$, —$OCHF_2$, —$S(O)_2NH_2$, —$SCH_3$, —$S(O)CH_3$ and —$S(O)_2CH_3$; and n is the integer 0, 1 or 2, stereoisomers thereof, and pharmaceutically acceptable salts thereof. In another aspect, is a Formula (2-A4), Formula (2-A5) or Formula (2-A6) compound, wherein $R^0$ is H, methyl, ethyl or propyl; $R^1$ is methyl; stereoisomers thereof, and pharmaceutically acceptable salts thereof.

In another aspect, is a composition comprising a Formula (2.1), Formula (2-A0), Formula (2-A2), Formula (2-A3), Formula (2-A4), Formula (2-A5) or Formula (2-A6) compound, stereoisomer thereof, or a pharmaceutically acceptable salt thereof. In another aspect, the composition further comprises a pharmaceutically acceptable carrier.

In another aspect, is a method of treating or preventing an inflammatory response in an animal by administering to said animal in need thereof, a therapeutically effective amount of a (2.1), Formula (2-A0), Formula (2-A2), Formula (2-A3), Formula (2-A4), Formula (2-A5) or Formula (2-A6) compound, stereoisomer thereof, or a pharmaceutically acceptable salt thereof. In another aspect of the method, the inflammatory response in the animal is due to a bacterial, viral, or fungal infection, stress, and/or an environmental factor. In another aspect of the method, treatment or prevention of the inflammatory response in the animal prevents or mitigates the progression of a respiratory disease or disorder in the animal. In another aspect of the method, the animal is livestock; and wherein the respiratory disease or disorder is bovine respiratory disease or swine respiratory disease. In another aspect of the method, IL-6 and TNF-α are down regulated in the animal.

In another aspect, is the use of a (2.1), Formula (2-A0), Formula (2-A2), Formula (2-A3), Formula (2-A4), Formula (2-A5) or Formula (2-A6) compound, stereoisomer thereof, or a pharmaceutically acceptable salt thereof, to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

Discussion

BRIEF DESCRIPTION OF FIGURES

FIG. 1. Mechanism of an Immunomodulator in Context of BRD Progression

FIG. 2. Clinical and Genomics Temporal Data Summary

FIG. 3. Plasma Cytokine (IL-6, IL-8, IL-10 and IFN-γ) Levels upon Arrival to the Feedlot for Calves at Risk for BRD FIG. 4. Biomarker Evaluation for M9 Intratracheal Lung Challenge; IL-6 (A) and CD163 Biomarker (B) Results It should be understood that this invention is not limited to the particular methodology, protocols, and reagents. etc., defined herein and as such may vary. The terminology used herein is for the purpose of describing embodiments only and is not intended to limit the scope of the present invention, which is defined solely by the claims.

Unless otherwise defined, scientific and technical terms used in connection with the compounds of the invention defined herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry synthesis, macrolides, and immunomodulation defined herein are those that are well known and commonly used in the art.

Definitions

For purposes of the present invention, as described and claimed herein, the following terms and phrases are defined as follows:

"Additional pharmaceutical agent(s)" as used herein, unless otherwise indicated, refers to other pharmaceutical compounds or products that provide a therapeutically effective amount of said agents that are useful for the treatment of a bacterial or parasitic infection in an animal and/or modulating an immune response, as defined herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —$OCH_3$, —$OCH_2CH_3$, —$OCH(CH_3)_2$, —$OC(CH_3)_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "($C_1$-$C_6$)alkyl" refers to a monovalent, straight or branched aliphatic group containing 1 to 6 carbon atoms; similarly, $C_1$-$C_3$ alkyl refers to a monovalent, straight or branched aliphatic group containing 1 to 3 carbon atoms, etc. Non-exclusive examples of ($C_1$-$C_6$)alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as defined herein. Further when used in compound words such as alkylphenyl, said alkyl moiety has the same meaning as herein defined and may be attached to the chemical moiety by any one of the carbon atoms of the aliphatic chain. Non-limiting examples of the compound word, $C_0$-$C_4$alkylphenyl include: $C_0$phenyl (phenyl), $C_1$alkylphenyl (—$CH_2$phenyl; benzyl), $C_2$alkylphenyl (—$CH_2CH_2$phenyl), and the like.

"Animal(s)", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat and horse. Non-exclusive examples of livestock include: swine, camel, rabbits, goat, sheep, deer, elk, bovine (cattle and bison). Preferred livestock is bovine.

"Antibacterial", as used herein, unless otherwise indicated, refers to a compound with a minimum inhibitory concentration (MIC) ≤64 µg/mL for any one strain of the BRD pathogens, *M. haemolytica* and *P. multocida*. The term "non-antibacterial" as used herein, unless otherwise indicated, refers to a compound with an MIC >64 µg/mL for the BRD pathogens (all strains tested), *M. haemolytica* and *P. multocida*.

"Aryl", as used herein, unless otherwise indicated, refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Further when used in compound words such as alkylaryl (e.g., alkylphenyl), said alkyl and aryl moiety have the same meaning as herein defined and may be attached to the chemical moiety by any one of the carbon atoms of the aliphatic chain or ring carbon. Examples of $C_0$-$C_3$alkylphenyl, for example: $C_0$alkylphenyl is phenyl; $C_1$-alkylphenyl is —$CH_2$phenyl (benzyl); and $C_2$-alkylphenyl is —$CH_2CH_2$phenyl. The phenyl ring is optionally substituted as defined herein.

"Azalide" as used herein, unless otherwise indicated, refers to a class of macrolides which contain a nitrogen atom in the macrolide ring which imparts different pharmacokinetic properties and is associated with greater stability of the molecule.

"Chiral", as used herein, unless otherwise indicated, refers to the structural characteristic of a molecule that makes it impossible to superimpose it on its mirror image, (e.g., "R" and "S" enantiomers).

"Composition", as used herein, unless otherwise indicated, refers to a compound of the invention that is formulated with at least one pharmaceutically acceptable excipient for dosing administration.

"Compounds of the invention" and "compounds", as used herein, unless otherwise indicated, includes a Formula (1), (1A), (1.1), (1-A0), (1-A1), (1-A1a), (1-A2), (1-A3), (1-A4), (1-A5), (1-A6), (2), (2A), (2.1), (2-A0), (2-A1), (2-A2), (2-A3), (2-A4), (2-A5) and (2-A6) azalide compound, stereoisomers thereof, and pharmaceutically acceptable salts thereof. The term(s) also include the respective 13-membered macrolides that are in equilibrium with the 15-membered macrolide ring. In addition, whenever an Example # is presented in the specification, for example, as a compound, composition comprising said compound, method of using said compound, and use of said compound as a medicament, then said Example # is equivalent to the compounds chemical name as further described herein. For example, B-113 is equivalent to (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-1-[(2S,3R,4S,6R)-3-hydroxy-6-methyl-4-[methyl-[methyl-[4-(trifluoromethyl)phenyl]sulfamoyl]amino]oxan-2-yl]oxy-3,5,8,10,12,14-hexamethyl-1-oxa-6-azacyclopentadecan-15-one, as defined under Table B.

"Cycloalkyl", as used herein, unless otherwise indicated, includes fully saturated or partially saturated carbocyclic alkyl moieties, i.e., a 3- to 6-membered ring containing only carbon atoms and can be monocyclic or part of a fused ring or bridged ring moiety. Examples of saturated carbocyclic (cycloalkyl) rings include, but are not limited to, cyclopropyl, cyclobutyl, cyclopentyl and cyclohexyl. Non-limiting examples of partially saturated cycloalkyls include: cyclopropene, cyclobutene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety have the same meaning as herein defined and may be attached to the chemical moiety by any one of the carbon atoms of the aliphatic chain. Examples of $C_0$-$C_4$alkyl$C_3$-$C_6$cycloalkyl include, for example: $C_0$alkyl$C_3$-$C_6$cycloalkyl is $C_3$-$C_6$cycloalkyl (i.e., cyclopropyl, cyclobutyl, cyclopentyl, cyclohexyl); $C_1$-alkyl$C_3$-$C_6$cycloalkyl is —$CH_2C_3$-$C_6$cycloalkyl (e.g., —$CH_2$-cyclopropyl, —$CH_2$-cyclohexyl, and the like); $C_2$-alkyl$C_3$-$C_6$cycloalkyl is —$CH_2CH_2C_3$-$C_6$cycloalkyl (e.g., —$CH_2CH_2$-cyclopropyl, —$CH_2CH_2$-cyclopentyl) and the like. Cycloalkyl moieties are optionally substituted as defined herein.

"Cytokine", as used herein, unless otherwise indicated, refers to general class of biological molecules which effect/affect all types of cells and influence immunological responses and non-immunological biologic processes. The definition is meant to include, but is not limited to, those biological molecules that act locally or systemically, and which, when used in the compositions or methods of the present invention serve to regulate or modulate an animal's immune response. Exemplary cytokines for use in practicing the invention include but are not limited to interleukins (e.g. among IL-1 to IL-29, in particular, IL-1, IL-1β, IL-6, IL-9, IL-10 and IL-12), chemokines (e.g. CCL2-5, CCL10, CCL11, CXCL8 (IL-8) and CXCL10), tumor necrosis factors (e.g., TNF-α and TNF-β), and in particular, NFK-B, which mediates the induction of pro-inflammatory cytokines, such as TNF-α, IL-1 and IL-6 in monocytes and macrophages.

"Halogen" or "halo", as used herein, unless otherwise indicated, refers to fluorine, chlorine, bromine and iodine. Further, when used in compound words such as "haloalkyl" or "haloalkoxy", said alkyl and alkoxy may be partially or fully substituted with halogen atoms which may be the same or different and said alkyl and alkoxy moiety has the same meaning as above and may be attached to the chemical moiety by any one of the carbon atoms of the aliphatic chain. Examples of "haloalkyl" include $F_3C—$, $ClCH_2—$, $CF_3CH_2—$ and $CF_3CH_2CH_2—$, and the like. The term "haloalkoxy" is defined analogously to the term "haloalkyl". Examples of "haloalkoxy" include $CF_3O—$, $CCl_3CH_2O—$, $HCF_2CH_2CH_2O—$ and $CF_3CH_2O—$ and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O and S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazolyl, and the like. The heteroaryl group may be attached to the chemical moiety by any one of the carbon atoms or nitrogen heteroatoms within the monocyclic or fused ring. Further when used in compound words such as alkylheteroaryl (e.g., $C_0$-$C_4$alkylheteroaryl), said alkyl and heteroaryl moiety have the same meaning as herein defined and may be attached to the chemical moiety by any one of the carbon atoms of the aliphatic chain. For example, $C_0$alkylheterocycle is heterocycle (e.g., pyrazolyl, imidazolyl, pyridinyl, piperazinyl, and the like), $C_1$alkylheteroaryl is —$CH_2$heteroaryl (e.g., —$CH_2$imidazolyl, —$CH_2$pyridinyl, and the like), $C_2$alkylheteroaryl is —$CH_2CH_2$heteroaryl (e.g., —$CH_2CH_2$ pyrazolyl, —$CH_2CH_2$oxazolyl, —$CH_2CH_2$pyrimidinyl, and the like) and the like. Heteroaryls are optionally substituted as defined herein.

"Heterocycle", as used herein, unless otherwise indicated, refers to a partially saturated or saturated 3- to 10-membered monocyclic ring, fused ring, or bridged ring structure containing one or more heteroatoms each independently selected from N, O and S, preferably from one to four heteroatoms. Non-exclusive examples of heterocycle include oxiranyl, thiaranyl, aziridinyl, oxetanyl, azetidinyl, thiatanyl, tetrahydrofuranyl, pyranyl, pyrazolidinyl, oxazolidinyl, tetrahydrothiophenyl, pyrrolidinyl, tetrahydropyranyl, piperidinyl, piperazinyl, morpholinyl, thiomorpholinyl, oxathianyl, tetrahydropyridinyl, 2H-azirinyl, 2,3-dihydroazetyl, 3,4-dihydro-2H-pyrrolyl and the like. The heterocycle group may be attached to the chemical moiety by any one of the carbon atoms or nitrogen heteroatoms within the ring. Further when used in compound words such as alkylheterocycle (e.g., $C_0$-$C_4$alkylheterocycle), said alkyl and heterocycle moiety have the same meaning as herein defined and may be attached to the chemical moiety by any one of the carbon atoms of the aliphatic chain. For example, $C_0$heterocycle is heterocycle (e.g., (piperidinyl, morpholinyl, azetidinyl and the like); $C_1$alkylheterocycle is —$CH_2$heterocycle (e.g., —$CH_2$morpholinyl, and the like), $C_2$alkylheterocycle is —$CH_2CH_2$heterocycle (e.g., $CH_2CH_2$pyrrolidinyl, —$CH_2CH_2$thiomorpholinyl and the like) and the like. Heterocycles are optionally substituted as defined herein.

"Macrolide(s)", as used herein, unless otherwise indicated, refers to compounds characterized by a large lactone ring containing from 12 to 16 carbon atoms to which are attached, via glycosidic bonds, one or more deoxy sugars; and includes the class of azalides.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with $(R^9)_n$," means that the number of substituents may vary from zero, one, two, or three possible substitutions since n is herein defined as the integer 0, 1, 2 or 3.

"Pharmaceutically acceptable" as used herein, unless otherwise indicated, indicates that the substance or composition must be compatible chemically and/or toxicologically, with the other ingredients comprising a formulation, composition, and/or the animal being treated therewith.

"Protecting group" or "Pg", as used herein, unless otherwise indicated, refers to a substituent that is commonly employed to block or protect an alcohol on the compound thereby protecting its functionality while allowing for the reaction of other functional groups on the compound. Non-exclusive examples of an alcohol-protecting group include: 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), ethoxyethyl acetal (EE), methoxymethyl acetal (MOM), methoxypropyl acetal (MOP), methyl ether, tetrahydropyranyl acetal (THP), triethylsilyl ether (TES), benzyloxycarbonyl (Cbz), triisopropylsilyl ether (TIPS), trimethylsilyl ether (TMS), tert-butyldimethylsilyl ether (TBS, TBDMS) and tert-butyldiphenylsilyl ether (TBDPS).

"Saturated" or "partially saturated", as used herein, unless otherwise indicated, refers to cycloalkyl rings having 3-6 carbon atoms and heterocyclic rings comprising 2-5 carbon atoms and at least one heteroatom selected from N, O, and S; and wherein each saturated ring contains single bonds between mutually adjacent carbon atoms or carbon heteroatoms; for example: cyclobutane, cyclopentane, cyclohexane, oxirane, oxetane, tetrahydofuran, piperadine, and the like. Partially saturated rings contain at least one double bond between mutually adjacent carbon atoms or carbon heteroatoms; for example: cyclobutene, cyclopentene, cyclohexa-1,3-diene, 2,3-dihydroazete, 2,5-dihydrofuran, 2H-thiopyran and the like.

"Stereoisomers", as used herein, unless otherwise indicated, refers to the compounds of the invention which have more than one asymmetric carbon atom. In the general Formulas depicted herein, the solid wedge shaped bond indicates that the bond is above the plane of paper and the broken wedge bond indicates that the bond is below the plane of the paper. The compounds of the invention may occur as individual enantiomers or diastereomers, or mixtures thereof, including racemic mixtures. All such isomeric forms are included within the present invention.

"Stress" or "stressful", as used herein, unless otherwise indicated, is a specific or non-specific response that varies in degree. Stressors are particular events, experiences, or environmental stimuli that affect an animal's health, that may be acute, chronic, disruptive, or perceived as uncontrollable. Non-exclusive examples of stressors in animal health include: natural disasters (e.g., floods, fires, and earthquakes), major life events (e.g., relocation/transportation, weaning, maternal and herd separation, comingling of animals from different sources, tail docking, needle teeth extraction, pain, feed and water deprivation and acute or chronic illness), and acute/chronic disruptions (e.g., temperature and humidity variation, confinement, shipping, improper nutrition and hydration and storms), loud noises (e.g., thunder, barking, fireworks and the like), environmental changes, pollutants and the like.

"Therapeutically effective amount", as used herein, unless otherwise indicated, refers to an amount of a compound of the invention that (i) treats or prevents the particular disease or disorder, (ii) attenuates, ameliorates, or eliminates one or more symptoms of the particular disease or disorder, or (iii) prevents or delays the onset of one or more symptoms of the particular disease or disorder.

"Treatment", "treating", and the like, as used herein, unless otherwise indicated, refers to control, preventative measures, reversing, alleviating, mitigating, or inhibiting inflammation driven by an environmental, bacterial-, viral-, fungal-, or parasitic-infection, and/or internal disease by moderating an immunological response. As used herein, these terms also encompass, depending on the condition of the animal, preventing the onset of a disorder or condition, or of symptoms associated with a disorder or condition, including reducing the severity of a disorder or condition or symptoms associated therewith. Treatment can also refer to administration of a compound of the invention to an animal that is not at the time of administration afflicted with the infection, immunological episode, or disease disorder or complex. As will be appreciated, it is not always possible to distinguish between "preventing" and "suppressing" a disease or disorder since the ultimate inductive event or events may be unknown or latent.

Other than in operating examples, or where otherwise indicated, all numbers expressing quantities of ingredients or reaction conditions used herein should be understood as modified in all instances by the term "about". "About", as used herein, refers to the indicated value of the variable and to all values of the variable that are within the experimental error of the indicated value (e.g., within the 95% confidence interval for the mean) or within 10 percent of the indicated value, whichever is greater.

The compounds of the present invention have several asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all steric forms of the compounds of the invention. The present invention includes all stereoisomers of compounds of the invention.

The independent syntheses of the stereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration. If desired, racemic mixtures of the compounds may be separated so that the individual enantiomers or diastereomers are isolated. The separation can be carried out by methods well known in the art, such as the coupling of a racemic mixture of compounds, followed by separation of the individual stereoisomers by standard methods, such as fractional crystallization or chromatography. The coupling reaction is often the formation of salts using an enantiomerically pure acid or base.

The derivatives may then be converted to the pure stereomers by cleavage of the added chiral residue. The racemic mixture of the compounds can also be separated directly by chromatographic methods using chiral stationary phases, which methods are well known in the art. Alternatively, any stereomers of a compound may be obtained by stereoselective synthesis using optically pure starting materials or reagents of known configuration by methods well known in the art.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Syn thesis, John Wiley & Sons, 1991. The protecting groups may be removed at a convenient subsequent stage using methods known from the art.

Macrolide Chemistry

The macrolides are known to have a strong binding affinity to the P-site on the 50S subunit of the bacterial ribosome and to inhibit protein synthesis. Modification of the desosamine group of the macrolide blocks this interaction by either modification of the dimethylamino group to block the salt bridge and/or modification of the neighboring hydroxy group affecting the hydrogen bond formed, thereby removing the antibacterial activity of said compounds of the invention. Although cladinose modifications have a comparatively smaller effect on the bacterial ribosome binding, they have the potential to affect the physicochemical properties, pharmacokinetics and cell permeability of the compound. By modifying macrolide structure therefore sequestering the molecule from entering the bacteria or enhancing efflux from the bacteria reduces or eliminates antibacterial activity even with the ability to bind the bacterial ribosome.

Lipophilicity

The lipophilicity of an organic compound can be described by a partition coefficient, log P, which can be defined as the ratio of the concentration of the unionized compound at equilibrium between organic and aqueous phases. Generally speaking, more lipophilic compounds are less soluble in aqueous media. A negative value for log P means the compound has a higher affinity for the aqueous phase (hydrophilic); when log P=0 the compound is equally partitioned between the lipid and aqueous phases; a positive value for log P denotes a higher concentration in the lipid phase (lipophilic). Lipophilicity is a major determining factor in a compound's absorption, distribution in the body, penetration across vital membranes and biological barriers, metabolism and excretion. The compounds of the invention are lipophilic (log P ~1 to 5.758) which aid in their transport and absorption into respiratory tissues, e.g., lungs.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying. Pharmaceutical compositions for use in accordance with the present invention may be formulated in conventional manner using one or more pharmaceutically acceptable carriers, which facilitate processing of the active compound into preparations for administration to the animal in need thereof. The formulations of the invention can be designed to be short-acting, fast-releasing, long-acting, and sustained-releasing. Thus, the pharmaceutical formulations can also be formulated for controlled release or for slow release; and are dependent upon the route of administration chosen.

Pharmaceutically acceptable excipients and carriers are generally known to those skilled in the art and are thus included in the instant invention. Such excipients and carriers (including water) are described, for example, in "Remington's Pharmaceutical Sciences" Mack Pub. Co., New Jersey (1991).

For BRD and SRD, pharmaceutical compositions are typically formulated for parenteral administration, e.g., in a liquid carrier or suitable for reconstitution into liquid solution or suspension for parenteral administration. In general, such compositions typically comprise a pharmaceutically acceptable carrier. Pharmaceutical carriers according to the invention can be sterile liquids, such as but not limited to water, saline solutions, aqueous dextrose solutions, aqueous glycerol solutions; and/or oils, including petroleum, animal, vegetable or synthetic origin, such as soybean oil, mineral oil, sesame oil and the like. Suitable pharmaceutical carriers are described in "Remington's Pharmaceutical Sciences" by E. W. Martin, 18th Edition. The pharmaceutical compositions comprising a compound of the invention can be administered orally, topically, parenterally (i.e., intramuscular, subcutaneous, intravenous, and intradermal injection). The pharmaceutical compositions comprising a compound of the invention can also be administered by intramammary and intra-uterine injection.

Pharmaceutical compositions and formulations as defined herein can be prepared by mixing a compound of the invention having the desired degree of purity with one or more pharmaceutically acceptable carrier(s) in the form of lyophilized formulations or aqueous solutions. The term "carrier" refers to a diluent, excipient, or vehicle with which the compound of the invention is administered. Pharmaceutically acceptable carriers are generally nontoxic to recipients at the dosages and concentrations employed, and include, but are not limited to: buffers (e.g., NaOH, KOH, HCl, phosphate, citrate and other organic acids (e.g., for example citric acid, acetic acid, benzoic acid, malic, and the like); antioxidants (e.g., butylated hydroxyanisole (BHA), butylated hydroxytoluene (BHT), sodium metabisulfite, monothioglycerol, propyl gallate, and the like); preservatives (e.g., octadecyldimethylbenzyl ammonium chloride, hexamethonium chloride, benzalkonium chloride, benzethonium chloride, phenol, butyl or benzyl alcohol, chlorobutanol, thimerosal's, alkyl parabens such as methyl or propyl paraben, catechol, resorcinol, cyclohexanol, 3-pentanol, m-cresol, and the like); hydrophilic polymers (e.g., polyvinylpyrrolidone (PVP), polyethylene glycol (PEG), polyvinyl alcohol (PVA), polyacrylic acid, polyacrylamides, xanthum gum, and the like); amino acids (e.g., glycine, glutamine, asparagine, histidine, arginine, lysine, and the like); chelating agents such as EDTA; monosaccharides, disaccharides, and other carbohydrates including sugars such as sucrose, mannitol, trehalose or sorbitol, glucose, mannose, or dextrins; and salt-forming counter-ions such as sodium; metal complexes (e.g., Zn-protein complexes). The carrier can be a solvent or reconstitution medium or dispersion medium containing, for example, water, ethanol, polyol (for example, glycerol, propylene glycol, and liquid polyethylene glycol, and the like), and suitable mixtures thereof. For intravenous administration, suitable carriers include physiological saline, bacteriostatic water, or phosphate buffered saline (PBS). Prolonged absorption of the injectable compositions can be brought about by including in the composition an agent which delays absorption, for example, aluminum monostearate and gelatin.

Solutions or suspensions used for parenteral application typically include one or more of the following components: a sterile carrier such as water for injection, saline solution, fixed oils, polyethylene glycols, glycerin, propylene glycol, or other synthetic solvents; antibacterial agents such as benzyl alcohol or methyl parabens; antioxidants such as ascorbic acid, BHA, BHT, monothioglycerol or sodium bisulfite; chelating agents such as ethylene-diaminetetraacetic acid; buffers such as acetates, citrates or phosphates; and agents for the adjustment of tonicity such as sodium chloride or dextrose. The pH can be adjusted with acids or bases, such as hydrochloric acid, citric acid or sodium hydroxide. Such preparations may be enclosed in ampoules, disposable syringes or multiple dose vials made of glass or plastic. The formulations to be used for in vivo administration are generally sterile. Sterility may be readily accomplished, e.g., by filtration through sterile filtration membranes, and radiation. The injectable compositions can contain the active component (drug) in the amounts ranging from about 1 to 250 mg/mL, and more preferably, in concentrations ranging from about 1 to 100 mg/mL. Without limiting the scope of the compositional components, an injectable composition comprising a Formula (1) compound, pharmaceutically acceptable salt thereof, (e.g., acetate) can be prepared by dissolving the compound (e.g., 1 to 25 mg/mL) in a composition comprising citric acid, propylene glycol, water and optionally an antioxidant (e.g., monothioglycerol). As described herein, the composition can contain about 90% (±~6%) of lactone A and 10% lactone B (±~6%) of a Formula (1) compound. The pH of the composition can be adjusted, as needed, with NaOH and/or HCl. Methods for preparation of such formulations will be apparent to those skilled in the art and can be prepared in accordance with procedures described in U.S. Pat. No. 6,514,945.

For oral use, the pharmaceutical compositions of the present invention, may be administered, for example, in the form of tablets or capsules, powders, dispersible granules, or cachets, or as aqueous solutions or suspensions. Oral compositions generally include an inert carrier or an edible carrier. They can be enclosed in gelatin capsules or compressed into tablets. For oral administration, the therapeutic agents can be combined with carriers and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, primogel, sodium starch glycolate, or corn starch; a lubricant such as magnesium stearate or stearates; a glidant such as colloidal silicon dioxide; a sweetening agent such as sucrose or saccharin; or a flavoring agent.

Dosage

Pharmaceutical compositions suitable for use in the present invention include compositions wherein the active ingredients are contained in an amount sufficient to achieve the intended purpose. More specifically, a therapeutically effective amount means an amount of a compound of the invention that is effective to prevent, alleviate or ameliorate symptoms/signs of disease or prolong the survival of the animal being treated. The quantity of active component, which is a compound of the invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 mg/kg to about 10 mg/kg of body weight, preferably about 0.02 mg/kg to about 1 mg/kg of body weight, more preferably about 0.04 mg/kg to about 0.8 mg/kg of body weight, even more preferably about 0.06 mg/kg to about 0.6 mg/kg of body weight. A preferred dosage regimen is parenteral administration of about 0.05 mg/kg to about 0.8 mg/kg of body weight by subcutaneous injection. It is to be understood that the dosages may vary depending upon the requirements of each animal and the severity of the disorders or diseases being treated. The desired dose may conveniently be presented in a single dose or as divided doses administered at appropriate intervals during the course of treatment. The preferred route of administration is parenteral. Parenteral administration includes intravenous, intramuscular, and subcutaneous injection. The preferred route of administration is by subcutaneous injection. The compounds of the invention can be administered to the animal at first signs of stress or bacterial infection, prior to shipment from a farm or ranch, or upon arrival to the feed lot.

A compound of the invention can be administered in a pharmaceutically acceptable form either alone or in combination with one or more additional agents which modulate a mammalian immune system or with anti-inflammatory agents or with one or more antibacterial agents. Additionally, the compounds of the invention can also be co-administered with vitamins and/or minerals. Non limiting examples of anti-inflammatory agents include: ketoprofen, cyclosporin A, rapamycin, FK-506 (tacrolimus), leflunomide, deoxyspergualin, mycophenolate, azathioprine, daclizumab, aspirin, acetaminophen, ibuprofen, naproxen, piroxicam, and anti-inflammatory steroids (e.g. prednisolone or dexamethasone). Non limiting examples of antibacterial agents include: novobiocin, aminoglycosides (e.g., gentamicin, neomycin, dihydrostreptomycin, spectinomycin, etc.), florfenicol, ceftiofur, cephapirin, ormetoprim, danofloxacin, enrofloxacin, bambermycins, ionophores (e.g., laidlomycin, lasalocid, monensin, narasin, salinomycin, lincomycin, pirlimycin, macrolides (e.g., erythromycin, gamithromycin, tildipirosin, tilmicosin, tulathroymycin, the M9-metabolite of tulathromycin, tylosin, tylvalosin, etc.), avilamycin, penicillins (e.g., amoxicillin, ampicillin, cloxacillin, penicillin, etc), tiamulin, polymyxin B, bacitracin, carbadox, virginiamycin, sulfadimethoxine, sulfamethazine, chlortetracycline, oxytetracycline, and tetracycline. Non-limiting examples of minerals include: calcium, magnesium, phosphorus, potassium, sodium, sulfur, cobalt, copper, iodine, iron, manganese, selenium, chromium, and zinc. Non-limiting examples of vitamins include: A, D, E, K, and B vitamins including: thiamin (B1), riboflavin (B2), niacin (B3), pantothenic acid (B5), pyridoxine (B6), biotin (B7) folate (B9), and B12. These additional combination agents may be administered as part of the same or separate dosage forms, via the same or different routes of administration, and on the same or different administration schedules according to standard medical or veterinary practice known to one skilled in the art.

Medical and Veterinary Uses

Methods defined herein are generally performed on an animal in need thereof. An animal in need can be an animal having, diagnosed with, suspected of having, or at risk for developing a disease, disorder, or condition associated with a bacterial infection, viral infection, parasitic infection, inflammation or an immune response. The disease or disorder can include respiratory disease, reproductive diseases like mastitis or metritis, inflammatory bowel disease, bovine viral diarrhea virus (BVDV), infectious bovine rhinotracheitis (IBR), bovine respiratory syncytial virus (BRSV), parainfluenza virus, bovine coronavirus, psoriasis, multiple sclerosis, rheumatoid arthritis, allergic autoinflammatory disease, or an autoimmune disease. Generally, a safe and effective amount of a compound of the invention is, for example, that amount that would cause the desired therapeutic effect in an animal while minimizing undesired side effects. In various embodiments, an effective amount of a compound of the invention can substantially mitigate inflammation or an immune response, slow the progress of a disease, disorder, or condition associated with inflammation or an immune response, or limit the development of a disease, disorder, or condition associated with inflammation or an immune response.

Compounds of the invention are macrolide (azalide) analogues that lack antibacterial activity against BRD pathogens and have been shown to have immunomodulatory properties that can prevent and/or control the symptoms of BRD in cattle. Accordingly, these macrolides are useful therapeutic agents for treating and/or controlling respiratory illnesses that may be provoked by environmental stimuli, stress, and bacterial infection. Some non-limiting macrolides used to treat BRD include: Draxxin® (tulathromycin), Zuprevo® (tildipirosin), and Zactran® (gamithromycin), and the like.

Draxxin®, an injectable solution, is indicated for the treatment of bovine respiratory disease (BRD) associated with *Mannheimia haemolytica, Pasteurella multocida, Histophilus somni*, and *Mycoplasma bovis*; and for the control of respiratory disease in cattle at high risk of developing BRD associated with *Mannheimia haemolytica, Pasteurella multocida, Histophilus somni*, and *Mycoplasma bovis*. Cattle receive a 2.5 mg/kg subcutaneous dose of Draxxin®. In swine, Draxxin® is indicated for the treatment of swine respiratory disease (SRD) associated with *Actinobacillus pleuropneumoniae, Pasteurella multocida, Bordetella bronchiseptica, Haemophilus parasuis*, and *Mycoplasma hyopneumoniae*; and for the control of SRD associated with *Actinobacillus pleuropneumoniae, Pasteurella multocida*, and *Mycoplasma hyopneumoniae* in groups of pigs where SRD has been diagnosed. Swine receive a 2.5 mg/kg intramuscular injection of Draxxin®.

A compound of the invention can treat, reduce, or prevent a disease, disorder, or condition associated with inflammation or an immune response. Inflammation is a critical response to potential danger signals and damage in organs of the body. Commonly referred to as the inflammatory cascade, the inflammatory response can be acute or chronic. Acute inflammation, part of the immune response, is the body's immediate response to injury or assault due to physical trauma, infection, stress, or a combination of all three. Acute inflammation helps to prevent further injury and facilitates the healing and recovery process. When inflammation becomes self-perpetuating however, it can result in chronic or long-term inflammation.

Trauma, inflammation, or infection leads to the activation of the inflammatory cascade. Initially, a proinflammatory activation occurs, but almost immediately thereafter a reactive suppressing anti-inflammatory response occurs. This systemic inflammatory response (SIR) usually manifests itself as increased systemic expression of both proinflammatory and anti-inflammatory species. Systemic inflammatory response starts with inflammation as a response to exogenous (microbial, physical, or chemical) agents or endogenous (immunologic or neurologic) factors. The response is initiated when inflammatory cells at the site of inflammation, such as macrophages, are activated and rapidly produce TNF-α and IL-1. These cytokines in turn activate the cytokine cascade resulting in the generation of pro-inflammatory cytokines, IL-6, and IL-8, as well as other chemokines. Inflammatory stimuli also trigger the synthesis of anti-inflammatory cytokines and specific cytokine inhibitors to control the extent of the inflammatory response. Anti-inflammatory cytokines such as IL-4, IL-10, IL-11, and IL-13 inhibit the synthesis of proinflammatory cytokines while the naturally occurring proinflammatory cytokine inhibitors neutralize proinflammatory cytokine activity by binding to pro-inflammatory cytokine receptors, decoy receptor antagonist, and cytokine binding proteins. The interplay among these proinflammatory cytokines, anti-inflammatory cytokines, and naturally occurring cytokine inhibitors determines the inflammatory response and its effectiveness to contain the inflammatory response and bring about resolution of the initiating process. The main known mediators involved in the evolution of SIRS are cytokines, nitric oxide, platelet activating factor (PAF), and eicosanoids. The systemic response to infection is mediated via macrophage-derived cytokines that target end organ receptors in response to injury or infection. However, production of anti-inflammatory protein and lipid molecules will also take place to attenuate and halt the inflammatory response. These mediators initiate overlapping processes that directly influence the endothelium, cardiovascular, hemodynamic, and coagulation mechanisms. If a balance between pro- and anti-inflammatory substances is not established and homeostasis restored, a massive pro-inflammatory reaction (i.e. SIRS) and multiple organ dysfunction (MODS) may ensue. Thus, after the first pro-inflammatory mediators are released, the body mounts a compensatory anti-inflammatory reaction to the initial inflammatory response. The anti-inflammatory reaction may be as robust and sometimes even more robust than the proinflammatory response. In addition to pro-inflammatory cytokines, other mediators such as NO, PAF, prostaglandins, and leukotrienes are also produced. These molecules are responsible for activating complement, coagulation, and kinin cascades as well.

Diseases associated with inflammation or an immune response can include: for example, but not limited to: bacterial infection; viral infection; fungal infection; parasitic infection; asthma; allergy; age related macular degeneration; dermatitis; pain; mastitis; metritis; autoinflammatory disease; autoimmune disease; inflammatory bowel disease; dermatitis, multiple sclerosis; osteoarthritis; osteoporosis; psoriasis; rheumatoid and osteoarthritis arthritis; synovitis, acne, pustulosis, hyperostosis, airway and respiratory diseases (e.g., equine airway disease and canine infectious respiratory disease); respiratory disease complex (bovine and swine), ischaemia-reperfusion, feline chronic kidney disease, feline and canine degenerative mitral valve disease (inflammatory complex; e.g., pro-inflammatory cytokines in heart failure via up-regulation of valvular and myocardial expression of cytokines, chemokines and adhesion molecules), psoriasis, multiple sclerosis, rheumatoid arthritis autoinflammatory disease, peptic ulcers, tuberculosis, periodontitis, otitis, ulcerative colitis, Crohn's disease, lupus, sinusitis, hepatitis, coeliac disease, pelvic inflammatory disease, glomerulonephritis, transplant rejection, chronic obstructive pulmonary disease, gout, ankylosing spondylitis, myositis, laminitis, gingivitis, scleroderma, vasculitis, malaria, Lyme, babesiosis, ehrlichiosis, anaplasmosis, tularemia, amebiasis, giardiasis, fascioliasis, fasciolopsiasis, elephantitis, cryptosporidiosis, leishmaniasis, microsporidiosis, trypanosomiasis, toxoplasmosis, and the like; and other inflammatory and immune diseases and disorders. A compound of the invention can treat a disease, disorder, or condition associated with inflammation by modulating cytokines, chemokines, and inflammatory markers, for example, IL6, IL-1β, NFKB, CSP136, LCN, CXCL8 (IL-8), TNFα, and induce TLR4 signaling.

Macrolide Immunomodulation

The chemistry of macrolides provides the basis to understand their immunomodulation effects. Macrolides are defined as cationic amphiphilic drugs; cellular penetration is primarily determined by their lipophilicity and cationic nature at physiological pH. Cellular membrane penetration by macrolides leads to depolarization of phospholipids, resulting in disposition of both drug and phospholipid into the cytosol and lysosomes, ultimately resulting in cellular state of phospholipidosis. Polar association with phospholipids, primarily phosphatidylcholine, within cells inhibits natural degradation by phospholipase enzymes; resulting in a reduction of primary cell signaling components, like arachidonic acid, among others. The decrease in arachidonic acid is postulated to prevent the normal production of the eicosanoid metabolites including prostaglandins, thromboxanes, leukotrienes and lipoxins. Additionally, indirect inhibition of the COX family of inflammatory mediators, NFkB and AP-1 and their resulting pro-inflammatory cytokine production are observed. The reduced ability for cells to signal, both intra and extracellularly is context dependent on the host. In healthy animals, macrolide treatment has been demonstrated to stimulate neutrophil and macrophage response upon disease stimulus. However, in the presence of an acute or chronic inflammation state, an inhibition or reversal of the inflammation is observed.

Modulation of host defense by azithromycin and other macrolide antibiotics occurs through interaction with structural cells, such as epithelial or endothelial cells, smooth muscle cells or fibroblasts, as well as with leukocytes (macrophages, poly-morphonuclear leukocytes or neutrophils, mononuclear leukocytes or monocytes, T cells and dendritic cells). Cellular accumulation of macrolides is a mechanism of passive transport into cells which does not require cellular energy, carrier proteins, and is unsaturable. The mechanism is distinct from ribosome binding associated with antibiotic activity and therefore unrelated. As an example, azithromycin aglycone which demonstrates no antibiotic activity demonstrates a high level of induced phospholipidosis (J. Parnham et al./Pharmacology & Therapeutics 143 (2014) 225-245). Azithromycin penetrates the cell membrane bilayer and stabilizes the membrane, reducing fluidity and neutralizing phospholipid charge on the inner leaflet membrane. This results in reduced fatty acid release and liberation of enzymes bound by electrostatic charge to the membrane, resulting in modulation of signaling pathways and inhibition of the activation of transcription factors including AP-1 and NFκB. The signaling pathway most affected is likely dependent on the particular cell, its activation state and the stimulus by which it is activated. Molecules dependent on negatively charged phospholipids are also affected. Azithromycin accumulates in lysosomes, modulating MPR transport of enzymes and lipids and through lipid remodeling in the lysosome membranes. One of the well documented aspects is their ability to moderate inflammatory responses as demonstrated by downregulation of exacerbated cytokine production (IL-1β, TNF-α, IL-6) through the NFκB pathway and effects on granulocytes and/or gene expression.

Immunological activity can also be assessed by analyzing CD163. CD163 is a scavenger receptor that binds hemoglobin/haptoglobin and is expressed on macrophages thought to be involved in innate immune sensing that aids in the clearance of activated macrophages thus preventing oxidative damage to tissue.

CD163 also functions as an innate immune sensor for gram-positive and gram-negative bacteria. Accordingly, a high CD163 expression in macrophages is a characteristic of tissues responding to inflammation, considered a highly correlative biomarker of inflammation. The scavenging of the oxidative and proinflammatory hemoglobin leading to stimulation of the heme-oxygenase-1 and production of anti-inflammatory heme metabolites indicates that CD163 thereby indirectly contributes to the anti-inflammatory response (Antioxid Redox Signal, Etzerodt et. al., 2013, 18(17), p. 2352-2363). CD163 may participate in the process leading to lung lesions in BRD. The expression of CD163 may also be correlated to elevated levels of IL-6 as observed in BRD, CD163 surface expression has been experimentally induced by 253+/−4.9% in monocytes and macrophages upon incubation with IL-6 (Journal of Leukocyte Biology; Buechler et al. vol. 67 January 2020; p. 97-103). Alternatively cross-linking of CD163 on alveolar macrophages with monoclonal antibody induced a protein tyrosine kinase-dependent signal that resulted in slow type calcium mobilization, inositol triphosphate production and secretion of IL-6 and GM-CSF (Journal of Leukocyte Biology; Van de Heuvel et al. vol. 66 November 1999; p. 858-866). The anti-inflammatory immune-modulating drug, tacrolimus, was shown to slightly increase the expression of CD163 (PLOS ONE; Kannegleter, et. al., January, 2017; p. 1-19); wherein a later study (HHS Public Access; Motta, et. al., Oral Dis. 2018, 24(4) p. 580-590) reported that therapy did not result in changes in the expression of CD163. Similarly, azithromycin (British Journal of Pharmacology, Vrancic, et. al; 2012, 165; p. 1348-1360) reported enhanced expression of CD163. CD163 expression upregulates glucocorticoids, IL-6, IL-10, and hemoglobin; and downregulates IL-4, IFN-γ, TNF-α, CXCL4, and GM-CSF. In contrast, CD163 was suppressed in cattle treated with M9 correlating with the proposed mechanism of inflammatory state reduction.

Cytokines are considered to be in a broad and loose category of small proteins (5-20 kDa) that are important in cell signaling. Their release has an effect on the behavior of cells around them. It can be said that cytokines are involved in autocrine signaling, paracrine signaling and endocrine signaling as immunomodulating agents. Cytokines are generally known to include chemokines, interferons, interleukins, lymphokines, and tumor necrosis factors (TNF) but generally not hormones or growth factors. Cytokines can be produced by a broad range of cells, including immune cells like macrophages, neutrophils, B lymphocytes, T lymphocytes and mast cells, as well as epithelial cells, endothelial cells, fibroblasts, and various stromal cells; a given cytokine may be produced by more than one type of cell. Cytokines can act through receptors and are especially important in the immune system. Cytokines can modulate the balance between humoral and cell based immune responses, and they can regulate the maturation, growth, or responsiveness of particular cell populations. Some cytokines can enhance or inhibit the action of other cytokines in complex ways. Cytokines can be important in health and disease, specifically in host responses to infection, immune responses, inflammation, stress, trauma, sepsis, cancer, and reproduction.

Interleukin 6 (IL-6) is a pleitropic cytokine that acts as both a pro-inflammatory cytokine and an anti-inflammatory myokine. IL-6 is produced and secreted by a variety of cells, including B cells, T cells, endothelial cells and macrophages to stimulate an immune response via the classic signaling pathway when it binds to the transmembrane IL-6 receptor (IL-6R) or via the trans-signaling pathway upon binding to the soluble form of IL-6R (sIL-6R); during infection and after tissue trauma leading to inflammation. The trans-signaling is responsible for the pro-inflammatory actions and most of the pathological effects of IL-6. Dysregulation of the IL-6 pathway has been reported to associate with development of several disease states, including a variety of inflammatory disorders. IL-6 is reported to induce vascular endothelial growth factor production, which enhances angiogenesis and increases vascular permeability, a feature of several inflammatory disorders. IL-6 is also implicated in enhancement of neutrophil, monocyte/macrophage recruitment and blockade of anti-inflammatory T-regulatory cells. In chronic inflammation, IL-6 has a detrimental role and leads to mononuclear cell accumulation at the site of injury. This may lead to an increase in serum levels of IL-6 and sIL-6R providing a foundation for the amplification step of chronic inflammatory responses. IL-6 has been implicated in the development of pulmonary neutrophilia by enhancing both neutrophil recruitment from blood and bone marrow and neutrophil survival. IL-6's role as an anti-inflammatory cytokine is mediated through its inhibitory effects on TNF-α and IL-1, and activation of IL-1ra and IL-10.

IL-6, like other inflammatory cytokines, has been shown to be elevated in different lung diseases in human and mice. IL-6 was elevated in the bovine BRD (*M. hemolytica*) challenge and was correlated with higher rectal temperature, lung lesions and mortality. The compounds of the invention, M9, and tulathromycin significantly reduced IL-6 levels which also correlated with overall animal survival. Therefore, the immune-modulatory compounds of the invention mitigate the pathologic increase in IL-6 consistent with dose and clinical outcome.

IL-36 is a member of the IL-1 superfamily of cytokines and includes three agonists (IL-36a, IL-36p, and IL-36γ) and an antagonist (IL-36RA). The IL-36 agonists bind to heterodimeric IL-36 receptor (IL-36R) complexes to produce a pro-inflammatory response. The antagonist binds to the IL-36R thereby prohibiting IL-36 signaling. IL-36 signaling occurs through the formation of a heterotrimeric complex IL-36, the IL-36R, and the IL-1AcP (IL-1 accessory protein) and activate the adaptor protein myeloid differentiated protein 88 (MyD88), mitogen-activated protein kinase (MAPK), and nuclear factor-kappa B (NF-κB) signaling pathways and induce inflammatory responses. IL-36RA prevents the interaction between the IL-1AcP and the receptor ligand complex. IL-36 proteins are widely expressed in T cells, keratinocytes, and skin, lung, and gut cells. IL-36 agonists bind to receptors [IL-36R and IL-1 receptor accessory protein (IL-1 RAcP)] and then activate. Finally, these pathways initiate the regulation of target genes. Recent evidence suggests that IL-36 regulates the function of both non-immune cells and immune cells; and is involved in immune cell activation, antigen presentation, and pro-inflammatory factor production. IL-36 has attracted great interest because of its dysregulation in inflammatory diseases. For example, serum and tissue IL-36 expression was increased in inflammatory and immune diseases and disorders like psoriasis, rheumatoid arthritis, and inflammatory bowel disease.

Chemokines

Chemokines are a family of small cytokines, or signaling proteins secreted by cells. Their name is derived from their ability to induce directed chemotaxis in nearby responsive cells (i.e., chemotactic cytokines); that stimulate recruitment of leukocytes. The main function of chemokines is to manage the migration of leukocytes (homing) in the respective anatomical locations in inflammatory and homeostatic processes. They are secondary pro-inflammatory mediators that are induced by primary pro-inflammatory mediators such as IL-1 or TNF. There are two major chemokine sub-families based upon the position of cysteine residues, i.e., CXC and CC. All members of the CXC chemokine sub-family have an intervening amino acid between the first two cysteines; members of the CC chemokine sub-family have two adjacent cysteines. As a general rule, members of the CXC chemokines are chemotactic for neutrophils, and CC chemokines are chemotactic for monocytes and a small sub-set of lymphocytes. Some chemokines are considered pro-inflammatory and can be induced during an immune response to recruit cells of the immune system to a site of infection or tissue damage, while others are considered homeostatic and are involved in controlling the migration of cells during normal processes of tissue maintenance or development (e.g., angiogenesis).

Inflammatory chemokines are formed under pathological conditions (on pro-inflammatory stimuli, such as IL-1, TNF-α, LPS, or viruses) and actively participate in the inflammatory response attracting immune cells to the site of inflammation and include: CXCL8 (IL-8), CCL2, CCL3, CCL4, CCL5, CCL11, CXCL10. These inflammatory chemokines are produced in high concentrations during infection or injury and determine the migration of inflammatory leukocytes into the damaged area. A typical example is CXCL8, which acts as a chemoattractant for neutrophils. In contrast to the homeostatic chemokine receptors, there is significant promiscuity (redundancy) associated with binding receptor and inflammatory chemokines.

Interleukin-8 (IL-8) is one of the proinflammatory chemokines that attract and activate immune and inflammatory cells. IL-8 mediates an array of biological effects, including several involving neutrophils: inflammatory cell activation and chemotaxis, production of reactive oxygen species, increased expression of the integrin CD11 b-CD18, enhancement of cell adhesion to endothelial cells, promotion of angiogenesis, and modulation of histamine release. IL-8 is produced by many cells, including neutrophils, monocytes, macrophages, mast cells, vascular endothelial cells, stromal cells and epithelial cells in response to an innate exogenous/endogenous stimulus. In target cells, IL-8 induces a series of physiological responses required for migration and phagocytosis, such as increases in intracellular $Ca^{2+}$ and exocytosis (e.g. histamine release).

Recruitment of inflammatory cells, such as neutrophils in response to tissue injury such as infection is a normal physiological response to eliminate the infectious agent, remove damaged or dead cells and initiate the healing process. However, excessive recruitment of these cells, the extended residence time and death of cells results in tissue damage. Influx of excessive inflammatory cells is therefore thought to be instrumental in the pathophysiology of pulmonary diseases such as in human inflammatory conditions such as chronic obstructive pulmonary disease (COPD), acute respiratory distress syndrome (ARDS), asthma, pulmonary fibrosis and bacterial pneumonia. This has also been observed in bovine respiratory disease (BRD) and bacterial pneumonia. Control of recruitment and activation of these cells in the lung would be an attractive strategy for therapeutic intervention. In all these conditions, IL-8 appears to be important for the recruitment and activation of neutrophils and T cells into the respiratory tract.

In an experimental cattle challenge study with *M. hemolytica*, one of the major causative agents of BRD, IL-8 levels were up-regulated in serum and tissues. The compounds of the invention were shown to downregulate IL-8 production in this challenge model and this correlated with a mitigated anti-inflammatory response and disease.

Biology of BRD

It has been long believed that the pathobiology of BRD originates from a stress-induced immune suppression leaving calves vulnerable to a myriad of microorganisms they encounter during the transition from cow-calf operation to feedlot. The dogma suggests that stimulation of the innate immune system would have a positive impact on the clinical outcome. However, to date, there has been little success with interventions consistent with this dogma, including the use of a DNA immunostimulant (Zelnate®). With the goal to better understand the progression of BRD, earlier studies suggest that it is the early unresolved heightened inflammatory state rather than immunosuppression that leads to the progression to BRD.

Based on current research driving BRD etiology, a novel understanding of the immunological status has shown that while a heightened pro-inflammatory state is ubiquitous in at-risk cattle, the perpetuation or lack of resolution/mitigation of this state coincides with disease outcome. After shipping on arrival to a feedlot, the pro-inflammatory state is especially characterized by innate immune components such as nasal-mucosal epithelial cell barrier damage and the release of pre-formed mediators such as members of the IL-1 cytokine family. Activation of danger-associated molecule patterns (DAMPs) including pattern recognition receptor (PRR) TLR-4 and inflammasome signaling demonstrate a response by epithelial and resident myeloid cells to the co-localized microbes in the upper airway. As bacterial components such as lipopolysaccharides (LPS; lipoglycans and endotoxins) induce TLR4 signaling, transcription factors such as NF-κB induce the expression of key cytokines involved in perpetuating the inflammatory process such as IL-1β, IL-6 and TNF-α and myeloid-derived granulocytes including macrophages and neutrophils are recruited and activated. These cascades lead to an environment where bacteria normally limited to the upper airway can transgress into the lung and cause disease. Associated with clinical disease are biomarkers of inflammatory processes such as elevated levels of secreted cytokines like IL-6 and acute phase proteins. Also associated with clinical disease are markers of cellular activation, for example expression of the scavenger receptor CD163 on macrophages and neutrophil-associated mediators such as LCN and CXCL8. The compounds of the invention effectively mitigates the heightened pro-inflammatory state in at-risk cattle by equilibrating the immune response and reducing the pathologic inflammatory cascade. This mechanism of an immunomodulator in the context of BRD progression is depicted in FIG. 1.

The compounds of the invention represent a new approach to a highly complex disease and have the potential to significantly reduce the incidence of BRD and the need for antibiotic treatment. They effectively moderate the pathologic innate inflammation occurring during the shipping period enabling the animal to restore homeostasis in a timeframe consistent with clinical disease protection.

Schemes and Experimentals

Tulathromycin A is a 15-membered (lactone A) closed ring antibacterial macrolide (azalide). The azalide converts to a 13-membered (lactone B) closed ring, tulathromycin B. This conversion is in an equilibrium ratio of about 9:1 (A:B), and is depicted below:

tetrahydro-2H-pyran-2-yl)oxy)-11-(((2S,3R,4S,6R)-3-hydroxy-6-methyl-4-(methylamino)tetrahydro-2H-pyran-2-yl)oxy)-3,5,8,10,12,14-hexamethyl-1-oxa-6-azacyclopentadecan-15-one (M9), depicted in the following diagrams below:

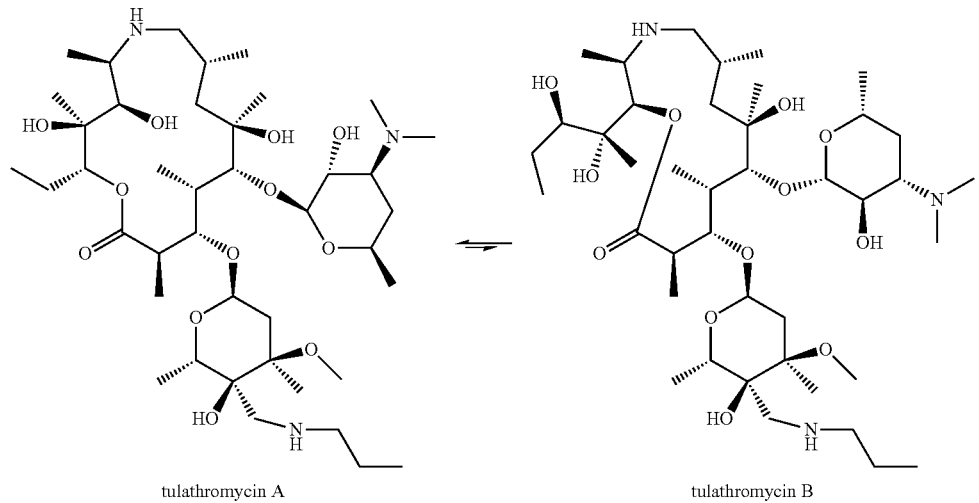 [SMILES: CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@@H](O)[C@](C)(O)[C@@H](CC)OC(=O)[C@@H]2C)C[C@@]1(C)OC ; CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@H]([C@](C)(O)[C@H](O)CC)OC(=O)[C@@H]2C)C[C@@]1(C)OC]

The tulathromycin azalides can also be represented by the following structures:

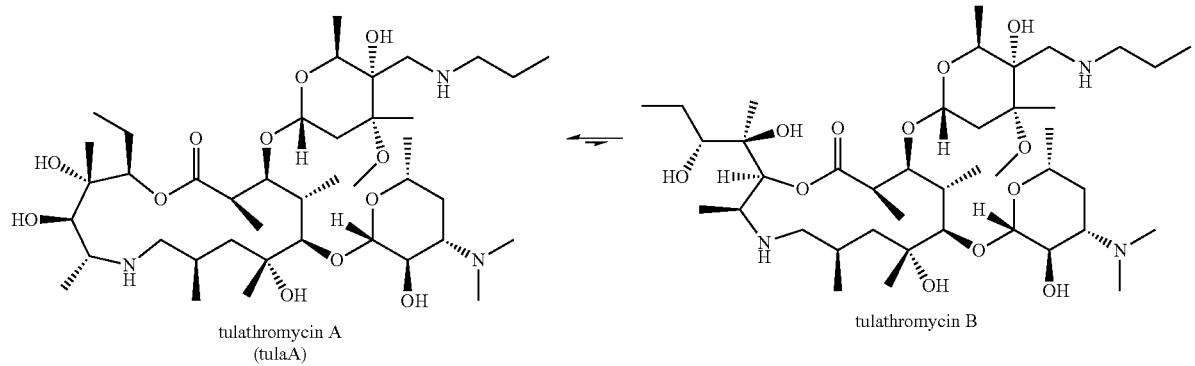 [SMILES: CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@@H](O)[C@](C)(O)[C@@H](CC)OC(=O)[C@@H]2C)C[C@@]1(C)OC ; CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@@H](C)[C@@H]([C@](C)(O)[C@H](O)CC)OC(=O)[C@@H]2C)C[C@@]1(C)OC]

Tulathromycin is (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((2R,4R,5S,6S)-5-hydroxy-4-methoxy-4,6-dimethyl-5-(((propylamino)methyl)tetrahydro-2H-pyran-2-yl)oxy)-3,5,8,10,12,14-hexamethyl-1-oxa-6-azacyclopentadecan-15-one; and a precursor to tulathromycin, tulathromycin epoxide (tula-epx), is (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one.

One of the metabolites of tulathromycin A is the desmethyl azalide, (2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)-

(M9)

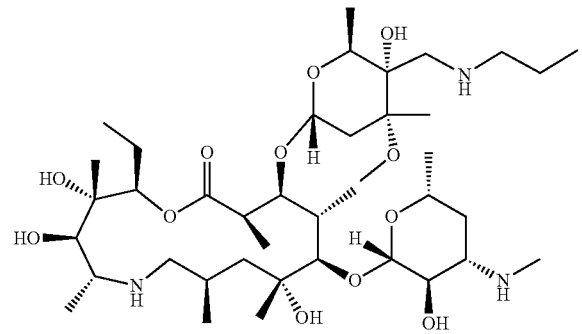

(M9)

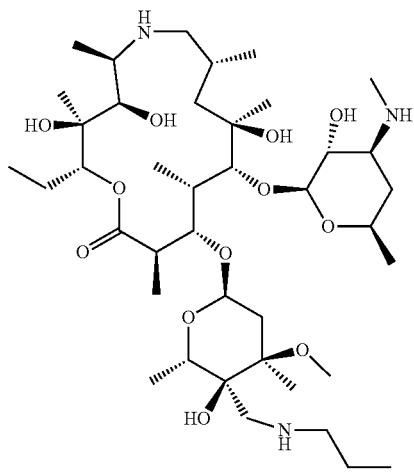

Tulathromycin B also metabolizes to the B-des-methyl azalide.

The M9 analogue can be used as a starting material for preparing compounds of the invention. The process to make des-methyl tulathromycin (M9) is a two-step process from tulathromycin A and the intermediate is generally not isolated, but it can be. The first step is an oxidation of the tertiary amine to the N-oxide using any number of oxidizing agents known to oxidize tertiary amines. The second step is a Polonovski-type demethylation which can employ any metal known to effect that type of transformation. It's generally iron, but a copper salt (Cu(II)) can also be used.

To a cold (<0° C.) solution of tulathromycin A (4.0 g, 5.0 mmol) in n-butanol (20 mL), 1.22 g (5.1 mmol) of a commercial 32% peracetic acid solution was added. After 30 minutes, the product was extracted into a 0.25M aqueous solution of disodium ethylenediamine-tetraacetic acid (EDTA, 15 mL). The aqueous solution was basified to pH 9.5 with concentrated aqueous ammonia and extracted with tert-butyl methyl ether (20 mL). The N-oxide product was concentrated to a thick oil but was not isolated, [M+H]$^+$=822. The oil was dissolved in methanol (16 mL). Copper (II) sulfate pentahydrate (1.5 g, 6.1 mmol) and acetic acid (0.28 mL) were added and the reaction was heated to 60° C. for 1-2 hours. The solution was cooled to 25° C. and hydroxyamine hydrochloride (0.75 g, 10 mmol) in water (8 mL) was added. After 2 hours, the product was partitioned between water (28 mL, adjusted to pH 9.5 with aqueous ammonia) and methylene chloride (20 mL). The organics were concentrated to an oil and the product was crystallized from hot acetonitrile (40 mL). The resulting white crystalline powder was dried to provide 3.2 g of M9. LCMS [M+H]$^+$=792.5. HPLC purity >98%. $^1$H NMR (600 MHz, d$_6$-DMSO): N-Me (3H, 2.42 ppm, S) compared to tulathromycin NMe$_2$ (6H, 2.26 ppm).

Alternatively, M9 can be prepared by mixing a 20° C. solution of tulathromycin A (4.0 g, 5.0 mmol) in n-butanol (10 mL) and then add hexafluoroacetone trihydrate (0.27 g, 1.2 mmol) followed by 30% aqueous hydrogen peroxide (0.62 g, 5.5 mmol). After 4 hours, acetic acid (0.31 g, 5.5 mmol) was added followed by methyl tert-butyl ether (6 mL) and water (25 mL). The upper organic layer was discarded. Methyl tert-butyl ether (8 mL) was added and the pH of the aqueous layer was adjusted to 9.8 with aqueous ammonia. The lower aqueous layer was discarded. The N-oxide product was concentrated to a thick oil but was not isolated. [M+H]$^+$=822. The oil was dissolved in methanol (12 mL). Anhydrous copper(II) sulfate (0.97 g, 6.1 mmol) and acetic acid (0.28 mL) were added and the reaction was heated to 60° C. for 1 hour. The solution was cooled to 25° C. and hydroxyamine hydrochloride (0.75 g, 10 mmol) in water (8 mL) was added. After 2 hours, the product was partitioned between water (28 mL, adjusted to pH 9.5 with aqueous ammonia) and methylene chloride (20 mL). The organics were concentrated to an oil and the product was crystallized from hot acetonitrile (40 mL). The resulting white crystalline powder was dried to provide 3.2 g of product; LCMS [M+H]$^+$=792.5. HPLC purity >98%. 1H NMR (600 MHz, d6-DMSO): N-Me (3H, 2.42 ppm, S) compared to tulathromycin NMe$_2$ (6H, 2.26 ppm).

Alternatively, M9 can be prepared by mixing a solution of tulathromycin epoxide (20.0 g, 27 mmol) in methanol (40 mL) and then add acetic acid (1.6 mL, 30 mmol), hexafluoroacetone trihydrate (0.38 mL, 3 mmol) and then 30% aqueous hydrogen peroxide (0.62 g, 30 mmol).

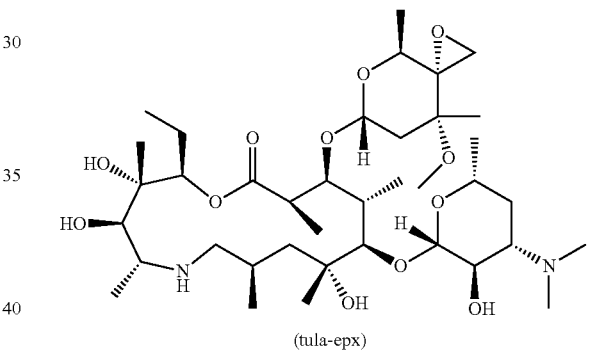

(tula-epx)

After 4 hours at 35° C., the reaction was cooled to 20° C. and anhydrous copper(II) sulfate (4.5 g, 29 mmol) was added and the reaction was heated to 60° C. for 1 hour. After cooling to 20° C., added 60 mL methylene chloride and 80 mL water. Basified the mixture to approximately pH 9.8 with concentrated aqueous ammonia. Concentrated the organics under vacuum to a solid and then added 2-propanol (40 mL) and n-propylamine (40 mL). Heated to 65° C. and stirred for 15 hours. Concentrated under vacuum to remove solvents. Added acetonitrile (120 mL) and heated to 78° C. Cooled to 10° C. and isolated product by filtration. The resulting white crystalline powder was dried to provide 12 g of product; LCMS [M+H]$^+$=792.5. HPLC purity >98%. 1H NMR (600 MHz, d6-DMSO): N-Me (3H, 2.42 ppm, S) compared to tulathromycin NMe$_2$ (6H, 2.26 ppm).

Azithromycin (depicted below), an azalide similar to tulathromycin, except the core ring N is substituted with a methyl group (1') and the cladinose sugar is not further substituted with N-methylpropan-1-amine (2'); depicted below.

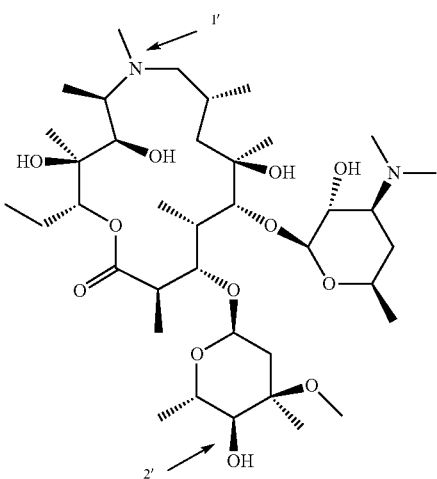

Azithromycin can be derivatized to prepare a des-methyl analogue, similar to M9. Further derivatizations can be conducted in accordance with the schemes and experimentals defined herein to prepare immune-modulating azithromycin derivatives that are not active (i.e., non-antibacterial) against BRD bacterial pathogens. In addition to azithromycin, other macrolides, for example, erythromycin, tilmicosin, clarithromycin, gamithromycin, fidaxomicin, roxithromycin, telithromycin, dirithromycin, josamycin, midecamycin, oleandomycin, roxithromycin, and others, can be modified in a similar manner as M9 to prepare immune-modulating analogues that lack antibacterial properties against BRD and other bacterial pathogens in animals, including humans.

For illustrative purposes, the reaction schemes depicted below demonstrate potential routes for synthesizing key intermediates and compounds of the invention. For a more detailed description of the individual reaction steps, see the Examples section below. Those skilled in the art will appreciate that other suitable starting materials, reagents, and synthetic routes may be used to synthesize the intermediates and compounds of the invention and a variety of derivatives thereof. Further, many of the compounds prepared by the methods described below can be prepared and/or modified using conventional chemistry.

The compounds of the invention may be used in their native form or as a salt. In cases where forming a stable nontoxic acid salt is desired, administration of the compound as a pharmaceutically acceptable salt may be appropriate. For the purpose of the present invention, the term "pharmaceutically acceptable salt" refers to those salts which are, within the scope of sound medical evaluation, suitable for use in contact with the tissues and organs of animals without displaying toxicity, irritation, allergic response and the like and are commensurate with a reasonable benefit/risk ratio. Further, the compounds of the invention have a secondary or tertiary amine group, which has basic character and thus can form acid addition salts, which may be pharmaceutically acceptable acids. Therefore, pharmaceutically acceptable salts according to the present invention include those pharmaceutically acceptable acid addition salts formed with organic and inorganic acids and those pharmaceutically acceptable salts formed with optically active acids. Representative acid addition salts include, but are not limited to, acetate, adipate, alginate, ascorbate, citrate, aspartate, benzoate, benzenesulfonate, besylate, bicarbonate/carbonate, bisulfate/sulfate, borate, butyrate, camphorate, camphorsulfonate, camsylate, citrate, digluconate, edisylate, etoglutarate, esylate, formate, fumarate, gluceptate, gluconate, glucuronate, glutamate, glycerophosphate, hemisulfate, heptanoate, hexafluorophosphate, hexanoate, hibenzate, fumarate, hydrochloride, hydrobromide, hydroiodide, 2-hydroxyethansulfonate, isethionate, lactate, malate, maleate, malonate, mesylate, methylsulphate, naphthylate, 2-napsylate, nicotinate, nitrate, orotate, oxalate, palmitate, pamoate, pectinate, persulfate, phosphate/hydrogen phosphate/dihydrogen phosphate, picrate, pivalate, proprionate, saccharate, stearate, succinate, tartrate, thiocyanate, tosylate and trifluoroacetate salts.

In the following Schemes, the demethylation or Polonovski reaction occurs when an amine oxide reacts with an acylating agent. The accepted mechanism involves proton removal to give a nitrogen ylide which loses acetate (using acetic anhydride) which attacks the carbon adjacent to the nitrogen atom giving an α-acetoxyamine. The central feature of the Polonovski reaction is the transformation of an N-oxide to an iminium ion intermediate. Depending on the structure of the substrate and the acid anhydride or other activating reagent employed, iminium ion formation can occur through loss of an α hydrogen, or through fragmentation of a Cα-carbon bond. Again, depending on conditions, the reaction will either stop at this stage and iminium ions become the Polonovski products, or proceed to give enamines or tertiary amides and/or secondary amines and aldehydes.

In principle, any reagent capable of activating the N-oxide oxygen could promote the Polonovski reaction. However, three major types of activating agents, acid anhydrides and chlorides (including chloroformate esters), iron salts and complexes, and sulfur dioxide, are usually employed.

In the following Schemes and experimental preparations, the following acronyms include: methanol (MeOH), ethanol (EtOH), dichloromethane (DCM), dichloroethane (DCE); hexafluoroisopropyl sulfamate (HFIPS); trifluoroacetic acid (TFA), hydrogen peroxide ($H_2O_2$), potassium cyanide (KCN), triethylamine (TEA), ethylenediaminetetraacetic acid (EDTA), acetic acid (AcOH), ammonium hydroxide ($NH_4OH$), acetonitrile (MeCN or Acn), ethyl acetate (EtOAc), tert-butyl alcohol (t-BuOH or TBA); sodium methoxide (MeONa); N-methyl-2-pyrrolidine (NMP); cerium(III) chloride ($CeCl_3$), sodium azide ($NaN_3$), sodium bicarbonate ($NaHCO_3$), ammonium chloride ($NH_4Cl$), N-iodosuccinimide (NIS), magnesium sulfate ($MgSO_4$); sodium sulfate ($Na_2SO_4$), ammonium sulfate ($(NH_4)_2SO_4$), copper sulfate ($CuSO_4$), sodium triacetoxyborohydride (STAB); N-(3-dimethylaminopropyl)-N'-ethylcarbodiimide hydrochloride (EDC.HCl); sodium cyanoborohydride ($NaBH_3CN$); N,N-diisopropylethylamine (DIPEA); dimethylformamide (DMF); 1-butanol (N-BuOH); hexafluoroacetone ($(CF_3)_2CO—H_2O$), hydrochloric acid (HCl); water ($H_2O$), methoxy (OMe); fluoro (F); chloro (Cl); methyl (Me); trifluoromethyl ($CF_3$); room temperature (RT); and overnight (ON).

In the following Schemes, for example, Scheme 1a, the formulas are depicted as s1a-A1 through s1a-A6; referring to Scheme 1a (s1a) and the -A1 refers to Formula A1 as described herein; and subsequently s1a-A2, s1a-A3, s1a-A4, s1a-A5 and s1a-A6 refer to the respective A2, A3, A4, A5 and A6 formulas as described herein.

Scheme 1a. Preparation of Formula (1) Sulfonamide Compounds 1-A1 through 1-A6

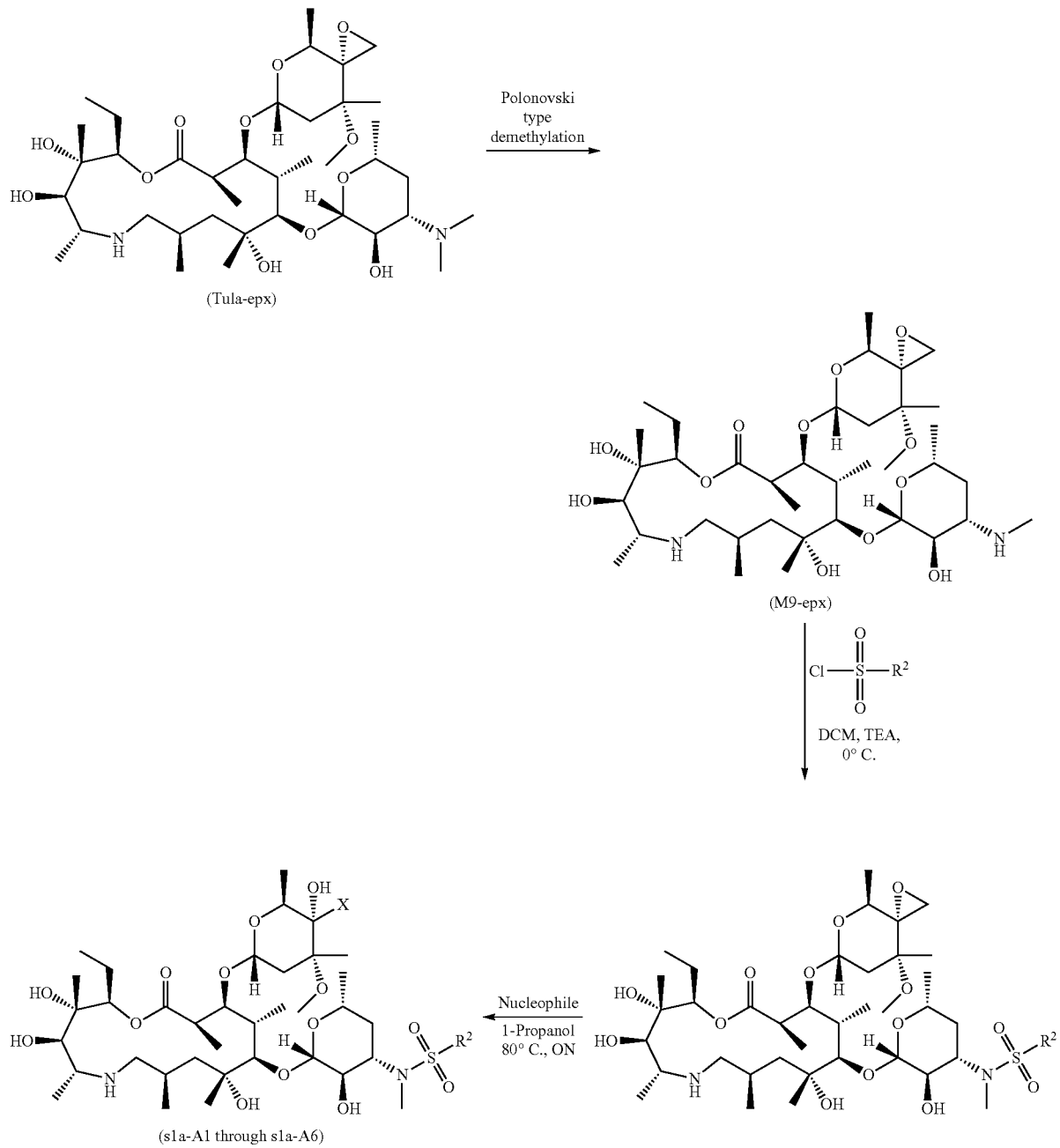

The sulfonamide analogs can be prepared following the 3-step procedure outlined in Scheme 1a above. First, the commercially available tulathromycin epoxide (tula-epx) can be demethylated under but not limited to the Polonovski reaction to give M9 epoxide (M9-epx). The N-oxide can be formed using different oxidizing agents such as iodine, N-iodosuccinimide, peracetic acid or hydrogen peroxide. The demethylation of the N-oxide can be triggered with iron or copper salts. The secondary amine thus formed can be transformed into various sulfonamides using sulfonylating reagents such as sulfonyl chlorides and fluorides and others. Mild bases such as TEA or DIPEA can be sometimes used to facilitate the sulfonamide formation reaction. In the last step, the epoxide functional group can be opened to give the final sulfonamide analogs using different nucleophiles such as primary and secondary amines, alcohols, thiols, cyanide, azide or halogen anions and others at higher temperature in alcoholic solvents such as but not limited to 1-propanol, 1-butanol or 2-propanol. This reaction can be completed overnight. Mild bases such as $NaHCO_3$ or salts such as $NH_4Cl$ or $(NH_4)_2SO_4$ can sometimes accelerate the epoxide opening reaction. For any of the Schemes presented herein, the "nucleophile" of the epoxide opening step on the cladinose ring, can be but is not limited to the following: $HNR^5R^6$, $HOR^7$, $HS(O)_pR^7$, $NaN_3$, $CeCl_3$, $TEA.3HF$, and KCN, wherein $R^5$, $R^6$, $R^7$ and p are as defined herein.

Scheme 1b Details for Scheme 1a Step 3 (Nucleophilic Epoxide Opening)

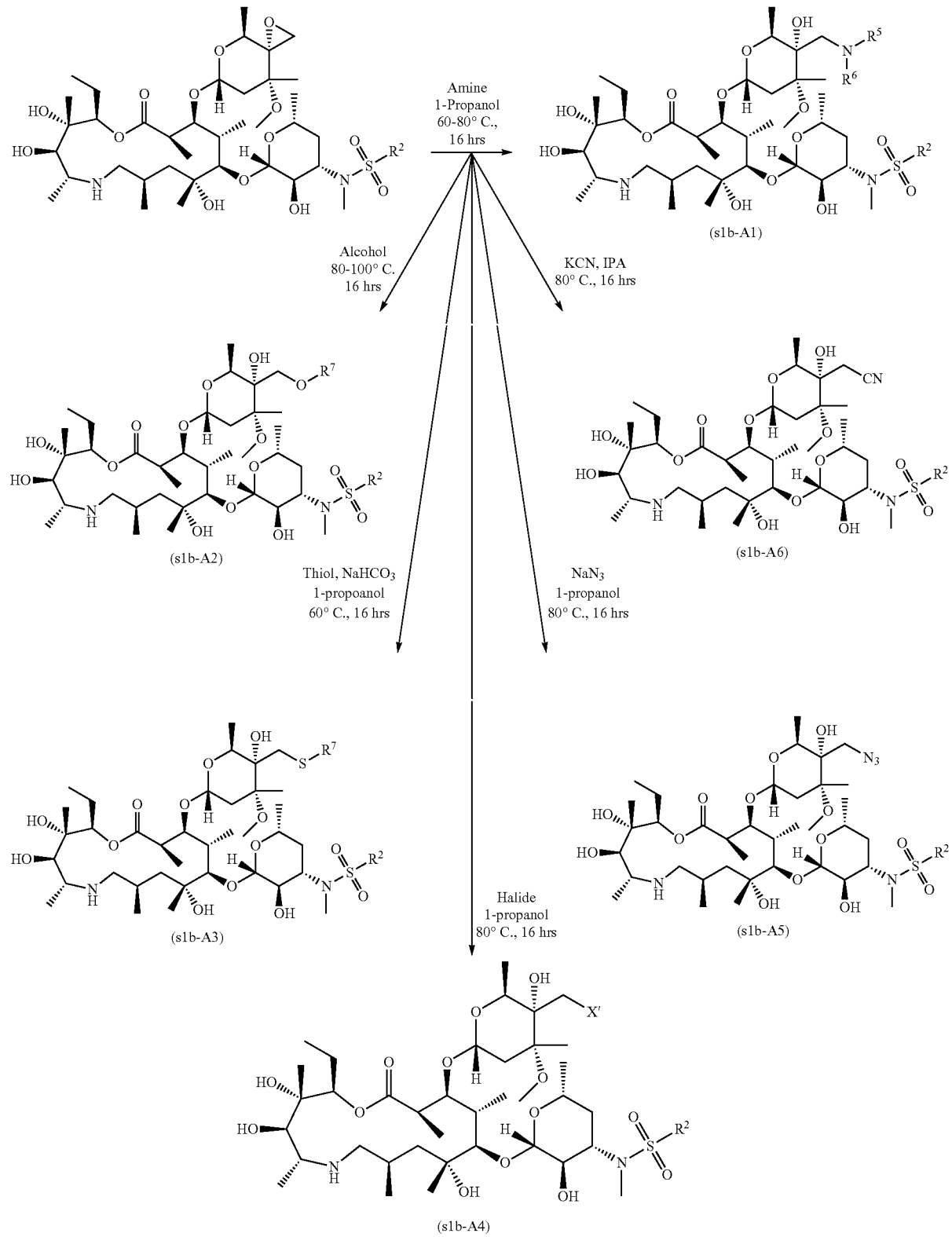

For the (s1b-A1) analogs, the epoxide functional group can be opened to give the final sulfonamide analogs using different primary or secondary amines in alcoholic solvents such as but not limited to methanol, ethanol. 1-propanol and others. For the (s1b-A2) analogs, the epoxide functional group can be opened to give the final sulfonamide analogs using different alcohols used as solvents such as but not limited to methanol, ethanol, 1-propanol and others. Mild bases such as NaHCO₃ or salts such as NH₄Cl or (NH₄)₂SO₄ can sometimes accelerate the epoxide opening reaction. For the (s1b-A3) analogs, the epoxide functional group can be opened to give the final sulfonamide analogs using different thiols such as but not limited to ethanethiol, propanethiol, isopropyl mercaptan and others in alcoholic solvents such as but not limited to ethanol or 1-propanol. Mild bases such as NaHCO₃ but not limited to are used to accelerate the epoxide opening reaction. For the (s1b-A4) analogs, the epoxide functional group can be opened to give the final sulfonamide analogs using different halides from reagents such as but not limited to CeCl₃ or Br₂ in alcoholic solvents such as but not limited to ethanol or 1-propanol. Mild bases such as NaHCO₃ or salts such as NH₄Cl or (NH₄)₂SO₄ can sometimes accelerate the epoxide opening reaction. For the (s1b-A5) analogs, the epoxide functional group can be opened to give the final sulfonamide analogs using different sources of the azide anion such as but not limited to NaN₃ in alcoholic solvents such as but not limited to ethanol or 1-propanol. Mild bases such as NaHCO₃ or salts such as NH₄Cl or (NH₄)₂SO₄ can sometimes accelerate the epoxide opening reaction. For the (s1b-A6) analogs, the epoxide functional group can be opened to give the final sulfonamide analogs using different sources of the cyanide anion such as but not limited to KCN in alcoholic solvents such as but not limited to IPA or 1-propanol. Mild bases such as NaHCO₃ or salts such as NH₄Cl or (NH₄)₂SO₄ can sometimes accelerate the epoxide opening reaction.

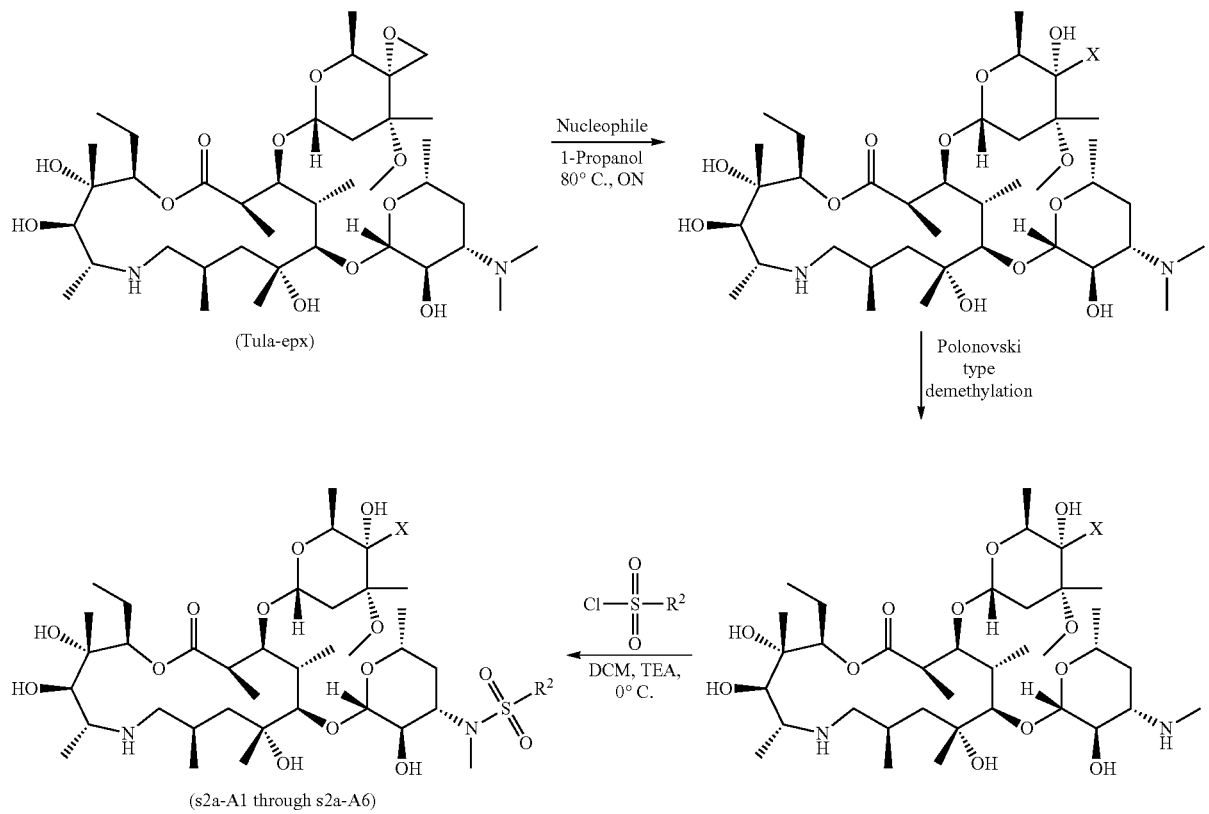

Scheme 2a. Preparation of Formula (1) Sulfonamide Compounds 1-A1 through 1-A6

Alternatively, the sulfonamide analogs can be prepared according to Scheme 2a. In the first step, the commercially available tulathromycin epoxide intermediate is treated with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol. This reaction can occur overnight. Mild bases such as NaHCO₃ or salts such as NH₄Cl or (NH₄)₂SO₄ can sometimes accelerate the epoxide opening reaction. In the second step, the tertiary dimethyl amine on the desosamine sugar can be demethylated using Polonovski type conditions as described above. The final sulfonamide analogs can be prepared by reacting the secondary methyl amine moiety with sulfonylating reagents such as sulfonyl chlorides or fluorides and the like.

Scheme 2b Details for Scheme 2a Step 1 (Nucleophilic Epoxide Opening)
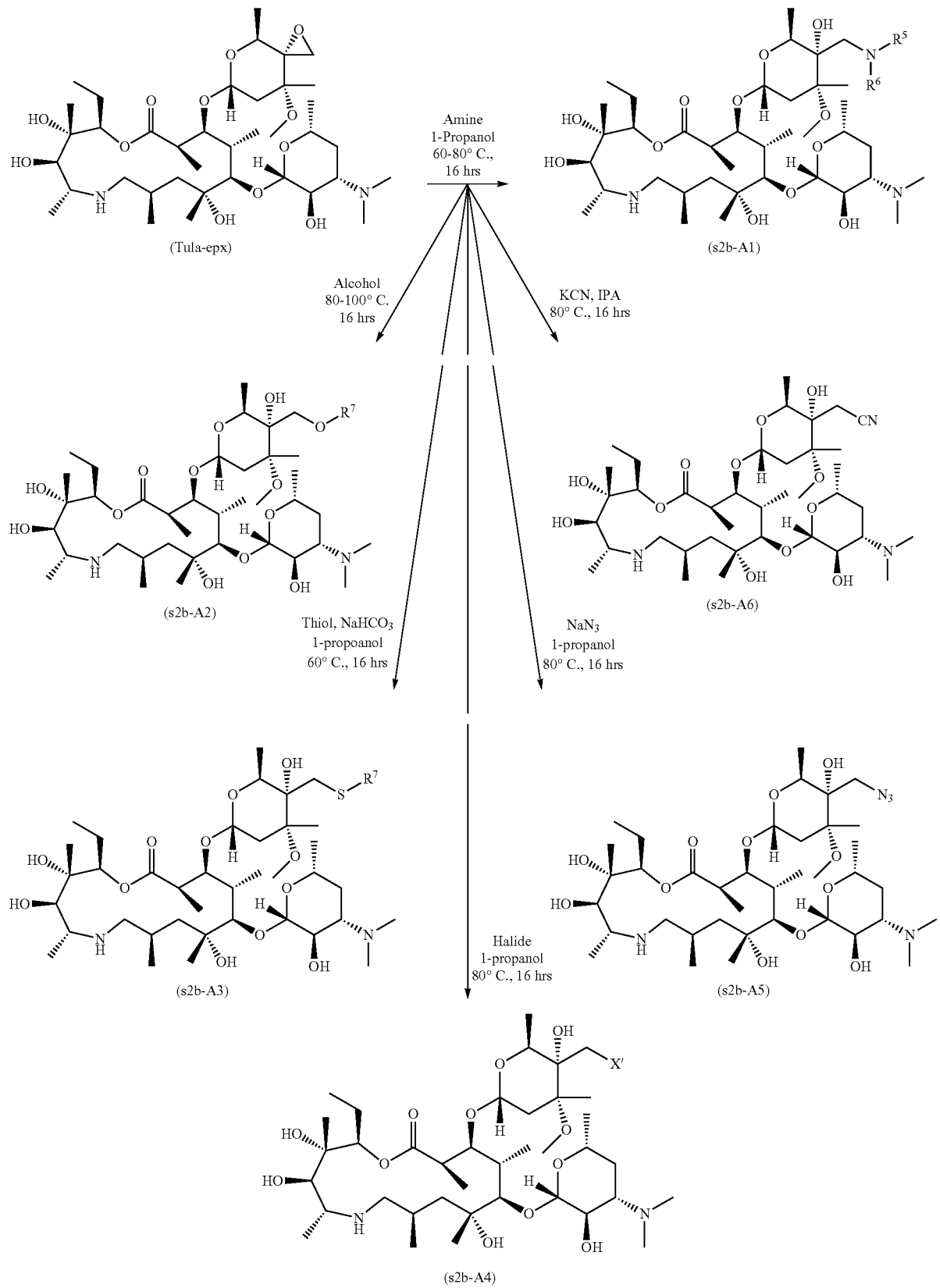

For the (s2b-A1) compounds, the epoxide functional group can be opened using different primary or secondary amines in alcoholic solvents such as but not limited to methanol, ethanol, 1-propanol and others. For the (s2b-A2) compounds, the epoxide functional group can be opened using different alcohols used as solvents such as but not limited to methanol, ethanol, 1-propanol and others. Mild bases such as NaHCO$_3$ or salts such as NH$_4$Cl or (NH$_4$)$_2$SO$_4$ can sometimes accelerate the epoxide opening reaction. For the (s2b-A3) compounds, the epoxide functional group can be opened using different thiols such as but not limited to ethanethiol, propanethiol, isopropyl mercaptan and others in alcoholic solvents such as but not limited to ethanol or 1-propanol. Mild bases such as NaHCO$_3$ but not limited to are used to accelerate the epoxide opening reaction. For the (s2b-A4) compounds, the epoxide functional group can be opened using different halides from reagents such as but not limited to CeCl$_3$ or Br$_2$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction. For the (s2b-A5) compounds, the epoxide functional group can be opened by the azide ion using different sources of the azide anion such as but not limited to NaN$_3$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction. For the (s2b-A6) compounds, the epoxide functional group can be opened by the cyanide ion using different sources of the cyanide anion such as but not limited to KCN in alcoholic solvents such as but not limited to IPA or 1-propanol. Mild bases such as NaHCO$_3$ or salts such as NH$_4$Cl or (NH$_4$)$_2$SO$_4$ can sometimes accelerate the epoxide opening reaction.

Scheme 2c Details for Scheme 2a Step 2 (Demethylation)

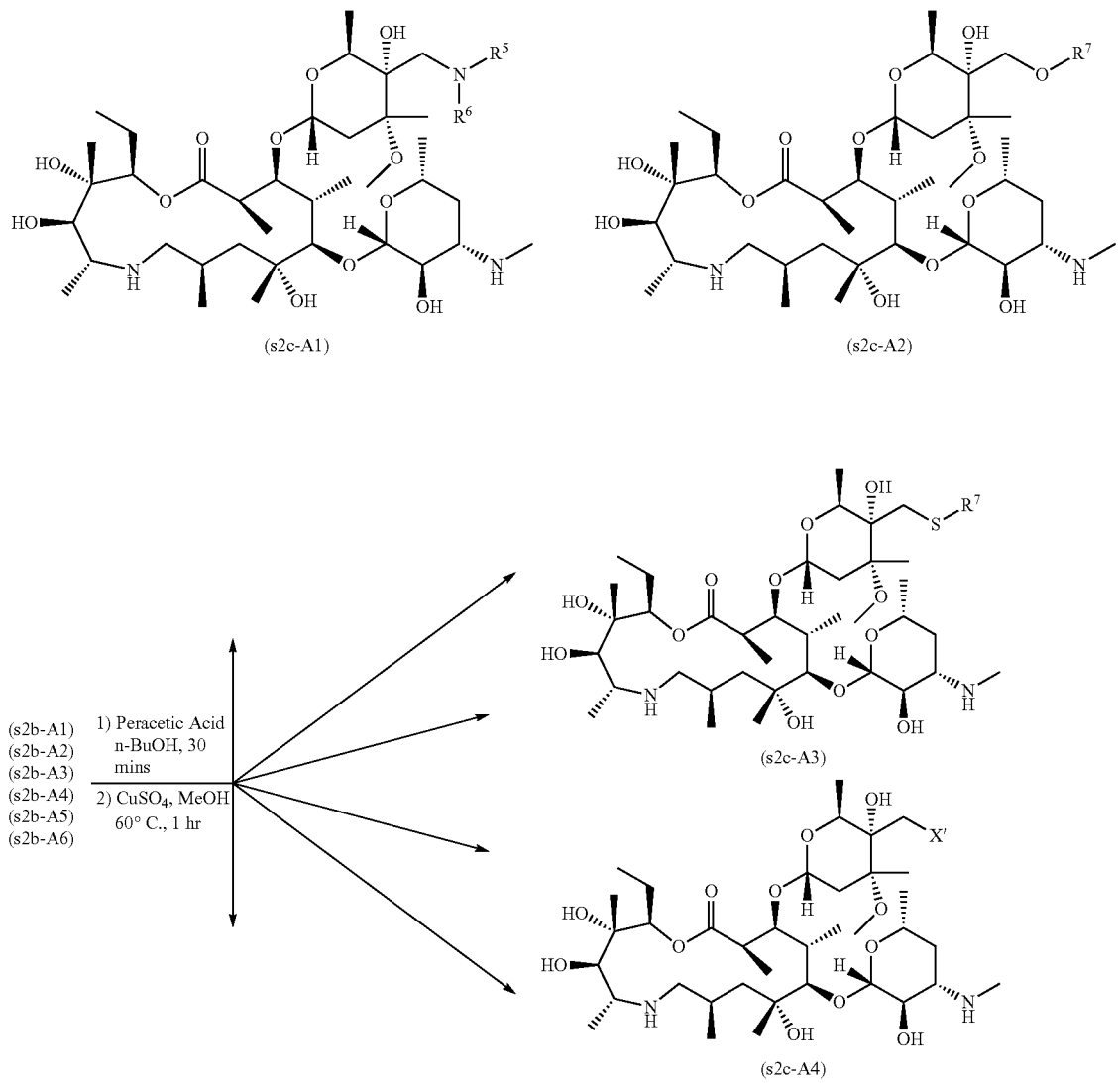

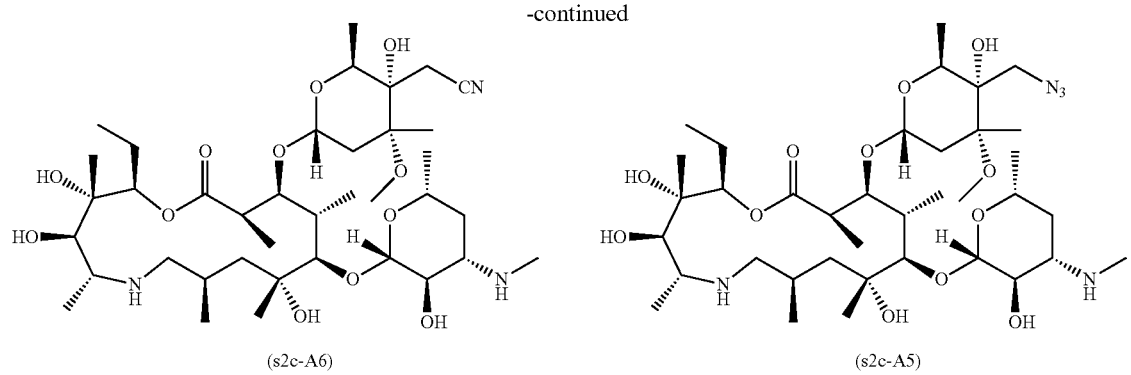

All compounds (s2b-A1) through (s2b-A6) can undergo a Polonovski type demethylation as described above, to give the corresponding compounds (s2c-A1) through (s2c-A6). The N-oxide can be formed using different oxidizing agents such as iodine, NIS, peracetic acid or hydrogen peroxide. The demethylation of the N-oxide can be triggered by such reagents as iron or copper salts.

Scheme 2d Details of Step 3 of Scheme 2a (Sulfonamide formation)

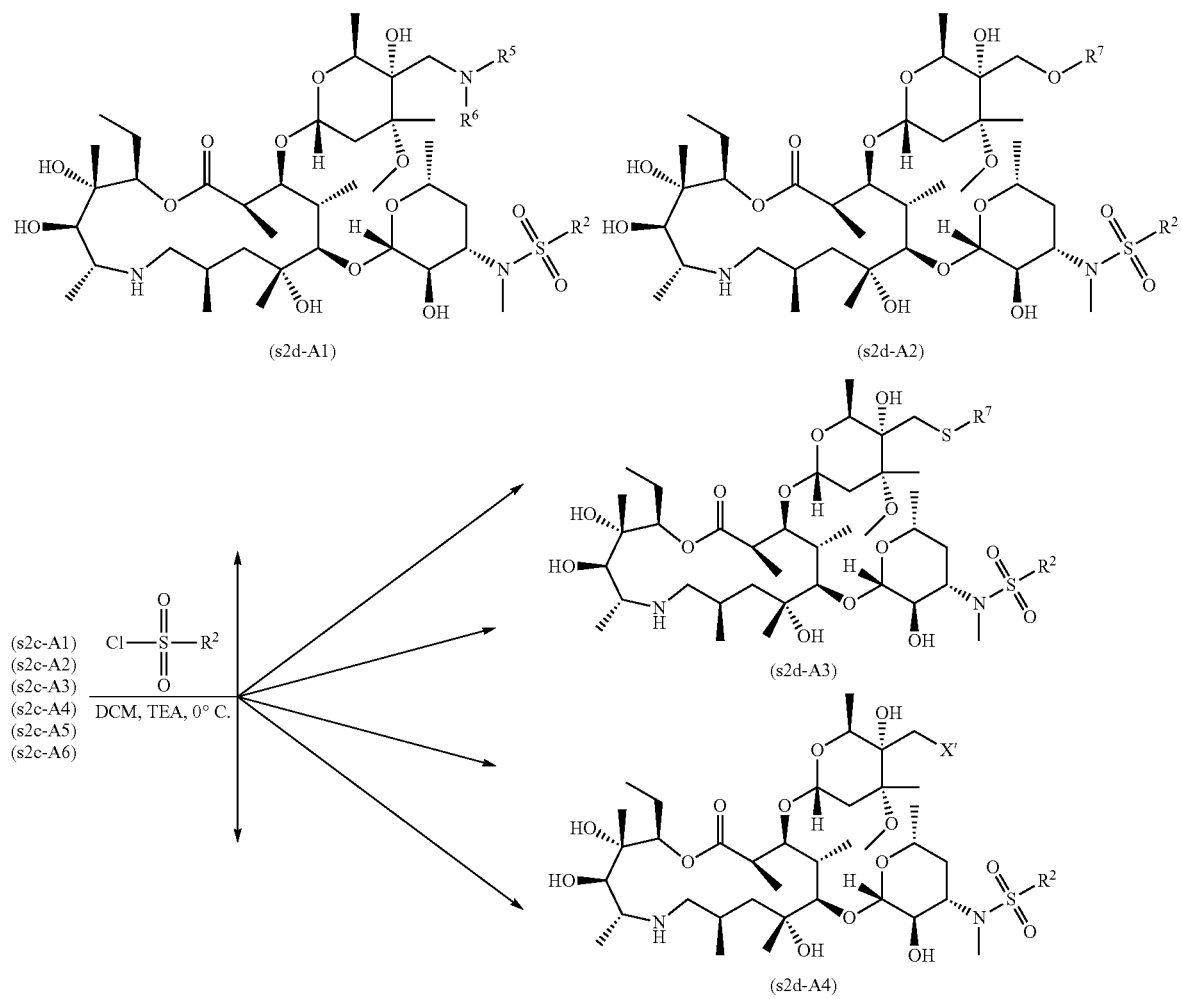

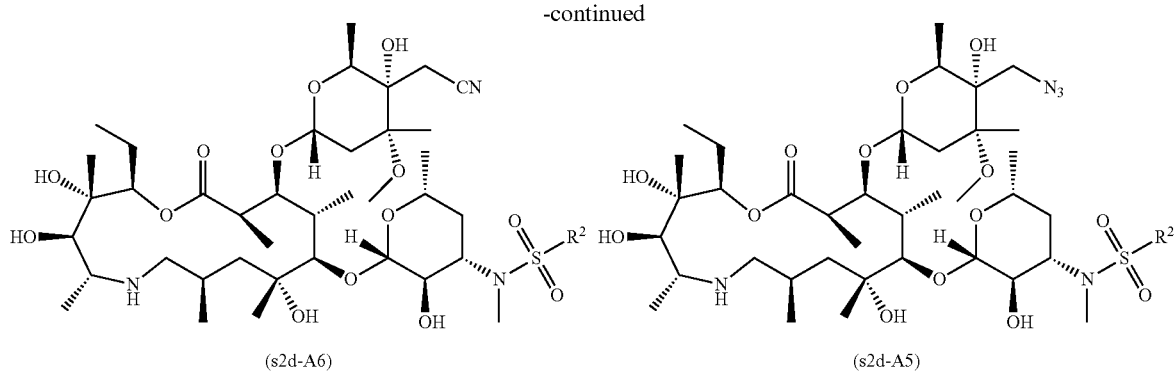

(s2d-A6)  (s2d-A5)

In the last step of the sequence the final analogs can be prepared by reacting the Polonovski reaction product (s2c-A1/A6) with sulfonylating reagents such as but not limited to sulfonyl chlorides and fluorides and the like. Details of this last transformation are shown in Scheme 2d above.

and others at higher temperature in alcoholic solvents such as but not limited to 1-propanol, 1-butanol or 2-propanol to open up the epoxide moiety. Mild bases such as $NaHCO_3$ or salts such as $NH_4Cl$ or $(NH_4)_2SO_4$ can sometimes accelerate the epoxide opening reaction. The details of this second step are shown below in Scheme 3b. In the last step, the final sulfonamide analogs can be prepared by reacting the secondary methyl amine moiety with sulfonylating reagents such as but not limited to sulfonyl chlorides or fluorides and the like. Details of this last transformation are shown in Scheme 3c below.

Scheme 3a. Preparation of Formula (1) Compounds 1-A1 through 1-A6

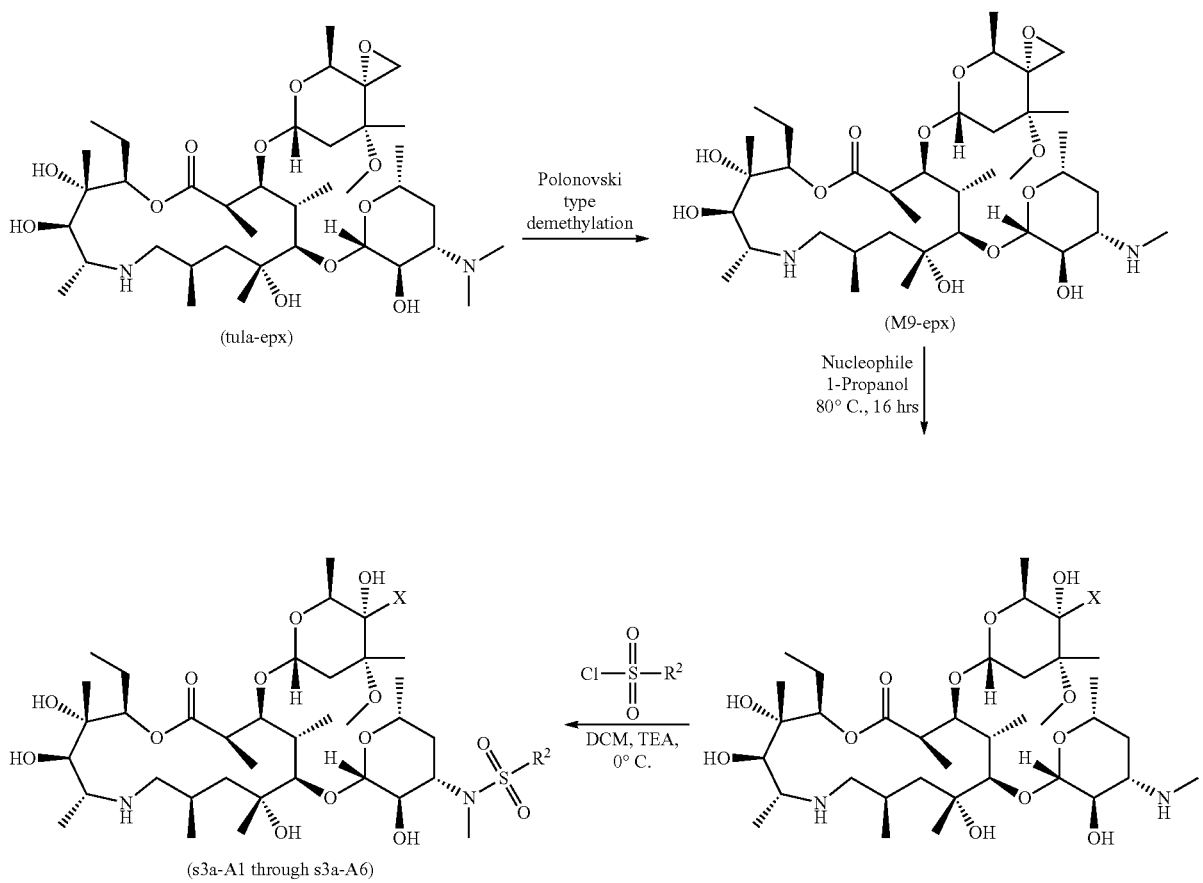

Alternatively, the analogs can be prepared as depicted in Scheme 3a. In the first step, the commercially available tulathromycin epoxide can be demethylated under but not limited to the Polonovski reaction as described above. M9-epoxide thus formed can be reacted with various nucleophiles such as but not limited to primary and secondary amines, alcohols, thiols, cyanide, azide or halogen anions Scheme 3b Details for Scheme 3a Step 2 (Nucleophilic Epoxide Opening)
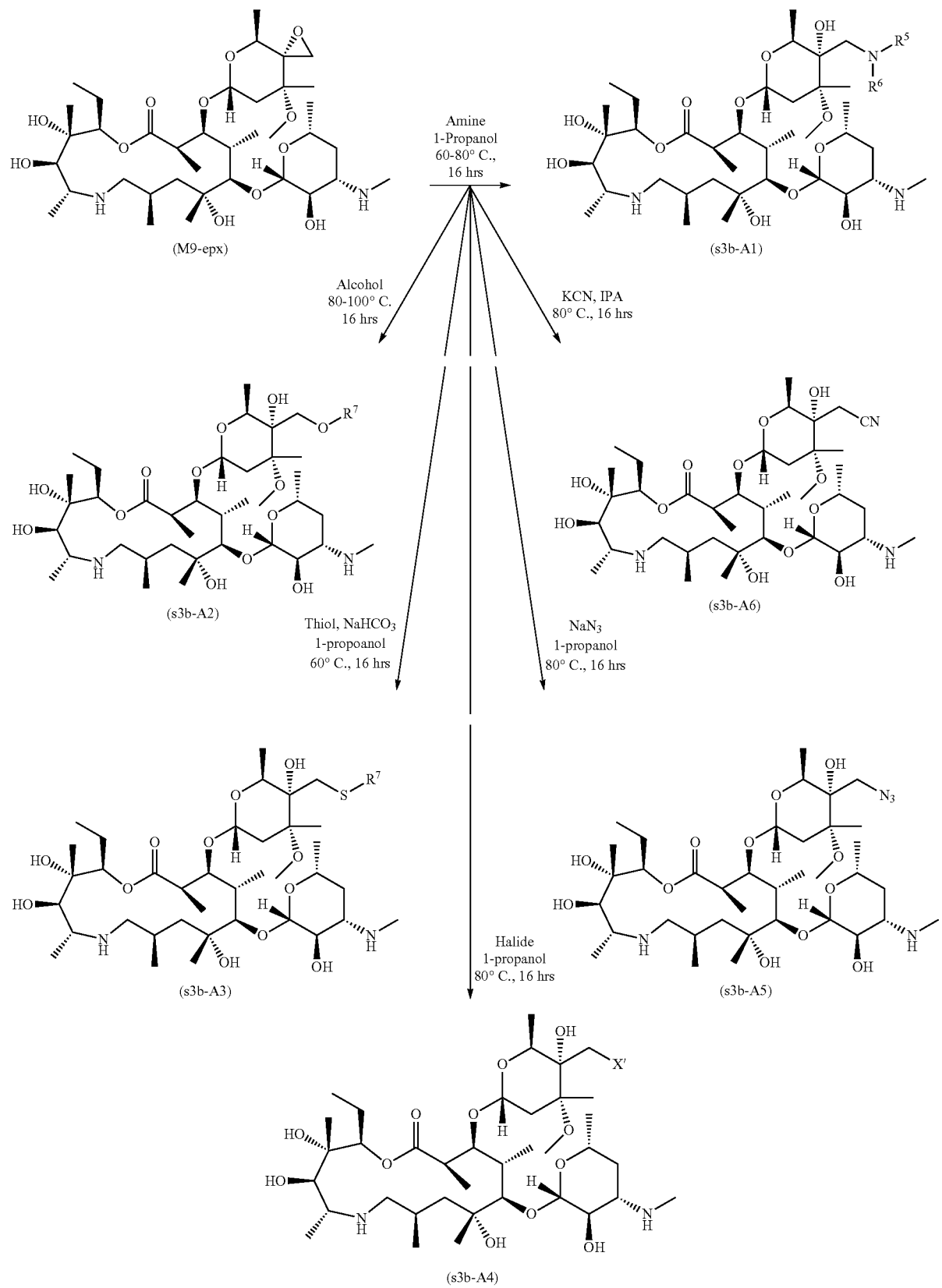

M9-epoxide formed from the demethylation of the commercially available tulathromycin epoxide (Scheme 3a) can be reacted to give the following compounds with Formula: (s3b-A1)—with various primary or secondary amines in alcoholic solvents such as but not limited to methanol, ethanol or 1-propanol; (s3b-A2)—with various alcohols used as solvent such as but not limited to methanol, ethanol or 1-propanol. Mild bases such as $NaHCO_3$ or salts such as $NH_4Cl$ or $(NH_4)_2SO_4$ can sometimes accelerate the epoxide opening reaction; (s3b-A3)—with various thiols such as but not limited to ethanethiol, propanethiol, isopropyl mercaptan and others in alcoholic solvents such as but not limited to ethanol or 1-propanol. Mild bases such as but not limited to $NaHCO_3$ are used to accelerate the epoxide opening reaction; (s3b-A4)—with halides from reagents such as but not limited to $CeCl_3$ or $Br_2$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction; (s3b-A5)—with the azide anion from sources such as but not limited to $NaN_3$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction; and (s3b-A6)—with the cyanide anion from sources such as but not limited to KCN in alcoholic solvents such as but not limited to IPA or 1-propanol. Mild bases such as $NaHCO_3$ or salts such as $NH_4Cl$ or $(NH_4)_2SO_4$ can sometimes accelerate the epoxide opening reaction.

Scheme 3c Details for Scheme 3a Step 3 (Sulfonamide formation)

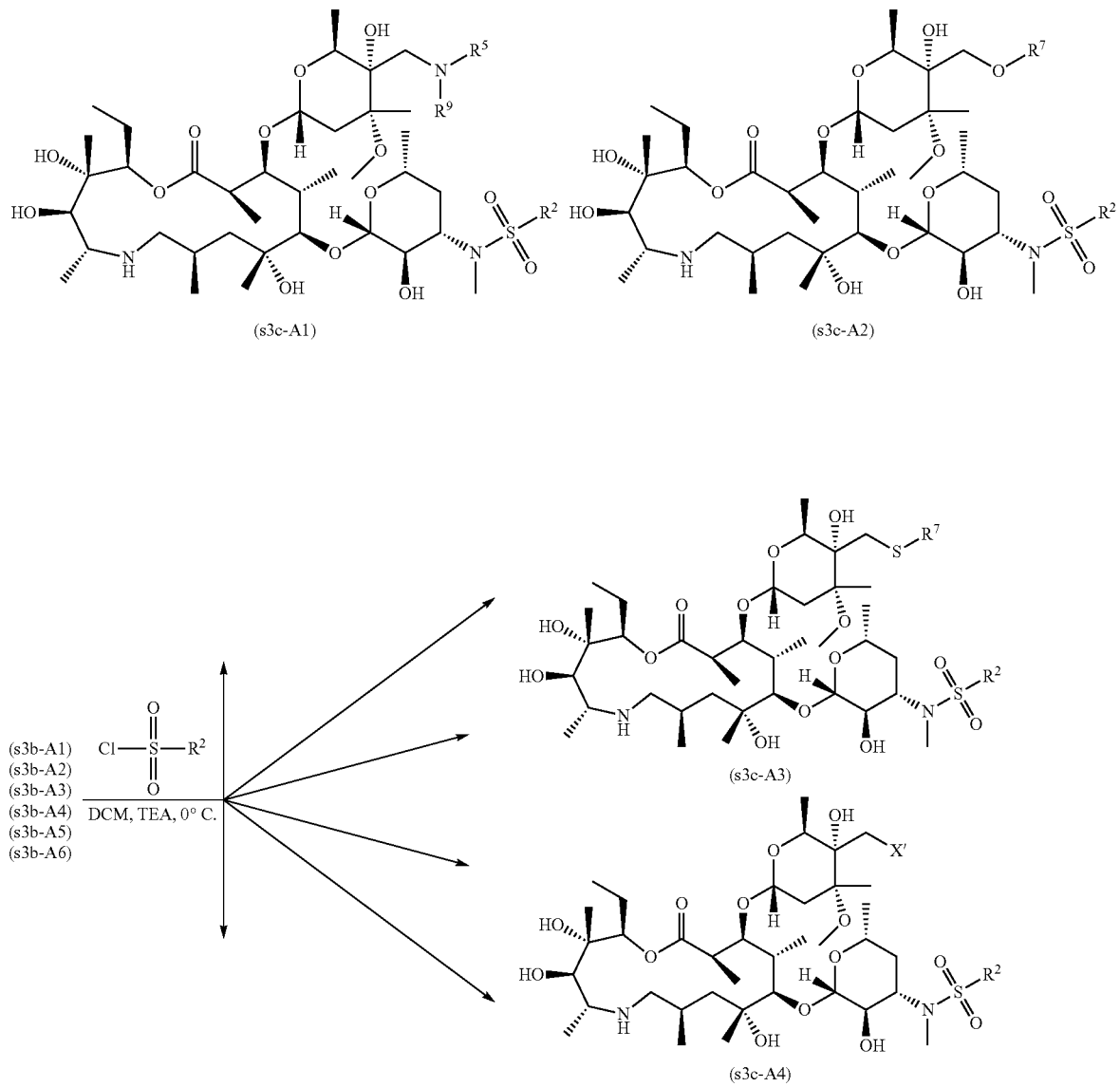

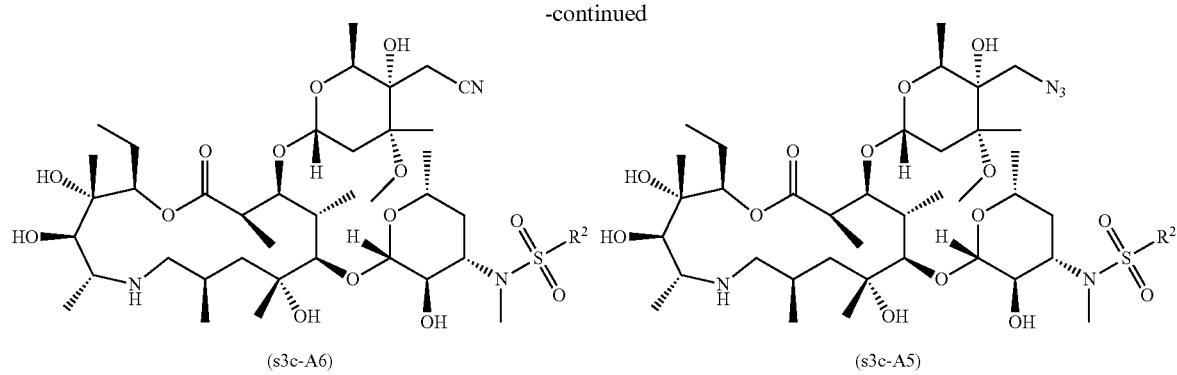

(s3c-A6)            (s3c-A5)

In the last step of the sequence, the final analogs of Formula (s3c-A1), (s3c-A2), (s3c-A3), (s3c-A4), (s3c-A5) and (s3c-A6) can be prepared by reacting the respective (s3b-A1/A6) analogs with sulfonylating reagents such as but not limited to sulfonyl chlorides or fluorides and the like in aprotic solvents such as DCM and mild bases such as but not limited to TEA or DIPEA.

Scheme 4a. Preparation of Formula (1) Sulfamide Compounds 1-A1 through 1-A6

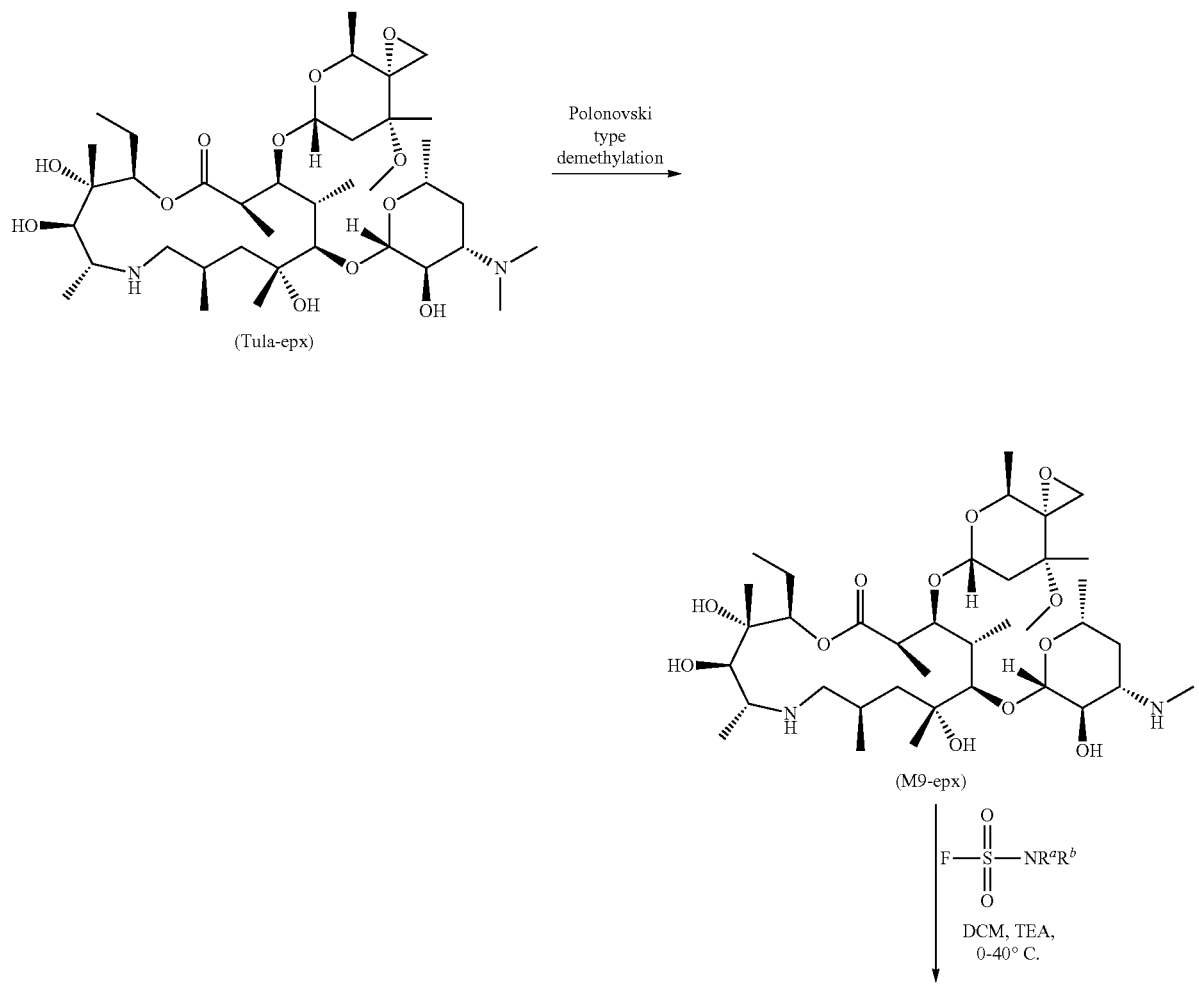

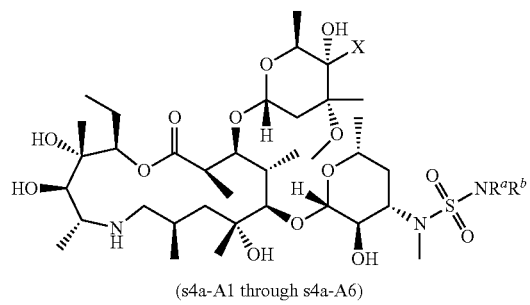
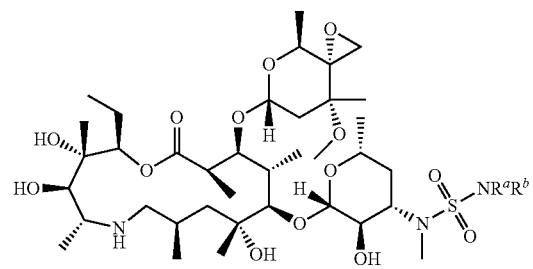

(s4a-A1 through s4a-A6)

Nucleophile
1-Propanol
80° C., ON

-continued

The sulfamide analogs can be prepared following the 3-step procedure outlined in Scheme 4a above. First, the commercially available tulathromycin epoxide (tula-epx) can be demethylated under but not limited to the Polonovski reaction to give M9 epoxide (M9-epx). The N-oxide can be formed using different oxidizing agents such as iodine, N-iodosuccinimide, peracetic acid or hydrogen peroxide. The demethylation of the N-oxide can be triggered with iron or copper salts. The secondary amine thus formed can be transformed into various sulfamides using sulfamoyl fluorides or chlorides and others.

Mild bases such as TEA or DIPEA can be sometimes used to facilitate the sulfamide formation reaction. Many sulfamoyl fluorides or chlorides are commercially available or can be easily prepared from the corresponding amines using procedures such as described in *Angew Chem. Int. Ed.* 2018, 57, 2605-2610. In the last step, the epoxide functional group can be opened to give the final sulfamide analogs using different nucleophiles such as primary and secondary amines, alcohols, thiols, cyanide, azide or halogen anions and others at higher temperature in alcoholic solvents such as but not limited to 1-propanol, 1-butanol or 2-propanol. This reaction can be completed overnight. Mild bases such as $NaHCO_3$ or salts such as $NH_4Cl$ or $(NH_4)_2SO_4$ can sometimes accelerate the epoxide opening reaction. For any of the Schemes presented here, the "nucleophile" of the epoxide opening step on the cladinose ring, can be but is not limited to the following: $HNR^5R^6$, $HOR^7$, $HS(O)_pR^7$, $NaN_3$, $CeCl_3$, $TEA.3HF$, and $KCN$, wherein $R^5$, $R^6$, $R^7$ and p are as defined herein.

Scheme 4b Details for Scheme 4a Step 3 (Nucleophilic Epoxide Opening)

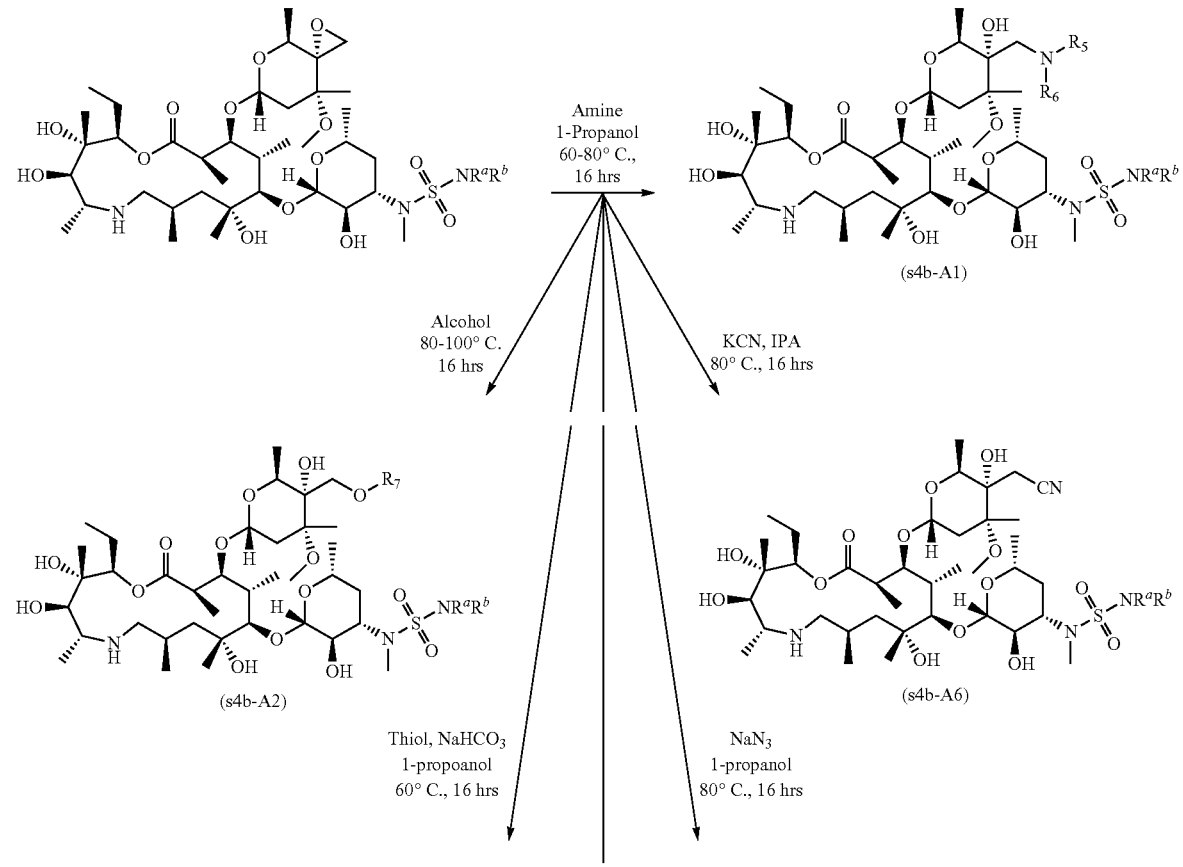

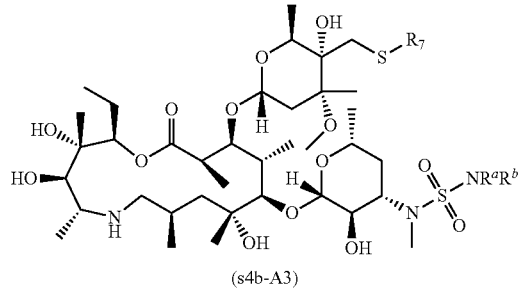
(s4b-A3)

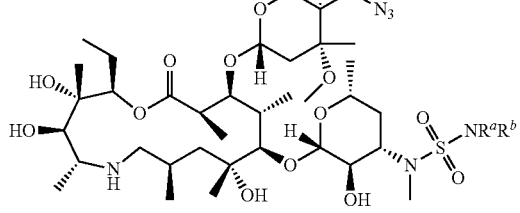
(s4b-A5)

Halide
1-propanol
80° C., 16 hrs

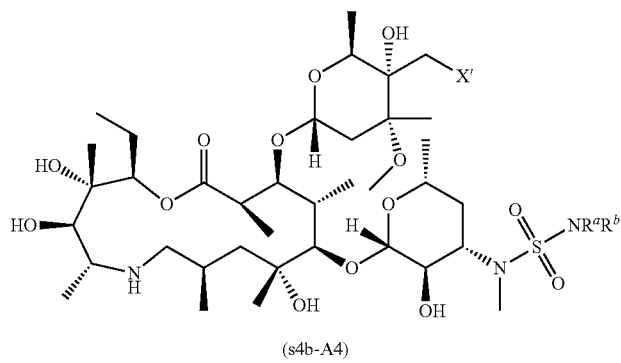
(s4b-A4)

For the (s4b-A1) analogs, the epoxide functional group can be opened to give the final sulfamide analogs using different primary or secondary amines in alcoholic solvents such as but not limited to methanol, ethanol, 1-propanol and others. For the (s4b-A2) analogs, the epoxide functional group can be opened to give the final sulfamide analogs using different alcohols used as solvents such as but not limited to methanol, ethanol, 1-propanol and others. Mild bases such as $NaHCO_3$ or salts such as $NH_4Cl$ or $(NH_4)_2SO_4$ can sometimes accelerate the epoxide opening reaction. For the (s4b-A3) analogs, the epoxide functional group can be opened to give the final sulfamide analogs using different thiols such as but not limited to ethanethiol, propanethiol, isopropyl mercaptan and others in alcoholic solvents such as but not limited to ethanol or 1-propanol. Mild bases such as $NaHCO_3$ but not limited to are used to accelerate the epoxide opening reaction. For the (s4b-A4) analogs, the epoxide functional group can be opened to give the final sulfamide analogs using different halides from reagents such as but not limited to $CeCl_3$ or $Br_2$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction. For the (s4b-A5) analogs, the epoxide functional group can be opened to give the final sulfamide analogs using different sources of the azide anion such as but not limited to $NaN_3$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction. For the (s4b-A6) analogs, the epoxide functional group can be opened to give the final sulfamide analogs using different sources of the cyanide anion such as but not limited to KCN in alcoholic solvents such as but not limited to IPA or 1-propanol. Mild bases such as $NaHCO_3$ or salts such as $NH_4Cl$ or $(NH_4)_2SO_4$ can sometimes accelerate the epoxide opening reaction.

Scheme 5a. Preparation of Formula (1) Sulfamide Compounds 1-A1 through 1-A6

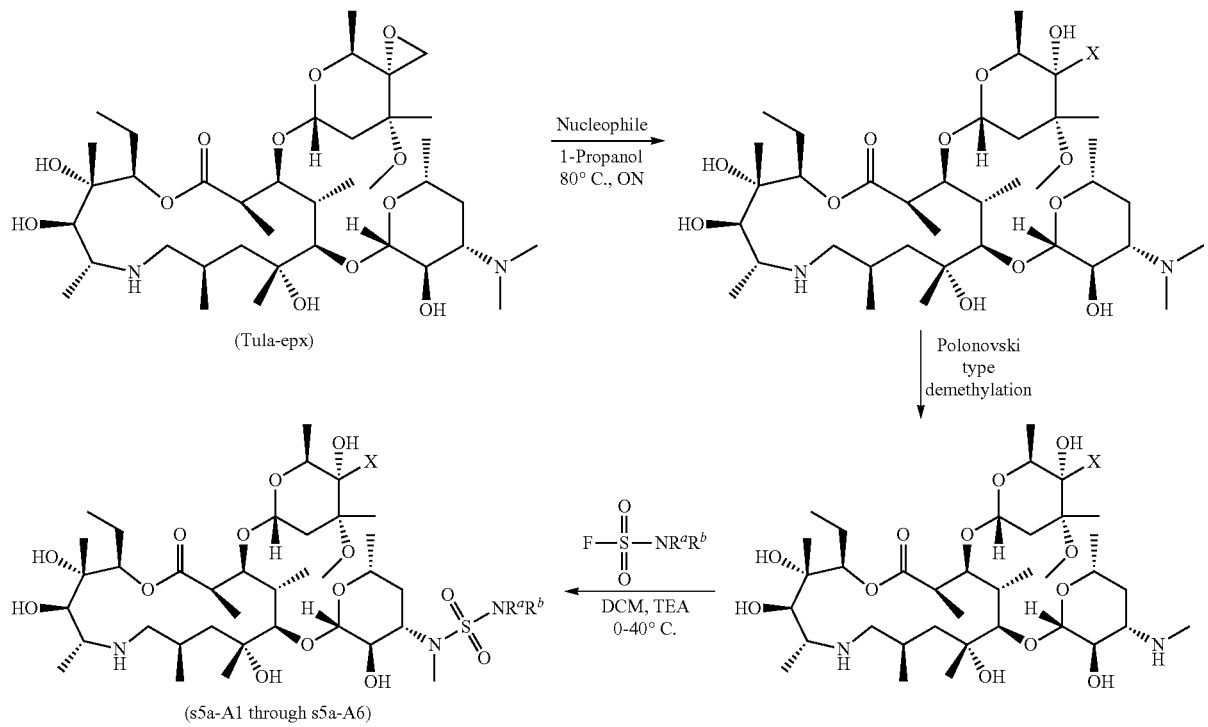

Alternatively, the sulfamide analogs can be prepared according to Scheme 5a. In the first step, the commercially available tulathromycin epoxide intermediate is treated with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol. This reaction can occur overnight. Mild bases such as $NaHCO_3$ or salts such as $NH_4Cl$ or $(NH_4)_2SO_4$ can sometimes accelerate the epoxide opening reaction. In the second step, the tertiary dimethyl amine on the desosamine sugar can be demethylated using Polonovski type conditions as described above. The final sulfamide analogs can be prepared by reacting the secondary methyl amine moiety with sulfamoyl fluorides or chlorides and others. Mild bases such as TEA or DIPEA can be sometimes used to facilitate the sulfamide formation reaction. Many sulfamoyl fluorides or chlorides are commercially available or can be easily prepared from the corresponding amines using procedures such as described in *Angew Chem. Int. Ed.* 2018, 57, 2605-2610.

Scheme 5b Details for Scheme 5a Step 1 (Nucleophilic Epoxide Opening)

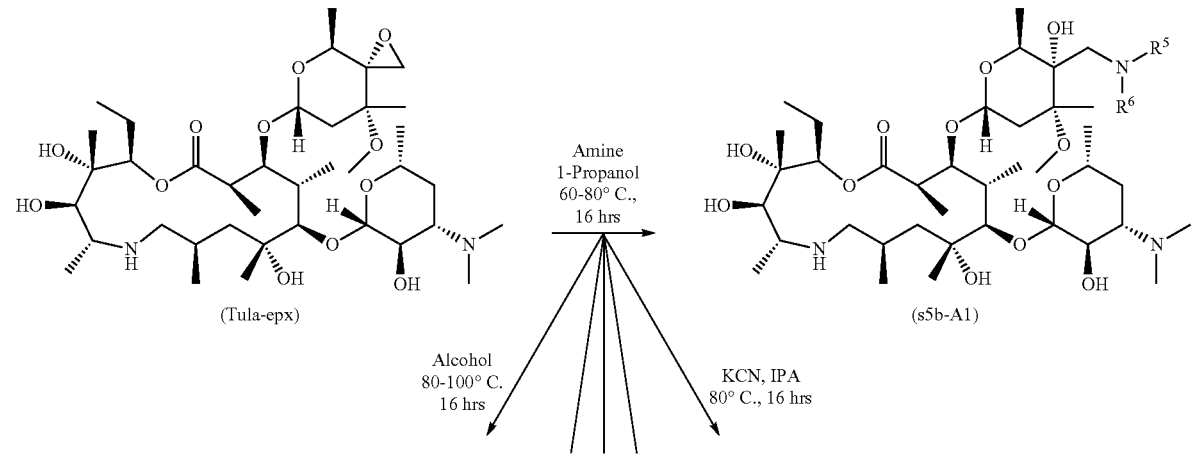

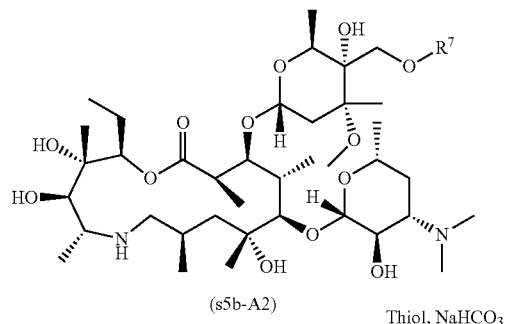

(s5b-A2)

Thiol, NaHCO₃
1-propoanol
60° C., 16 hrs

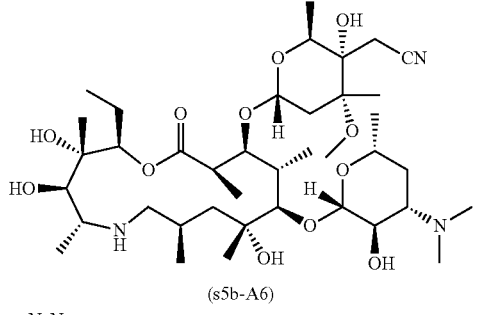

(s5b-A6)

NaN₃
1-propanol
80° C., 16 hrs

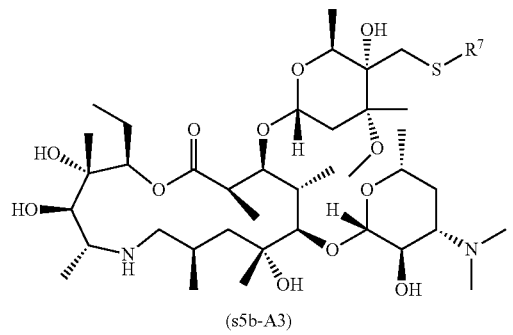 [SMILES: CC[C@H]1OC(=O)[C@H](C)[C@@H](O[C@H]2C[C@@](C)(OC)[C@]3(CO3)[C@H](C)O2)[C@H](C)[C@@H](O[C@@H]2O[C@H](C)C[C@H](N(C)C)[C@H]2O)[C@](C)(O)C[C@@H](C)CN[C@H](C)[C@@H](O)[C@]1(C)O]

(s5b-A3)

Halide
1-propanol
80° C., 16 hrs

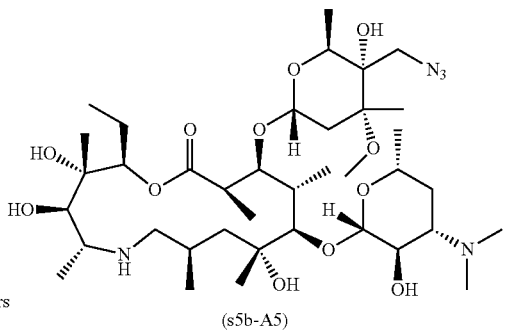

(s5b-A5)

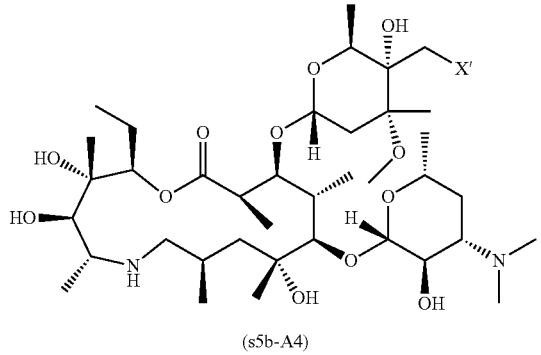

(s5b-A4)

For the (s5b-A1) compounds, the epoxide functional group can be opened using different primary or secondary amines in alcoholic solvents such as but not limited to methanol, ethanol, 1-propanol and others. For the (s5b-A2) compounds, the epoxide functional group can be opened using different alcohols used as solvents such as but not limited to methanol, ethanol, 1-propanol and others. Mild bases such as NaHCO₃ or salts such as NH₄Cl or (NH₄)₂SO₄ can sometimes accelerate the epoxide opening reaction. For the (s5b-A3) compounds, the epoxide functional group can be opened using different thiols such as but not limited to ethanethiol, propanethiol, isopropyl mercaptan and others in alcoholic solvents such as but not limited to ethanol or 1-propanol. Mild bases such as NaHCO₃ but not limited to are used to accelerate the epoxide opening reaction. For the (s5b-A4) compounds, the epoxide functional group can be opened using different halides from reagents such as but not limited to CeCl₃ or Br₂ in alcoholic solvents such as but not limited to ethanol or 1-propanol. Mild bases such as NaHCO₃ or salts such as NH₄Cl or (NH₄)₂SO₄ can sometimes accelerate the epoxide opening reaction. For the (s5b-A5) compounds, the epoxide functional group can be opened by the azide ion using different sources of the azide anion such as but not limited to NaN₃ in alcoholic solvents such as but not limited to ethanol or 1-propanol. Mild bases such as NaHCO₃ or salts such as NH₄Cl or (NH₄)₂SO₄ can sometimes accelerate the epoxide opening reaction. For the (s5b-A6) compounds, the epoxide functional group can be opened by the cyanide ion using different sources of the cyanide anion such as but not limited to KCN in alcoholic solvents such as but not limited to IPA or 1-propanol. Mild bases such as NaHCO₃ or salts such as NH₄Cl or (NH₄)₂SO₄ can sometimes accelerate the epoxide opening reaction.

Scheme 5c Details for Scheme 5a Step 2 (Demethylation)

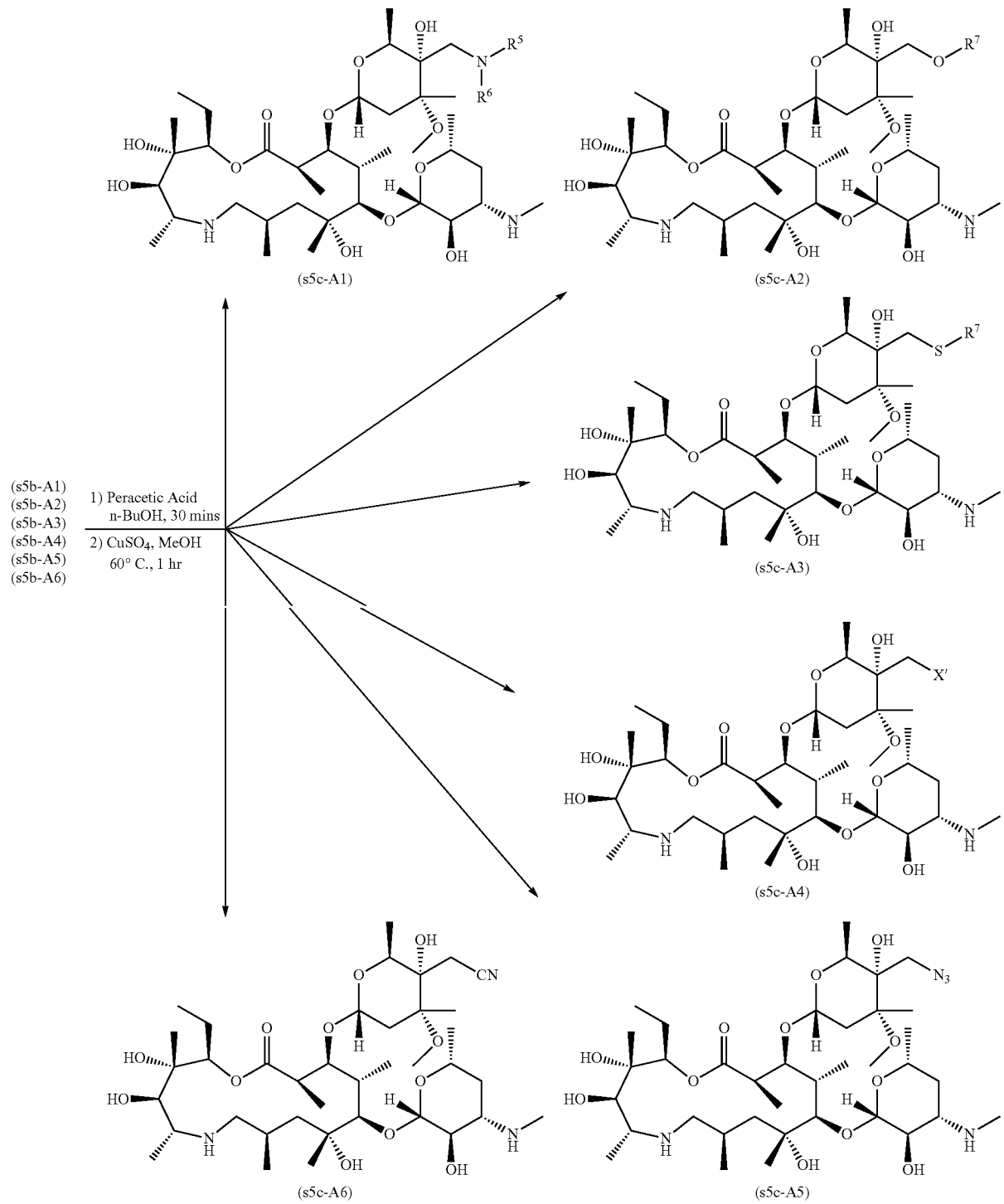

All compounds (s5b-A1) through (s5b-A6) can undergo a Polonovski type demethylation as described above, to give the corresponding compounds (s5c-A1) through (s5c-A6). The N-oxide can be formed using different oxidizing agents such as iodine, NIS, peracetic acid or hydrogen peroxide. The demethylation of the N-oxide can be triggered by such reagents as iron or copper salts.

Scheme 5d Details of Step 3 of Scheme 5a (Sulfamide formation)

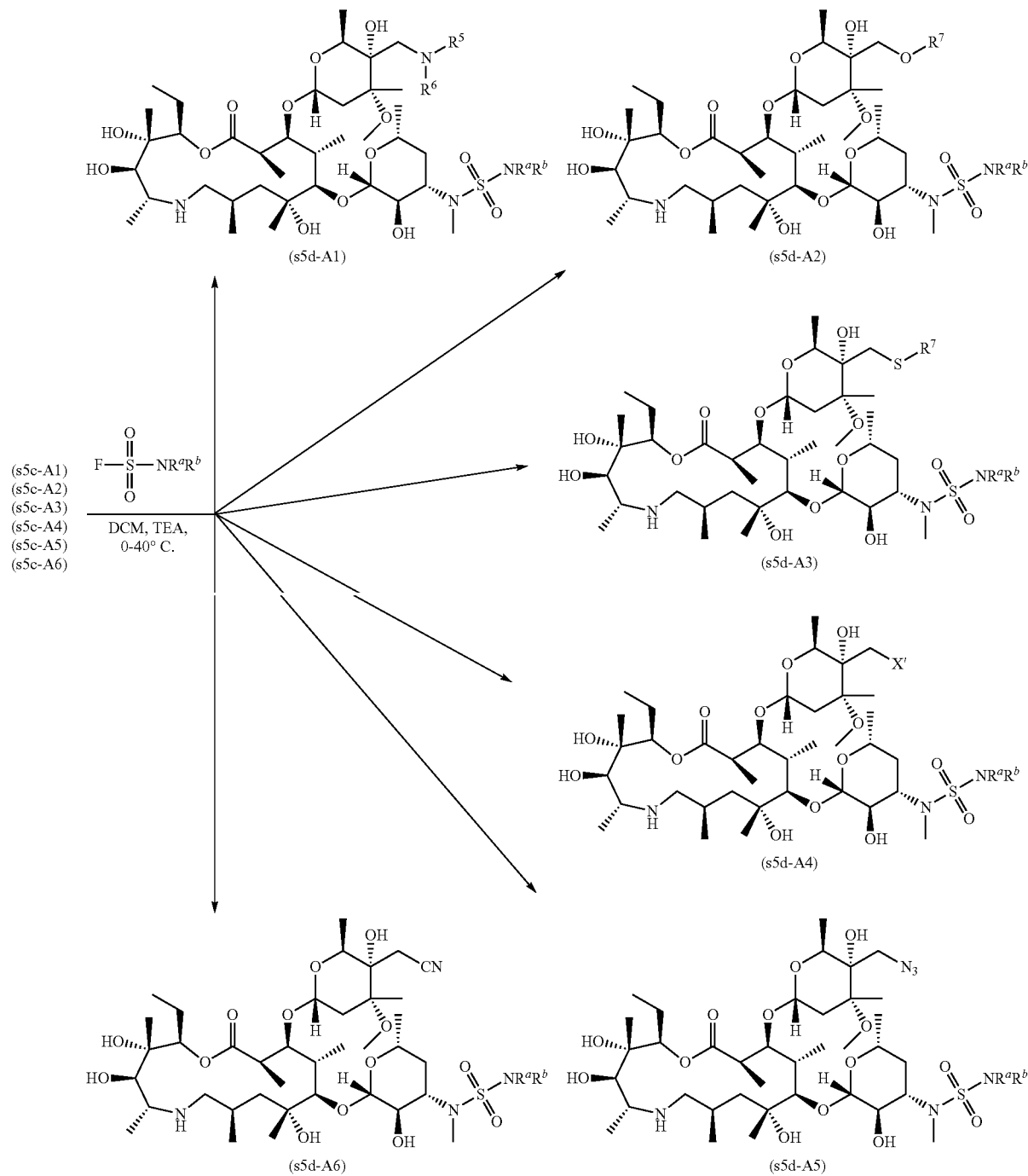

In the last step of the sequence the final analogs can be prepared by reacting the Polonovski reaction product (s5c-A1/A6) with sulfamoyl fluorides or chlorides and others. Mild bases such as TEA or DIPEA can be sometimes used to facilitate the sulfamide formation reaction. Many sulfamoyl fluorides or chlorides are commercially available or can be easily prepared from the corresponding amines using procedures such as described in *Angew Chem. Int. Ed.* 2018, 57, 2605-2610. Details of this last transformation are shown in Scheme 5d above.

Scheme 6a. Preparation of Cyclic Sulfamate Formula (1) Compounds by Fluoro Sulfonamide Intramolecular Cyclization

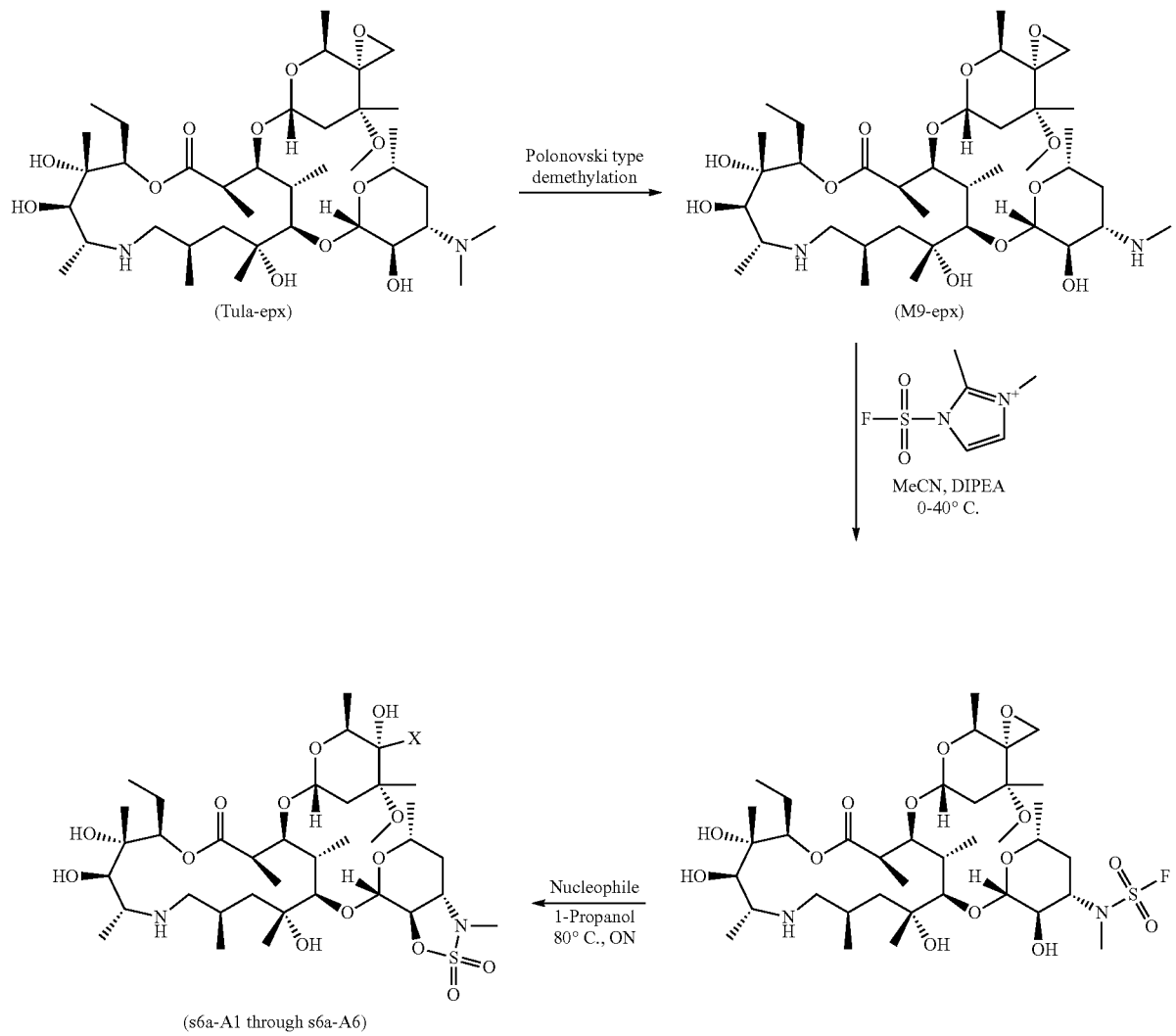

Cyclic sulfamate analogs can be prepared according to Scheme 6a. First, the commercially available tulathromycin epoxide (tula-epx) can be demethylated under but not limited to the Polonovski reaction to give M9 epoxide (M9-epx). The N-oxide can be formed using different oxidizing agents such as iodine, N-iodosuccinimide, peracetic acid or hydrogen peroxide. The demethylation of the N-oxide can be triggered with iron or copper salts. The secondary amine thus formed can be transformed into a fluoro sulfonamide by reacting M9 epoxide with commercially available 1-(fluorosulfonyl)-2,3-dimethyl-1H-imidazol-3-ium trifluoromethanesulfonate. In the last step, two transformations occur upon heating in alcoholic solvents such as 1-propanol. First, the epoxide functional group can be opened using different nucleophiles such as primary and secondary amines, alcohols, thiols, cyanide, azide or halogen anions and others at higher temperature in alcoholic solvents such as but not limited to 1-propanol, 1-butanol or 2-propanol. This reaction can be completed overnight. Second, the fluoro sulfonamide functional group undergoes an intramolecular cyclization to give the cyclic sulfamate moiety under the same conditions. Mild bases such as $NaHCO_3$, TEA or DIPEA or salts such as $NH_4Cl$ or $(NH_4)_2SO_4$ can sometimes accelerate the epoxide opening reaction and sulfamate cylcization. For any of the Schemes presented here, the "nucleophile" of the epoxide opening step on the cladinose ring, can be but is not limited to the following: $HNR^5R^6$, $HOR^7$, $HS(O)_pR^7$, $NaN_3$, $CeCl_3$, $TEA·3HF$, and $KCN$, wherein $R^5$, $R^6$, $R^7$ and p are as defined herein.

Scheme 6b Details for Scheme 6a Step 3 (Epoxide Opening and Cyclization)
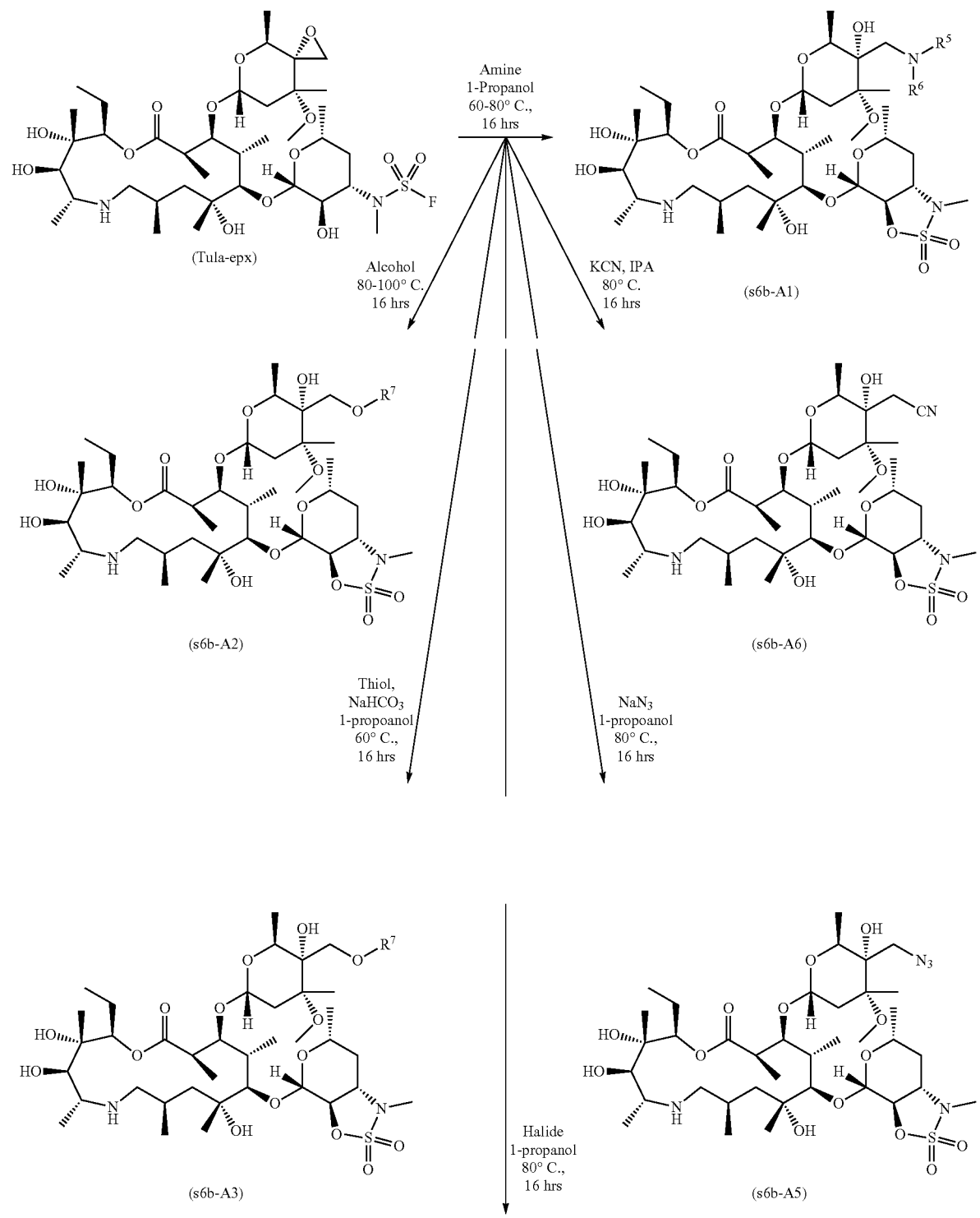

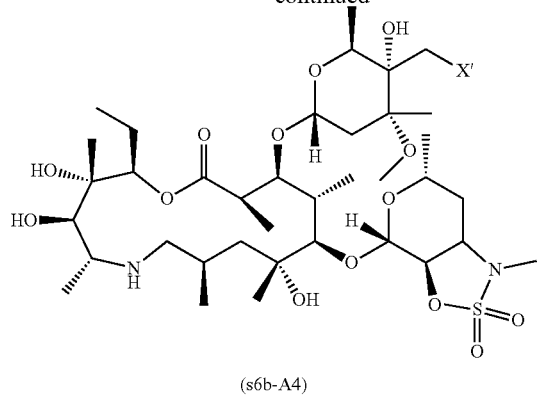

(s6b-A4)

For the (s6b-A1) compounds, the epoxide functional group can be opened using different primary or secondary amines in alcoholic solvents such as but not limited to methanol, ethanol, 1-propanol and others while the cyclization towards the cyclic sulfamate occurs simultaneously. For the (s6b-A2) compounds, the epoxide functional group can be opened using different alcohols used as solvents such as but not limited to methanol, ethanol, 1-propanol and others while the cyclization towards the cyclic sulfamate occurs simultaneously. Mild bases such as $NaHCO_3$ or salts such as $NH_4Cl$ or $(NH_4)_2SO_4$ can sometimes accelerate the epoxide opening reaction. For the (s6b-A3) compounds, the epoxide functional group can be opened using different thiols such as but not limited to ethanethiol, propanethiol, isopropyl mercaptan and others in alcoholic solvents such as but not limited to ethanol or 1-propanol while the cyclization towards the cyclic sulfamate occurs simultaneously. Mild bases such as $NaHCO_3$ but not limited to are used to accelerate the epoxide opening reaction. For the (s6b-A4) compounds, the epoxide functional group can be opened using different halides from reagents such as but not limited to $CeCl_3$ or $Br_2$ in alcoholic solvents such as but not limited to ethanol or 1-propanol while the cyclization towards the cyclic sulfamate occurs simultaneously. Mild bases such as $NaHCO_3$ or salts such as $NH_4Cl$ or $(NH_4)_2SO_4$ can sometimes accelerate the epoxide opening reaction. For the (s6b-A5) compounds, the epoxide functional group can be opened by the azide ion using different sources of the azide anion such as but not limited to $NaN_3$ in alcoholic solvents such as but not limited to ethanol or 1-propanol while the cyclization towards the cyclic sulfamate occurs simultaneously. Mild bases such as $NaHCO_3$ or salts such as $NH_4Cl$ or $(NH_4)_2SO_4$ can sometimes accelerate the epoxide opening reaction. For the (s6b-A6) compounds, the epoxide functional group can be opened by the cyanide ion using different sources of the cyanide anion such as but not limited to KCN in alcoholic solvents such as but not limited to IPA or 1-propanol while the cyclization towards the cyclic sulfamate occurs simultaneously. Mild bases such as $NaHCO_3$ or salts such as $NH_4Cl$ or $(NH_4)_2SO_4$ can sometimes accelerate the epoxide opening reaction.

Scheme 7. Preparation of Alkylated Core Nitrogen Sulfonamide Formula (1) Compounds by Reductive Amination

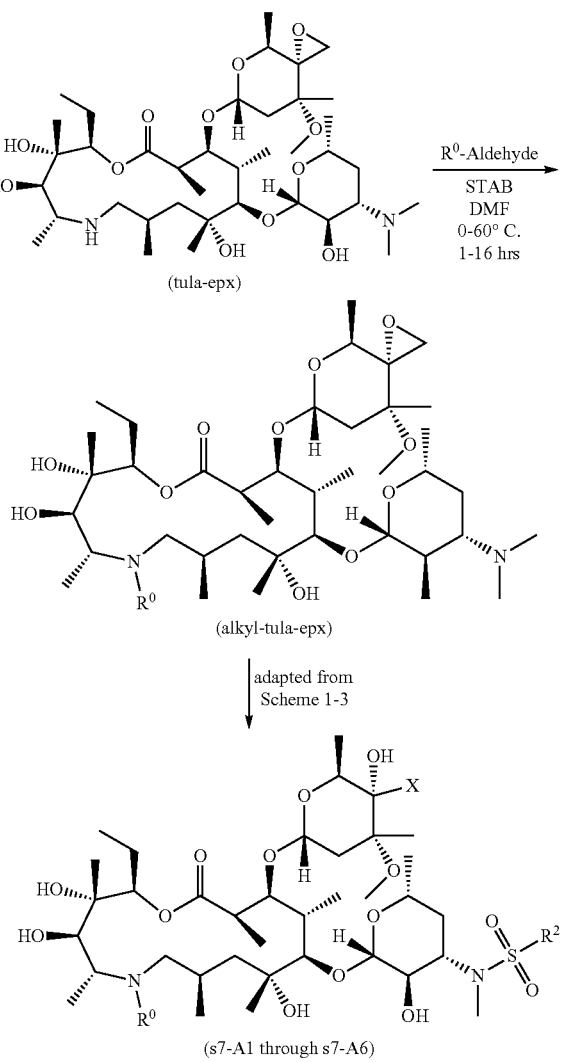

The alkyl-tula-epx intermediate can be easily synthesized from tula epoxide (tula-epx) by a variety of methods such as but not limited to reductive aminations with the corresponding aldehyde and a hydride source such as but not limited to STAB or NaBH₃CN in solvents such as alcohols or DMF and temperatures between 0° C. and 60° C. Subsequent chemistry to make compounds of the invention wherein the macrolide core nitrogen is alkylated with various $R^o$ groups can be accomplished with Schemes 1-3, e.g., a Polonovski type demethylation, epoxide opening and sulfonamide formation by replacing the starting material Tula-epoxide in Schemes 1-3 by $R^o$ alkylated tulathromycin epoxide intermediate (alkyl-tula-epx); e.g., wherein $R^o$ is propyl.

Scheme 8. Preparation of Alkylated Core Nitrogen Sulfamide Formula (1) Compounds by Reductive Amination

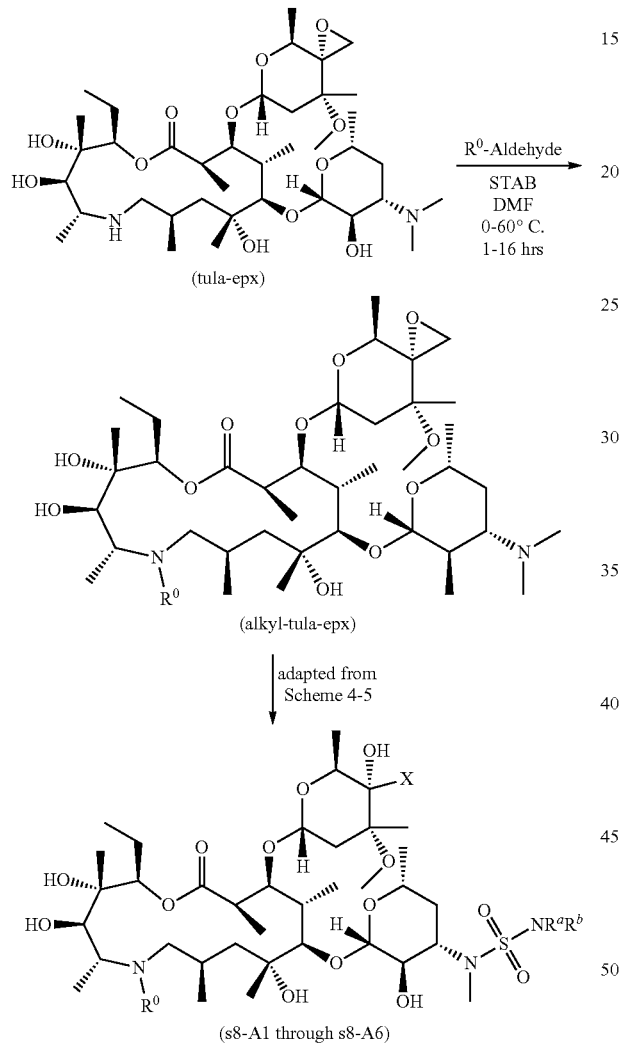

(s8-A1 through s8-A6)

Scheme 9. Preparation of Alkylated Core Nitrogen Cyclic Sulfamate Formula (1) Compounds by Reductive Amination

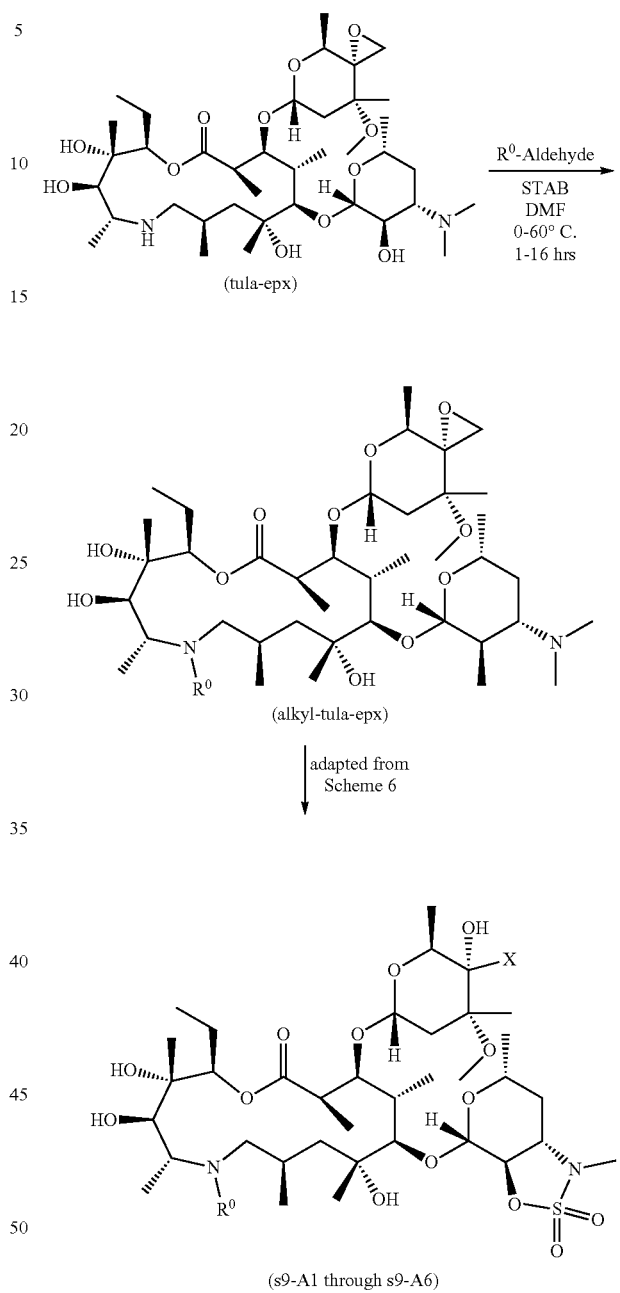

(s9-A1 through s9-A6)

The alkyl-tula-epx intermediate can be easily synthesized from tula epoxide (tula-epx) by a variety of methods such as but not limited to reductive animations with the corresponding aldehyde and a hydride source such as but not limited to STAB or NaBH₃CN in solvents such as alcohols or DMF and temperatures between 0° C. and 60° C. Subsequent chemistry to make compounds of the invention wherein the macrolide core nitrogen is alkylated with various $R^o$ groups can be accomplished with Schemes 4-5, e.g., a Polonovski type demethylation, epoxide opening and sulfamide formation by replacing the starting material Tula-epoxide in Schemes 4-5 by $R^o$ alkylated tulathromycin epoxide intermediate (alkyl-tula-epx); e.g., wherein $R^o$ is propyl.

The alkyl-tula-epx intermediate can be easily synthesized from tula epoxide (tula-epx) by a variety of methods such as but not limited to reductive animations with the corresponding aldehyde and a hydride source such as but not limited to STAB or NaBH₃CN in solvents such as alcohols or DMF and temperatures between 0° C. and 60° C. Subsequent chemistry to make compounds of the invention wherein the macrolide core nitrogen is alkylated with various $R^o$ groups can be accomplished with Schemes 6, e.g., a Polonovski type demethylation, fluoro sulfonamide formation followed by epoxide opening and simultaneous cyclization by replacing the starting material Tula-epoxide in Scheme 6(a/b) by $R^o$ alkylated tulathromycin epoxide intermediate (alkyl-tula-epx); e.g., wherein $R^o$ is propyl.

Scheme 10. Preparation of Formula (1) Compounds Substituted with Various R¹ Groups: Preparation of a Common Intermediate M8 Epoxide (M8-epx)

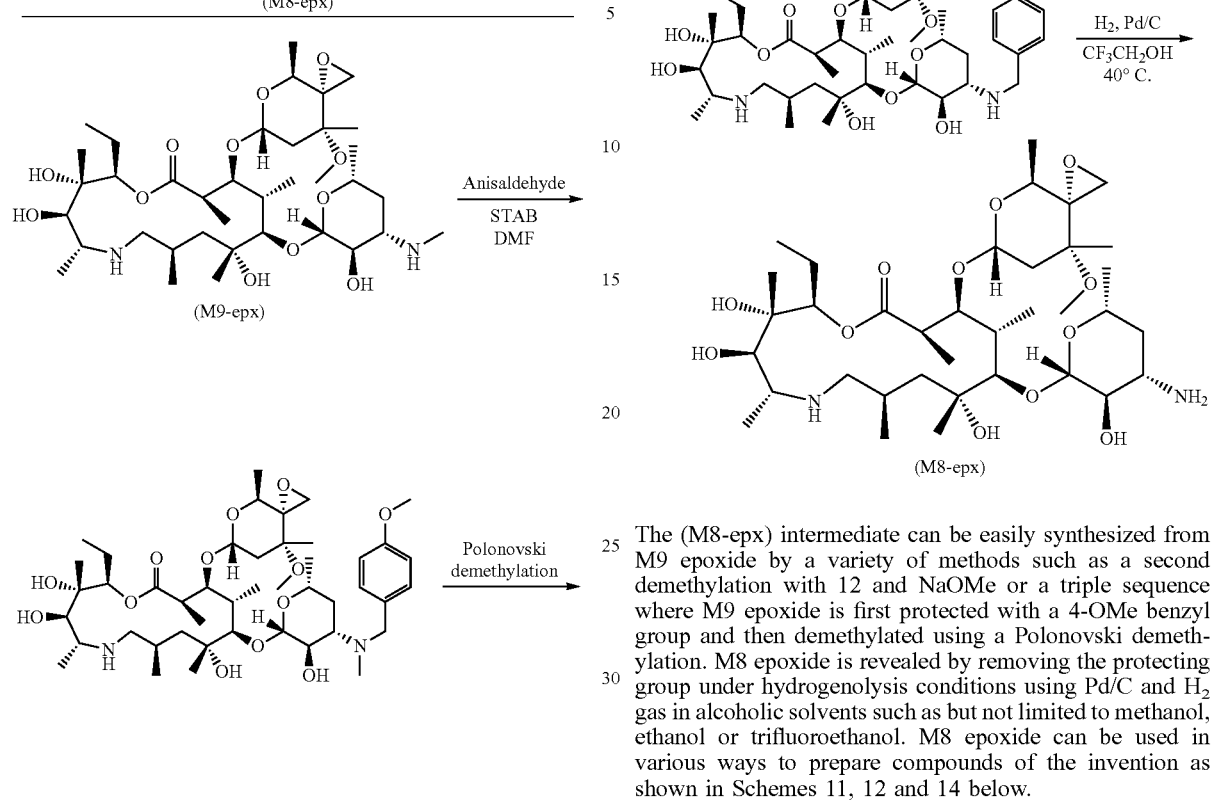

The (M8-epx) intermediate can be easily synthesized from M9 epoxide by a variety of methods such as a second demethylation with $I_2$ and NaOMe or a triple sequence where M9 epoxide is first protected with a 4-OMe benzyl group and then demethylated using a Polonovski demethylation. M8 epoxide is revealed by removing the protecting group under hydrogenolysis conditions using Pd/C and $H_2$ gas in alcoholic solvents such as but not limited to methanol, ethanol or trifluoroethanol. M8 epoxide can be used in various ways to prepare compounds of the invention as shown in Schemes 11, 12 and 14 below.

Scheme 11. Preparation of Sulfonamide Formula (1) Compounds Substituted with Various R¹ Groups from M8 Epoxide (M8-epx)

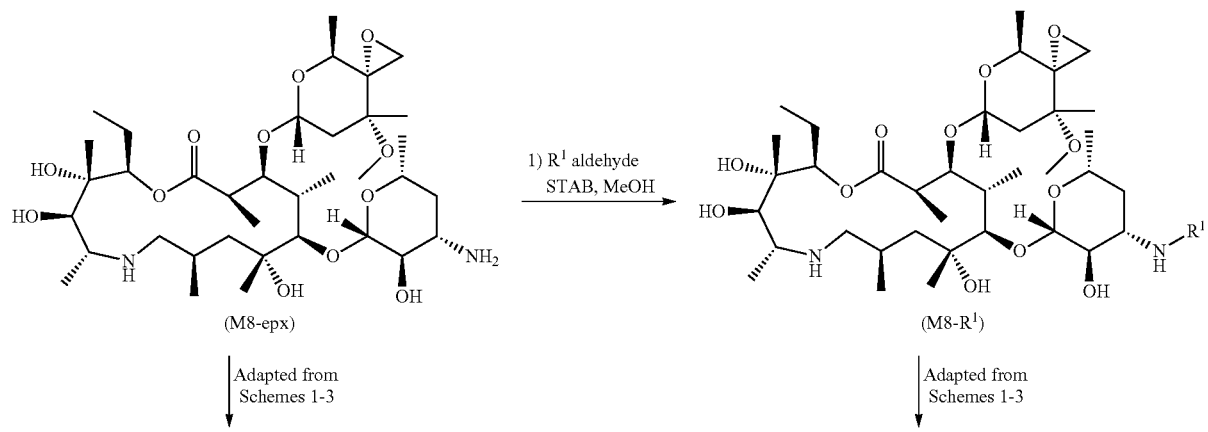

107

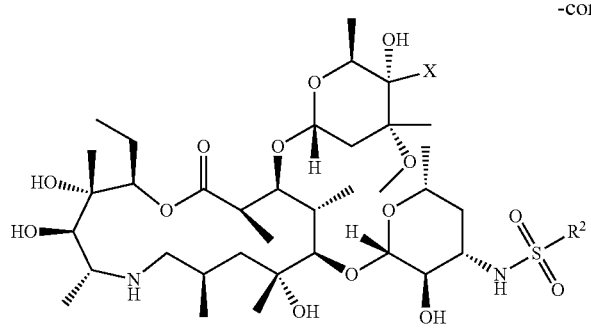

(s11a-A1 through s11a-A6)

108

-continued

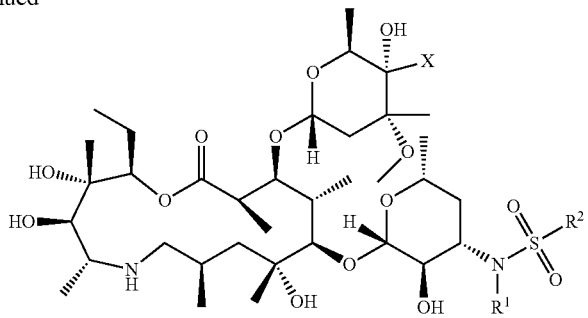

(s11b-A1 through s11b-A6)

M8 epoxide can be reacted with sulfonamide forming reagents such as sulfonyl chlorides, fluorides in aprotic solvents such as DCM and mild bases such as but not limited to TEA or DIPEA as shown in Scheme 11 to give sulfonamide compounds of the invention s11a-A1 through s11a-A6. M8 epoxide can also undergo a reductive amination with the corresponding $R^1$ aldehyde and a hydride source such as but not limited to STAB or NaBH$_3$CN in solvents such as alcohols, DMF, MeCOH, DCM or DCE and temperatures between 0° C. and 60° C. Subsequent chemistry to make sulfonamide compounds of the invention wherein $R^1$ is not CH$_3$ as in the tulathromycin derived analogs can be accomplished with sulfonyl chlorides or fluorides in aprotic solvents such as DCM and mild bases such as but not limited to TEA or DIPEA as shown on Scheme 11 to give compounds of the invention s11 b-A1 through s11 b-A6.

M8 epoxide can be reacted with sulfamide forming reagents such as sulfamoyl chlorides or fluorides in aprotic solvents such as DCM and mild bases such as but not limited to TEA or DIPEA as shown in Scheme 12 to give sulfamide compounds of the invention s12a-A1 through s12a-A6. M8 epoxide can also undergo a reductive amination with the corresponding $R^1$ aldehyde and a hydride source such as but not limited to STAB or NaBH$_3$CN in solvents such as alcohols, DMF, MeCOH, DCM or DCE and temperatures between 0° C. and 60° C. Subsequent chemistry to make sulfamide compounds of the invention wherein $R^1$ is not CH$_3$ as in the tulathromycin derived analogs can be accomplished with sulfamoyl chlorides or fluorides in aprotic solvents such as DCM and mild bases such as but not limited to TEA or DIPEA as shown on Scheme 12 to give compounds of the invention s12b-A1 through s12b-A6.

Scheme 12. Preparation of Sulfamide Formula (1) Compounds Substituted with Various $R^1$ Groups from M8 Epoxide (M8-epx)

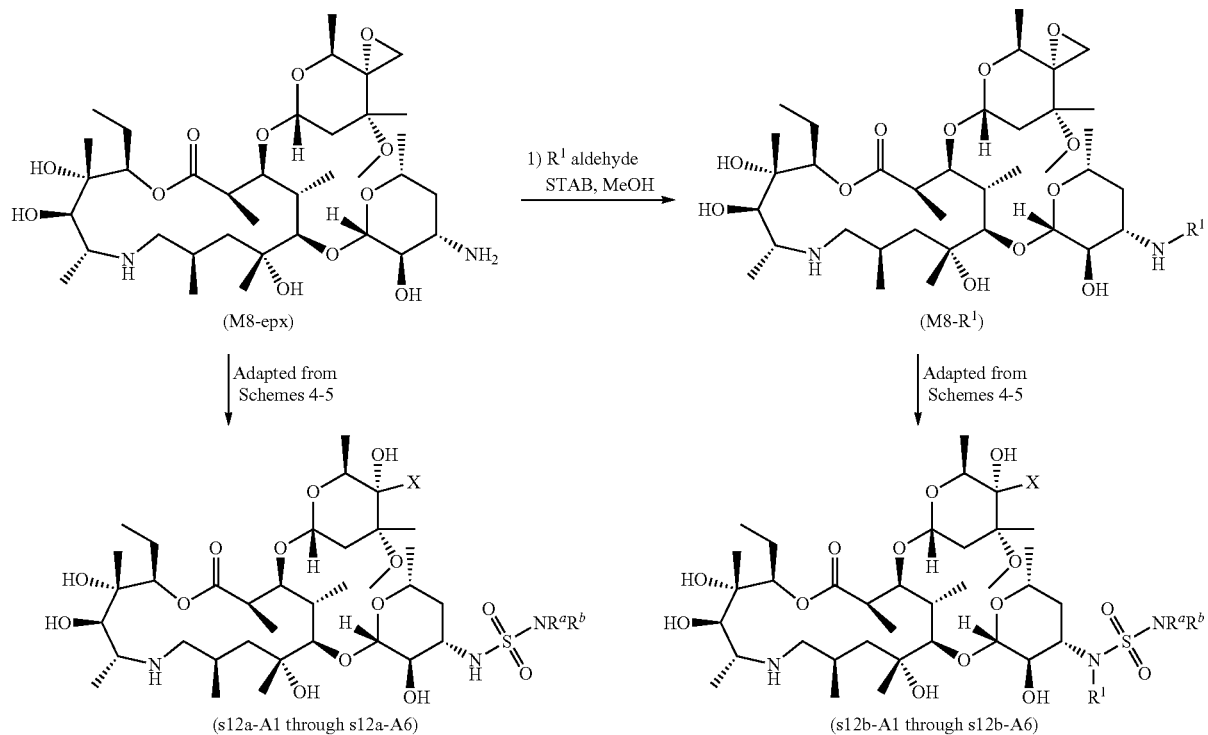

Scheme 13. Preparation of Primary Sulfonamides of Formula (1) Compounds Substituted with Various $R^0$ Groups from Tulathromycin Epoxide (tula-epx)

Tulathromycin epoxide can be demethylated under but not limited to the Polonovski reaction to give M9 epoxide (M9-epx). The N-oxide can be formed using different oxidizing agents such as iodine, N-iodosuccinimide, peracetic acid or hydrogen peroxide. The demethylation of the N-oxide can be triggered with iron or copper salts. The secondary amine thus formed can be transformed into a primary sulfonamide using various sulfonylating reagents such as HFIPS described in OL, 2021, pp 3373-3378. In the last step, the epoxide functional group can be opened to give the final sulfonamide analogs using different nucleophiles such as primary and secondary amines, alcohols, thiols, cyanide, azide or halogen anions and others at higher temperature in alcoholic solvents such as but not limited to 1-propanol, 1-butanol or 2-propanol to form the final compounds of the invention s13a-A1 through s13a-A6. This reaction can be completed overnight. Mild bases such as NaHCO$_3$ or salts such as NH$_4$Cl or (NH$_4$)$_2$SO$_4$ can sometimes accelerate the epoxide opening reaction. For any of the Schemes presented here, the "nucleophile" of the epoxide opening step on the cladinose ring, can be but is not limited to the following: HNR$^5$R$^6$, HOR$^7$, HS(O)$_p$R$^7$, NaN$_3$, CeCl$_3$, TEA.3HF, and KCN, wherein R$^5$, R$^6$, R$^7$ and p are as defined herein.

In a similar fashion, Tulathromycin epoxide can be alkylated on the core Nitrogen to form alkyl-tula-epx intermediate by a variety of methods such as but not limited to reductive animations with the corresponding aldehyde and a hydride source such as but not limited to STAB or NaBH$_3$CN in solvents such as alcohols or DMF and temperatures between 0° C. and 60° C. Subsequent chemistry to make compounds of the invention s13b-A1 through s13b-A6 wherein the macrolide core nitrogen is alkylated with various R$^0$ groups can be accomplished following the same steps as explained above, namely primary sulfonamide formation followed by the epoxide moiety opening.

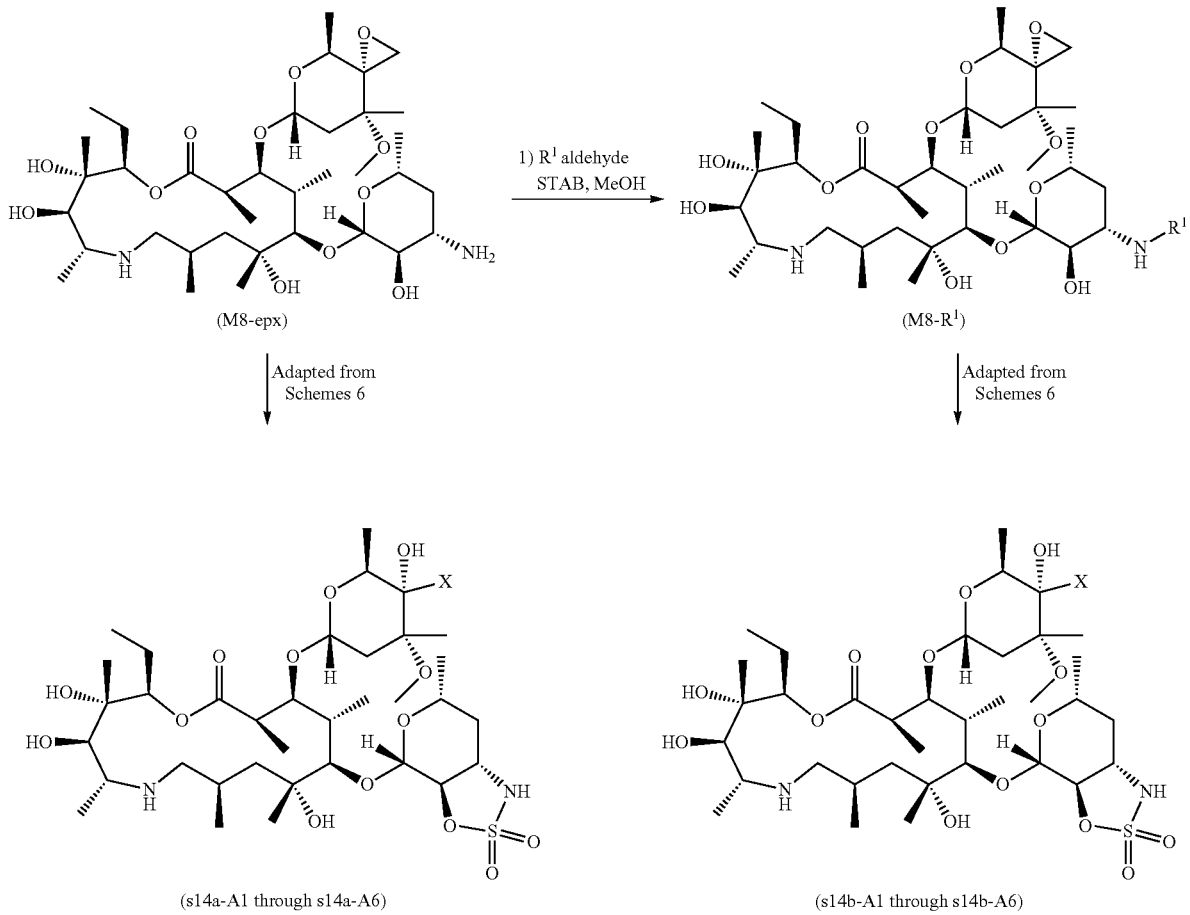

Scheme 14. Preparation of Cyclic Sulfamate Formula (1) Compounds Substituted with Various R$^1$ Groups from M8 Epoxide (M8-epx)

M8 epoxide can be reacted with 1-(fluorosulfonyl)-2,3-dimethyl-1H-imidazol-3-ium trifluoromethanesulfonate to give the fluoro sulfonamide that can be cyclized towards the cyclic sulfamate upon the epoxide opening reaction as detailed previously. Scheme 14 (left side) shows the preparation of cyclic sulfamate compound s14a-A1 through s14a-A6 where R$^1$=H. M8 epoxide can also undergo a reductive amination with the corresponding R$^1$ aldehyde and a hydride source such as but not limited to STAB or NaBH$_3$CN in solvents such as alcohols, DMF, MeCOH, DCM or DCE and temperatures between 0° C. and 60° C. Subsequent chemistry to make cyclic sulfamate compounds of the invention wherein R$^1$ is not CH$_3$ as in the tulathromycin derived analogs can be accomplished the same way as detailed on Scheme 6. Scheme 14 (right side) shows the preparation of cyclic sulfamate compound s14b-A1 through s14b-A6 where R$^1$ is different from H or methyl.

Scheme 15. Preparation of Sulfonamide Formula (1-A0) Compounds of Formula (1) by Reductive Amination from Azithromycin

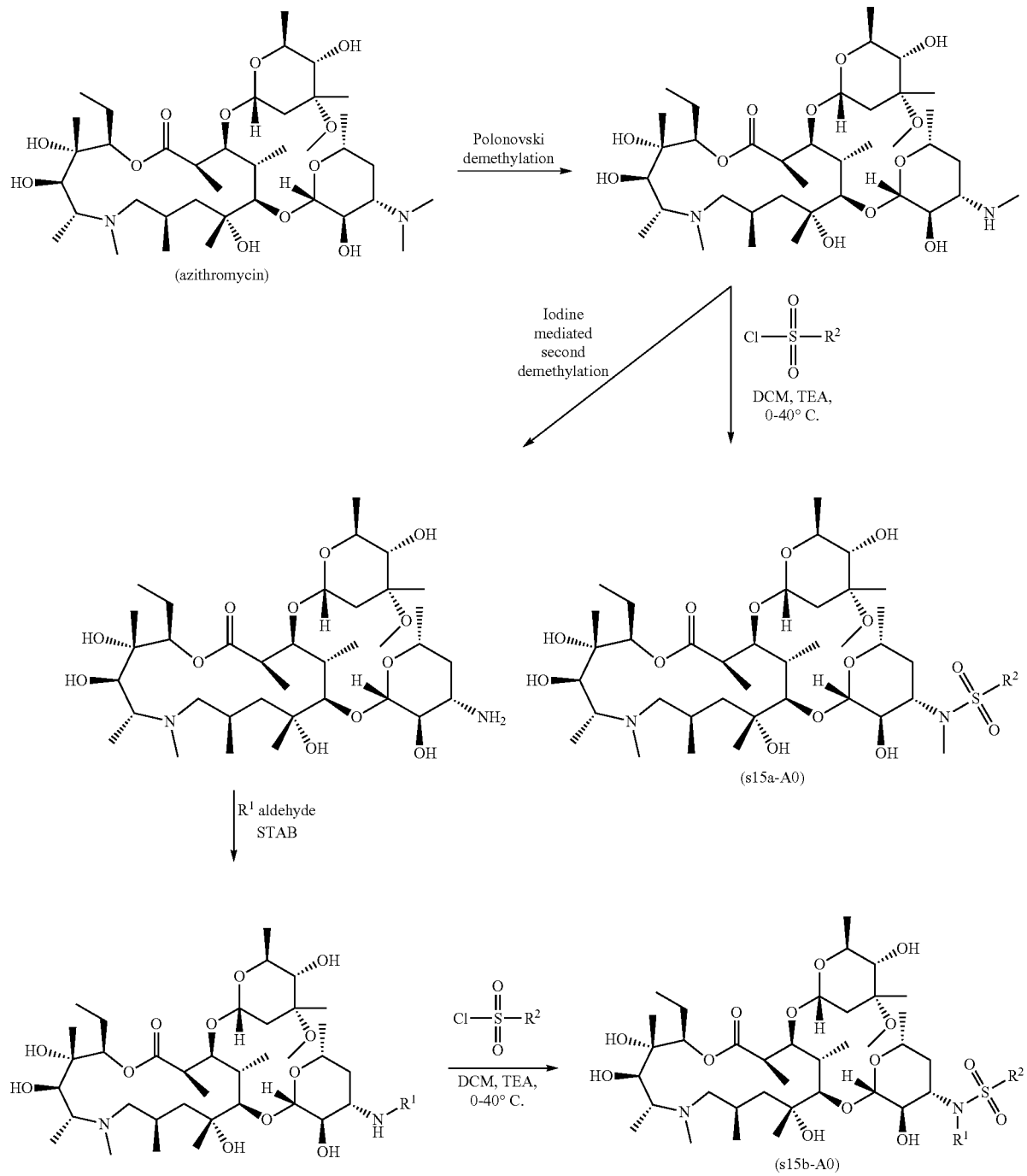

Azithromycin can be used as a starting material for the synthesis of Sulfonamide Formula (1) compounds of the invention as shown in Scheme 15. Azithromycin can undergo a demethylation reaction similar to tulathromycin under similar conditions such as but not limited to the Polonovski reaction defined herein. Demethylated azithromycin can be reacted with sulfonamide forming reagents such as but not limited to sulfonyl chlorides, fluorides in aprotic solvents such as DCM and mild bases such as but not limited to TEA or DIPEA as shown in Scheme 15 to give compounds of the invention s15a-A0.

Moreover, des-methyl azithromycin can undergo a second demethylation as described above using 12 and NaOMe followed by reductive amination with $R^1$ corresponding aldehydes. Compounds of the invention s15b-A0 can be synthesized by reacting the $R^1$ substituted azithromycin with sulfonamide forming reagents such as but not limited to sulfonyl chlorides, fluorides in aprotic solvents such as DCM and mild bases such as but not limited to TEA or DIPEA as shown in Scheme 15.

Scheme 16. Preparation of Sulfamide Formula (1-A0) Compounds of Formula (1) by Reductive Amination from Azithromycin

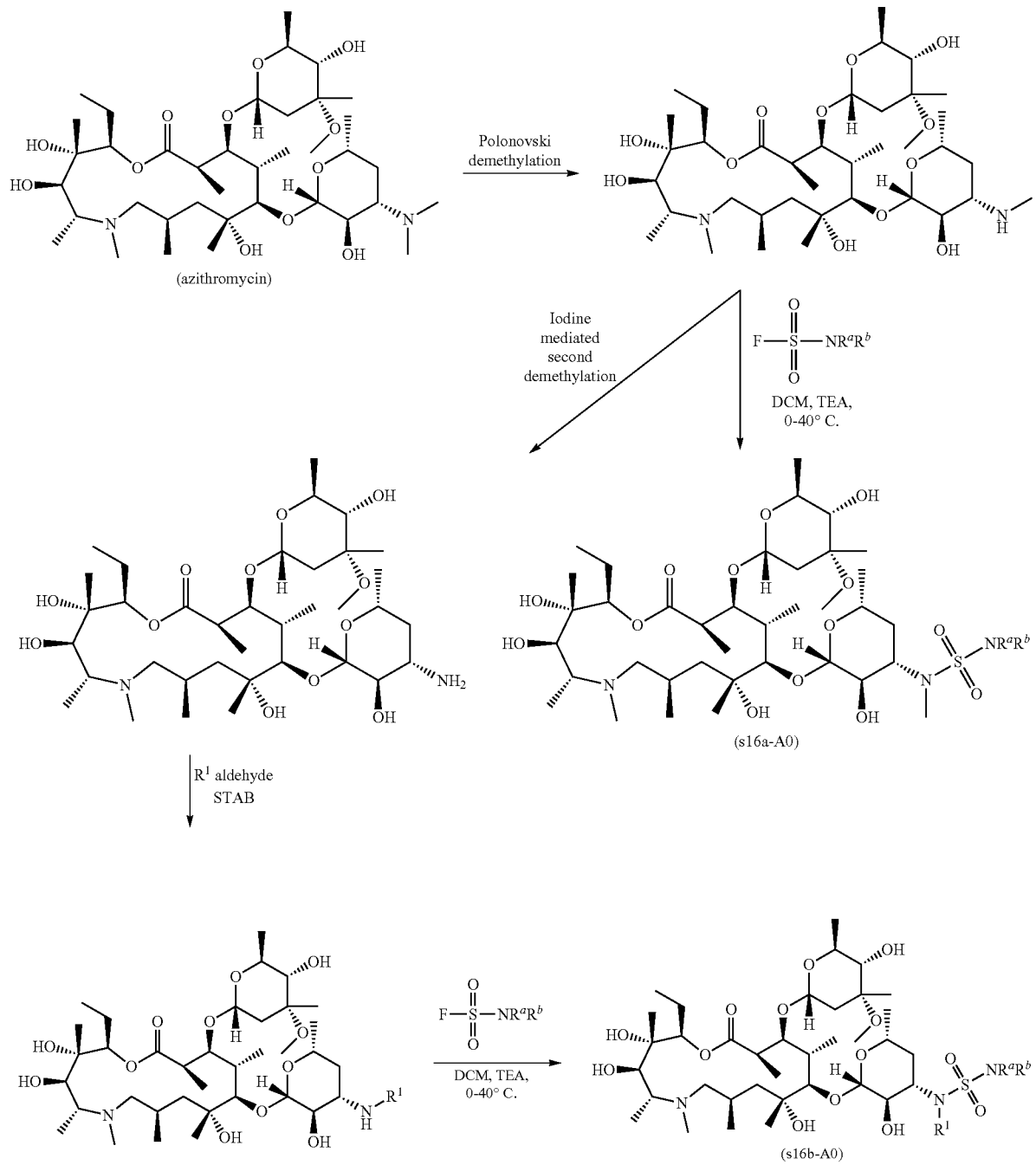

Azithromycin can be used as a starting material for the synthesis of sulfamide Formula (1) compounds of the invention as shown in Scheme 16. Azithromycin can undergo a demethylation reaction similar to tulathromycin under similar conditions such as but not limited to the Polonovski reaction defined herein. Demethylated azithromycin can be reacted with sulfamide forming reagents such as but not limited to sulfamoyl chlorides or fluorides in aprotic solvents such as DCM and mild bases such as but not limited to TEA or DIPEA to give compounds of the invention s16a-A0.

Moreover, des-methyl azithromycin can undergo a second demethylation as described above using 12 and NaOMe followed by reductive amination with $R^1$ corresponding aldehydes. Compounds of the invention s16b-A0 can be synthesized by reacting the $R^1$ substituted azithromycin sulfamide forming reagents such as but not limited to sulfamoyl chlorides or fluorides in aprotic solvents such as DCM and mild bases such as but not limited to TEA or DIPEA.

Scheme 17. Preparation of Formula (1) Sulfonamide O-Aryl/Heteroaryl Compounds

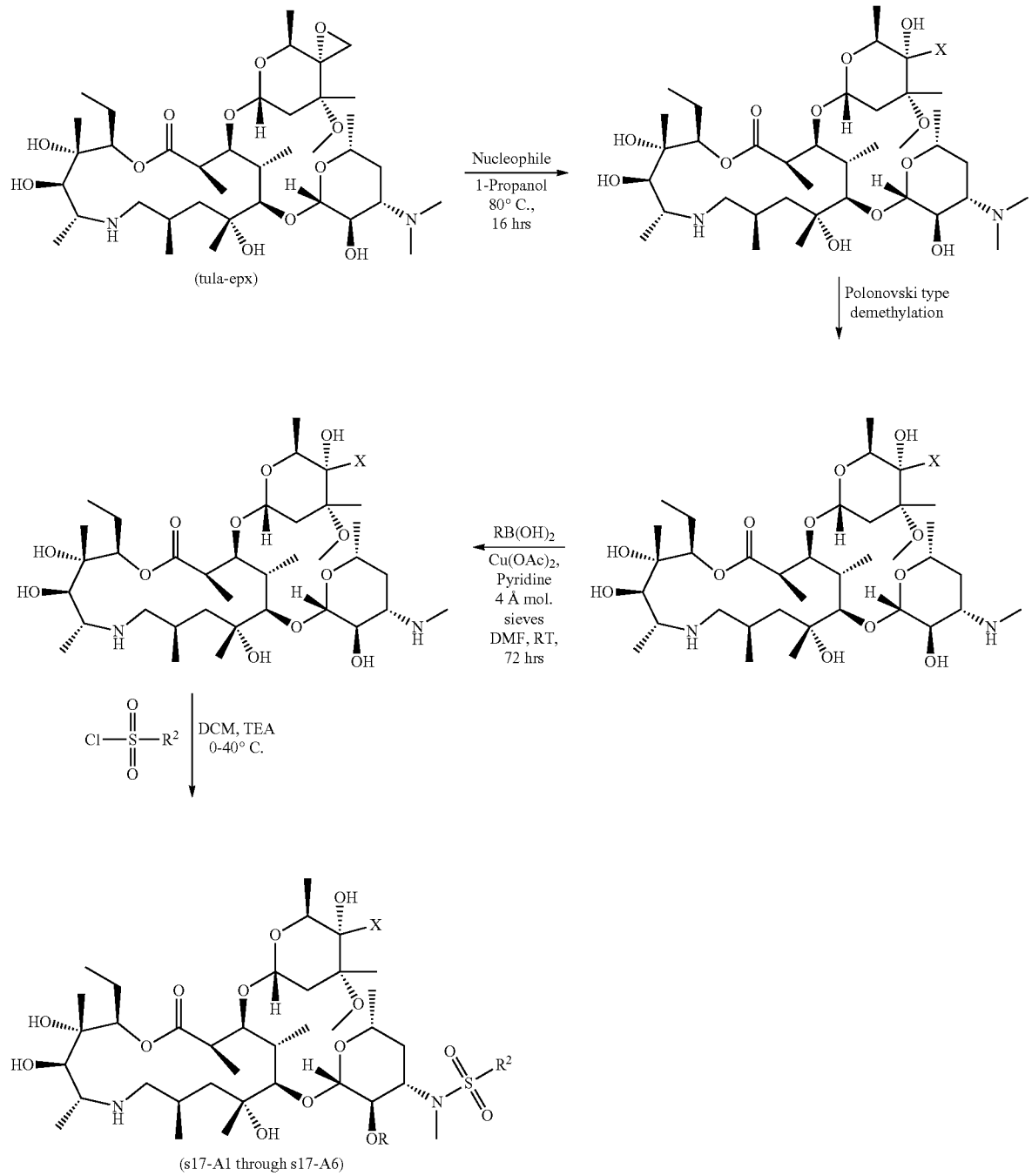

(s17-A1 through s17-A6)

Formula (1) compounds additionally substituted by an aryl/heteroaryl R group on the hydroxyl group of the desosamine sugar can be synthesized according to the sequence shown in Scheme 17. The first three steps of the sequence are shown in details in Schemes 2a, 2b and 2c and consist of opening the epoxide moiety of tula epoxide, followed by a Polonovski demethylation. The third step is a Chan-Lam type coupling with selectivity for the desosamine sugar hydroxyl. Aryl or heteroaryl boronic acids or boronate esters can be selectively coupled to the desosamine hydroxyl when stirred with copper salts such as but not limited to copper (II) acetate in the presence of weak bases such as pyridine, a drying agent such as molecular sieves and oxygen. The last step of the sequence is a sulfonamide formation reaction employing reagents such as but not limited to sulfonyl chlorides, fluorides and others in aprotic solvents and mild bases such as but not limited to TEA or DIPEA to give the desired O-aryl/heteroaryl sulfonamide combination compounds s17-A1 through s17-A6.

Scheme 18. Preparation of Formula (1) Sulfamide O-Aryl/Heteroaryl Compounds

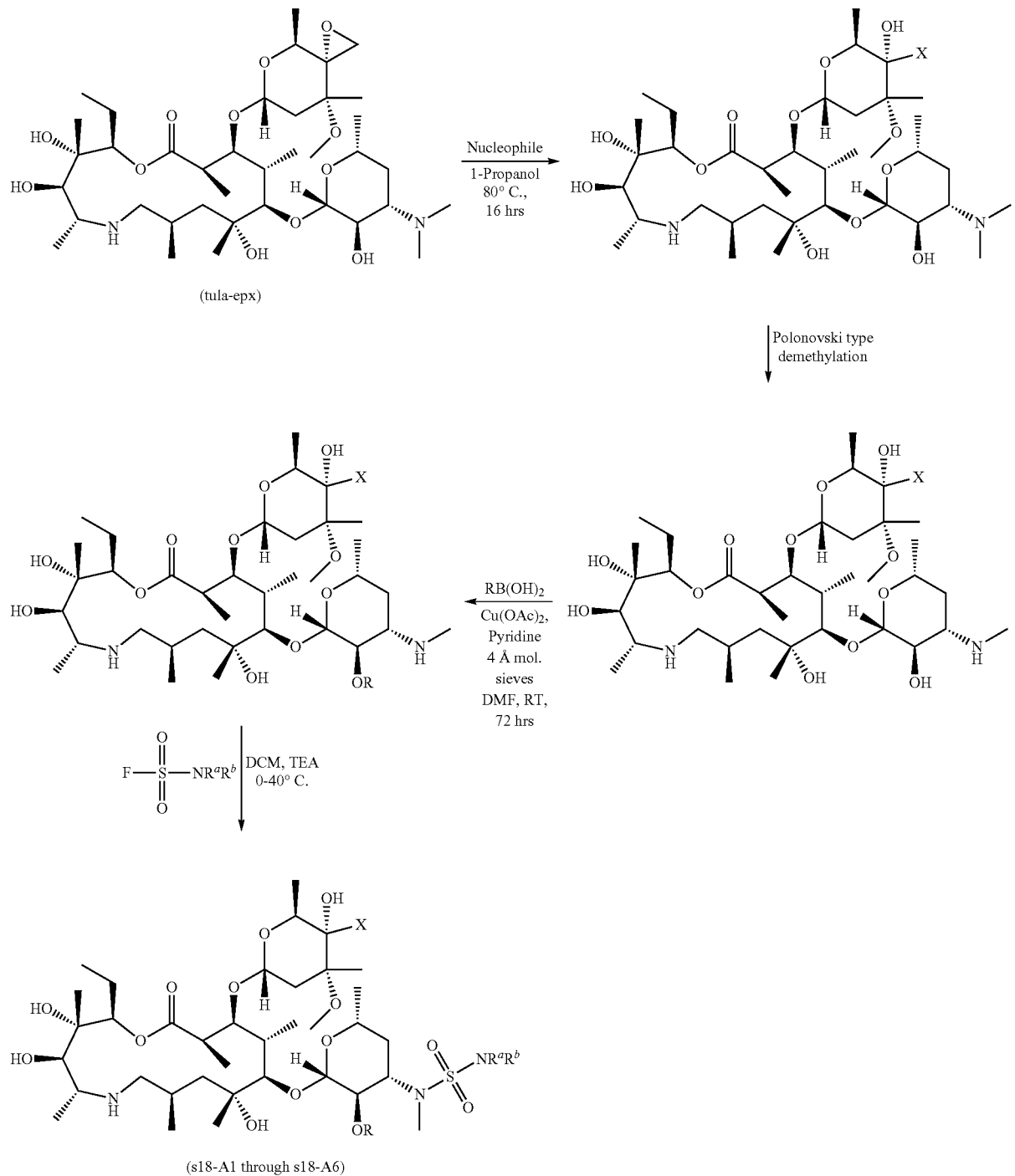

Formula (1) compounds additionally substituted by an aryl/heteroaryl R group on the hydroxyl group of the desosamine sugar can be synthesized according to the sequence shown in Scheme 18. The first three steps of the sequence are shown in details in Schemes 5a, 5b and 5c and consist of opening the epoxide moiety of tula epoxide, followed by a Polonovski demethylation. The third step is a Chan-Lam type coupling with selectivity for the desosamine sugar hydroxyl. Aryl or heteroaryl boronic acids or boronate esters can be selectively coupled to the desosamine hydroxyl when stirred with copper salts such as but not limited to copper (II) acetate in the presence of weak bases such as pyridine, a drying agent such as molecular sieves and oxygen. The last step of the sequence is a sulfamide formation reaction employing reagents such as but not limited to sulfamoyl chlorides, fluorides and others in aprotic solvents and mild bases such as but not limited to TEA or DIPEA to give the desired O-aryl/heteroaryl sulfamide combination compounds s18-A1 through s18-A6.

Scheme 19. Preparation of Formula (1.1) Des-Cladinose Sulfonamide Compounds

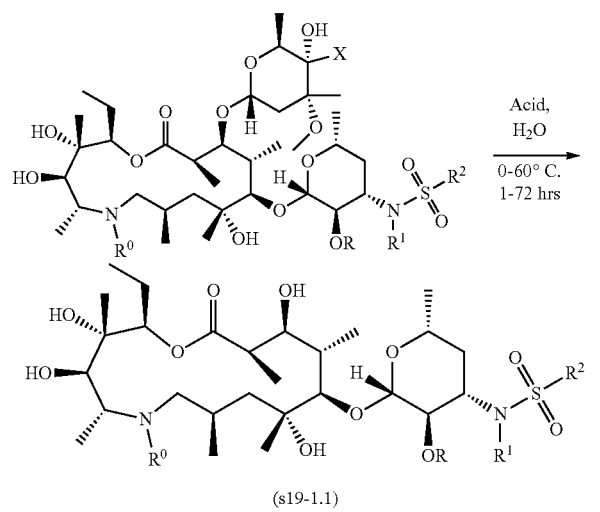

(s19-1.1)

Scheme 20. Preparation of Formula (1.1) Des-cladinose Sulfamide Compounds

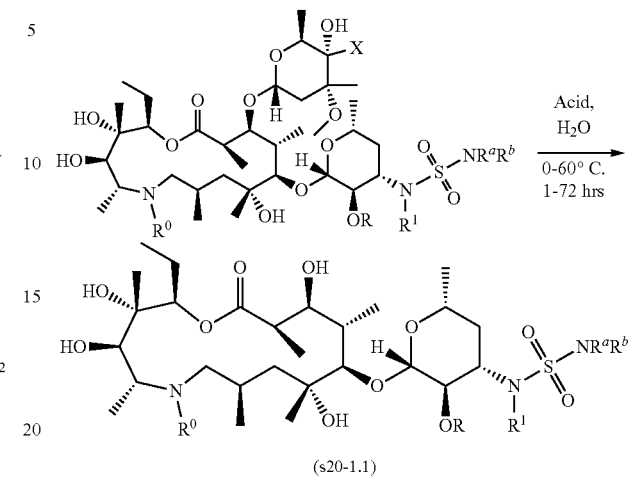

(s20-1.1)

Des-cladinose sulfonamide compounds of Formula (1.1) can be easily synthesized from Formula (1A) compounds, by stirring said compound in aqueous acetic acid or hydrochloric acid at temperatures between 0° C. and 60° C. in solvents such as but not limited THF, MeCN or $H_2O$ for 1 to 72 hours as shown.

Des-cladinose sulfamide compounds of Formula (1.1) can be easily synthesized from Formula (1A) compounds, by stirring said compound in aqueous acetic acid or hydrochloric acid at temperatures between 0° C. and 60° C. in solvents such as but not limited THF, MeCN or $H_2O$ for 1 to 72 hours as shown.

EXAMPLES

Preparation of a Des-Cladinose Sulfonamide Compound Example (A-20) of Formula (1.1)

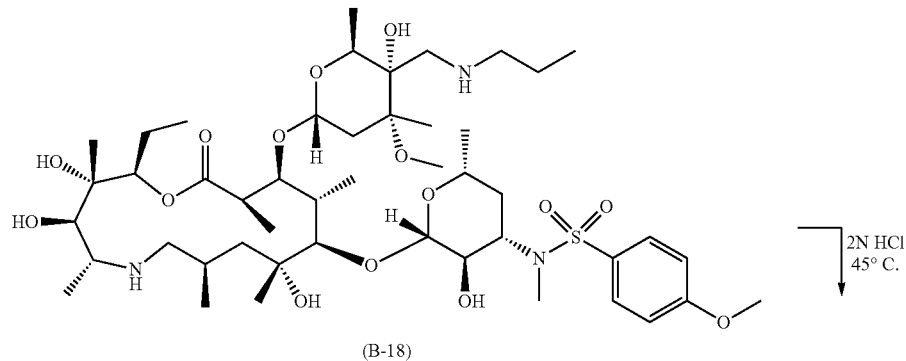

(B-18)

2N HCl
45° C.

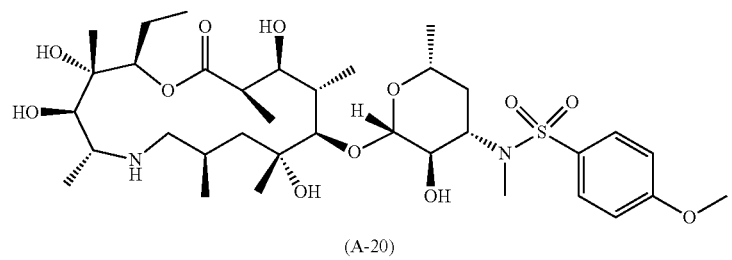

(A-20)

To crude example B-18 (300.0 mg) was added 2N HCl (5.0 mL) and the resulting mixture was heated at 45° C. for 2 hours before being cooled to room temperature. The crude reaction mixture was poured into an ice cooled solution of NH$_4$OH (pH>7), stirred for 5 minutes, then concentrated and lyophilized. The crude material was purified by Prep HPLC using ammonium acetate as a buffer and the purified material was passed through an SCX column to afford the title compound as the free base.

Formula (1.1) compounds can be made similarly to that shown above for example A-20 under similar conditions but for the Formula (1-A1) compound starting materials instead of those used for example B-18.

Preparation of a Des-Cladinose Sulfamide Compound Example A-37 of Formula (1.1)

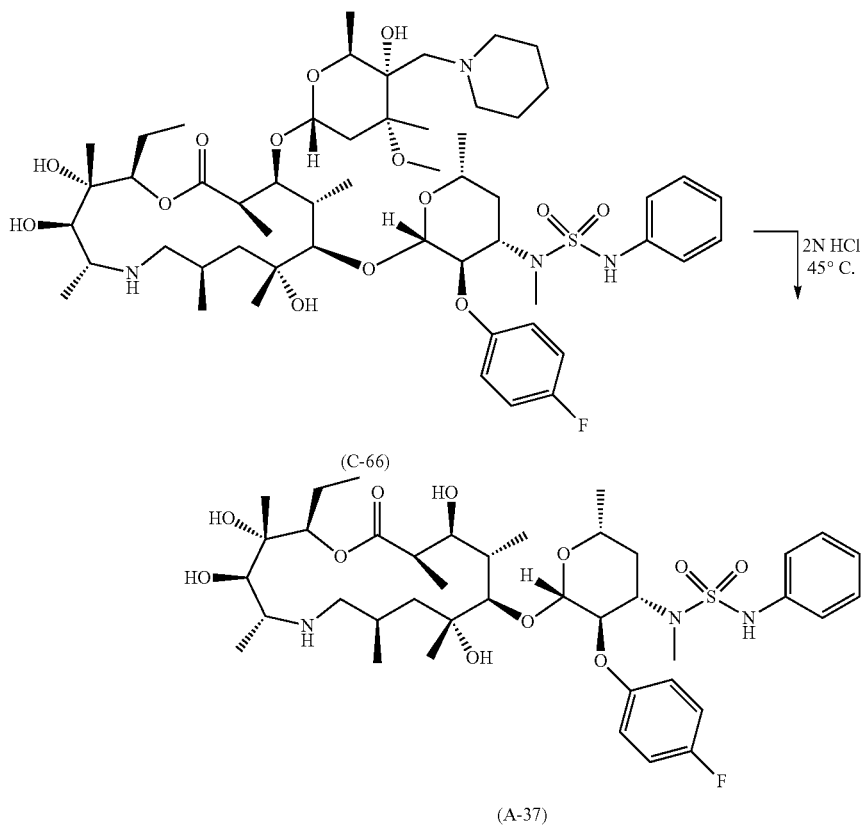

(C-66)

(A-37)

To crude example C-66 (100.0 mg) was added 2N HCl (2.0 mL) and the resulting mixture was heated at 45° C. for 2 hours before being cooled to room temperature. The crude reaction mixture was poured into an ice cooled solution of NH$_4$OH (pH>7), stirred for 5 minutes, then concentrated and lyophilized. The crude material was purified by Prep HPLC using ammonium acetate as a buffer and the purified material was passed through an SCX column to afford the title compound as the free base.

Formula (1.1) compounds can be made similarly to that shown above for example A-37 under similar conditions but for the Formula (1-A1a) compound starting materials instead of those used for example C-66.

Preparation of a Sulfonamide Compound Example (B-8) of Formula (1-A1)

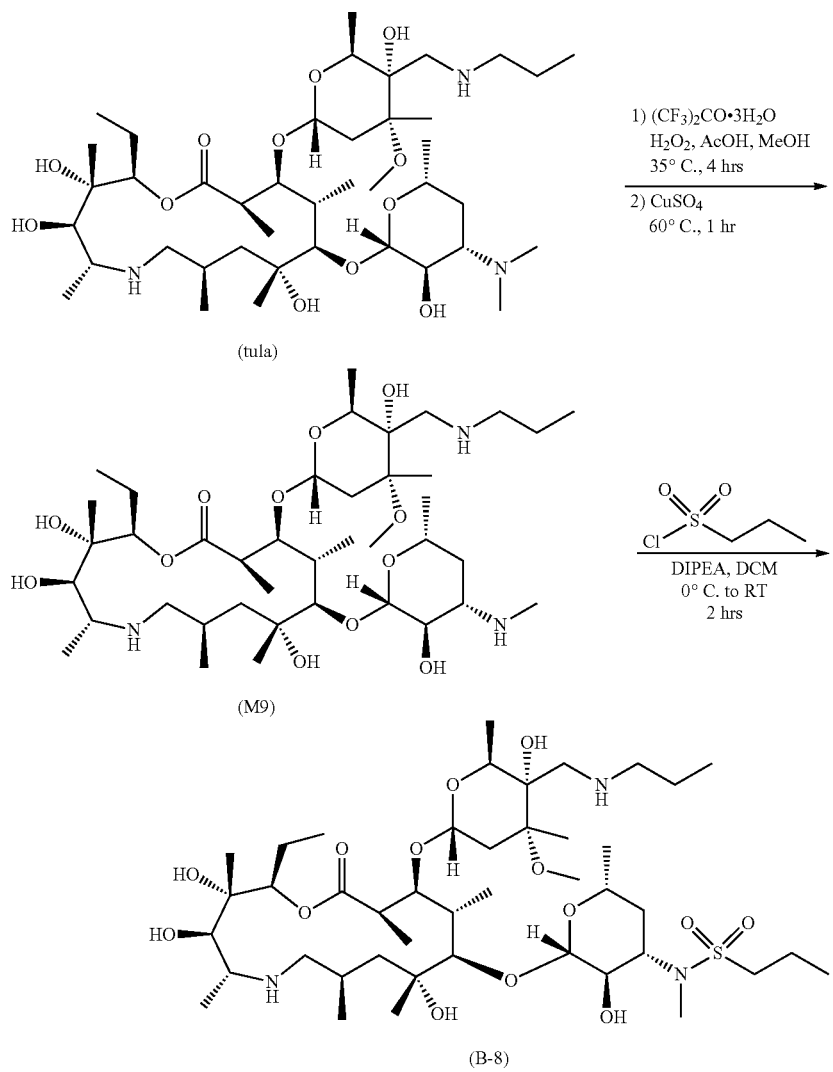

Step 1: To a solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-1-oxa-6-azacyclopentadecan-15-one (tula) (20.0 g, 24.8 mmol) in methanol (40 mL) and acetic acid (1.6 mL, 28 mmol), hexafluoroacetone trihydrate (0.62 g, 2.8 mmol) and then 30% aqueous hydrogen peroxide (2.88 ml, 28 mmol) were added together and stirred for 4 hours at 35° C. After consumption of the starting material as judged by LCMS, the reaction was cooled to 20° C. and anhydrous copper(II) sulfate (4.35 g, 28 mmol) was added and the reaction was heated to 60° C. for 2 hours. After completion of the reaction as judged by LCMS, the reaction mixture was cooled to 20° C. and 60 mL DCM and 80 mL H$_2$O were added. The mixture was basified to approximately pH 9.8 with concentrated aqueous ammonia. The mixture was concentrated under vacuum to a solid and recrystallized from acetone/water to give 14.2 g of a white crystalline product (M9) that was >95% pure by LCMS and used as is in the next step.

Step 2: M9 from Step 1 (0.38 mmol, 300 mg, 1.0 eq) was dissolved in DCM (5 mL) and DIPEA (1.5 eq, 100 µL, 0.57 mmol) followed by propane-1-sulfonyl chloride (1.1 eq, 59 mg, 0.42 mmol) were added at 0° C. The reaction mixture was stirred initially at 0° C. and then warmed to room temperature over 2 hours. After completion of the reaction as judged by LCMS analysis, the reaction mixture was diluted with DCM, washed with water and brine. The organic part was dried with anhydrous Na$_2$SO$_4$ and concentrated under reduced pressure to afford crude product purified by C18 reverse flash chromatography with 0.5% AcOH as modifier (0 to 100% MeCN in H$_2$O). The fractions containing the desired product were lyophilized to give the desired compound as the acetate salt (16 mg).

Formula (1-A1) compounds shown in Table B where R$^5$ is H and R$^6$ is propyl can be made similarly to that shown above for Example B-8 under similar conditions by either varying the sulfonamide forming reagent or the starting material and using (alkyl-tula-epx) as the starting material instead of tulathromycin epoxide as shown in the schemes herein.

Preparation of a Sulfamide Compound Example (B-50) of Formula (1-A1)

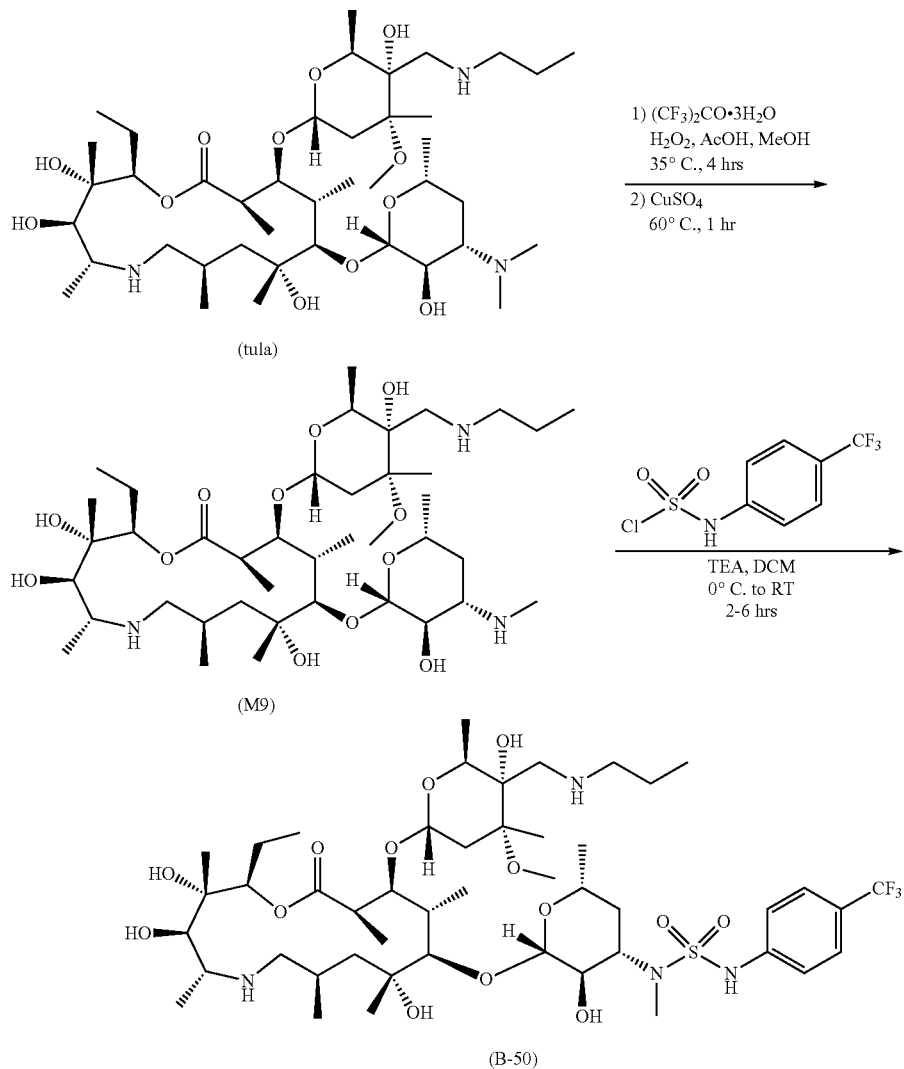

Step 1: To a solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-1-oxa-6-azacyclopentadecan-15-one (tula) (20.0 g, 24.8 mmol) in methanol (40 mL) and acetic acid (1.6 mL, 28 mmol), hexafluoroacetone trihydrate (0.62 g, 2.8 mmol) and then 30% aqueous hydrogen peroxide (2.88 ml, 28 mmol) were added together and stirred for 4 hours at 35° C. After consumption of the starting material as judged by LCMS, the reaction was cooled to 20° C. and anhydrous copper(II) sulfate (4.35 g, 28 mmol) was added and the reaction was heated to 60° C. for 2 hours. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 14.2 g of a white crystalline product (M9) that was >95% pure by LCMS and used as is in the next step.

Step 2: M9 from Step 1 (0.51 mmol, 400 mg, 1.0 eq) was dissolved in DCM (10 ml) and TEA (3.0 eq, 210 uL, 0.56 mmol) followed by N-[4-(trifluoromethyl)phenyl]sulfamoyl fluoride (1.1 eq, 135 mg, 0.42 mmol) were added at 0° C. The reaction mixture was stirred initially at 0° C. for 2 hours and then warmed to room temperature over 4 hours. After completion of the reaction as judged by LCMS analysis the reaction mixture was diluted with DCM, washed with water and brine. The organic part was dried with anhydrous $Na_2SO_4$ and concentrated under reduced pressure to afford crude product purified by C18 reverse flash chromatography with 0.5% AcOH as modifier (0 to 100% MeCN in $H_2O$). The fractions containing the desired product were lyophilized to give the desired compound (B-50) as the acetate salt (194 mg).

Formula (1-A1) compounds shown in Table B where $R^5$ is H and $R^6$ is propyl can be made similarly to that shown above for Example B-50 under similar conditions by either varying the sulfamide forming reagent or the starting material and using (alkyl-tula-epx) as the starting material instead of tulathromycin epoxide as shown in the schemes herein.

Preparation of a Sulfonamide Compound that is Example B-93 of Formula (1-A1)
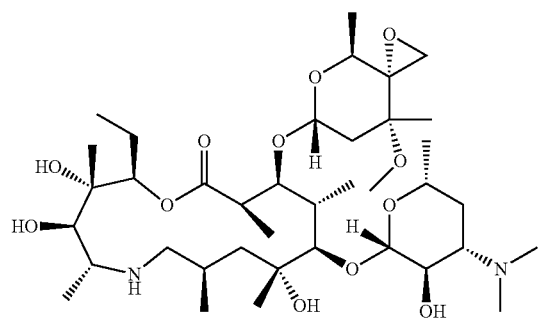
(tula-epx)
1) (CF$_3$)$_2$CO•3H$_2$O
   H$_2$O$_2$, AcOH, MeOH
   35° C., 4 hrs
2) CuSO$_4$
   60° C., 1 hr
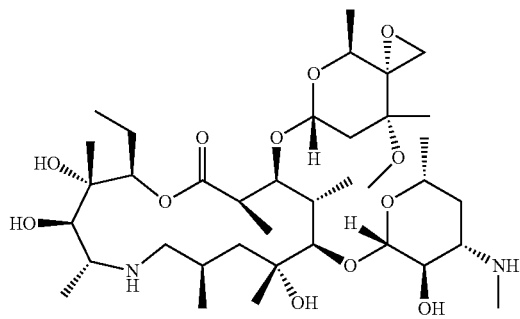
(M9-epx)
N-ethylamine
1-Propanol
80° C., 16 hrs
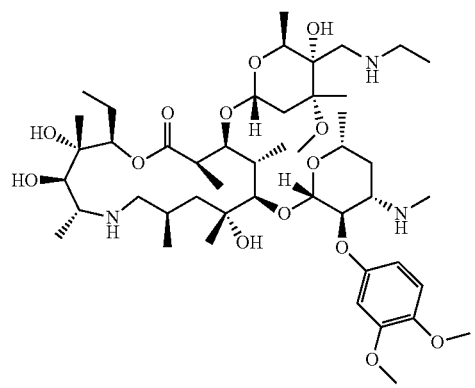
Cu(OAc)$_2$,
Pyridine
4 Å mol.
sieves
DMF, RT,
72 hrs
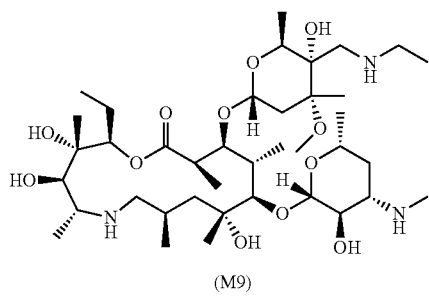
(M9)
DCM, DIPEA
RT, 16 hrs

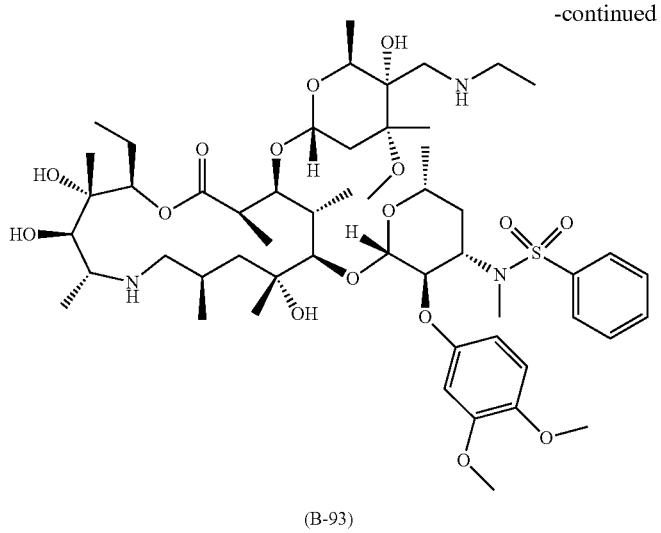

(B-93)

Step 1: A solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: A solution of 10 g (13.14 mmol) M9-epx from Step 1 and 10.9 mL N-ethylamine (10.0 eq, 131.4 mmol) in 100 mL 1-propanol was heated to 80° C. for 16 hours. After completion of the reaction as judged by LCMS analysis, the volatiles were removed under reduced pressure, then dissolved in 100 ml DCM and $H_2O$ and the pH was adjusted to ~9.8 with $NH_4OH$. The aqueous layer was extracted 3 times with DCM and the organic layers combined, dried over anhydrous magnesium sulfate. The volatiles were removed under reduced pressure to give the crude material that was purified on C18 silica using reverse flash chromatography with 1.0% AcOH as the modifier (0 to 100% MeCN in $H_2O$). The desired fractions were combined, the pH adjusted to ~9.8 with $NH_4OH$ and extracted 3 times with DCM. The organic layers were combined, dried over anhydrous magnesium sulfate and the volatiles removed under reduced pressure to give the desired material as an off-white amorphous solid.

Step 3: A mixture of the product of Step 2 (250 mg, 0.32 mmol, 1.0 eq), (3,4-dimethoxyphenyl)boronic acid (88 mg, 0.47 mmol, 1.5 eq), copper (II) acetate (143 mg, 2.5 equiv., 0.79 mmol) molecular sieves (4 Å, activated, 0.2 g) and pyridine (51 uL, 2 eq, 0.63 mmol) in DMF (5.0 mL) was stirred at room temperature in dry air for 3 days. Upon the completion of the reaction as judged by LCMS analysis the mixture was filtered on Celite and the volatiles removed under reduced pressure. The crude material was purified on C18 silica using reverse flash chromatography with 1.0% AcOH as the modifier (0 to 100% MeCN in $H_2O$). The desired fractions were combined, the pH adjusted to ~9.8 with $NH_4OH$ and extracted 3 times with DCM. The organic layers were combined, dried over anhydrous magnesium sulfate and the volatiles removed under reduced pressure to give the desired material as an off-white amorphous solid.

Step 4: The material from Step 3 (150 mg, 0.16 mmol, 1.0 eq) was dissolved in dry DCM (3 ml) in a dry round bottom flask and DIPEA (69 uL, 2.5 eq.) was added followed by benzenesulfonyl chloride (32 mg, 1.2 eq, 0.19 mmol). The mixture was stirred overnight after which the LCMS analysis indicated all starting material being consumed. The volatiles were removed under a stream of $N_2$ and the crude material was purified by reverse phase chromatography using a C18 column with a gradient of 1% AcOH in MeCN and $H_2O$. The fractions containing the desired product were lyophilized to give the desired product as an acetate salt (99 mg, 55% yield).

Preparation of the Sulfonamide Compound Example B-107 of Formula (1-A1)
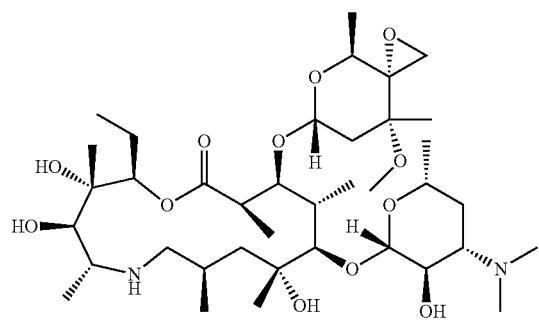
(tula-epx)
1) (CF$_3$)$_2$CO•3H$_2$O
H$_2$O$_2$, AcOH, MeOH
35° C., 4 hrs
2) CuSO$_4$
60° C., 1 hr
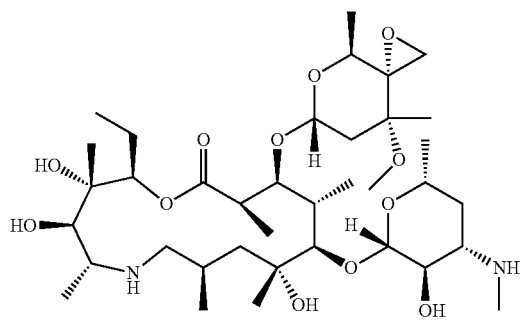
(M9-epx)
N-ethylamine
1-Propanol
80° C., 16 hrs
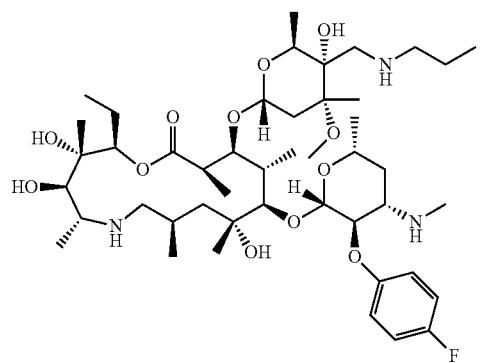
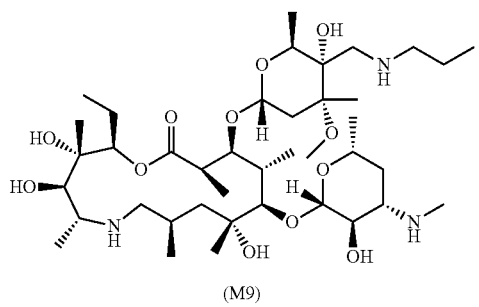
(M9)
B(OH)$_2$ / 4-F-phenyl
Cu(OAc)$_2$,
Pyridine
4 Å mol. sieves
DMF, RT,
72 hrs
DCM, DIPEA
0° C., 2 hrs
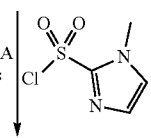

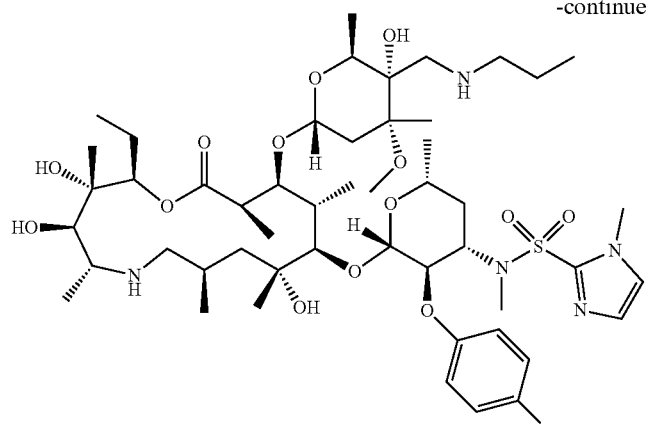

(B-107)

Step 1: A solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL H₂O were added. The mixture was basified to approximately pH 9.8 with concentrated aqueous ammonia. The mixture was concentrated under vacuum to a solid and recrystallized from acetone/water to give 16 g of a white crystalline product (M9-epx) that was 95% pure by LCMS and used as is in the next step.

Step 2: A solution of 10 g (13.14 mmol) M9-epx from Step 1 and 10.9 mL n-propylamine (10.0 eq, 131.4 mmol) in 100 mL 1-propanol was heated to 80° C. for 16 hours. After completion of the reaction as judged by LCMS analysis, the volatiles were removed under reduced pressure, the remaining crude solid was then dissolved in 100 mL DCM and H₂O and the pH was adjusted to ~9.8 with NH₄OH. The aqueous layer was extracted 3 times with DCM and the organic layers combined and dried over anhydrous magnesium sulfate. The volatiles were removed under reduced pressure to give the crude material that was purified on C18 silica using reverse flash chromatography with 1.0% AcOH as the modifier (0 to 100% MeCN in H₂O). The desired fractions were combined, the pH adjusted to ~9.8 with NH₄OH and extracted 3 times with DCM. The organic layers were combined, dried over anhydrous magnesium sulfate and the volatiles removed under reduced pressure to give the desired material as an off-white amorphous solid.

Step 3: A mixture of the product from Step 2 (3.6 g, 4.5 mmol), (4-fluorophenyl)boronic acid (2.5 g, 18.0 mmol, 4 eq), copper (II) acetate (1.24 g, 1.5 equiv., 6.8 mmol) molecular sieves (4 Å, activated, 4.0 g) and pyridine (1.5 mL, 4 eq, 18.0 mmol) in DMF (35.0 mL) was stirred at room temperature in dry air for 3 days. Upon the completion of the reaction as judged by LCMS analysis, the mixture was poured into MTBE (70 mL) and 20 mL of 10% NH₃ before filtering through celite. The mixture was then separated and washed with water (50 mL), 2M NaOH (10 mL) and brine (10 mL) before evaporating to give a lilac solid (5.0 g) as the crude material. The crude was purified by reverse flash chromatography on a C18 column with 0.5% AcOH as the modifier. The fractions containing the desired product were lyophilized to give the desired compound as the acetate salt.

Step 4: The material from Step 3 (642 mg, 0.72 mmol, 1.0 eq) was dissolved in dry DCM (20 mL) in a dry round bottom flask and TEA (203 μL, 2.0 eq.) was added followed by 1-methyl-1H-imidazole-2-sulfonyl chloride (165 mg, 1.2 eq, 0.87 mmol) at 0° C. The mixture was stirred overnight with reaction temperature slowly coming to RT after which the LCMS analysis indicated all starting material being consumed. The volatiles were removed under a stream of N₂ and the crude material was purified by reverse phase chromatography using a C18 column with a gradient of 1% AcOH in MeCN and H₂O. The fractions containing the desired product were lyophilized to give the desired product (B-107) as an acetate salt (150 mg, 19% yield).

Preparation of the Sulfamide Compound Example (B-113) of Formula (1-A1)

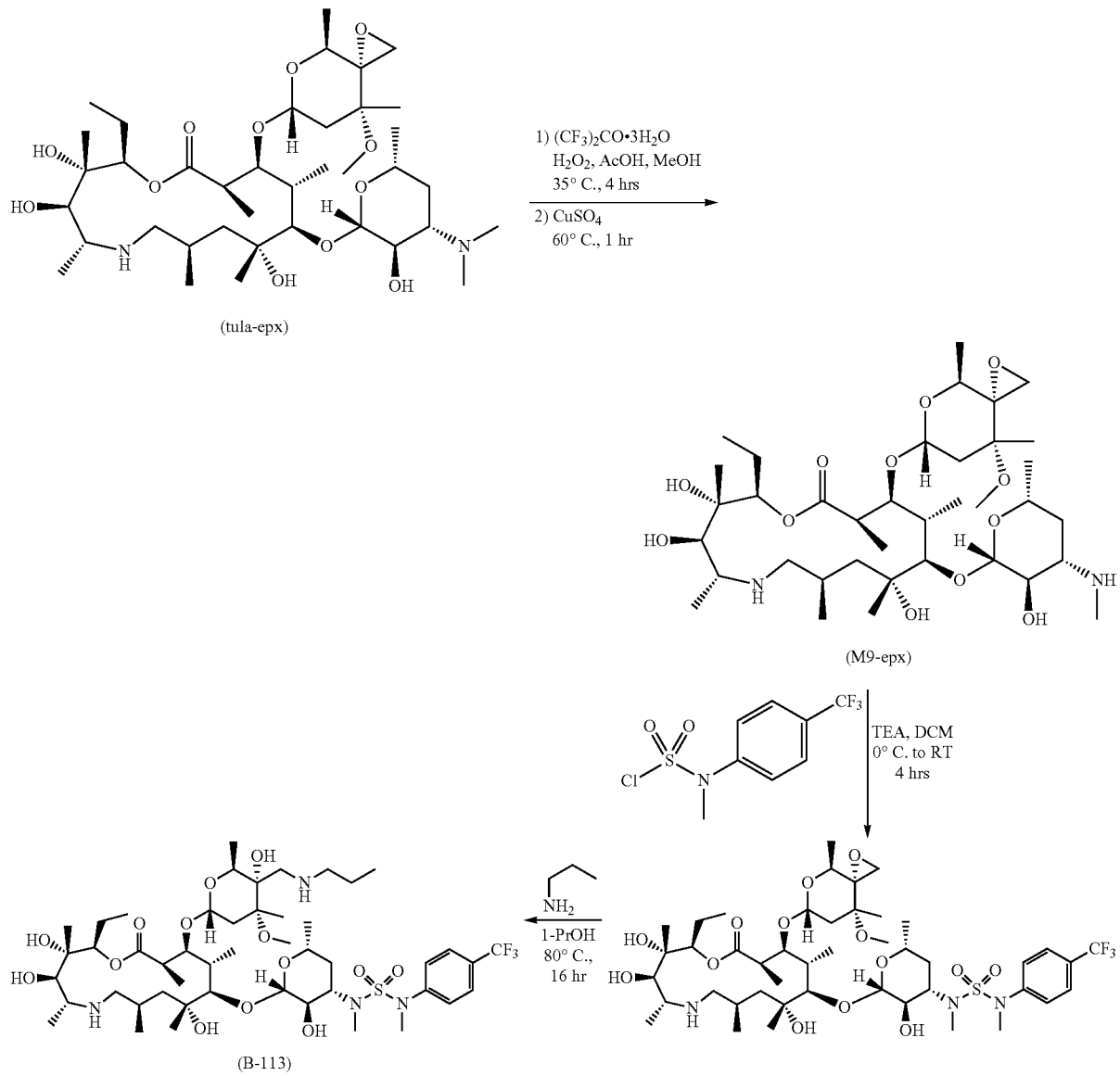

Step 1: A solution of (2R,3S,4R,5R,8R,10R,11R,12S,13S, 14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL H$_2$O were added. The mixture was basified to approximately pH 9.8 with concentrated aqueous ammonia. The mixture was concentrated under vacuum to a solid and recrystallized from acetone/water to give 16 g of a white crystalline product (M9-epx) that was 95% pure by LCMS and used as is in the next step.

Step 2: To a solution of 5.0 g (6.83 mmol) M9-epx from Step 1 and 1.8 mL TEA (1.5 eq, 10.2 mmol) in 50 mL dry DCM at 0° C. was added a solution of N-methyl-4-(trifluoromethyl)phenylsulfamoyl chloride (1.2 eq.) in DCM (5 mL) over 5 minutes. The reaction mixture was stirred initially at 0° C. and then warmed slowly to room temperature over 24 hours. After completion of the reaction as judged by LCMS analysis, the reaction mixture was diluted with DCM and washed with water, followed by a brine solution. The organic layer was dried over anhydrous Na$_2$SO$_4$, concentrated under reduced pressure and triturated the resulting material with 30% Et$_2$O in pentane to obtain a free solid material (~5.2 g) that was used as is in the following step.

Step 3: The product from Step 2 (0.22 mmol, 200 mg, 1.00 eq) was dissolved in n-PrOH (2.5 mL) and n-propylamine (5.0 eq, 0.11 mL, 1.10 mmol) was added. The resulting solution was stirred at 70° C. overnight. After completion of the reaction as judged by LCMS analysis, the volatiles were removed under a stream of $N_2$ and the crude purified by C18 reverse flash chromatography with 0.5% AcOH as modifier (0 to 100% MeCN in $H_2O$). The fractions containing the desired product were lyophilized to give the desired compound (B-113) as the acetate salt (48 mg, 25%).

Preparation of a sulfonamide compound of Formula (1-A1) that is Example B-142 using a modification of Scheme 7 wherein the nucleophile used in the last step to open the epoxide is N-propylamine and such that $R^1$ is propyl from a reductive amination reaction with propionaldehyde is shown below:

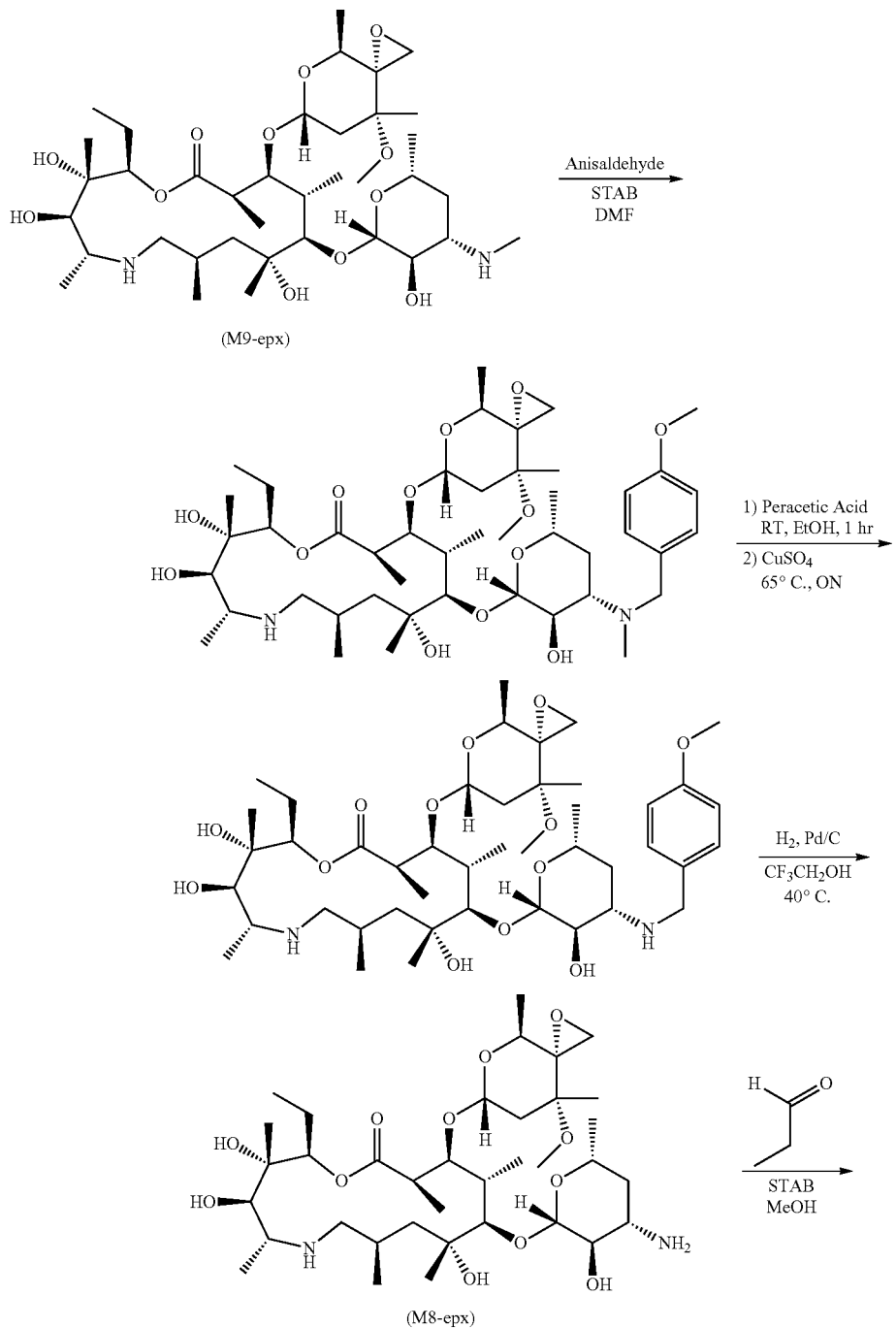

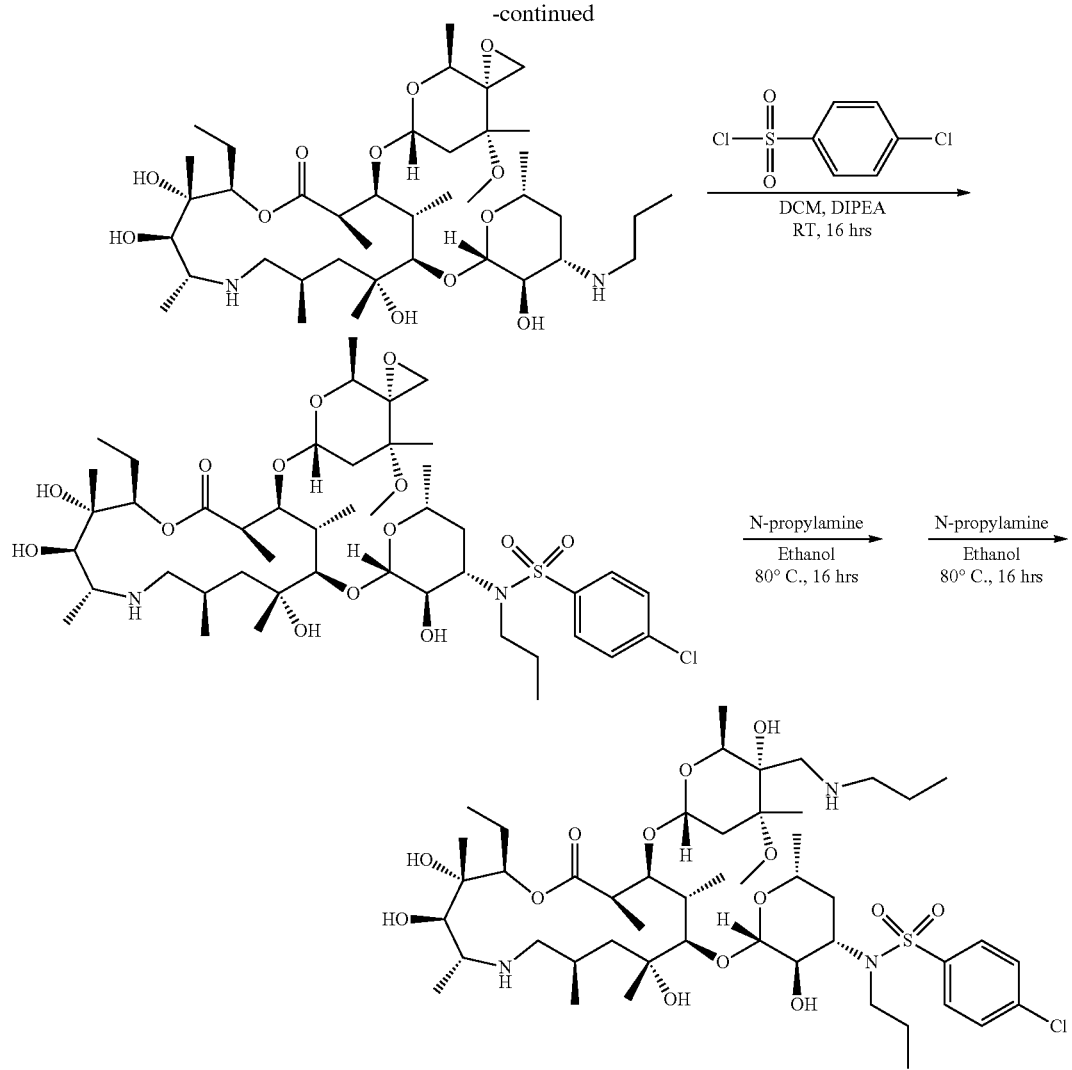

(B-142)

Step 1: 1.0 g (1.36 mmol, 1.00 eq) of M9 Epoxide was dissolved in 10 mL dry DMF in a 50 mL round bottom flask and 2.0 eq p-anisaldehyde was added (0.332 mL, 2.73 mmol) followed by 1.17 g sodium triacetoxyborohydride (STAB, 4.0 eq, 5.5 mmol). The resulting solution was heated at 40° C. for 2 hours. An additional 0.6 g, (2.7 mmol, 2.0 eq) STAB was added and the resulting solution was heated at 40° C. overnight after which the LCMS analysis showed full consumption of the starting material. The reaction mixture was then cooled to 0° C. and 5 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH-12 with $NH_4OH$ and extracted 3 times with 20 mL DCM. The organics were combined and dried over $MgSO_4$ and removed under reduced pressure to afford the crude material that was purified by reverse phase chromatography on a C18 column eluting with a gradient of 1% AcOH in MeCN and $H_2O$. The fractions containing the desired product were combined, the pH was adjusted to pH-12 with $NH_4OH$ and extracted 3 times with 50 mL DCM to give the desired product as a free base (1008 mg, 87%)

Step 2: 1008 mg of product from step 1 (1.18 mmol, 1.00 eq) was dissolved in 10 mL dry EtOH and peracetic acid was added (32% dilute solution in acetic acid; 1.5 eq 304 μL). The resulting solution was stirred at room temperature for 45 minutes after which the LCMS showed a full conversion to the corresponding N-oxide. After that copper sulfate (II) anhydrous was added (3.0 eq; 566 mg) and the solution was stirred at 65° C. for 4 hours after which the LCMS showed a complete reaction with 41% debenzylated product and 44% demethylated product. The reaction mixture was diluted with 20 mL DCM and $H_2O$ and the pH adjusted to ~12 with $NH_4OH$. The crude material was extracted 3 times with DCM and the organics were combined, dried over $MgSO_4$ and the volatiles removed under reduced pressure. The crude was purified by reverse phase chromatography on a C18 column with a gradient of 1% AcOH in MeCN and $H_2O$. The fractions containing the desired product were combined, the pH was adjusted to pH-12 with $NH_4OH$ and extracted 3 times with 50 mL DCM to give the desired product as a free base (250 mgs 25% yield).

Step 3: The product from Step 2 (250 mg, 0.30 mmol, 1.0 eq) was dissolved in 10 mL $CF_3CH_2OH$. 5% Pd/C (25 mgs)

was added and the resulting slurry was hydrogenated under balloon pressure $H_2$ at 40° C. overnight after which the LCMS showed complete reaction. The Pd/C was filtered off on Celite and the volatiles removed under reduced pressure to give the desired product (M8 epoxide; M8-epx) as a white powder (195 mgs, 91%).

Step 4: The product from Step 3 (M8-epx, 250 mgs, 1.0 eq, 0.35 mmol) was dissolved in 5 mL dry MeCOH in a 25 mL round bottom flask and the solution was cooled to 0° C. Propionaldehyde (1.2 eq, 30 μL) was added followed by a portion wise addition of sodium triacetoxyborohydride (5 eq, 369 mg). The solution was stirred at 0° C. to room temperature for 2 hours after which the LCMS showed a full conversion to the desired product. The reaction mixture was then cooled to 0° C. and 1 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH-12 with $NH_4OH$ and extracted 3 times with 20 mL DCM. The organics were combined and dried over $MgSO_4$ and removed under reduced pressure to afford the desired product (250 mg) as a white solid material with ~80% LCMS purity that was used as is in subsequent epoxide opening.

Step 5: The material from Step 4 (200 mg, 0.32 mmol, 1.0 eq) was dissolved in dry DCM (5 ml) in a dry round bottom flask and DIPEA (0.141 mL, 2.5 eq.) was added followed by 4-chlorobenzenesulfonyl chloride (1.2 eq) in DCM (5 mL). The mixture was stirred overnight after which the LCMS analysis indicated all starting material being consumed. The volatiles were removed under a stream of $N_2$ and the crude material was purified by reverse phase chromatography on a C18 column with a gradient of 1% AcOH in MeCN and $H_2O$. The fractions containing the desired product were combined, the pH was adjusted to pH-12 with $NH_4OH$ and extracted 3 times with 50 mL DCM to give the desired product as a free base (93 mgs 32% yield).

Step 6: To a pressure vial was added the product from Step 5 (93 mg, 0.10 mmol, 1 eq) and EtOH (2 mL) followed by N-propylamine (103 ul, 1.25 mmol, 12 eq). The reaction mixture was stirred at 80° C. for 16 hours. The reaction mixture was then concentrated under vacuum and the crude product was purified by reverse phase chromatography on a C18 column with a gradient of 1% AcOH in MeCN and $H_2O$. The fractions containing the desired product were lyophilized to give the desired product as the acetate salt as a white solid (35 mg, 33% yield).

Following this example, the alkyl group $R^1$ on the desosamine nitrogen can be varied by replacing propionaldehyde in the fourth step of the sequence by any other alkyl aldehyde such as but not limited to acetaldehyde or isobutylaldehyde or carbaldehydes such as benzaldehyde, or 2-pyridyl carbaldehyde and others. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

Preparation of a Sulfonamide Compound Example C-4 of Formula (1-A1a)

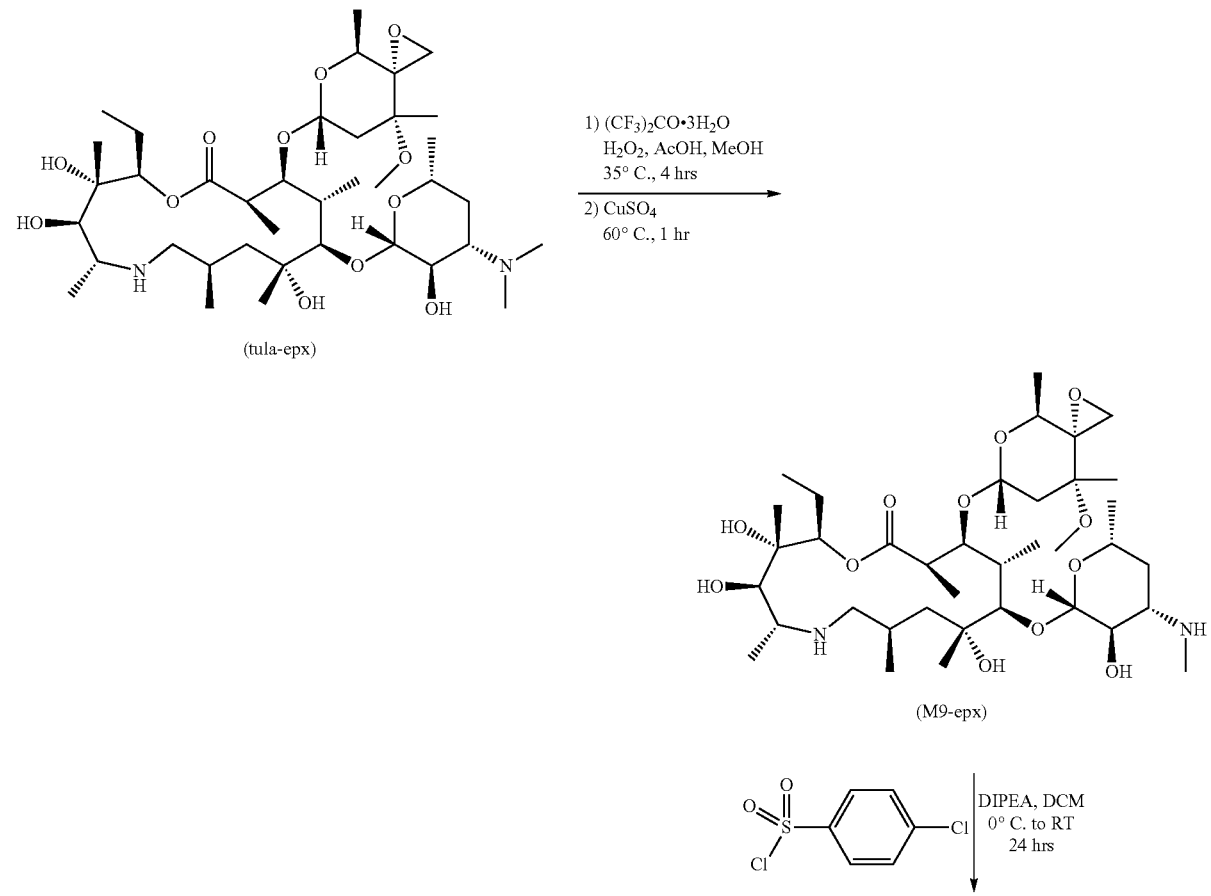

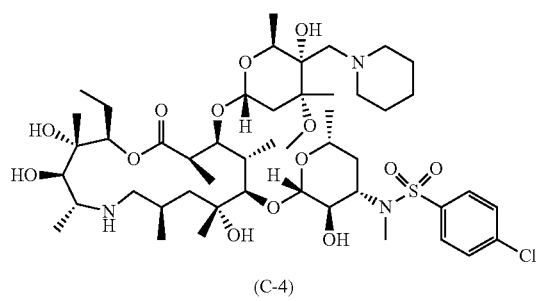
(C-4)

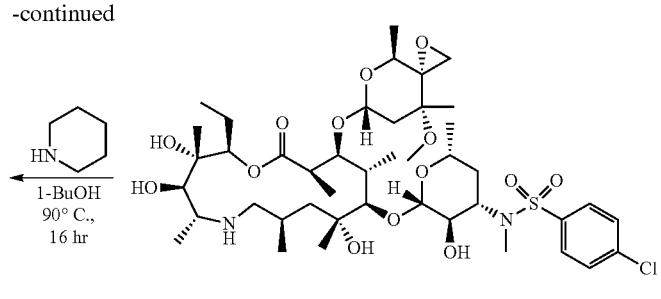

-continued

Step 1: A solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: A solution of 5.0 g (6.83 mmol) M9-epx from Step 1 and 1.8 mL DIPEA (1.5 eq, 10.2 mmol) in 50 mL DCM at 0° C. was added a solution of 4-chlorobenzenesulfonyl chloride (1.2 eq) in DCM (5 mL) was slowly. The reaction mixture was stirred initially at 0° C. and then warmed slowly to room temperature over 24 hours. After completion of the reaction as judged by LCMS analysis, the reaction mixture was diluted with DCM and washed with water, followed by brine solution. The organic layer was dried over anhydrous $Na_2SO_4$, concentrated under reduced pressure and triturated the resultant material with 30% $Et_2O$ in pentane to obtain a free solid material (~5.2 g) that was used as is in the following step.

Step 3: The product from Step 2 (0.22 mmol, 200 mg, 1.00 eq) in n-BuOH (1.5 mL) was added to piperidine (5.0 eq, 0.11 mL, 1.10 mmol) and the resulting solution was stirred at 90° C. overnight. After completion of the reaction as judged by LCMS analysis, the volatiles were removed under a stream of $N_2$ and the crude purified by C18 reverse flash chromatography with 0.5% AcOH as modifier (0 to 100% MeCN in $H_2O$). The fractions containing the desired product were lyophilized to give the desired compound as the acetate salt (48 mg).

Formula (1-A1a) compounds shown in Table C can be made similarly to that shown above for Example C-4 under similar conditions by either varying the amine used in the third step to open the epoxide functional group or the sulfonamide forming reagent or the starting material and using (alkyl-tula-epx) as the starting material instead of tulathromycin epoxide as shown in the schemes herein.

Preparation of a Sulfamide Compound Example (C-54) of Formula (1-A1a)

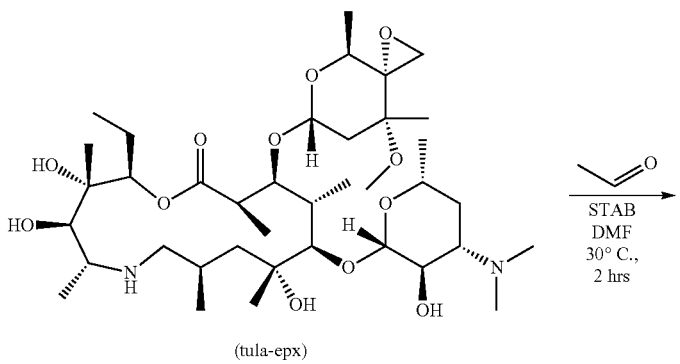
(tula-epx)

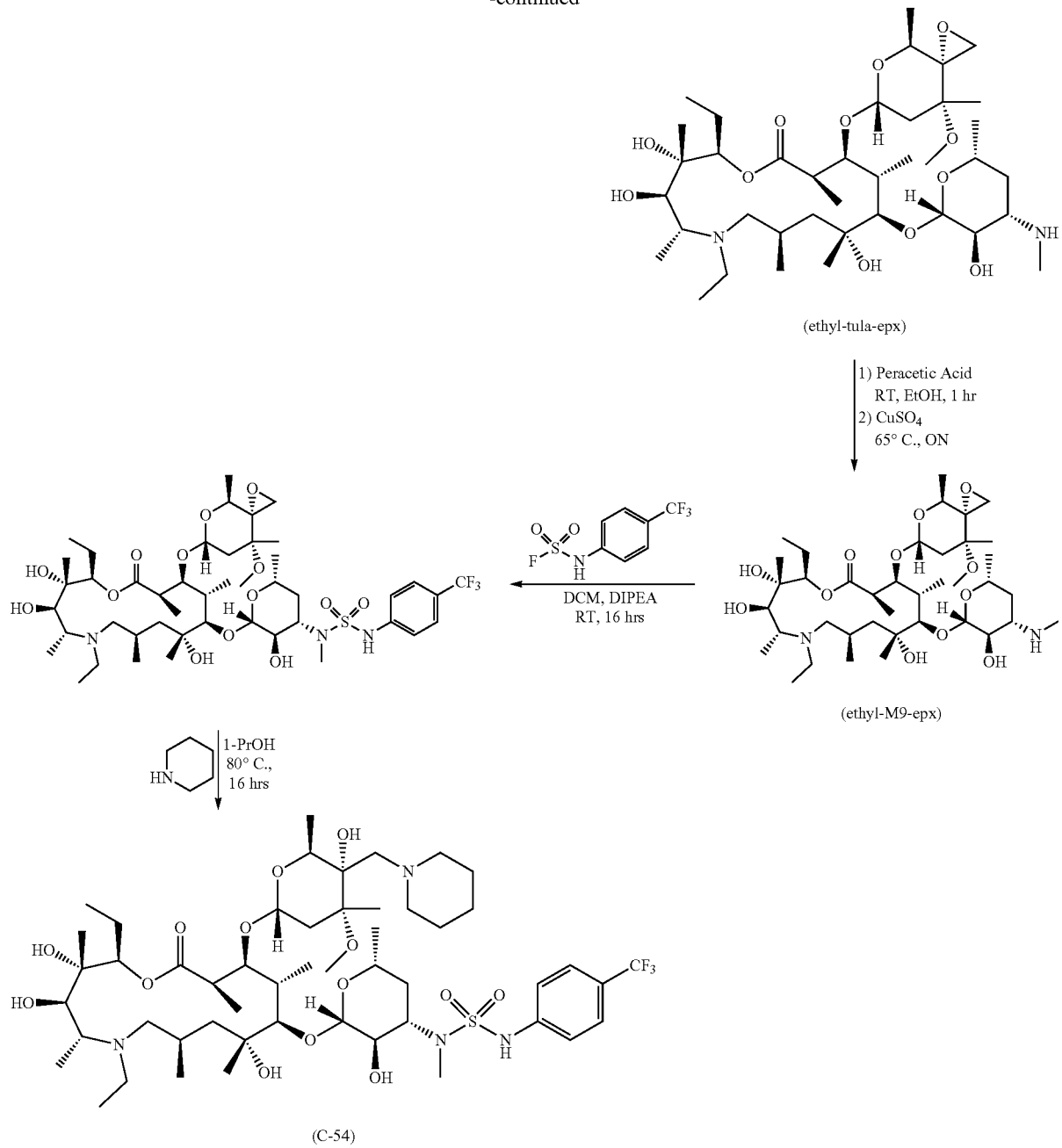

Step 1: To a solution of (2R,3S,4R,5R,8R,10R,11R,12S, 13S,14R)-11-(((2S,3R,4S,6R)-4-(dimethylamino)-3-hydroxy-6-methyltetrahydro-2H-pyran-2-yl)oxy)-2-ethyl-3,4, 10-trihydroxy-13-(((3S,4S,6R,8R)-8-methoxy-4,8-dimethyl-1,5-dioxaspiro[2.5]octan-6-yl)oxy)-3,5,8,10,12, 14-hexamethyl-1-oxa-6-azacyclopentadecan-15-one (tula-epx) (1.0 g, 1.34 mmol) and acetaldehyde (3.0 eq) in dry DMF (10 mL) was added STAB (6.0 eq) and the resulting solution was stirred for 2 hours at 30° C. After consumption of the starting material as judged by LCMS, the reaction was cooled to 0° C. and 2 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH-12 with $NH_4OH$ and extracted 3 times with 20 mL DCM. The organics were combined and dried over $MgSO_4$ and removed under reduced pressure to afford the crude material that was purified by reverse phase chromatography on a C18 column with a gradient of 1% AcOH in MeCN and $H_2O$. The fractions containing the desired product were combined, the pH was adjusted to pH-12 with $NH_4OH$ and extracted 3 times with 50 mL DCM to give the desired product as a free base (590 mgs, 53% yield).

Step 2: 590 mg of product from Step 1 (0.76 mmol, 1.00 eq) was dissolved in 10 mL dry EtOH and peracetic acid was added (32% dilute solution in acetic acid; 1.2 eq 192 µL). The resulting solution was stirred at room temperature for 45 minutes after which the LCMS showed a full conversion to the corresponding N-oxide. The reaction mixture was then diluted with DCM (30 mL and H₂O) and transferred to a separatory funnel. The pH was adjusted to pH-12 with NH₄OH and extracted 3 times with 20 mL DCM. The organics were combined and dried over MgSO₄ and removed under reduced pressure to afford the crude N-oxide. The crude N-oxide (0.76 mmol, 1.0 eq) was dissolved in 10 mL dry ethanol and copper sulfate (II) pentahydrate was added (5.0 eq; 950 mg) and the solution was stirred at 65° C. for 16 hours after which the LCMS showed a complete reaction. The reaction mixture was diluted with 20 mL DCM and H₂O and the pH adjusted to ~12 with NH₄OH. The crude material was extracted 3 times with DCM and the organics were combined, dried over MgSO₄ and the volatiles removed under reduced pressure to give the crude desired product with LCMS purity >90% that was used as is in the following step.

Step 3: The material from Step 2 (250 mg, 0.32 mmol, 1.0 eq) was dissolved in dry DCM (5 ml) in a dry round bottom flask and DIPEA (0.141 mL, 2.5 eq.) was added followed by N-[4-(trifluoromethyl)phenyl]sulfamoyl fluoride (1.3 eq, 135 mg, 0.42 mmol). The reaction was stirred for 16 hours at room temperature after which the LCMS analysis indicated all starting material being consumed. The volatiles were removed under a stream of N₂ and the crude material was purified by reverse phase chromatography on a C18 column with a gradient of 1% AcOH in MeCN and H₂O. The fractions containing the desired product were combined, the pH was adjusted to pH-12 with NH₄OH and extracted 3 times with 50 mL DCM to give the desired product as a free base (150 mgs 51% yield).

Step 4: To a pressure vial was added the product from step 3 (150 mg, 0.17 mmol, 1 eq) and N-propanol (5 mL) followed by addition piperidine (117 µl, 2.0 mmol, 12 eq). The reaction mixture was stirred at 70° C. for 16 hours. The reaction mixture was then concentrated under vacuum and the crude product was purified by reverse phase chromatography using a C18 column with a gradient of 1% AcOH in MeCN and H₂O. The fractions containing the desired product were lyophilized to give the desired product (C-54) as an acetate salt (90 mg, 53% yield).

Following this example, the alkyl group $R^o$ on the core nitrogen can be varied by replacing acetaldehyde in the first step of the sequence by any other alkyl aldehyde such as but not limited to formaldehyde or propionaldehyde and others. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

Formula (1-A1a) compounds shown in Table C can be made similarly to that shown above for Example C-54 under similar conditions by either varying the amine used in the fourth step to open the epoxide functional group or the sulfonamide or sulfamide forming reagent or the starting material and using (alkyl-tula-epx) as the starting material instead of tulathromycin epoxide as shown in the schemes herein.

Preparation of a Cyclic Sulfamate Compound Example (C-17) of Formula (1-A1a)

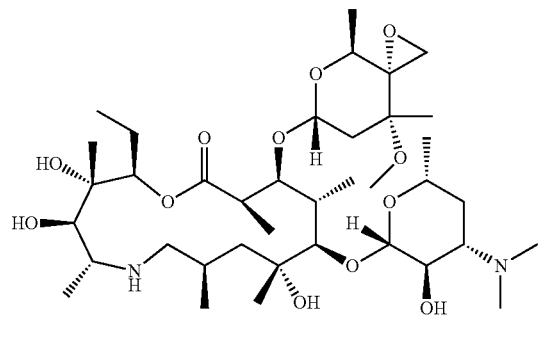

(tula-epx)

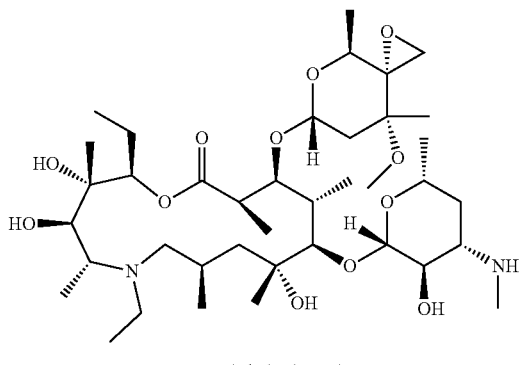

(ethyl-tula-epx)

1) Peracetic Acid
   RT, EtOH, 1 hr
2) CuSO₄
   65° C., ON

-continued

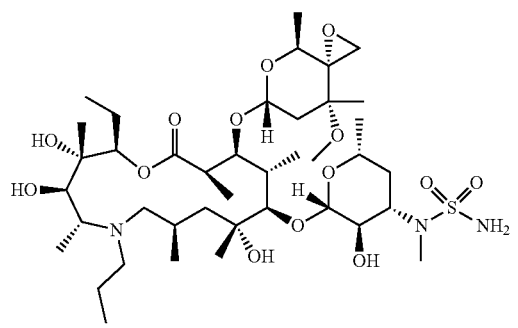

151

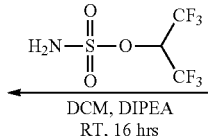

DCM, DIPEA
RT, 16 hrs

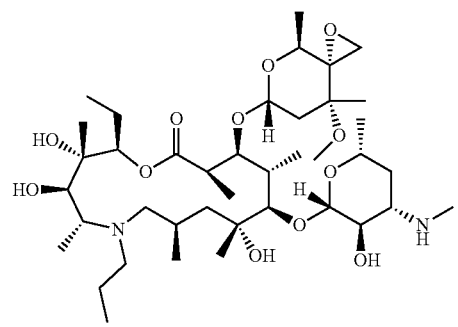

152

(ethyl-M9-epx)

1-PrOH
80° C.,
16 hrs
NH₂

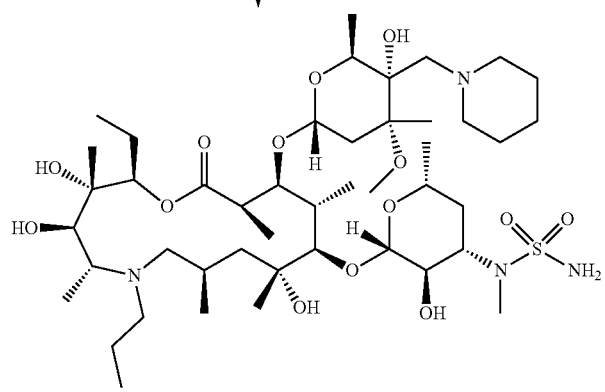

(C-17)

Step 1: To a solution of (2R,3S,4R,5R,8R,10R,11R,12S, 13S,14R)-11-(((2S,3R,4S,6R)-4-(dimethylamino)-3-hydroxy-6-methyltetrahydro-2H-pyran-2-yl)oxy)-2-ethyl-3,4, 10-trihydroxy-13-(((3S,4S,6R,8R)-8-methoxy-4,8-dimethyl-1,5-dioxaspiro[2.5]octan-6-yl)oxy)-3,5,8,10,12, 14-hexamethyl-1-oxa-6-azacyclopentadecan-15-one (tula-epx) (1.0 g, 1.34 mmol) and propionaldehyde (2.0 eq, 2.68 mmol) in dry DMF (10 mL) was added STAB (4.0 eq, 5.36 mmol) and the resulting solution was heated for 4 hours at 45° C. After consumption of the starting material as judged by LCMS, the reaction was cooled to 0° C. and 2 mL of a saturated solution of NH₄Cl was added and the solution stirred for 5 minutes. The reaction mixture was then diluted with DCM (30 mL and H₂O) and transferred to a separatory funnel. The pH was adjusted to pH-12 with NH₄OH and extracted 3 times with 20 mL DCM. The organics were combined and dried over MgSO₄ and removed under reduced pressure to afford the crude material that was purified by reverse phase chromatography on a C18 column with a gradient of 1% AcOH in MeCN and H₂O. The fractions containing the desired product were combined, the pH was adjusted to pH-12 with NH₄OH and extracted 3 times with 50 mL DCM to give the desired product as a free base (600 mgs, 57% yield).

Step 2: 590 mg of product from Step 1 (0.76 mmol, 1.00 eq) was dissolved in 10 mL dry EtOH and peracetic acid was added (32% dilute solution in acetic acid; 1.2 eq 192 µL). The resulting solution was stirred at room temperature for 45 minutes after which the LCMS showed a full conversion to the corresponding N-oxide. The reaction mixture was then diluted with DCM (30 mL and H₂O) and transferred to a separatory funnel. The pH was adjusted to pH-12 with NH₄OH and extracted 3 times with 20 mL DCM. The organics were combined and dried over MgSO₄ and removed under reduced pressure to afford the crude N-oxide. The crude N-oxide (0.76 mmol, 1.0 eq) was dissolved in 10 mL dry ethanol and copper sulfate (II) pentahydrate was added (5.0 eq; 950 mg) and the solution was stirred at 65° C. for 16 hours after which the LCMS showed a complete reaction. The reaction mixture was diluted with 20 mL DCM and H₂O and the pH adjusted to ~12 with NH₄OH. The crude material was extracted 3 times with DCM and the organics were combined, dried over MgSO₄ and the volatiles removed under reduced pressure to give the crude desired product with LCMS purity >85% that was used as is in the following step.

Step 3: The material from Step 2 (150 mg, 0.19 mmol, 1.0 eq) was dissolved in dry DCM (1.4 ml) in a dry round bottom flask and pyridine (0.6 mL, 40.0 eq.) was added followed by [2,2,2-trifluoro-1-(trifluoromethyl)ethyl] sulfamate (Organic Letters, Vol. 23, 2021, pp 3373-3378) (1.2 eq, 0.57 mg, 0.23 mmol) upon which the solution was stirred at 40° C. for 24 hours after which the LCMS analysis indicated all starting material being consumed. The volatiles were removed under a stream of N₂ and the crude material was purified by reverse phase chromatography on a C18 column with a gradient of 1% AcOH in MeCN and H₂O. The fractions containing the desired product were combined, the pH was adjusted to pH-12 with NH₄OH and extracted 3 times with 50 mL DCM to give the desired product as a free base (105 mgs 64% yield).

Step 4: To a pressure vial was added the product from Step 3 (250 mg, 0.29 mmol, 1 eq) and N-propanol (4 mL) followed by addition piperidine (434 µl, 4.4 mmol, 15 eq). The reaction mixture was stirred at 75° C. for 16 hours. The reaction mixture was then concentrated under vacuum and the crude product was purified by reverse phase chromatography using a C18 column with a gradient of 1% AcOH in MeCN and H₂O. The fractions containing the desired product were lyophilized to give the desired product (C-17) as an acetate salt (58 mg, 20% yield).

Following this example, the alkyl group R⁰ on the core nitrogen can be varied by replacing acetaldehyde in the first step of the sequence by any other alkyl aldehyde such as but not limited to formaldehyde or propionaldehyde and others. The sequence can also be started from tulathromycin epoxide and the reductive amination step skipped so that R⁰═H. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

Preparation of a Cyclic Sulfamate Compound Example (D-2) of Formula (2-A1)

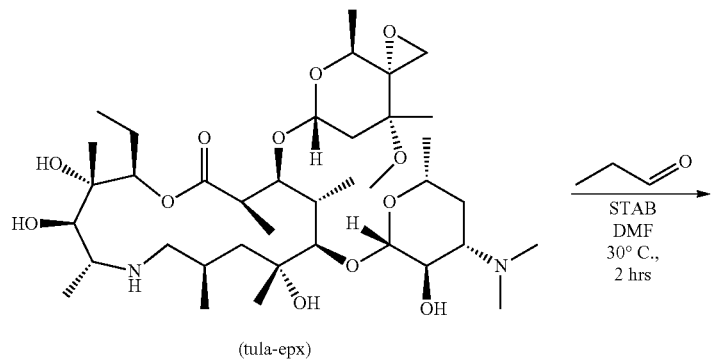

(tula-epx)

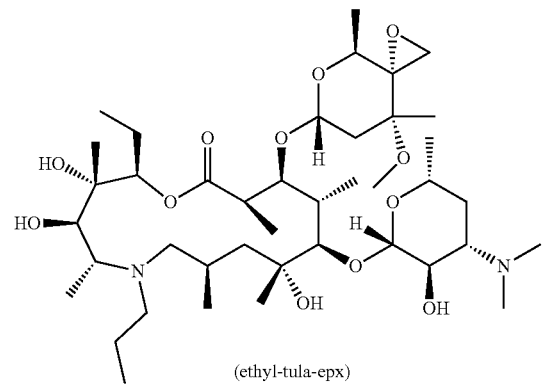

(ethyl-tula-epx)

1) Peracetic Acid
   RT, EtOH, 1 hr
2) CuSO₄
   65° C., ON

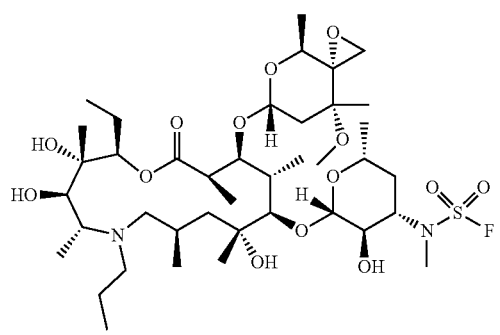

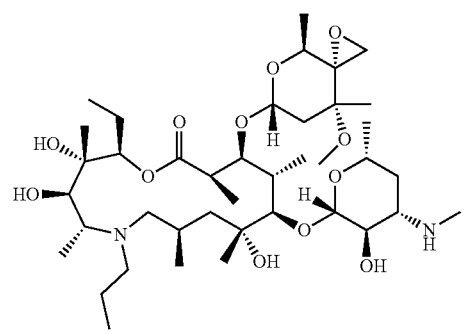

(ethyl-M9-epx)

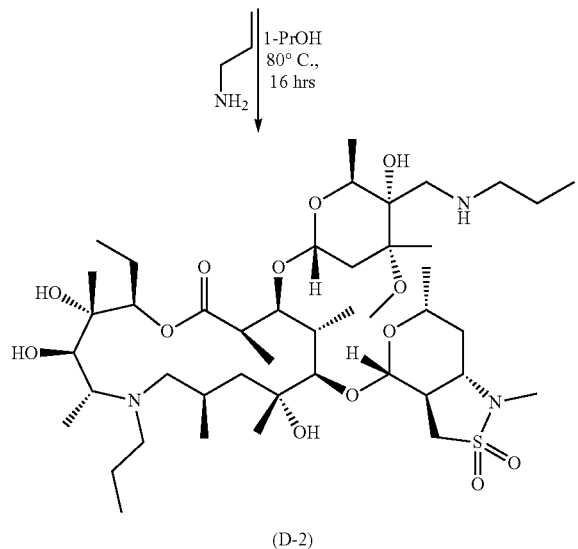

(D-2)

Step 1: To a solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (1.0 g, 1.34 mmol) and propionaldehyde (2.0 eq, 2.68 mmol) in dry DMF (10 mL) was added STAB (4.0 eq, 5.36 mmol) and the resulting solution was heated for 4 hours at 45° C. After consumption of the starting material as judged by LCMS, the reaction was cooled to 0° C. and 2 mL of a saturated solution of NH$_4$Cl was added and the solution stirred for 5 minutes. The reaction mixture was then diluted with DCM (30 mL and H$_2$O) and transferred to a separatory funnel. The pH was adjusted to pH-12 with NH$_4$OH and extracted 3 times with 20 mL DCM. The organics were combined and dried over MgSO$_4$ and removed under reduced pressure to afford the crude material that was purified by reverse phase chromatography on a C18 column with a gradient of 1% AcOH in MeCN and H$_2$O. The fractions containing the desired product were combined, the pH was adjusted to pH-12 with NH$_4$OH and extracted 3 times with 50 mL DCM to give the desired product as a free base (600 mgs, 57% yield).

Step 2: 590 mg of product from Step 1 (0.76 mmol, 1.00 eq) was dissolved in 10 mL dry EtOH and peracetic acid was added (32% dilute solution in acetic acid; 1.2 eq 192 µL). The resulting solution was stirred at room temperature for 45 minutes after which the LCMS showed a full conversion to the corresponding N-oxide. The reaction mixture was then diluted with DCM (30 mL and H$_2$O) and transferred to a separatory funnel. The pH was adjusted to pH-12 with NH$_4$OH and extracted 3 times with 20 mL DCM. The organics were combined and dried over MgSO$_4$ and removed under reduced pressure to afford the crude N-oxide. The crude N-oxide (0.76 mmol, 1.0 eq) was dissolved in 10 mL dry ethanol and copper sulfate (II) pentahydrate was added (5.0 eq; 950 mg) and the solution was stirred at 65° C. for 16 hours after which the LCMS showed a complete reaction. The reaction mixture was diluted with 20 mL DCM and H$_2$O and the pH adjusted to ~12 with NH$_4$OH. The crude material was extracted 3 times with DCM and the organics were combined, dried over MgSO$_4$ and the volatiles removed under reduced pressure to give the crude desired product with LCMS purity >85% that was used as is in the following step.

Step 3: The material from Step 2 (150 mg, 0.19 mmol, 1.0 eq) was dissolved in dry MeCN (1.5 ml) in a dry round bottom flask and. DIPEA (0.338 mL, 10.0 eq.) was added followed by 1-(Fluorosulfonyl)-2,3-dimethyl-1H-imidazol-3-ium trifluoromethanesulfonate (1.3 eq, 0.84 mg, 0.25 mmol) upon which the solution turned immediately orange. The reaction was stirred for 15 minutes at room temperature after which the LCMS analysis indicated all starting material being consumed. The volatiles were removed under a stream of N$_2$ and the crude material was purified by reverse phase chromatography on a C18 column with a gradient of 1% AcOH in MeCN and H$_2$O. The fractions containing the desired product were combined, the pH was adjusted to pH-12 with NH₄OH and extracted 3 times with 50 mL DCM to give the desired product as a free base (39 mgs 24% yield).

Step 4: To a pressure vial was added the product from Step 3 (39 mg, 0.046 mmol, 1 eq) and Ethanol (3 mL) followed by addition 1-propylamine (187 µl, 2.27 mmol, 50 eq). The reaction mixture was stirred at 75° C. for 6 hours upon which the LCMS analysis showed reaction completion. The reaction mixture was then concentrated under vacuum and the crude product was purified by reverse phase chromatography using a C18 column with a gradient of 1% AcOH in MeCN and H₂O. The fractions containing the desired product were lyophilized to give the desired product (D-2) as an acetate salt (20 mg, 49% yield).

Following this example, the alkyl group $R^0$ on the core nitrogen can be varied by replacing acetaldehyde in the first step of the sequence by any other alkyl aldehyde such as but not limited to formaldehyde or propionaldehyde. The sequence can also be started from tulathromycin epoxide and the reductive amination step skipped so that $R^0$=H. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

Formula (1-A1a) compounds shown in Table C can be made similarly to that shown above for Example C-54 under similar conditions by either varying the amine used in the fourth step to open the epoxide functional group or the sulfonamide or sulfamide forming reagent or the starting material and using (alkyl-tula-epx) as the starting material instead of tulathromycin epoxide as shown in the schemes herein.

The following Formula (1.1) compounds were prepared according to the schemes and procedures described herein; are shown in Table A. The respective Formula (1.1) compound names are provided below the table.

(1.1)

TABLE A

| | Formula (1.1) Compounds | | |
|---|---|---|---|
| Ex# | R | $R^2$ | Mass [M+H]⁺ |
| | $R^0$ and $R^1$ are methyl | | |
| A-1 | 4-methoxyphenyl | phenyl | 823 |
| A-2 | 3-CF₃, 4-fluorophenyl | phenyl | 879 |
| A-3 | phenyl | phenyl | 793 |
| | $R^0$ is H and $R^1$ is methyl | | |
| A-4 | phenyl | —NHphenyl | 794 |
| A-5 | 3-chloro, 4-CF₃phenyl | 3-chloro, 4-fluorophenyl | 934 |
| A-6 | 4-fluoro, 3-CF₃phenyl | 3-chloro, 4-fluorophenyl | 917 |
| A-7 | 3-chloro, 4-CF₃phenyl | phenyl | 881 |
| A-8 | 3,4-dimethoxyphenyl | phenyl | 839 |
| A-9 | 4-methoxyphenyl | phenyl | 809 |
| A-10 | 4-fluoro, 3-CF₃phenyl | phenyl | 865 |
| A-11 | H | 3-methoxyphenyl | 733 |
| A-12 | H | 2-methyl, 3-bromophenyl | 739 |
| A-13 | H | 3,4-difluorophenyl | 739 |
| A-14 | H | 3-chloro, 4-fluorophenyl | 755 |
| A-15 | H | 3-cyano, 4-fluorophenyl | 746 |
| A-16 | H | phenyl | 703 |
| A-17 | H | 4-fluorophenyl | 721 |
| A-18 | H | 2-nitrophenyl | 748 |
| A-19 | H | 4-nitrophenyl | 748 |
| A-20 | H | 4-methoxyphenyl | 733 |
| A-21 | 4-fluorophenyl | 4-(morpholin-4-yl)pyridin-2-yl substituent | 883 |
| A-22 | 4-fluorophenyl | thiophen-2-yl substituent | 803 |
| A-23 | 4-fluorophenyl | phenyl | 797 |

TABLE A-continued

Formula (1.1) Compounds

| Ex# | R | R² | Mass [M+H]⁺ |
|---|---|---|---|
| A-24 | 4-fluorophenyl | benzofuran-2-yl | 837 |
| A-25 | 4-fluorophenyl | 4-fluorophenyl | 815 |
| A-26* | 4-fluorophenyl | 4-methylthiazol-5-yl | 818 |
| A-27 | 4-fluorophenyl | 1-methylimidazol-2-yl | 801 |
| A-28 | 4-fluorophenyl | 6,7-dihydro-5H-pyrrolo[1,2-a]imidazol-3-yl | 827 |
| A-29 | 4-fluorophenyl | 6-chloropyridin-2-yl | 832 |
| A-30 | 4-fluorophenyl | 4-chlorophenyl | 831 |
| A-31 | 3-chloro, 4-CF₃phenyl | 1-methylimidazol-2-yl | 885 |
| A-32 | phenyl | cyclopropyl | 743 |
| A-33 | 4-fluorophenyl | 5-bromopyridin-2-yl | 877 |
| A-34 | 4-fluoro, 3-CFsphenyi | 1-methylimidazol-2-yl | 869 |
| A-35 | 3-chloro, 4-methoxyphenyl | 1-methylimidazol-2-yl | 848 |
| A-36 | 4-methoxyphenyl | —NHphenyl | 824 |
| A-37 | 4-fluorophenyl | —NHphenyl | 812 |

*MIC ≤64 μg/mL for at least one BRD pathogenic strain

Formula (1.1) Table A Example Names:

A-1. N-[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-(4-methoxyphenoxy)-6-methyloxan-4-yl]-N-methylbenzenesulfonamide;

A-2. N-((2S,3R,4S,6R)-2-(((2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-N-methylbenzenesulfonamide;

A-3. N-((2S,3R,4S,6R)-2-(((2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl)oxy)-6-methyl-3-phenoxytetrahydro-2H-pyran-4-yl)-N-methylbenzenesulfonamide;

A-4. (2R,3S,4R,5R,8R,10R,11R,12S,13S,14R)-2-ethyl-3,4,10,13-tetrahydroxy-3,5,8,10,12,14-hexamethyl-11-[(2R,3S,4R,6S)-6-methyl-4-[methyl(phenylsulfamoyl)amino]-3-phenoxyoxan-2-yl]oxy-15-oxo-1-oxa-6-azacyclopentadecane;

A-5. 3-chloro-N-((2S,3R,4S,6R)-3-(3-chloro-4-(trifluoromethyl)phenoxy)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyltetrahydro-2H-pyran-4-yl)-4-fluoro-N-methylbenzenesulfonamide;

A-6. 3-chloro-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-4-fluoro-N-methylbenzenesulfonamide;

A-7. N-((2S,3R,4S,6R)-3-(3-chloro-4-(trifluoromethyl)phenoxy)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

A-8. N-((2S,3R,4S,6R)-3-(3,4-dimethoxyphenoxy)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

A-9. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-methoxyphenoxy)-6-methyltetrahydro-2H-pyran-4-yl)-N-methylbenzenesulfonamide;

A-10. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-N-methylbenzenesulfonamide;

A-11. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-methoxy-N-methylbenzenesulfonamide;

A-12. 3-bromo-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N,2-dimethylbenzenesulfonamide;

A-13. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3,4-difluoro-N-methylbenzenesulfonamide;

A-14. 3-chloro-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-fluoro-N-methylbenzenesulfonamide;

A-15. 3-cyano-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-fluoro-N-methylbenzenesulfonamide;

A-16. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

A-17. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-fluoro-N-methylbenzenesulfonamide;

A-18. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-2-nitrobenzenesulfonamide;

A-19. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-nitrobenzenesulfonamide;

A-20. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-methoxy-N-methylbenzenesulfonamide;

A-21. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methyl-6-morpholinopyridine-3-sulfonamide;

A-22. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylthiophene-2-sulfonamide;

A-23. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylbenzenesulfonamide;

A-24. N-[(2S,3R,4S,6R)-2-[[(2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadec-11-yl]oxy]-3-(4-fluorophenoxy)-6-methyloxan-4-yl]-N-methyl-1-benzofuran-2-sulfonamide;

A-25. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-4-fluoro-N-methylbenzenesulfonamide A-26. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylthiazolyl-5-sulfonamide;

A-27. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N,1-dimethyl-1H-imidazole-2-sulfonamide;

A-28. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methyl-6,7-dihydro-5H-pyrrolo[1,2-a]imidazole-3-sulfonamide;

A-29. 6-chloro-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylpyridine-2-sulfonamide A-30. 4-chloro-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylbenzenesulfonamide;

A-31. N-((2S,3R,4S,6R)-3-(3-chloro-4-(trifluoromethyl)phenoxy)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyltetrahydro-2H-pyran-4-yl)-N,1-dimethyl-1H-imidazole-2-sulfonamide;

A-32. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyl-3-phenoxytetrahydro-2H-pyran-4-yl)-N-methylcyclopropanesulfonamide;

A-33. 5-bromo-N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylpyridine-2-sulfonamide;

A-34. N-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-N,1-dimethyl-1H-imidazole-2-sulfonamide;

A-35. N-((2S,3R,4S,6R)-3-(3-chloro-4-methoxyphenoxy)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-6-methyltetrahydro-2H-pyran-4-yl)-N,1-dimethyl-1H-imidazole-2-sulfonamide;

A-36. (2R,3S,4R,5R,8R,10R,11R,12S,13S,14R)-2-ethyl-3,4,10,13-tetrahydroxy-11-[(2R,3S,4R,6S)-3-(4-methoxy-phenoxy)-6-methyl-4-[methyl(phenylsulfamoyl)amino]oxan-2-yl]oxy-3,5,8,10,12,14-hexamethyl-15-oxo-1-oxa-6-azacyclopentadecane; and A-37. (2R,3S,4R,5R,8R,10R,11R,12S,13S,14R)-2-ethyl-11-[(2R,3S,4R,6S)-3-(4-fluorophenoxy)-6-methyl-4-[methyl(phenylsulfamoyl)amino]oxan-2-yl]oxy-3,4,10,13-tetrahydroxy-3,5,8,10,12,14-hexamethyl-15-oxo-1-oxa-6-azacyclopentadecane.

The following Formula (1-A1) compounds were prepared according to the schemes and procedures described herein and are shown in Table B. The respective compound names are provided below the table.

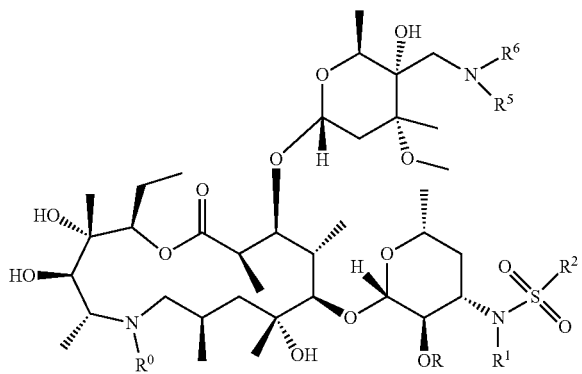

(1-A1)

For clarity, the substitution —NH-4-CF$_3$phenyl in the following tables is

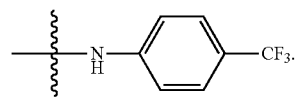

TABLE B

| | | Formula (1-A1) Compounds | | | |
|---|---|---|---|---|---|
| Ex # | R | R$^2$ | R$^5$ | R$^6$ | Mass [M + H]$^+$ |
| | | R$^0$ is H and R$^1$ is methyl | | | |
| B-1 | H | —CH$_2$CH$_2$OCH$_3$ | H | propyl | 914 |
| B-2* | H | 4-nitrophenyl | H | propyl | 977 |
| B-3 | H | cyclohexyl | H | propyl | 938 |

TABLE B-continued

Formula (1-A1) Compounds

| B-4 | H | [3,5-dimethylisoxazol-4-yl structure] | H | propyl | 951 |
| B-5 | H | [1,2-dimethylimidazol-4-yl structure] | H | propyl | 950 |
| B-6 | H | [6-fluoropyridin-3-yl structure] | H | propyl | 1001 |
| B-7 | H | phenyl | H | propyl | 932 |
| B-8 | H | propyl | H | propyl | 898 |
| B-9 | H | [thieno[3,2-b]pyridin-6-yl structure] | H | propyl | 989 |
| B-10 | H | [cyclopropylmethyl structure] | H | propyl | 910 |
| B-11 | H | [4-(methylsulfonyl)phenyl structure] | H | propyl | 1010 |
| B-12* | H | pyridin-3yl | H | propyl | 933 |
| B-13 | H | 4-cyanophenyl | H | propyl | 957 |
| B-14 | H | 4-CF₃pheny | H | propyl | 1000 |
| B-15 | H | [4-sulfamoylphenyl structure] | H | propyl | 1011 |
| B-16 | H | [1-methylimidazol-4-yl structure] | H | propyl | 936 |
| B-17 | H | [6-cyanopyridin-3-yl structure] | H | propyl | 958 |
| B-18 | H | 4-methoxyphenyl | H | propyl | 962 |
| B-19 | H | [4-(1H-pyrazol-1-yl)phenyl structure] | H | propyl | 998 |
| B-20 | H | 4-chlorophenyl | H | benzyl | 1015 |
| B-21 | H | 4-chlorophenyl | H | —(CH₂)₂CH(CH₃)₂ | 995 |
| B-22 | H | 4-chlorophenyl | H | cyclopentyl | 993 |
| B-23* | H | 4-chlorophenyl | H | cyclopropyl | 965 |

TABLE B-continued

Formula (1-A1) Compounds

| | | | | | |
|---|---|---|---|---|---|
| B-24 | H | 4-chlorophenyl | H |  | 979 |
| B-25 | H | 4-chlorophenyl | H | 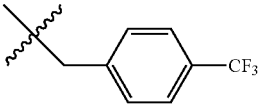 [SMILES: *Cc1ccc(C(F)(F)F)cc1] | 1083 |
| B-26 | H | 4-methylphenyl | H | propyl | 946 |
| B-27 | H | 4-chlorophenyl | H | 4-methoxyphenyl | 1031 |
| B-28 | H | 4-chlorophenyl | methyl | —$(CH_2)_2N(CH_3)_2$ | 1010 |
| B-29 | H | 4-chlorophenyl | H | 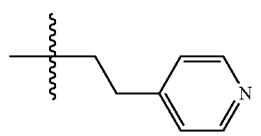 [SMILES: *CCc1ccncc1] | 1030 |
| B-30 | H | 4-chlorophenyl | H | 4-chlorophenyl | 1035 |
| B-31* | H | 4-chlorophenyl | H | 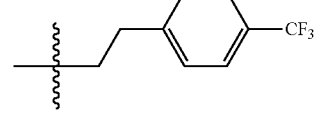 | 1097 |
| B-32 | H | 4-chlorophenyl | H | phenyl | 1001 |
| B-33 | H | 4-chlorophenyl | H | ethyl | 953 |
| B-34 | H | 4-chlorophenyl | H | 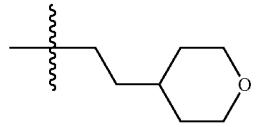 [SMILES: *CCC1CCOCC1] | 1037 |
| B-35 | H | 4-chlorophenyl | H | —$(CH_2)_2N(CH_3)_2$ | 996 |
| B-36 | H | 4-chlorophenyl | H | —$(CH_2)_2OCH_3$ | 983 |
| B-37 | H | 4-chlorophenyl | H | 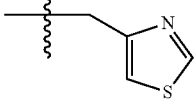 | 1022 |
| B-38 | H | 4-chlorophenyl | H | methyl | 939 |
| B-39 | H | 4-chlorophenyl | H | 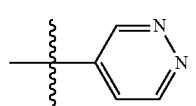 [SMILES: *c1ccnnc1] | 1003 |
| B-40* | H | —$NH(CH_2)_2$phenyl | H | propyl | 975 |
| B-41 | H | 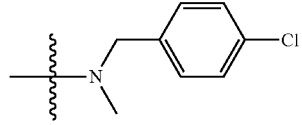 | H | propyl | 1010 |
| B-42 | H | 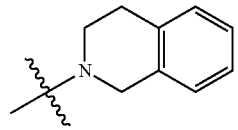 [SMILES: *N1CCc2ccccc2C1] | H | propyl | 987 |
| B-43 | H | —$CH_2CF_3$ | H | propyl | 953 |

TABLE B-continued

Formula (1-A1) Compounds

| B-44 | H | 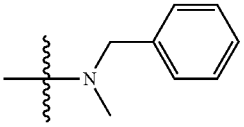 [SMILES: *N(C)Cc1ccccc1] | H | propyl | 975 |
| --- | --- | --- | --- | --- | --- |
| B-45 | H | 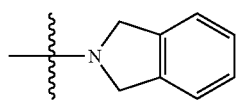 | H | propyl | 973 |
| B-46 | H | 4-chlorophenyl | H | pyridin-4yl | 1002 |
| B-47 | H | 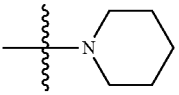 [SMILES: *N1CCCCC1] | H | propyl | 039 |
| B-48 | H | —NHphenyl | H | propyl | 947 |
| B-49 | H | 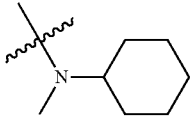 [SMILES: *N(C)C1CCCCC1] | H | propyl | 967 |
| B-50 | H | —NH-4-CF$_3$phenyl | H | propyl | 1015 |
| B-51 | H | —N(CH$_3$)$_2$ | H | propyl | 899 |
| B-52 | H | —NHCH$_2$phenyl | H | propyl | 961 |
| B-53 | H | —NH-4-fluorophenyl | H | propyl | 965 |
| B-54 | H | 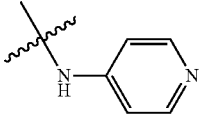 | H | propyl | 948 |
| B-55 | H | —NHCH$_3$ | H | propyl | 885 |
| B-56 | H | —NHcyclohexyl | H | propyl | 953 |
| B-57 | H | 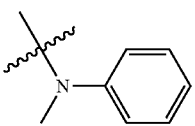 | H | propyl | 961 |
| B-58 | H | 4-chlorophenyl | H | 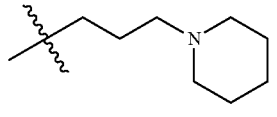 [SMILES: *CCCN1CCCCC1] | 1050 |
| B-59 | H | methyl | H | propyl | 870 |
| B-60 | H | 4-chlorophenyl | H | propyl | 967 |
| B-61 | H | 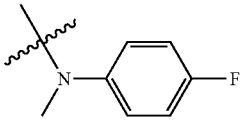 [SMILES: *N(C)c1ccc(F)cc1] | H | propyl | 979 |
| B-62 | H | 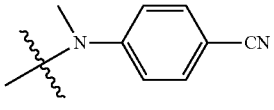 [SMILES: *N(C)c1ccc(C#N)cc1] | H | propyl | 986 |

TABLE B-continued

Formula (1-A1) Compounds

| | | | | | |
|---|---|---|---|---|---|
| B-63 | H | (cyclopropyl-NH-phenyl structure) | H | propyl | 987 |
| B-64 | H | —NH-4-CF$_3$phenyl | H | phenyl | 1049 |
| B-65* | H | —NH-4-CF$_3$phenyl | H | —(CH$_2$)$_2$CF$_3$ | 987 |
| B-66 | H | —NH-4-CF$_3$phenyl | H | (CH$_2$)$_2$-tetrahydropyran | 1085 |
| B-67 | H | —NH-4-CF$_3$phenyl | H | (CH$_2$)$_2$-cyclopropyl | 1041 |
| B-68 | H | —NH-4-CF$_3$phenyl | H | (CH$_2$)$_2$-pyrrolidinyl | 1070 |
| B-69 | H | —NH-4-CF$_3$phenyl | H | cyclohexyl | 1055 |
| B-70 | H | —NH-4-CF$_3$phenyl | H | cyclopropyl | — |
| B-71 | H | —NH-4-CF$_3$phenyl | H | —(CH$_2$)$_2$C(CH$_2$)$_3$ | 1057 |
| B-72 | H | —NH-4-CF$_3$phenyl | H | butyl | 1029 |
| B-73 | H | —NH-4-CF$_3$phenyl | H | —(CH$_2$)$_2$CH(CH$_3$)$_2$ | 1043 |
| B-74 | H | —NH-4-CF$_3$phenyl | H | —(CH$_2$)$_3$N(CH$_3$)$_2$ | 1058 |
| B-75 | H | —NH-4-CF$_3$phenyl | H | (CH$_2$)$_3$-piperidinyl | 1098 |
| B-76 | H | —NH-4-CF$_3$phenyl | H | methyl | 987 |
| B-77 | H | —NH-4-CF$_3$phenyl | H | ethyl | 1001 |
| B-78 | H | —NH-4-CF$_3$phenyl | H | —(CH$_2$)$_3$OCH$_3$ | 1045 |
| B79* | H | —NH-4-CF$_3$phenyl | H | CF | 1145 |
| B-80 | H | —NH-4-CF$_3$phenyl | H | cyclobutyl | 1027 |
| B-81 | H | —NH-4-CF$_3$phenyl | H | —(CH$_2$)$_2$NHC(O)CH$_3$ | 1058 |
| B-82 | H | —NH-4-CF$_3$phenyl | H | —(CH$_2$)N(CH$_3$)$_2$ | 1044 |
| B-83 | H | —NH-4-CF$_3$phenyl | H | —(CH$_2$)$_2$OCH$_2$CH$_3$ | 1045 |
| B-84 | H | —NH-4-CF$_3$phenyl | H | —(CH$_2$)$_2$OCH$_3$ | 1031 |
| B-85 | H | —NH-4-CF$_3$phenyl | H | —CH$_2$CH(CH$_3$)$_2$ | 1029 |
| B-86 | H | —NH-4-CF$_3$phenyl | H | CH$_2$-biphenyl | 1139 |
| B-87 | H | —NH-4-CF$_3$phenyl | H | (CH$_2$)$_3$-(2-oxopyrrolidinyl) | 1098 |
| B-88 | H | —NH-4-CF$_3$phenyl | H | (CH$_2$)$_3$NHC(O)CH$_3$ | 1072 |

TABLE B-continued

Formula (1-A1) Compounds

| | | | | | |
|---|---|---|---|---|---|
| B-89 | H | —NH-4-CF$_3$phenyl | H | 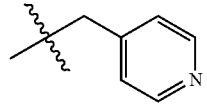 [SMILES: *Cc1ccncc1] | 1064 |
| B-90 | H | —NH-4-CF$_3$phenyl | H | benzyl | 1063 |
| B-91 | H | —NH-4-CF$_3$phenyl | H | —(CH$_2$)$_2$CH$_2$F | 1033 |
| B-92 | H | —NH-4-CF$_3$phenyl | H | —(CH$_2$)$_2$S(O)$_2$N(CH$_3$)$_2$ | 1108 |
| B-93 | 3,4-dimethoxy phenyl | phenyl | H | ethyl | 1040 |
| B-94 | 3,4-dimethoxy phenyl | phenyl | ethyl | —S(O)$_2$phenyl | 1180 |
| B-95 | 3-Cl, 4-CF$_3$ phenyl | phenyl | H | propyl | 1097 |
| B-96 | 3-Cl, 4-CF$_3$ phenyl | 3-Cl, 4-fluorophenyl | H | propyl | 1149 |
| B-97 | 3-Cl, 4-OMe phenyl | phenyl | H | propyl | 1059 |
| B-98 | 4-F, 3-CF$_3$ phenyl | 3-Cl, 4-fluorophenyl | H | propyl | 1133 |
| B-99 | 4-F, 3-CF$_3$ phenyl | phenyl | H | propyl | 1080 |
| B-100 | 4-F, 3-CF$_3$ phenyl | phenyl | propyl | —S(O)$_2$phenyl | 1220 |
| B-101 | 3-Cl, 4-OMe phenyl | 3-Cl, 4-fluorophenyl | H | propyl | 1111 |
| B-102 | 3,4-dimethoxy phenyl | 3-Cl, 4-fluorophenyl | H | propyl | 1107 |
| B-103 | 4-methoxy phenyl | 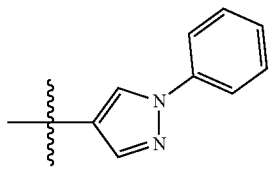 [SMILES: *c1cnn(-c2ccccc2)c1] | H | propyl | 1118 |
| B-104 | 4-methoxy phenyl | 4-bromophenyl | H | propyl | 1117 |
| B-105* | 4-methoxy phenyl | 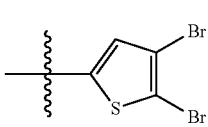 [SMILES: *c1cc(Br)c(Br)s1] | H | propyl | 1202 |
| B-106 | 4-fluorophenyl | 4-chlorophenyl | H | propyl | 1061 |
| B-107 | 4-fluorophenyl | 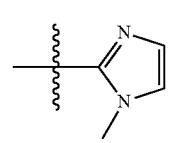 [SMILES: *c1nccn1C] | H | propyl | 1030 |
| B-108 | 4-fluorophenyl | 4-fluorophenyl | H | propyl | 1044 |
| B-109 | 4-fluorophenyl | phenyl | H | propyl | 1026 |
| B-110 | 2-F, 6-methyl phenyl | 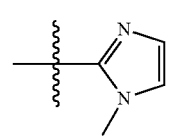 | H | propyl | 1044 |
| B-111 | 4-methoxy phenyl | 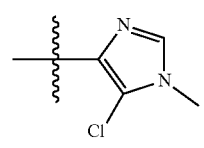 | H | propyl | 1077 |
| B-112 | H | 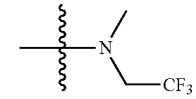 | H | propyl | 967 |

TABLE B-continued
Formula (1-A1) Compounds
| | | | | | |
|---|---|---|---|---|---|
| B-113 | H | 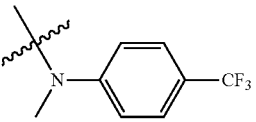 [SMILES: *N(C)c1ccc(C(F)(F)F)cc1] | H | propyl | 1029 |
| B-114 | 4-fluorophenyl | 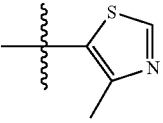 [SMILES: *c1scnc1C] | H | propyl | 1047 |
| B-115 | 4-fluorophenyl | 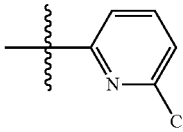 | H | propyl | 1062 |
| B-116* | 4-methoxy phenyl | 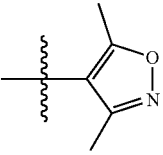 [SMILES: *c1c(C)noc1C] | H | propyl | 1057 |
| B-117 | 4-methoxy phenyl | 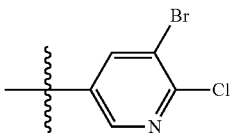 [SMILES: *c1cnc(Cl)c(Br)c1] | H | propyl | 1153 |
| B-118 | 4-methoxy phenyl | 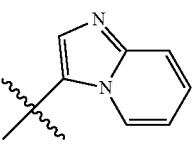 [SMILES: *c1cnc2ccccn12] | H | propyl | 1078 |
| B-119 | 4-methoxy phenyl | 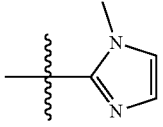 [SMILES: *c1nccn1C] | H | propyl | 1042 |
| B-120* | 4-methoxy phenyl | 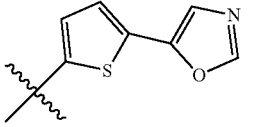 [SMILES: *c1ccc(-c2cnco2)s1] | H | propyl | 1111 |
| B-121 | 4-F, 2-methyl phenyl | 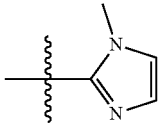 [SMILES: *c1nccn1C] | H | propyl | 1044 |
| B-122 | 3-cyano, 4-fluorophenyl | 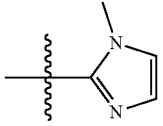 | H | propyl | 1055 |
| B-123 | 4-methoxy phenyl | 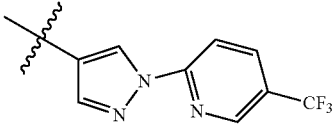 [SMILES: *c1cnn(-c2ccc(C(F)(F)F)cn2)c1] | H | propyl | 1173 |

TABLE B-continued
Formula (1-A1) Compounds
| B-124 | 4-methoxy phenyl | 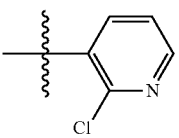 [SMILES: *c1cccnc1Cl] | H | propyl | 1074 |
|---|---|---|---|---|---|
| B-125 | H | —NH₂ | H | 4-methoxyphenyl | 935 |
| B-126 | H | 4-CF₃phenyl | H | —(CH₂)₂SO₂CH₃ | 1044 |
| B-127 | H | 4-CF₃phenyl | H | 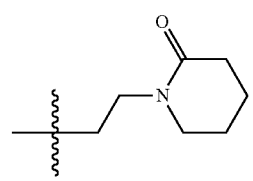 [SMILES: *CCN1CCCCC1=O] | 1083 |
| B-128 | H | —NH-4-CF₃phenyl | H | —(CH₂)₂SO₂phenyl | 1141 |
| B-129 | H | —NH-4-CF₃phenyl | H | —(CH₂)₂OCF₃ | 1085 |
| B-130 | pyridin-2-yl | phenyl | H | propyl | 1009 |
| B-131 | pyridin-2-yl | 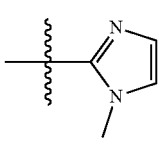 [SMILES: *c1nccn1C] | H | propyl | 1013 |
| B-132 | 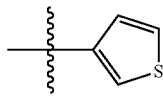 | 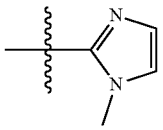 [SMILES: *c1nccn1C] | H | propyl | 1018 |
| B-133 | 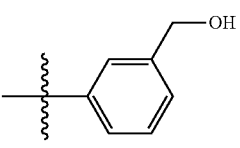 | phenyl | H | propyl | 1038 |
| B-134 | 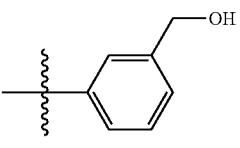 [SMILES: *c1cccc(CO)c1] | 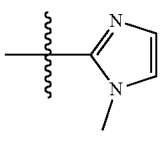 [SMILES: *c1nccn1C] | H | propyl | 1042 |
| B-135 | 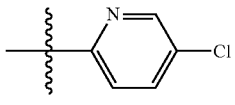 | phenyl | H | propyl | 1044 |
| B-136 | 4-chlorophenyl | 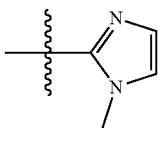 | H | propyl | 1047 |
| B-137 | 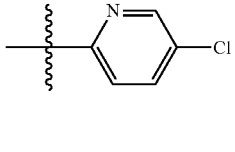 | 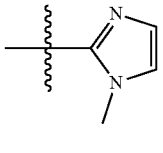 [SMILES: *c1nccn1C] | H | propyl | 1048 |

TABLE B-continued

Formula (1-A1) Compounds

| Ex # | R¹ | R² | R⁵ | R⁶ | Mass [M + H]⁺ |
|---|---|---|---|---|---|
| B-138 | 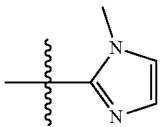 [SMILES: *c1nccn1C] | phenyl | H | propyl | 1070 |
| B-139 | 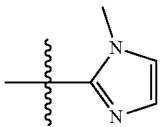 [SMILES: *c1nccn1C] | 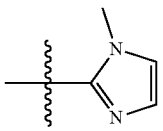 | H | propyl | 1074 |
| B-140 | H | —NH₂ | H | propyl | 871 |
| B-141 | 4-fluorophenyl | 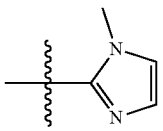 | H | benzyl | 1078 |

| Ex # | R¹ | R² | R⁵ | R⁶ | Mass [M + H]⁺ |
|---|---|---|---|---|---|
| R⁰ and R are H | | | | | |
| B-142 | propyl | 4-chlorophenyl | H | propyl | 995 |
| B-143 | benzyl | 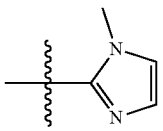 | H | propyl | 1012 |
| B-144 | benzyl | 4-methoxyphenyl | H | propyl | 1038 |
| B-145 | benzyl | phenyl | H | propyl | 1008 |
| B-146 | 4-methoxy benzyl | 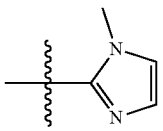 | H | propyl | 1042 |
| B-147 | 4-methoxy benzyl | 4-methoxyphenyl | H | propyl | 1068 |
| B-148 | 4-methoxy benzyl | phenyl | H | propyl | 1038 |
| B-149 | isobutyl | 4-methoxyphenyl | H | propyl | 1024 |
| B-150 | isobutyl | 4-chlorophenyl | H | propyl | 1028 |

| Ex # | R⁰ | R² | R⁵ | R⁶ | Mass [M + H]⁺ |
|---|---|---|---|---|---|
| R is H and R¹ is methyl | | | | | |
| B-151 | propyl | 4-chlorophenyl | H | propyl | 1008 |
| B-152 | ethyl | 4-chlorophenyl | H | propyl | 994 |
| B-153 | methyl | 4-chlorophenyl | H | propyl | 978 |
| B-154 | propyl | 4-methylphenyl | H | propyl | 988 |
| B-155 | ethyl | 4-methylphenyl | H | propyl | 974 |
| B-156 | methyl | 4-methylphenyl | H | propyl | 960 |
| B-157 | propyl | amino | H | 4-methoxyphenyl | 977 |
| B-158 | propyl | amino | H | propyl | 913 |
| B-159* | methyl | —NH-4-CF₃phenyl | H | propyl | 1049 |
| R is 4-fluorophenyl and R¹ is methyl | | | | | |
| B-160 | propyl | phenyl | H | propyl | 1068 |
| B-161* | ethyl | phenyl | H | propyl | 1054 |

TABLE B-continued

Formula (1-A1) Compounds

| B-162* | methyl | 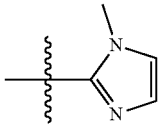 | H | propyl | 1064 |

*MIC ≤64 μg/mL for at least one BRD pathogenic strain

Formula (1-A1) Table B Example Names:

B-1. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-2-methoxy-N-methylethane-1-sulfonamide;

B-2. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-nitrobenzenesulfonamide;

B-3. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylcyclohexanesulfonamide;

B-4. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,3,5-trimethylisoxazole-4-sulfonamide;

B-5. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,1,2-trimethyl-1H-imidazole-4-sulfonamide;

B-6. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-6-fluoro-N-methylpyridine-3-sulfonamide;

B-7. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-8. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpropane-1-sulfonamide;

B-9. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylthieno[3,2-b]pyridine-6-sulfonamide;

B-10. 1-cyclopropyl-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylmethanesulfonamide;

B-11. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(methylsulfonyl)benzenesulfonamide;

B-12. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpyridine-3-sulfonamide;

B-13. 4-cyano-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-14. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(trifluoromethyl)benzenesulfonamide;

B-15. N1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N1-methylbenzene-1,4-disulfonamide;

B-16. N-((2S,3R,4S,6R)-2-(((2R,3S,4R,5R,8R,10R,11R,12S,13S,14R)-2-ethyl-3,4,10-trihydroxy-13-(((2R,4R,5S, 6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,1-dimethyl-1H-imidazole-4-sulfonamide;

B-17. 6-cyano-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpyridine-3-sulfonamide;

B-18. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-4-methoxy-N-methylbenzenesulfonamide;

B-19. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(1H-pyrazol-1-yl)benzenesulfonamide;

B-20. N-((2S,3R,4S,6R)-2-(((2R,3S,4R,5R,8R,10R,11R,12S,13S,14R)-13-(((2R,4R,5S,6S)-5-((benzylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;

B-21. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-5-((isopentylamino)methyl)-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-22. 4-chloro-N-((2S,3R,4S,6R)-2-(((2R,3S,4R,5R,8R,10R,11R,12S,13S,14R)-13-(((2R,4R,5S,6S)-5-((cyclopentylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-23. 4-chloro-N-((2S,3R,4S,6R)-2-(((2R,3S,4R,5R,8R,10R,11R,12S,13S,14R)-13-(((2R,4R,5S,6S)-5-((cyclopropylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-24. 4-chloro-N-((2S,3R,4S,6R)-2-(((2R,3S,4R,5R,8R,10R,11R,12S,13S,14R)-13-(((2R,4R,5S,6S)-5-(((cyclopropylmethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-25. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)benzyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-26. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,4-dimethylbenzenesulfonamide;

B-27. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((4-methoxybenzyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-28. 4-chloro-N-((2S,3R,4S,6R)-2-(((2R,3S,4R,5R,8R,10R,11R,12S,13S,14R)-13-(((2R,4R,5S,6S)-5-(((2-(dimethylamino)ethyl)(methyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-29. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(pyridin-4-yl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-30. 4-chloro-N-((2S,3R,4S,6R)-2-(((2R,3S,4R,5R,8R,10R,11R,12S,13S,14R)-13-(((2R,4R,5S,6S)-5-(((4-chlorophenyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-31. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)phenethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-32. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((phenylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-33. 4-chloro-N-((2S,3R,4S,6R)-2-(((2R,3S,4R,5R,8R,10R,11R,12S,13S,14R)-2-ethyl-13-(((2R,4R,5S,6S)-5-((ethylamino)methyl)-5-hydroxy-4-methoxy-4,6-dimethyltetrahydro-2H-pyran-2-yl)oxy)-3,4,10-trihydroxy-3,5, 8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-34. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(tetrahydro-2H-pyran-4-yl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-35. 4-chloro-N-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-36. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((2-methoxyethyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-37. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((thiazol-4-ylmethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-38. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((methylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-39. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((pyridazin-4-ylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-40. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(2-phenylethylsulfamoyl)amino]oxan-2-yl]oxy-3,5,8,10,12,14-hexamethyl-15-oxo-1-oxa-6-azacyclopentadecane;

B-41. (2R,3S,4R,5R,8R,10R,11R,12S,13S,14R)-11-[(2S,3R,4S,6R)-4-[[(4-chlorophenyl)methyl-methylsulfamoyl]-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one;

B-42. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-3,4-dihydroisoquinoline-2(1H)-sulfonamide;

B-43. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(2,2,2-trifluoroethylsulfamoyl)amino]oxan-2-yl]oxy-3,5,8,10,12,14-hexamethyl-15-oxo-1-oxa-6-azacyclopentadecane;

B-44. (2R,3S,4R,5R,8R,10R,11R,12S,13S,14R)-11-[(2S,3R,4S,6R)-4-[[benzyl(methyl)sulfamoyl]-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one;

B-45. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylisoindoline-2-sulfonamide;

B-46. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((pyridin-4-ylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-47. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpiperidine-1-sulfonamide;

B-48. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(phenylsulfamoyl)amino]oxan-2-yl]oxy-3,5,8,10,12,14-hexamethyl-15-oxo-1-oxa-6-azacyclopentadecane;

B-49. (2R,3S,4R,5R,8R,10R,11R,12S,13S,14R)-11-[(2S,3R,4S,6R)-4-[[cyclohexyl(methyl)sulfamoyl]-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one;

B-50. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-51. (2R,3S,4R,5R,8R,10R,11R,12S,13S,14R)-11-[(2S,3R,4S,6R)-4-[dimethylsulfamoyl(methyl)amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one;

B-52. (2R,3S,4R,5R,8R,10R,11R,12S,13S,14R)-11-[(2S,3R,4S,6R)-4-[benzylsulfamoyl(methyl)amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadecane;

B-53. (2R,3S,4R,5R,8R,10R,11R,12S,13S,14R)-2-ethyl-11-[(2S,3R,4S,6R)-4-[(4-fluorophenyl)sulfamoyl-methylamino]-3-hydroxy-6-methyloxan-2-yl]oxy-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadecane;

B-54. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(pyridin-4-ylsulfamoyl)amino]oxan-2-yl]oxy-3,5,8,10,12,14-hexamethyl-15-oxo-1-oxa-6-azacyclopentadecane;

B-55. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(methylsulfamoyl)amino]oxan-2-yl]oxy-3,5,8,10,12,14-hexamethyl-15-oxo-1-oxa-6-azacyclopentadecane;

B-56. (2R,3S,4R,5R,8R,10R,11R,12S,13S,14R)-11-[(2S,3R,4S,6R)-4-[cyclohexylsulfamoyl(methyl)amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadecane;

B-57. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl[methyl(phenyl)sulfamoyl]amino]oxan-2-yl]oxy-3,5,8,10,12,14-hexamethyl-1-oxa-6-azacyclopentadecan-15-one;

B-58. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((3-(piperidin-1-yl)propyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-59. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylmethanesulfonamide;

B-60. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-61. (2R,3S,4R,5R,8R,10R,11R,12S,13S,14R)-2-ethyl-11-[(2S,3R,4S,6R)-4-[[(4-fluorophenyl)-methylsulfamoyl]-methylamino]-3-hydroxy-6-methyloxan-2-yl]oxy-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one;

B-62. 4-[[[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-methylsulfamoyl]-methylamino]benzonitrile;

B-63. 2-(cyclopropylamino)-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-N-methylbenzenesulfonamide;

B-64. (2R,3S,4R,5R,8R,10R,11R,12S,13S,14R)-13-[(2R,4R,5S,6S)-5-(anilinomethyl)-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-65. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(3,3,3-trifluoropropylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-66. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[[2-(oxan-4-yl)ethylamino]methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-67. (2R,3S,4R,5R,8R,10R,11R,12S,13S,14R)-13-[(2R,4R,5S,6S)-5-[(2-cyclopropylethylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-68. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(2-pyrrolidin-1-ylethylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-69. (2R,3S,4R,5R,8R,10R,11R,12S,13S,14R)-13-[(2R,4R,5S,6S)-5-[(cyclohexylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-70. (2R,3S,4R,5R,8R,10R,11R,12S,13S,14R)-13-[(2R,4R,5S,6S)-5-[(cyclopropylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-71. (2R,3S,4R,5R,8R,10R,11R,12S,13S,14R)-13-[(2R,4R,5S,6S)-5-[(3,3-dimethylbutylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl- 4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-72. (2R,3S,4R,5R,8R,10R,11R,12S,13S,14R)-13-[(2R,4R,5S,6S)-5-(butylaminomethyl)-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-73. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(3-methylbutylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-74. (2R,3S,4R,5R,8R,10R,11R,12S,13S,14R)-13-[(2R,4R,5S,6S)-5-[[3-(dimethylamino)propylamino]methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-75. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(3-piperidin-1-ylpropylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-76. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(methylaminomethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-77. (2R,3S,4R,5R,8R,10R,11R,12S,13S,14R)-2-ethyl-13-[(2R,4R,5S,6S)-5-(ethylaminomethyl)-5-hydroxy-4-methoxy-4,6-dimethyloxan-2-yl]oxy-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-78. 2R,3S,4R,5R,8R,10R,11R,12S,13S,14R)-2-ethyl-13-[(2R,4R,5S,6S)-5-(ethylaminomethyl)-5-hydroxy-4-methoxy-4,6-dimethyloxan-2-yl]oxy-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-79. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[[2-[4-(trifluoromethyl)phenyl]ethylamino]methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane B-80. (2R,3S,4R,5R,8R,10R,11R,12S,13S,14R)-13-[(2R,4R,5S,6S)-5-[(cyclobutylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-81. N-(2-(((((2S,3S,4R,6R)-6-(((2R,3S,4R,5R,8R,10R,11R,12S,13S,14R)-2-ethyl-3,4,10-trihydroxy-11-(((2S,3R,4S,6R)-3-hydroxy-6-methyl-4-(methyl(N-(4-(trifluoromethyl)phenyl)sulfamoyl)amino)tetrahydro-2H-pyran-2-yl)oxy)-3,5,8,10,12,14-hexamethyl-15-oxo-1-oxa-6-azacyclopentadecan-13-yl)oxy)-3-hydroxy-4-methoxy-2,4-dimethyltetrahydro-2H-pyran-3-yl)methyl)amino)ethyl)acetamide;

B-82. (2R,3S,4R,5R,8R,10R,11R,12S,13S,14R)-13-[(2R,4R,5S,6S)-5-[[2-(dimethylamino)ethylamino]methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-83. (2R,3S,4R,5R,8R,10R,11R,12S,13S,14R)-13-[(2R,4R,5S,6S)-5-[(2-ethoxyethylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-84. (2R,3S,4R,5R,8R,10R,11R,12S,13S,14R)-2-ethyl-3,4,10-trihydroxy-13-[(2R,4R,5S,6S)-5-hydroxy-4-methoxy-5-[(2-methoxyethylamino)methyl]-4,6-dimethyloxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-85. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(2-methylpropylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-86. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[[(4-phenylphenyl)methylamino]methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-87. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[[3-(2-oxopyrrolidin-1-yl)propylamino]methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-88. N-[3-[[(2S,3S,4R,6R)-6-[[(2R,3S,4R,5R,8R,10R,11R,12S,13S,14R)-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadec-13-yl]oxy]-3-hydroxy-4-methoxy-2,4-dimethyloxan-3-yl]methylamino]propyl]acetamide;

B-89. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[(pyridin-4-ylmethylamino)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-90. (2R,3S,4R,5R,8R,10R,11R,12S,13S,14R)-13-[(2R,4R,5S,6S)-5-[(benzylamino)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-91. (2R,3S,4R,5R,8R,10R,11R,12S,13S,14R)-2-ethyl-13-[(2R,4R,5S,6S)-5-[(3-fluoropropylamino)methyl]-5-hydroxy-4-methoxy-4,6-dimethyloxan-2-yl]oxy-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-92. 2-[[(2S,3S,4R,6R)-6-[[(2R,3S,4R,5R,8R,10R,11R,12S,13S,14R)-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadec-13-yl]oxy]-3-hydroxy-4-methoxy-2,4-dimethyloxan-3-yl]methylamino]-N,N-dimethylethanesulfonamide;

B-93. N-((2S,3R,4S,6R)-3-(3,4-dimethoxyphenoxy)-2-(((2R,3S,4R,5R,8R,10R,11R,12S,13S,14R)-2-ethyl-13-(((2R,4R,5S,6S)-5-((ethylamino)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

B-94. N-((2S,3R,4S,6R)-3-(3,4-dimethoxyphenoxy)-2-(((2R,3S,4R,5R,8R,10R,11R,12S,13S,14R)-2-ethyl-13-(((2R,4R,5S,6S)-5-((N-ethylphenylsulfonamido)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

B-95. N-((2S,3R,4S,6R)-3-(3-chloro-4-(trifluoromethyl)phenoxy)-2-(((2R,3S,4R,5R,8R,10R,11R,12S,13S,14R)-2-ethyl-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

B-96. 3-chloro-N-((2S,3R,4S,6R)-3-(3-chloro-4-(trifluoromethyl)phenoxy)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-4-yl)-4-fluoro-N-methylbenzenesulfonamide;

B-97. N-((2S,3R,4S,6R)-3-(3-chloro-4-methoxyphenoxy)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-4-yl)-N-methylbenzenesulfonamide;

B-98. 3-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-4-fluoro-N-methylbenzenesulfonamide;

B-99. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-(4-fluoro-3-(trifluoromethyl)phenoxy)-6-methyltetrahydro-2H-pyran-4-yl)-N-methylbenzenesulfonamide;

B-100. N-(((2S,3S,4R,6R)-6-(((2R,3S,4R,5R,8R,10R,11R,12S,13S,14R)-2-ethyl-11-(((2S,3R,4S,6R)-3-(4-fluoro-3-(trifluoromethyl)phenoxy)-6-methyl-4-(N-methylphenylsulfonamido)tetrahydro-2H-pyran-2-yl)oxy)-3,4,10-trihydroxy-3,5,8,10,12,14-hexamethyl-15-oxo-1-oxa-6-azacyclopentadecan-13-yl)oxy)-3-hydroxy-4-methoxy-2,4-dimethyltetrahydro-2H-pyran-3-yl)methyl)-N-propylbenzenesulfonamide;

B-101. 3-chloro-N-((2S,3R,4S,6R)-3-(3-chloro-4-methoxyphenoxy)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-4-yl)-4-fluoro-N-methylbenzenesulfonamide;

B-102. 3-chloro-N-((2S,3R,4S,6R)-3-(3,4-dimethoxyphenoxy)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-4-yl)-4-fluoro-N-methylbenzenesulfonamide;

B-103. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N,5-dimethyl-1-phenylpyrazole-4-sulfonamide;

B-104. 4-bromo-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methylbenzenesulfonamide;

B-105. 4,5-dibromo-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methylthiophene-2-sulfonamide;

B-106. 4-chloro-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N-methylbenzenesulfonamide;

B-107. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,1-dimethylimidazole-2-sulfonamide;

B-108. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-4-fluoro-N-methylbenzenesulfonamide;

B-109. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N-methylbenzenesulfonamide;

B-110. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(2-fluoro-6-methylphenoxy)-6-methyloxan-4-yl]-N,1-dimethylimidazole-2-sulfonamide;

B-111. 5-chloro-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N,1-dimethylimidazole-4-sulfonamide;

B-112. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[methyl(2,2,2-trifluoroethyl)sulfamoyl]amino]oxan-2-yl]oxy-3,5,8,10,12,14-hexamethyl-1-oxa-6-azacyclopentadecan-15-one;

B-113. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[methyl-[4-(trifluoromethyl)phenyl]sulfamoyl]amino]oxan-2-yl]oxy-3,5,8,10,12,14-hexamethyl-1-oxa-6-azacyclopentadecan-15-one;

B-114. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,4-dimethyl-1,3-thiazole-5-sulfonamide;

B-115. 6-chloro-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N-methylpyridine-2-sulfonamide;

B-116. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N,3,5-trimethyl-1,2-oxazole-4-sulfonamide;

B-117. 5-bromo-6-chloro-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methylpyridine-3-sulfonamide;

B-118. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methylimidazo[1,2-a]pyridine-3-sulfonamide;

B-119. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N,1-dimethylimidazole-2-sulfonamide;

B-120. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methyl-5-(1,3-oxazol-5-yl)thiophene-2-sulfonamide;

B-121. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-fluoro-2-methylphenoxy)-6-methyloxan-4-yl]-N,1-dimethylimidazole-2-sulfonamide;

B-122. N-[(2S,3R,4S,6R)-3-(3-cyano-4-fluorophenoxy)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyloxan-4-yl]-N,1-dimethylimidazole-2-sulfonamide;

B-123. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methyl-1-[5-(trifluoromethyl)pyridin-2-yl]pyrazole-4-sulfonamide;

B-124. 2-chloro-N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-(4-methoxyphenoxy)-6-methyloxan-4-yl]-N-methylpyridine-3-sulfonamide;

B-125. (2R,3S,4R,5R,8R,10R,11R,12S,13S,14R)-2-ethyl-3,4,10-trihydroxy-13-[(2R,4R,5S,6S)-5-hydroxy-methoxy-5-[(4-methoxyanilino)methyl]-4,6-dimethyl-oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-1-oxa-6-azacyclopentadecane;

B-126. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(methylsulfonyl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(trifluoromethyl)benzenesulfonamide;

B-127. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(2-oxopiperidin-1-yl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(trifluoromethyl)benzenesulfonamide;

B-128. (2R,3S,4R,5R,8R,10R,11R,12S,13S,14R)-13-[(2R,4R,5S,6S)-5-[[2-(benzenesulfonyl)ethylamino]methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-129. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-[[2-(trifluoromethoxy)ethylamino]-methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

B-130. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)-oxan-2-yl]oxy-3,5,8,10,12,14-hexamethyl-15-oxo-1-oxa-6-azacyclopentadec-11-yl]oxy]-6-methyl-3-pyridin-2-yloxyoxan-4-yl]-N-methylbenzenesulfonamide;

B-131. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)-oxan-2-yl]oxy-3,5,8,10,12,14-hexamethyl-15-oxo-1-oxa-6-azacyclopentadec-11-yl]oxy]-6-methyl-3-pyridin-2-yloxyoxan-4-yl]-N,1-dimethylimidazole-2-sulfonamide;

B-132. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyl-3-thiophen-3-yloxyoxan-4-yl]-N,1-dimethylimidazole-2-sulfonamide;

B-133. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-[3-(hydroxymethyl)phenoxy]-6-methyloxan-4-yl]-N-methylbenzenesulfonamide;

B-134. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-[3-(hydroxymethyl)phenoxy]-6-methyloxan-4-yl]-N,1-dimethylimidazole-2-sulfonamide;

B-135. N-[(2S,3R,4S,6R)-3-(5-chloropyridin-2-yl)oxy-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyloxan-4-yl]-N-methylbenzenesulfonamide;

B-136. N-[(2S,3R,4S,6R)-3-(4-chlorophenoxy)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyloxan-4-yl]-N,1-dimethylimidazole-2-sulfonamide;

B-137. N-[(2S,3R,4S,6R)-3-(5-chloropyridin-2-yl)oxy-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyloxan-4-yl]-N,1-dimethylimidazole-2-sulfonamide;

B-138. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyl-3-(3-methylsulfinylphenoxy)oxan-4-yl]-N-methylbenzenesulfonamide;

B-139. N-[(2S,3R,4S,6R)-2-[[(2R,3S,4R,5R,8R,10R,11R,12S,13S,14R)-2-ethyl-3,4,10-trihydroxy-13-[(4S,5R,6R)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-6-methyl-3-(3-methylsulfinylphenoxy)oxan-4-yl]-N,1-dimethylimidazole-2-sulfonamide;

B-140. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-1-oxa-6-azacyclopentadecane;

B-141. N-((2S,3R,4S,6R)-2-(((2R,3S,4R,5R,8R,10R,11R,12S,13S,14R)-13-(((4S,5R,6R)-5-((benzylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N,1-dimethyl-1H-imidazole-2-sulfonamide;

B-142. 4-chloro-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-N-propylbenzenesulfonamide;

B-143. N-benzyl-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-1H-imidazole-2-sulfonamide;

B-144. N-benzyl-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-4-methoxybenzenesulfonamide;

B-145. N-benzyl-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6- azacyclopentadecan-11-yl)oxy)-3-hydroxy-6-methyltetrahydro-2H-pyran-4-yl)benzenesulfonamide;

B-146. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-(4-methoxybenzyl)-1-methyl-1H-imidazole-2-sulfonamide;

B-147. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-4-methoxy-N-(4-methoxybenzyl)benzenesulfonamide;

B-148. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-(4-methoxybenzyl)benzenesulfonamide;

B-149. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-isobutyl-4-methoxybenzenesulfonamide;

B-150. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-isobutylbenzenesulfonamide;

B-151. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-N-methylbenzenesulfonamide;

B-152. 4-chloro-N-((2S,3R,4S,6R)-2-(((2R,3S,4R,5R,8R,10R,11R,12S,13S,14R)-2,6-diethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

B-153. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-N-methylbenzenesulfonamide;

B-154. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-N,4-dimethylbenzenesulfonamide;

B-155. N-((2S,3R,4S,6R)-2-(((2R,3S,4R,5R,8R,10R,11R,12S,13S,14R)-2,6-diethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N,4-dimethylbenzenesulfonamide;

B-156. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-N,4-dimethylbenzenesulfonamide;

B-157. (2R,3S,4R,5R,8R,10R,11R,12S,13S,14R)-2-ethyl-3,4,10-trihydroxy-13-[(2R,4R,5S,6S)-5-hydroxy-4-methoxy-5-[(4-methoxyanilino)methyl]-4,6-dimethyl-oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-6-propyl-1-oxa-6-azacyclopentadecane;

B-158. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-6-propyl-1-oxa-6-azacyclopentadecane;

B-159. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-11-[(2S,3R,4S,6R)-3-hydroxy-6-methyl-4-[methyl-[[4-(trifluoromethyl)phenyl]sulfamoyl]-amino]oxan-2-yl]oxy-3,5,6,8,10,12,14-heptamethyl-15-oxo-1-oxa-6-azacyclopentadecane;

B-160. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-(4-fluorophenoxy)-6-methyltetrahydro-2H-pyran-4-yl)-N-methylbenzenesulfonamide;

B-161. N-((2S,3R,4S,6R)-2-(((2R,3S,4R,5R,8R,10R,11R,12S,13S,14R)-2,6-diethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-(4-fluorophenoxy)-6-methyltetrahydro-2H-pyran-4-yl)-N-methylbenzenesulfonamide; and B-162. N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-(4-fluorophenoxy)-6-methyltetrahydro-2H-pyran-4-yl)-N,1-dimethyl-1H-imidazole-2-sulfonamide.

The following Formula (1-A1a) compounds were prepared according to the schemes and procedures described herein, are presented in Table C. The respective compound names are provided below the table.

(1-A1a)

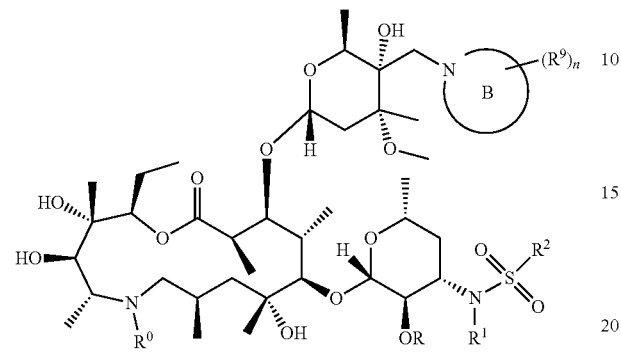

TABLE C

Formula (1-A1a) Compounds

| Ex# | $R^0$ | $R^2$ | Ring B ± $(R^9)_n$ | Mass $[M + H]^+$ |
|---|---|---|---|---|
| R is H and $R^1$ is methyl | | | | |
| C-1 | H | 4-chlorophenyl | morpholine | 995 |
| C-2 | H | 4-chlorophenyl | azetidine | 965 |
| C-3 | H | 4-chlorophenyl | pyrrolidine | 979 |
| C-4 | H | 4-chlorophenyl | piperidine | 993 |
| C-5 | H | 4-chlorophenyl | imidazolyl | 976 |
| C-6 | H | 4-chlorophenyl | thiomorpholine | 1011 |
| C-7 | H | 4-chlorophenyl | N-methylpiperazine | 1008 |
| C-8 | H | 4-chlorophenyl | pyrazolyl | 976 |
| C-9 | H | 4-chlorophenyl | tetrazolyl | 978 |
| C-10 | H | 4-chlorophenyl | tetrahydroisoquinoline | 1041 |
| C-11 | H | —NH-4-CF$_3$pheny | piperidine | 1041 |

TABLE C-continued

Formula (1-A1a) Compounds

| C-12 | H | —NH-4-CF₃phenyl | (piperazine-N-ethyl) | 1070 |
| C-13 | H | —NH-4-CF₃phenyl | (thiomorpholine-S,S-dioxide) | 1091 |
| C-14 | H | —NH-4-CF₃phenyl | (piperazine-N-isopropyl) | 1084 |
| C-15 | H | —NH-4-CF₃phenyl | (piperazine-N-SO₂CH₃) | 1120 |
| C-16 | H | amino | piperidine | 897 |
| C-17 | propyl | amino | piperidine | 939 |
| C-18 | H | 4-CF₃phenyl | piperidine | 1026 |
| C-19 | H | 4-fluorophenyl | piperidine | 976 |
| C-20 | ethyl | —NHphenyl | piperidine | 1001 |
| C-21 | propyl | —NHphenyl | piperidine | 1015 |
| C-22 | H | —NH-4-t-butylphenyl | piperidine | 1029 |
| C-23 | H | —NH-3-chlorophenyl | piperidine | 1008 |
| C-24* | H | —NH-3-fluorophenyl | piperidine | 991 |
| C-25* | H | —NH-3-di-methylamino | piperidine | 1016 |
| C-26* | H | —NH-3-methylphenyl | piperidine | 987 |
| C-27* | H | —NH-4-methoxyphenyl | piperidine | 1003 |
| C-28 | H | —NH-3,4-di-chlorophenyl | piperidine | 1042 |
| C-29 | H | —NH-4-bromophenyl | piperidine | 1052 |
| C-30 | H | —NH-4-iodophenyl | piperidine | 1099 |
| C-31 | H | —NH-4-chloro, 3-CF₃ phenyl | piperidine | 1076 |
| C-32 | H | —NH-4-methylphenyl | piperidine | 987 |
| C-33 | H | —NH-3,4-di-methylphenyl | piperidine | 1001 |
| C-34 | H | (HN-2-(1-methylimidazolyl)) | piperidine | 977 |
| C-35 | H | —N(CH₂CH₃)₂ | piperidine | 953 |
| C-36 | ethyl | —NH-4-CF₃phenyl | piperidine | 1069 |
| C-37 | H | —CH₂SO₂CH₃ | piperidine | 974 |
| C-38* | methyl | 4-chlorophenyl | piperidine | 1007 |

| Ex. # | $R^1$ | $R^2$ | Ring B ± $(R^9)_n$ | Mass [M + H]⁺ |
|---|---|---|---|---|

R and $R^0$ are both H

| C-39 | (3-pyridylmethyl) | —NH-4-CF₃phenyl | piperidine | 1118 |
| C-40 | propyl | 4-chlorophenyl | piperidine | 1021 |
| C-41 | propyl | 4-methoxyphenyl | piperidine | 1016 |
| C-42 | —CH₂CH(CH₃)₂ | 4-chlorophenyl | piperidine | 1035 |
| C-43 | —CH₂CH(CH₃)₂ | 4-methoxyphenyl | piperidine | 1030 |
| C-44 | —CH₂CH(CH₃)₂ | —NH-4-CF₃phenyl | piperidine | 1083 |
| C-45 | cyclohexyl | 4-trifluoromethylphenyl | piperidine | 1109 |

TABLE C-continued

Formula (1-A1a) Compounds

| Ex # | R | R² | Ring B ± (R⁹)ₙ | Mass [M + H]⁺ |
|---|---|---|---|---|
| C-46 | H | N-CH₂-thiazole, N-(4-CF₃-phenyl) | piperidine | 1180 |
| C-47 | methyl | 4-SF₅phenyl | piperidine | 1083 |

| Ex # | R | R² | Ring B ± (R⁹)ₙ | Mass [M + H]⁺ |
|---|---|---|---|---|

R⁰ is H; R¹ is methyl

| Ex # | R | R² | Ring B ± (R⁹)ₙ | Mass [M + H]⁺ |
|---|---|---|---|---|
| C-48 | 5-chloropyridin-2-yl | phenyl | piperidine | 1070 |
| C-49 | 2-fluoropyridin-4-yl | 1-methylimidazol-2-yl | piperidine | 1057 |
| C-50 | 4-methoxyphenyl | —NHphenyl | piperidine | 1079 |
| C-51 | 4-fluorophenyl | —NHphenyl | piperidine | 1067 |
| C-52 | phenyl | —NHphenyl | piperidine | 1049 |
| C-53 | phenyl | phenyl | piperidine | 1034 |
| C-54 | 4-fluorophenyl | phenyl | piperidine | 1052 |
| C-55 | 2-fluoropyridin-4-yl | phenyl | piperidine | 1053 |
| C-56 | 4-fluorophenyl | 1-methylimidazol-2-yl | piperidine | 1056 |

| Ex # | R⁰ | R² | Ring B ± (R⁹)ₙ | Mass [M + H]⁺ |
|---|---|---|---|---|

R and R¹ are H

| Ex # | R⁰ | R² | Ring B ± (R⁹)ₙ | Mass [M + H]⁺ |
|---|---|---|---|---|
| C-57* | methyl | —NH-4-CF₃phenyl | piperidine | 1055 |
| C-58* | propyl | —NH-4-CF₃phenyl | piperidine | 1083 |

*MIC ≤64 µg/mL for at least one BRD pathogenic strain

C-1. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(morpholinomethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-2. N-((2S,3R,4S,6R)-2-(((2R,3S,4R,5R,8R,10R,11R,12S,13S,14R)-13-(((2R,4R,5S,6S)-5-(azetidin-1-ylmethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;

C-3. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(pyrrolidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-4. 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10, 12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-5. N-((2S,3R,4S,6R)-2-(((2R,3S,4R,5R,8R,10R,11R,12S, 13S,14R)-13-(((2R,4R,5S,6S)-5-((1H-imidazol-1-yl)methyl)-5-hydroxy-4-methoxy-4,6-dimethyltetrahydro-2H-pyran-2-yl)oxy)-2-ethyl-3,4,10-trihydroxy-3,5,8,10, 12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;

C-6. 4-chloro-N-((2S,3R,4S,6R)-2-(((2R,3S,4R,5R,8R,10R, 11R,12S,13S,14R)-2-ethyl-3,4,10-trihydroxy-13-(((2R, 4R,5S,6S)-5-hydroxy-4-methoxy-4,6-dimethyl-5-(thiomorpholinomethyl)tetrahydro-2H-pyran-2-yl)oxy)-3,5, 8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-7. 4-chloro-N-((2S,3R,4S,6R)-2-(((2R,3S,4R,5R,8R,10R, 11R,12S,13S,14R)-2-ethyl-3,4,10-trihydroxy-13-(((2R, 4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-8. N-((2S,3R,4S,6R)-2-(((2R,3S,4R,5R,8R,10R,11R,12S, 13S,14R)-13-(((2R,4R,5S,6S)-5-((1H-pyrazol-1-yl)methyl)-5-hydroxy-4-methoxy-4,6-dimethyltetrahydro-2H-pyran-2-yl)oxy)-2-ethyl-3,4,10-trihydroxy-3,5,8,10, 12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;

C-9. N-((2S,3R,4S,6R)-2-(((2R,3S,4R,5R,8R,10R,11R,12S, 13S,14R)-13-(((2R,4R,5S,6S)-5-((1H-tetrazol-1-yl)methyl)-5-hydroxy-4-methoxy-4,6-dimethyltetrahydro-2H-pyran-2-yl)oxy)-2-ethyl-3,4,10-trihydroxy-3,5,8,10, 12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;

C-10. 4-chloro-N-((2S,3R,4S,6R)-2-(((2R,3S,4R,5R,8R, 10R,11R,12S,13S,14R)-13-(((2R,4R,5S,6S)-5-((3,4-dihydroisoquinolin-2(1H)-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;

C-11. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-12. (2R,3S,4R,5R,8R,10R,11R,12S,13S,14R)-2-ethyl-13-[(2R,4R,5S,6S)-5-[(4-ethylpiperazin-1-yl)methyl]-5-hydroxy-4-methoxy-4,6-dimethyloxan-2-yl]oxy-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-13. (2R,3S,4R,5R,8R,10R,11R,12S,13S,14R)-13-[(2R, 4R,5S,6S)-5-[(1,1-dioxo-1,4-thiazinan-4-yl)methyl]-5-hydroxy-4-methoxy-4,6-dimethyloxan-2-yl]oxy-2-ethyl-3,4,10-trihydroxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-14. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-[(4-propan-2-ylpiperazin-1-yl)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-15. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-[(4-methylsulfonylpiperazin-1-yl)methyl]oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-16. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-1-oxa-6-azacyclopentadecane;

C-17. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl(sulfamoyl)amino]oxan-2-yl]oxy-3,5,8,10,12,14-hexamethyl-15-oxo-6-propyl-1-oxa-6-azacyclopentadecane;

C-18. N-[(2S,3R,4S,6R)-2-[[(2R,3S,4R,5R,8R,10R,11R, 12S,13S,14R)-2-ethyl-3,4,10-trihydroxy-13-[(2R,4R,5S, 6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-N-methyl-4-(trifluoromethyl)benzenesulfonamide;

C-19. N-[(2S,3R,4S,6R)-2-[[(2R,3S,4R,5R,8R,10R,11R, 12S,13S,14R)-2-ethyl-3,4,10-trihydroxy-13-[(2R,4R,5S, 6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-4-fluoro-N-methylbenzenesulfonamide;

C-20. (2R,3S,4R,5R,8R,10R,11R,12S,13S,14R)-2,6-diethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl(phenylsulfamoyl)amino]-oxan-2-yl]oxy-3,5,8, 10,12,14-hexamethyl-15-oxo-1-oxa-6-azacyclopentadecane;

C-21. (2R,3S,4R,5R,8R,10R,11R,12S,13S,14R)-2-ethyl-3, 4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl(phenylsulfamoyl)amino]-oxan-2-yl]oxy-3,5,8, 10,12,14-hexamethyl-15-oxo-6-propyl-1-oxa-6-azacyclopentadecane;

C-22. (2R,3S,4R,5R,8R,10R,11R,12S,13S,14R)-11-[(2R, 3S,4R,6S)-4-[(4-tert-butylphenyl)sulfamoyl-methyl-amino]-3-hydroxy-6-methyloxan-2-yl]oxy-2-ethyl-3,4, 10-trihydroxy-13-[(2R,4R,5S,6S)-5-hydroxy-4-methoxy-4,6-dimethyl-5-(piperidin-1-ylmethyl)oxan-2-yl]oxy-3,5, 8,10,12,14-hexamethyl-15-oxo-1-oxa-6-azacyclopentadecane;

C-23. (2R,3S,4R,5R,8R,10R,11R,12S,13S,14R)-11-[(2R, 3S,4R,6S)-4-[(3-chlorophenyl)sulfamoyl-methylamino]-

3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)-oxan-2-yl]oxy-3,5,8,10,12,14-hexamethyl-15-oxo-1-oxa-6-azacyclopentadecane;

C-24. (2R,3S,4R,5R,8R,10R,11R,12S,13S,14R)-2-ethyl-11-[(2R,3S,4R,6S)-4-[(3-fluorophenyl)sulfamoyl-methylamino]-3-hydroxy-6-methyloxan-2-yl]oxy-3,4,10-trihydroxy-13-[(2R,4R,5S,6S)-5-hydroxy-4-methoxy-4,6-dimethyl-5-(piperidin-1-ylmethyl)-oxan-2-yl]oxy-3,5,8,10,12,14-hexamethyl-15-oxo-1-oxa-6-azacyclopentadecane;

C-25. (2R,3S,4R,5R,8R,10R,11R,12S,13S,14R)-11-[(2R,3S,4R,6S)-4-[[3-(dimethylamino)phenyl]sulfamoyl-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-26. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-hydroxy-6-methyl-4-[methyl-[(3-methylphenyl)sulfamoyl]-amino]oxan-2-yl]oxy-3,5,8,10,12,14-hexamethyl-15-oxo-1-oxa-6-azacyclopentadecane;

C-27. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-hydroxy-4-[(4-methoxyphenyl) sulfamoyl-methylamino]-6-methyloxan-2-yl]oxy-3,5,8,10,12,14-hexamethyl-15-oxo-1-oxa-6-azacyclopentadecane;

C-28. (2R,3S,4R,5R,8R,10R,11R,12S,13S,14R)-11-[(2R,3S,4R,6S)-4-[(3,4-dichlorophenyl)sulfamoyl-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)-oxan-2-yl]oxy-3,5,8,10,12,14-hexamethyl-15-oxo-1-oxa-6-azacyclopentadecane;

C-29. (2R,3S,4R,5R,8R,10R,11R,12S,13S,14R)-11-[(2R,3S,4R,6S)-4-[(4-bromophenyl)sulfamoyl-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-30. (2R,3S,4R,5R,8R,10R,11R,12S,13S,14R)-2-ethyl-3,4,10-trihydroxy-11-[(2R,3S,4R,6S)-3-hydroxy-4-[(4-iodophenyl)sulfamoyl-methylamino]-6-methyloxan-2-yl]oxy-13-[(2R,4R,5S,6S)-5-hydroxy-4-methoxy-4,6-dimethyl-5-(piperidin-1-ylmethyl)-oxan-2-yl]oxy-3,5,8,10,12,14-hexamethyl-15-oxo-1-oxa-6-azacyclopentadecane;

C-31. (2R,3S,4R,5R,8R,10R,11R,12S,13S,14R)-11-[(2R,3S,4R,6S)-4-[[4-chloro-3-(trifluoromethyl)phenyl]sulfamoyl-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-32. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-hydroxy-6-methyl-4-[methyl-[(4-methylphenyl)sulfamoyl]amino]oxan-2-yl]oxy-3,5,8,10,12,14-hexamethyl-15-oxo-1-oxa-6-azacyclopentadecane;

C-33. (2R,3S,4R,5R,8R,10R,11R,12S,13S,14R)-11-[(2R,3S,4R,6S)-4-[(3,4-dimethylphenyl)sulfamoyl-methylamino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-34. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-hydroxy-6-methyl-4-[methyl-[(1-methylimidazol-2-yl)sulfamoyl]amino]oxan-2-yl]oxy-3,5,8,10,12,14-hexamethyl-15-oxo-1-oxa-6-azacyclopentadecane;

C-35. (2R,3S,4R,5R,8R,10R,11R,12S,13S,14R)-11-[(2S,3R,4S,6R)-4-[diethylsulfamoyl(methyl)amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-1-oxa-6-azacyclopentadecan-15-one;

C-36. (2R,3S,4R,5R,8R,10R,11R,12S,13S,14R)-2,6-diethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]-sulfamoyl]amino]oxan-2-yl]oxy-3,5,8,10,12,14-hexamethyl-15-oxo-1-oxa-6-azacyclopentadecane;

C-37. N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-N-methyl-1-methylsulfonylmethanesulfonamide;

C-38. 4-chloro-N-((2S,3R,4S,6R)-2-(((2R,3S,4R,5R,8R,10R,11R,12S,13S,14R)-2-ethyl-3,4,10-trihydroxy-13-(((6R)-5-hydroxy-4-methoxy-4,6-dimethyl-5-(piperidin-1-ylmethyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-N-methylbenzenesulfonamide;

C-39. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[pyridin-3-ylmethyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-40. 4-chloro-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclo-pentadec-11-yl]oxy]-3-hydroxy-6-methyloxan-4-yl]-N-propylbenzenesulfonamide;

C-41. N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-4-methoxy-N-propylbenzenesulfonamide;

C-42. 4-chloro-N-cyclohexyl-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]benzenesulfonamide;

C-43. N-cyclohexyl-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-4-methoxybenzenesulfonamide;

C-44. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[2-methylpropyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

C-45. (2R,3S,4R,5R,8R,10R,11R,12S,13S,14R)-11-[(2S,3R,4S,6R)-4-[cyclohexyl-[[4-(trifluoromethyl)phenyl]sulfamoyl]amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-46. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[[1,3-thiazol-2-ylmethyl-[4-(trifluoromethyl)phenyl]sulfamoyl]amino]oxan-2-yl]oxy-3,5,8,10,12,14-hexamethyl-15-oxo-1-oxa-6-azacyclopentadecane, acetic acid;

C-47. N-((2S,3R,4S,6R)-2-(((2R,3S,4R,5R,8R,10R,11R,12S,13S,14R)-2-ethyl-3,4,10-trihydroxy-13-(((6R)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(pentafluoro-16-sulfanyl)benzenesulfonamide;

C-48. N-[(2S,3R,4S,6R)-3-(5-chloropyridin-2-yl)oxy-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-6-methyloxan-4-yl]-N-methylbenzenesulfonamide;

C-49. N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(2-fluoropyridin-4-yl)oxy-6-methyloxan-4-yl]-N,1-dimethylimidazole-2-sulfonamide;

C-50. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-(4-methoxyphenoxy)-6-methyl-4-[methyl(phenylsulfamoyl)amino]oxan-2-yl]oxy-3,5,8,10,12,14-hexamethyl-15-oxo-1-oxa-6-azacyclopentadecane;

C-51. (2R,3S,4R,5R,8R,10R,11R,12S,13S,14R)-2-ethyl-11-[(2R,3S,4R,6S)-3-(4-fluorophenoxy)-6-methyl-4-[methyl(phenylsulfamoyl)amino]oxan-2-yl]oxy-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

C-52. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-11-[(2R,3S,4R,6S)-6-methyl-4-[methyl(phenylsulfamoyl)amino]-3-phenoxyoxan-2-yl]oxy-15-oxo-1-oxa-6-azacyclopentadecane;

C-53. N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-6-methyl-3-phenoxyoxan-4-yl]-N-methylbenzenesulfonamide;

C-54. N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N-methylbenzenesulfonamide;

C-55. N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(2-fluoropyridin-4-yl)oxy-6-methyloxan-4-yl]-N-methylbenzenesulfonamide;

C-56. N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,1-dimethylimidazole-2-sulfonamide;

C-57. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,6,8,10,12,14-heptamethyl-15-oxo-1-oxa-6-azacyclopentadecane, acetic acid; and C-58. (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-6-propyl-1-oxa-6-azacyclopentadecane, acetic acid.

The following Formula (2-A1) compounds were prepared in accordance with the

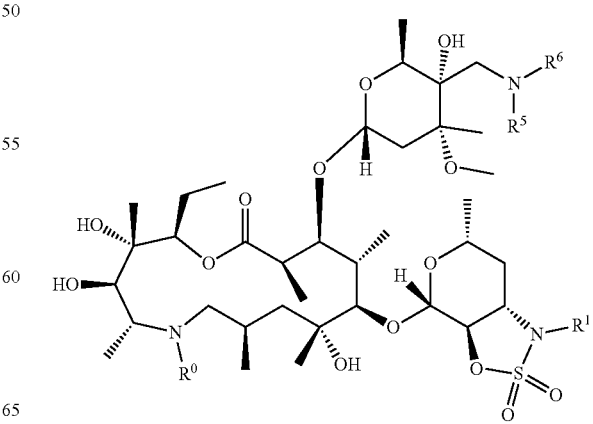

(2-A1)

schemes and procedures described herein, wherein $R^0$, $R^1$, $R^5$ and $R^6$ are as defined below in Table D; or $R^5$ and $R^6$ join together to Form Ring B, which is also defined below in Table D. The respective compound names are provided below the table.

TABLE D

Formula (2-A1) Compounds

| Example# | $R^0$ | $R^1$ | $R^5$ | $R^6$ | Mass $[M + H]^+$ |
|---|---|---|---|---|---|
| D-1 | H | methyl | H | propyl | 854 |
| D-2 | propyl | methyl | H | propyl | 896 |
| D-3 | propyl | 4-methoxybenzyl | H | propyl | 1002 |
| D-4 | H | 4-methoxybenzyl | H | propyl | 960 |

| Example# | $R^0$ | $R^1$ | Ring B | Mass $[M + H]^+$ |
|---|---|---|---|---|
| D-5 | H | methyl | piperidine | 880 |
| D-6 | propyl | methyl | piperidine | 922 |
| D-7 | H | 4-methoxybenzyl | piperidine | 986 |

Formula (2-A1) Table D Example Names:
D-1. (2R,3S,4R,5R,8R,10R,11R,12S,13S,14R)-11-[[(3aR,4S,6R,7aS)-1,6-dimethyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one; acetic acid;

D2. (2R,3S,4R,5R,8R,10R,11R,12S,13S,14R)-11-[[(3aR,4S,6R,7aS)-1,6-dimethyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-6-propyl-1-oxa-6-azacyclopentadecan-15-one; acetic acid;

D3. (2R,3S,4R,5R,8R,10R,11R,12S,13S,14R)-11-[[(3aR,4S,6R,7aS)-1-[(4-methoxyphenyl)methyl]-6-methyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-6-propyl-1-oxa-6-azacyclopentadecan-15-one; acetic acid;

D4. (2R,3S,4R,5R,8R,10R,11R,12S,13S,14R)-11-[[(3aR,4S,6R,7aS)-1-[(4-methoxyphenyl)methyl]-6-methyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-1-oxa-6-azacyclopentadecan-15-one; acetic acid;

D5. (2R,3S,4R,5R,8R,10R,11R,12S,13S,14R)-11-[[(3aR,4S,6R,7aS)-1,6-dimethyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-1-oxa-6-azacyclopentadecan-15-one; acetic acid;

D6. (2R,3S,4R,5R,8R,10R,11R,12S,13S,14R)-11-[[(3aR,4S,6R,7aS)-1,6-dimethyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-6-propyl-1-oxa-6-azacyclopentadecan-15-one; and D7. (2R,3S,4R,5R,8R,10R,11R,12S,13S,14R)-11-[[(3aR,4S,6R,7aS)-1-[(4-methoxyphenyl)methyl]-6-methyl-2,2-dioxo-4,6,7,7a-tetrahydro-3aH-pyrano[4,3-d]oxathiazol-4-yl]oxy]-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-1-oxa-6-azacyclopentadecan-15-one; acetic acid.

Example NMR's

A-1. $^1$H NMR (400 MHz, CHLOROFORM-d) δ ppm 0.36-1.25 (m, 23H) 1.27-2.13 (m, 17H) 2.16-2.67 (m, 7H) 3.36-3.62 (m, 4H) 3.69-3.84 (m, 1H) 4.03-4.32 (m, 2H) 4.49-4.71 (m, 1H) 4.78-5.00 (m, 1H) 6.42-6.74 (m, 3H) 6.48-6.72 (m, 2H) 7.25-7.52 (m, 2H) 7.58-7.80 (m, 2H);

A-2. $^1$H NMR (400 MHz, CHLOROFORM-d) δ ppm 0.31-1.54 (m, 25H) 1.59-2.14 (m, 10H) 2.25-2.73 (m, 2H) 3.43-3.68 (m, 3H) 3.80-3.92 (m, 1H) 4.14-4.33 (m, 1H) 4.53-4.71 (m, 1H) 4.84-5.00 (m, 1H) 6.76-7.07 (m, 3H) 6.78-6.97 (m, 2H) 7.25-8.08 (m, 5H) 7.30-7.58 (m, 3H) 7.35-7.56 (m, 3H) 7.58-7.85 (m, 2H);

A-3. $^1$H NMR (400 MHz, CHLOROFORM-d) δ ppm 0.29-1.67 (m, 32H) 1.70-2.14 (m, 5H) 2.39-2.98 (m, 6H) 3.52-3.76 (m, 3H) 3.82-4.27 (m, 3H) 4.62-5.07 (m, 4H) 4.98-5.13 (m, 1H) 6.54-6.83 (m, 3H) 6.88-7.10 (m, 2H) 7.24-7.51 (m, 3H) 7.71 (br d, J=7.82 Hz, 2H);

A-4. $^1$H NMR (400 MHz, DMSO-d6) δ ppm 0.8-1.5 (m, 32H), 1.6-2.0 (m, 11H) (including 2 units of acetate salt), 2.1-2.5 (m, 4H), 2.6-2.9 (m, 3H), 3.2-3.5 (m, 5H), 4.00-4.02 (m, 3H), 4.9-5.2 (m, 3H), 6.83-7.02 (m, 4H), 7.12-7.24 (m, 6H);

A-5. $^1$H NMR (400 MHz, CHLOROFORM-d) δ ppm 0.17-1.43 (m, 20H) 1.47-2.26 (m, 5H) 2.47-3.16 (m, 6H) 3.26-3.52 (m, 3H) 3.54-3.85 (m, 5H) 3.85-4.03 (m, 1H) 4.20-4.34 (m, 1H) 4.65-5.10 (m, 3H) 5.14-5.41 (m, 1H) 5.43-5.71 (m, 1H) 6.52-6.87 (m, 2H) 6.60-6.87 (m, 2H) 7.02-7.18 (m, 1H) 7.48 (s, 1H) 7.55-7.97 (m, 4H) 8.26-8.64 (m, 1H) 9.18-9.56 (m, 1H);

A-6. $^1$H NMR (400 MHz, CHLOROFORM-d) δ ppm 0.40-1.67 (m, 32H) 1.85-2.35 (m, 4H) 2.49-3.20 (m, 6H) 3.29-3.90 (m, 6H) 4.18-4.34 (m, 1H) 4.71-4.99 (m, 2H) 5.58-5.69 (m, 1H) 6.76-7.00 (m, 2H) 7.07-7.26 (m, 2H) 7.55-7.67 (m, 1H) 7.69-7.87 (m, 1H);

A-7. $^1$H NMR (400 MHz, CHLOROFORM-d) δ ppm −0.23-2.25 (m, 41H) 2.49-2.93 (m, 2H) 3.04-4.01 (m, 6H) 4.15-4.44 (m, 1H) 4.77-5.08 (m, 2H) 6.59-6.76 (m, 1H) 6.90-7.09 (m, 1H) 7.29-7.55 (m, 1H) 7.29-7.58 (m, 2H) 7.62-7.83 (m, 1H) 8.27-8.59 (m, 1H) 9.33-9.56 (m, 1H);

A-8. $^1$H NMR (400 MHz, CHLOROFORM-d) δ ppm 0.44-1.60 (m, 32H) 1.68-2.69 (m, 12H) 2.92-3.45 (m, 4H) 3.50-3.90 (m, 9H) 4.08-4.26 (m, 1H) 4.70-4.83 (m, 1H) 4.85-4.97 (m, 1H) 6.26-6.41 (m, 2H) 6.46-6.62 (m, 1H) 6.51-6.69 (m, 1H) 7.33-7.61 (m, 3H) 7.64-7.87 (m, 2H);

A-9. $^1$H NMR (400 MHz, CHLOROFORM-d) δ ppm 0.50-1.53 (m, 30H) 1.67-2.34 (m, 9H) 2.49-3.04 (m, 6H) 3.12-3.27 (m, 1H) 3.45 (d, J=2.20 Hz, 1H) 3.62-3.85 (m, 6H) 3.86-4.08 (m, 2H) 4.17-4.41 (m, 2H) 4.73-4.88 (m, 1H) 4.96 (d, J=7.58 Hz, 1H) 6.58-6.78 (m, 3H) 6.60-6.63 (m, 1H) 7.39-7.64 (m, 3H) 7.71-7.80 (m, 1H) 7.77-7.84 (m, 1H) 7.79-7.87 (m, 1H) 7.84-7.87 (m, 1H);

A-10. $^1$H NMR (400 MHz, CHLOROFORM-d) δ ppm 0.43-1.68 (m, 31H) 1.70-2.18 (m, 7H) 2.30-2.98 (m, 5H) 3.10-3.90 (m, 5H) 4.01-4.30 (m, 1H) 4.80-5.07 (m, 2H) 6.46-6.75 (m, 4H) 7.26-7.52 (m, 3H) 7.62-7.81 (m, 2H);

A-11. ¹H NMR (400 MHz, METHANOL-d4) δ ppm 0.69-1.87 (m, 38H), 2.00-2.18 (m, 6H), 2.39-2.73 (m, 5H), 2.86-3.61 (m, 3H), 3.62-4.01 (m, 4H) 6.98-7.11 (m, 1H) 7.18-7.46 (m, 3H);

A-12. ¹H NMR (400 MHz, METHANOL-d4) δ ppm 0.73-1.57 (m. 30H), 1.58-1.72 (m, 8H). 2.44-2.71 (m 8H), 3.03-3.20 (m, 1H) 3.22-3.28 (m, 2H) 3.43 (s, 1H) 3.50 (d, J=10.27 Hz, 2H) 3.61 (s, 1H) 3.74 (br d, J=3.67 Hz, 1H) 4.60 (br d, J=7.34 Hz, 2H) 7.10-7.14 (m, 1H) 7.71-7.75 (m, 1H) 7.90-7.97 (m, 1H);

A-13. ¹H NMR (400 MHz, METHANOL-d4) δ ppm 0.76-1.20 (m, 35H). 1.33-2.17 (m, 9H), 2.39-2.98 (m, 6H), 3.08-3.19 (m, 1H) 3.37 (s, 1H), 3.84 (td, J=11.07, 4.77 Hz, 1H) 7.30-7.33 (m, 1H) 7.62 (m, 1H) 7.68-7.81 (m, 1H);

A-14. ¹H NMR (400 MHz, METHANOL-d4) δ ppm 0.76-1.57 (m, 38H), 1.68-2.15 (m, 6H), 2.50-3.00 (m, 6H), 3.09-3.19 (m, 1H) 3.37 (s, 1H), 3.85 (br d, J=3.91 Hz, 1H) 7.29 (t, J=8.68 Hz, 1H) 7.72-7.77 (m, 1H), 7.91 (dd, J=6.60, 1.22 Hz, 1H);

A-15. ¹H NMR (400 MHz, METHANOL-d4) δ ppm 0.77-1.55 (m, 36H), 1.58-2.19 (m, 6H), 2.42-2.73 (m, 5H), 3.01 (br d, J=9.05 Hz, 1H) 3.08-3.21 (m, 1H) 3.39 (s, 1H), 3.72-3.95 (m, 4H) 4.59 (br d, J=7.34 Hz, 2H) 7.43 (t, J=8.80 Hz, 1H) 8.01-8.17 (m, 1H) 8.22 (m, 1H);

A-16. ¹H NMR (400 MHz, METHANOL-d4) δ ppm 0.81-1.47 (M, 32H), 1.57-2.24 (M, 9H), 2.56-3.02 (m, 5H), 3.07-3.19 (m, 2H) 3.41 (s, 1H) 3.50 (br d, J=10.27 Hz, 2H) 3.58 (s, 1H) 3.88 (br d, J=6.36 Hz, 1H) 7.41-7.54 (m, 3H) 7.78 (d, J=7.82 Hz, 2H);

A-17. ¹H NMR (400 MHz, METHANOL-d4) δ ppm 0.76-1.51 (m, 35H), 1.59-2.62 (m, 11H), 2.66-3.19 (m, 5H), 3.37 (s, 1H) 3.86 (td, J=10.94, 5.01 Hz, 1H) 7.16 (t, J=8.68 Hz, 2H) 7.83 (dd, J=8.44, 5.26 Hz, 2H);

A-18. ¹H NMR (400 MHz, METHANOL-d4) δ ppm 0.76-1.51 (m, 36H), 1.57-2.18 (m, 9H), 2.55-2.99 (m, 6H), 3.37 (s, 1H), 3.88 (br d, J=3.42 Hz, 1H) 7.59-7.70 (m, 3H) 8.08 (d, J=7.58 Hz, 1H);

A-19. ¹H NMR (400 MHz, METHANOL-d4) δ ppm 0.75-1.50 (m, 32H) 1.53-2.18 (m, 11H) 2.43-2.97 (br d, J=9.05 Hz, 6H) 3.12 (dd, J=10.03, 7.58 Hz, 1H) 3.21 (br d, J=0.98 Hz, 1H) 3.35 (s, 1H) 3.85 (td, J=11.19, 4.52 Hz, 1H) 7.99 (m, J=8.56 Hz, 2H) 8.25 (m, J=8.56 Hz, 2H);

A-20. ¹H NMR (400 MHz, METHANOL-d4) δ ppm 0.76-1.52 (m, 32H), 1.67-2.17 (m, 9H), 2.53-3.19 (m, 7H), 3.38 (s, 1H) 3.50 (d, J=14.18 Hz, 3H) 3.77 (s, 3H) 3.85 (td, J=10.82, 5.50 Hz, 1H) 6.94 (d, J=8.56 Hz, 2H) 7.70 (d, J=8.80 Hz, 2H);

A-21. ¹H NMR (400 MHz, CHLOROFORM-d) δ ppm 0.35-1.53 (m, 29H) 1.62-2.26 (m, 9H) 2.44-2.98 (m, 7H) 3.34-3.80 (m, 2H) 3.80-3.94 (m, 2H) 4.14-4.27 (m, 2H) 4.90-5.01 (m, 2H) 5.01-5.11 (m, 1H) 5.37-5.48 (m, 1H) 6.37-6.47 (m, 1H) 6.57-6.76 (m, 5H) 7.55-7.74 (m, 2H) 8.37-8.50 (m, 2H) 8.50-8.68 (m, 1H) 9.27-9.47 (m, 1H);

A-22. ¹H NMR (400 MHz, CHLOROFORM-d) δ ppm 0.41-1.40 (m, 25H) 1.51-2.25 (m, 12H) 2.34-3.00 (m, 6H) 3.22-3.93 (m, 3H) 4.15-4.25 (m, 1H) 4.84-5.08 (m, 2H) 5.34-5.55 (m, 1H) 6.57-7.02 (m, 5H) 7.32-7.56 (m, 2H) 8.29-8.65 (m, 2H) 9.25-9.57 (m, 1H);

A-23. ¹H NMR (400 MHz, CHLOROFORM-d) δ ppm 0.41-1.52 (m, 23H) 1.56-2.69 (m, 17H) 2.82-3.03 (m, 2H) 3.34-3.51 (m, 3H) 3.59-3.95 (m, 4H) 4.14-4.29 (m, 1H) 4.79-5.06 (m, 2H) 6.53-6.79 (m, 4H) 7.31-7.56 (m, 2H) 7.70-7.86 (m, 2H) 8.38-8.56 (m, 1H) 9.24-9.53 (m, 1H);

A-24. ¹H NMR (400 MHz, CHLOROFORM-d) δ ppm 0.35-1.56 (m, 30H) 1.69-2.29 (m, 4H) 2.35-3.08 (m, 7H) 3.28-4.02 (m, 3H) 4.09-4.37 (m, 2H) 4.77-5.10 (m, 3H) 5.35 (br s, 1H) 6.30-6.73 (m, 4H) 7.23 (s, 4H) 7.52-7.65 (m, 1H) 8.44-8.63 (m, 1H) 9.21-9.51 (m, 1H);

A-25. ¹H NMR (400 MHz, CHLOROFORM-d) δ ppm 0.51-1.47 (m, 24H) 1.56-2.11 (m, 11H) 2.11-2.56 (m, 6H) 2.87-4.06 (m, 1H) 4.08-4.45 (m, 3H) 4.56-4.92 (m, 3H) 4.98-5.22 (m, 1H) 5.33-5.53 (m, 1H) 6.39-6.99 (m, 4H) 7.32-7.54 (m, 2H) 7.62-7.78 (m, 2H) 8.63-8.96 (m, 1H) 9.38-9.65 (m, 1H);

A-26. ¹H NMR (400 MHz, CHLOROFORM-d) δ ppm 0.41-1.52 (m, 25H) 1.69-2.29 (m, 8H) 2.45-2.94 (m, 8H) 3.08-3.73 (m, 7H) 3.82-4.05 (m, 2H) 4.09-4.33 (m, 2H) 4.58-5.05 (m, 3H) 6.42-7.02 (m, 4H) 8.72-8.93 (m, 1H);

A-27. ¹H NMR (400 MHz, CHLOROFORM-d) δ ppm 0.49-1.68 (m, 30H) 1.78-2.16 (m, 5H) 2.43-2.84 (m, 6H) 3.11-3.48 (m, 4H) 3.47-3.75 (m, 3H) 3.75-3.91 (m, 4H) 4.15-4.30 (m, 1H) 4.71-4.82 (m, 1H) 4.88-5.01 (m, 1H) 6.73-7.06 (m, 6H);

A-28. ¹H NMR (400 MHz, CHLOROFORM-d) δ ppm 0.45-1.33 (m, 29H) 1.36-2.05 (m, 9H) 2.42-2.80 (m, 6H) 3.22 (br s, 2H) 3.40 (br s, 1H) 3.48-3.83 (m, 2H) 3.76-3.98 (m, 4H) 4.15-4.37 (m, 2H) 4.68-4.98 (m, 3H) 6.72-6.92 (m, 4H) 7.27-7.32 (m, 1H);

A-29. ¹H NMR (400 MHz, CHLOROFORM-d) δ ppm 0.48-1.75 (m, 29H) 1.96-2.05 (m, 1H) 2.00-2.91 (m, 6H) 3.27-3.52 (m, 5H) 3.54-3.74 (m, 3H) 3.75-4.12 (m, 4H) 4.23-4.35 (m, 1H) 4.69-4.91 (m, 2H) 5.03-5.13 (m, 1H) 6.60-6.68 (m, 2H) 6.71-6.86 (m, 4H) 7.68-7.84 (m, 1H);

A-30. ¹H NMR (400 MHz, CHLOROFORM-d) δ ppm 0.38-1.53 (m, 22H) 1.56-2.25 (m, 15H) 2.50-2.59 (m, 3H) 2.86-3.01 (m, 2H) 3.23-3.81 (m, 2H) 3.82-3.92 (m, 1H) 4.07-4.27 (m, 2H) 4.76-5.01 (m, 3H) 6.43-6.59 (m, 2H) 6.65-6.81 (m, 2H) 7.28-7.45 (m, 2H) 7.49-7.73 (m, 2H) 8.16-8.36 (m, 1H) 8.57-8.72 (m, 1H);

A-31. ¹H NMR (400 MHz, CHLOROFORM-d) δ ppm 0.41-1.56 (m, 30H) 1.80-2.61 (m, 15H) 2.63-3.01 (m, 1H) 3.16-3.22 (m, 1H) 3.35-3.53 (m, 1H) 3.48-3.64 (m, 1H) 3.69-3.78 (m, 3H) 3.84-4.09 (m, 1H) 4.34-4.50 (m, 1H) 4.94-5.15 (m, 1H) 6.71-6.84 (m, 1H) 6.86-6.97 (m, 1H) 6.97-7.10 (m, 1H) 7.11-7.20 (m, 2H);

A-32. ¹H NMR (400 MHz, CHLOROFORM-d) δ ppm 0.50-1.40 (m, 32H), 1.40-2.26 (m, 11H), 2.30-3.36 (m, 6H) 3.31-3.93 (m, 5H) 3.94-4.14 (m, 1H) 4.67-4.86 (m, 2H) 6.76-7.00 (m, 3H) 7.04-7.17 (m, 2H);

A-33. ¹H NMR (400 MHz, CHLOROFORM-d) δ ppm 0.04-1.34 (m, 29H), 1.39-2.20 (m, 16H), 2.52-3.02 (m, 4H) 3.39-4.01 (m, 2H) 4.19-4.37 (m, 1H) 4.70-5.03 (m, 3H) 6.45-6.62 (m, 2H) 6.66-6.85 (m, 2H) 7.65-7.80 (m, 1H) 7.85-7.95 (m, 1H) 8.28-8.46 (m, 1H);

A-34. ¹H NMR (400 MHz, CHLOROFORM-d) δ ppm 0.39-1.60 (m, 22H) 1.69-2.41 (m, 1H) 1.69-3.08 (m, 5H) 1.76-2.26 (m, 10H) 2.51-3.15 (m, 1H) 2.54-3.11 (m, 1H) 2.67-3.01 (m, 4H) 2.85-3.04 (m, 1H) 3.34-3.52 (m, 3H) 3.55-4.00 (m, 2H) 4.01-4.44 (m, 3H) 4.91-5.13 (m, 2H) 6.77-7.17 (m, 5H);

A-35. ¹H NMR (400 MHz, CHLOROFORM-d) δ ppm 0.32-1.47 (m, 30H), 1.46-2.73 (m, 7H) 2.75-3.50 (m, 4H) 3.58-3.84 (m, 2H) 3.87-4.06 (m, 1H) 4.13-4.28 (m, 1H) 4.84-5.10 (m, 1H) 5.10-5.22 (m, 1H) 6.96-7.17 (m, 3H) 7.24-7.44 (m, 1H) 7.45-7.60 (m, 1H);

A-36. ¹H NMR (400 MHz, DMSO-d6) δ ppm 0.8-1.5 (m, 32H), 1.6-2.0 (m, 9H) (including 1 unit of acetate salt), 2.1-2.5 (m, 4H), 2.6-2.9 (m, 3H), 3.2-3.5 (m, 4H), 3.6-3.8 (m, 5H), 4.0-4.3 (m, 2H), 4.9-5.2 (m, 3H), 6.86 (d, 2H, J=8.92 Hz), 7.00-7.04 (m, 1H), 7.13 (d, 2H, J=7.6 Hz), 7.24-7.28 (m, 2H);

A-37. $^1$H NMR (400 MHz, DMSO-d6) δ ppm 0.5-1.5 (m, 33H), 1.6-2.1 (m, 7H) (including 1 unit of acetate salt), 2.4-2.9 (m, 5H), 3.1-3.5 (m, 5H), 3.9-4.2 (m, 3H), 4.9-5.2 (m, 3H), 6.92-7.03 (m, 5H), 7.12 (d, 2H, J=7.92 Hz), 7.23-7.27 (m, 2H), 9.82 (bs, 1H);

B-1. $^1$H NMR (400 MHz, DMSO-d6) δ ppm 0.8-1.5 (m, 48H), 1.6-2.3 (m, 10H) (including 1 unit of acetate salt), 2.4-2.8 (m, 10H), 3.1-3.7 (m, 13H), 4.09 (s, 1H), 4.3-4.4 (m, 2H), 4.7-4.9 (m, 2H), 5.1-5.2 (m, 1H);

B-2. $^1$H NMR (400 MHz, DMSO-d6) δ ppm 0.8-1.5 (m, 48H), 1.6-2.3 (m, 12H) (including 2 units of acetate salt), 2.4-2.8 (m, 9H), 3.0-3.5 (m, 5H), 3.7-3.8 (m, 4H), 4.07 (s, 1H), 4.37-4.39 (m, 2H), 4.81-4.84 (m, 3H), 8.01 (d, 2H, J=8.64 Hz), 8.33 (d, 2H, J=8.64 Hz);

B-3. $^1$H NMR (400 MHz, DMSO-d6) δ ppm 0.8-1.5 (m, 54H), 1.6-2.3 (m, 14H) (including 2 units of acetate salt), 2.4-2.9 (m, 13H), 3.0-3.7 (m, 8H), 4.06 (bs, 1H), 4.40-4.41 (m, 2H), 4.82-4.86 (m, 2H), 5.1-5.2 (m, 1H);

B-4. $^1$H NMR (400 MHz, DMSO-d6) δ ppm 0.8-1.5 (m, 47H), 1.6-2.3 (m, 10H) (including 1 unit of acetate salt), 2.4-2.8 (m, 14H), 3.1-3.5 (m, 6H), 3.6-3.8 (m, 2H), 4.08 (s, 1H), 4.1-4.2 (bs, 1H), 4.36-4.40 (m, 2H), 4.81-4.85 (m, 2H), 4.99-5.01 (m, 1H);

B-5. $^1$H NMR (400 MHz, DMSO-d6) δ ppm 0.8-1.5 (m, 48H), 1.6-2.3 (m, 16H) (including 2 units of acetate salt), 2.4-2.8 (m, 10H), 3.1-3.3 (m, 4H), 3.4-3.5 (m, 4H), 3.6-3.9 (m, 2H), 4.12 (s, 1H), 4.40-4.43 (m, 2H), 4.82-4.87 (m, 2H), 5.18 (bs, 1H), 7.66 (s, 1H);

B-6. $^1$H NMR (400 MHz, DMSO-d6) δ ppm 0.8-1.5 (m, 47H), 1.6-2.3 (m, 12H) (including 2 units of acetate salt), 2.4-2.9 (m, 10H), 3.0-3.5 (m, 5H), 3.7-3.9 (m, 4H), 4.07 (s, 1H), 4.4-4.5 (m, 2H), 4.82-4.86 (m, 3H), 8.06 (d, 1H, J=8.28 Hz), 8.37 (d, 1H, J=8.32 Hz), 9.04 (s, 1H);

B-7. $^1$H NMR (400 MHz, DMSO-d6) δ ppm 0.8-1.5 (m, 48H), 1.6-2.3 (m, 12H) (including 2 units of acetate salt), 2.6-2.8 (m, 10H), 3.0-3.5 (m, 6H), 3.6-3.9 (m, 2H), 4.07 (s, 1H), 4.39-4.41 (m, 2H), 4.82-4.87 (m, 3H), 7.30-7.31 (m, 1H), 7.51-7.60 (m, 2H), 7.79 (d, 2H, J=7.48 Hz);

B-8. $^1$H NMR (400 MHz, DMSO-d6) δ ppm 0.8-1.5 (m, 46H), 1.6-2.2 (m, 16H) (including 2 units of acetate salt), 2.3-2.8 (m, 12H), 3.0-3.2 (m, 3H), 3.3-3.4 (m, 5H), 3.6-3.8 (m, 3H), 4.08 (s, 1H), 4.39-4.41 (m, 2H), 4.82-4.86 (m, 2H), 5.15-5.16 (m, 1H);

B-9. $^1$H NMR (400 MHz, DMSO-d6) δ ppm 0.8-1.5 (m, 44H), 1.6-2.3 (m, 12H) (including 2 units of acetate salt), 2.4-2.8 (m, 10H), 3.0-3.5 (m, 5H), 3.7-3.9 (m, 4H), 4.07 (s, 1H), 4.38-4.39 (m, 2H), 4.81-4.85 (m, 4H), 7.66 (d, 2H, J=5.32 Hz), 8.41 (d, 2H, J=5.4 Hz), 8.93 (s, 2H);

B-10. $^1$H NMR (400 MHz, DMSO-d6) δ ppm 0.2-0.3 (m, 2H), 0.5-0.6 (m, 2H), 0.8-1.5 (m, 50H), 1.6-2.2 (m, 12H) (including 2 units of acetate salt), 2.4-2.8 (m, 10H), 3.0-3.5 (m, 7H), 3.6-3.7 (m, 2H), 4.09 (s, 1H), 4.39-4.41 (m, 2H), 4.81-4.85 (m, 2H), 5.10 (m, 1H);

B-11. $^1$H NMR (400 MHz, DMSO-d6) δ ppm 0.8-1.5 (m, 48H), 1.6-2.3 (m, 9H) (including 1 unit of acetate salt), 2.4-2.8 (m, 10H), 3.1-3.3 (m, 5H), 3.4-3.9 (m, 4H), 4.06 (s, 1H), 4.20 (bs, 1H), 4.38-4.41 (m, 2H), 4.83-4.87 (m, 3H), 8.01 (d, 2H, J=8.48 Hz), 8.06 (d, 2H, J=8.48 Hz);

B-12. $^1$H NMR (400 MHz, DMSO-d6) δ ppm 0.8-1.5 (m, 46H), 1.6-2.3 (m, 10H) (including 1 unit of acetate salt), 2.4-2.8 (m, 9H), 3.1-3.5 (m, 5H), 3.6-3.9 (m, 3H), 4.08 (s, 1H), 4.20 (bs, 1H), 4.3-4.4 (m, 2H), 4.82-4.86 (m, 3H), 7.55-7.58 (m, 1H), 8.13 (d, 1H, J=8.04 Hz), 8.76 (d, 1H, J=3.84 Hz), 8.91 (s, 1H);

B-13. $^1$H NMR (400 MHz, DMSO-d6) δ ppm 0.8-1.5 (m, 44H), 1.6-2.3 (m, 14H) (including 2 units of acetate salt), 2.4-2.8 (m, 13H), 3.0-3.5 (m, 5H), 3.6-3.9 (m, 2H), 4.08 (s, 1H), 4.37-4.40 (m, 2H), 4.82-4.86 (m, 3H), 7.92 (d, 2H, J=8.32 Hz), 8.01 (d, 2H, J=8.32 Hz);

B-14. $^1$H NMR (400 MHz, DMSO-d6) δ ppm 0.8-1.5 (m, 46H), 1.6-2.3 (m, 9H) (including 1 unit of acetate salt), 2.4-2.9 (m, 9H), 3.0-3.5 (m, 6H), 3.7-3.9 (m, 4H), 4.09 (s, 1H), 4.4-4.5 (m, 2H), 4.81-4.85 (m, 3H), 7.90 (d, 2H, J=7.88 Hz), 7.98 (d, 2H, J=8.04 Hz);

B-15. $^1$H NMR (400 MHz, DMSO-d6) δ ppm 0.8-1.5 (m, 46H), 1.6-2.3 (m, 9H) (including 1 unit of acetate salt), 2.4-2.9 (m, 9H), 3.0-3.5 (m, 6H), 3.6-3.9 (m, 5H), 4.4-4.5 (m, 3H), 4.8-4.9 (m, 3H), 7.5-7.7 (bs, 1H), 7.93-7.98 (m, 4H);

B-16. $^1$H NMR (400 MHz, DMSO-d6) δ ppm 0.8-1.5 (m, 48H), 1.6-2.3 (m, 10H) (including 1 unit of acetate salt), 2.6-2.9 (m, 9H), 3.1-3.7 (m, 8H), 3.8-4.0 (m, 1H), 4.09 (s, 1H), 4.20 (bs, 1H), 4.4-4.5 (m, 2H), 4.84-4.87 (m, 2H), 5.11 (s, 1H), 7.56 (s, 1H), 7.79 (s, 1H);

B-17. $^1$H NMR (400 MHz, DMSO-d6) δ ppm 0.8-1.5 (m, 43H), 1.6-2.3 (m, 11H) (including 1 unit of acetate salt), 2.4-2.9 (m, 12H), 3.0-3.5 (m, 6H), 3.7-3.9 (m, 2H), 4.04 (s, 1H), 4.34-4.40 (m, 2H), 4.83-4.85 (m, 3H), 8.21 (d, 1H, J=8.16 Hz), 8.32 (dd, 1H, J=8.16 Hz, 2 Hz), 8.98 (d, 1H, J=1.6 Hz);

B-18. $^1$H NMR (400 MHz, DMSO-d6) δ ppm 0.8-1.5 (m, 46H), 1.6-2.3 (m, 10H) (including 1 unit of acetate salt), 2.4-2.9 (m, 12H), 3.0-3.5 (m, 5H), 3.6-3.9 (m, 6H), 4.09 (bs, 1H), 4.39-4.41 (m, 2H), 4.8-4.9 (m, 3H), 7.05 (d, 1H, J=8.76 Hz), 7.72 (d, 1H, J=8.76 Hz);

B-19. $^1$H NMR (400 MHz, DMSO-d6) δ ppm 0.8-1.5 (m, 43H), 1.6-2.3 (m, 10H) (including 1 unit of acetate salt), 2.4-2.8 (m, 10H), 3.1-3.5 (m, 5H), 3.6-3.9 (m, 2H), 4.09 (s, 1H), 4.40-4.42 (m, 2H), 4.82-4.87 (m, 3H), 6.61 (s, 1H), 7.82 (s, 1H), 7.89 (d, 2H, J=8.68 Hz), 8.01 (d, 2H, J=8.72 Hz), 8.64 (s, 1H);

B-20. $^1$H NMR (400 MHz, DMSO-d$_6$) δ ppm 0.77-1.5 (m, 39H), 1.7-2.3 (m, 18H) (including 2 unit of acetate salt), 2.4-2.8 (m, 6H), 3.13 (bs, 2H), 3.31-3.39 (m, 3H), 3.66-3.80 (m, 4H), 3.98 (bs, 1H), 4.16 (bs, 1H), 4.35-4.38 (m, 3H), 4.82-4.88 (m, 3H), 7.25-7.34 (m, 5H), 7.60 (d, 2H, J=8 Hz), 7.78 (d, 2H, J=8 Hz);

B-21. $^1$H NMR (400 MHz, DMSO-d$_6$) δ ppm 0.77-1.5 (m, 42H), 1.7-2.3 (m, 12H) (including 1 unit of acetate salt), 2.4-2.8 (m, 16H), 3.13 (bs, 1H), 3.69 (bs, 2H), 3.72-3.79 (m, 4H), 3.85 (s, 1H), 4.11 (bs, 1H), 4.38 (d, 2H, J=8 Hz), 4.81-4.84 (m, 2H), 7.60 (d, 2H, J=8 Hz), 7.78 (d, 2H, J=8 Hz);

B-22. $^1$H NMR (400 MHz, DMSO-d$_6$) δ ppm 0.77-1.5 (m, 39H), 1.7-2.3 (m, 18H) (including 3 unit of acetate salt), 2.4-2.8 (m, 13H), 3.13 (bs, 1H), 3.25-3.70 (m, 6H), 3.75-3.82 (bs, 4H), 4.07 (bs, 1H), 4.42-4.46 (m, 2H), 4.81-4.84 (m, 3H), 7.60 (d, 2H, J=8 Hz), 7.77 (d, 2H, J=8 Hz);

B-23. $^1$H NMR (400 MHz, DMSO-d$_6$) δ ppm 0.19-0.25 (m, 2H), 0.37 (bs, 2H), 0.77-1.5 (m, 35H), 1.7-2.3 (m, 12H) (including 1 unit of acetate salt), 2.4-2.8 (m, 8H), 3.13 (bs, 1H), 3.25-3.50 (m, 5H), 3.79 (bs, 1H), 3.80

(bs, 1H), 4.10-4.23 (m, 4H), 4.39 (bs, 1H), 4.49 (d, 2H, J=8 Hz), 4.82-4.84 (m, 3H), 7.60 (d, 2H, J=8 Hz), 7.78 (d, 2H, J=8 Hz);

B-24. $^1$H NMR (400 MHz, DMSO-d$_6$) δ ppm 0.08-0.10 (m, 2H), 0.39-0.42 (m, 2H), 0.77-1.5 (m, 37H), 1.7-2.3 (m, 15H) (including 1 unit of acetate salt), 2.4-2.8 (m, 8H), 3.13 (bs, 2H), 3.31-3.45 (m, 6H), 3.80 (bs, 1H), 3.98 (bs, 1H), 4.09 (bs, 1H), 4.38-4.40 (m, 2H), 4.81-4.87 (m, 2H), 7.60 (d, 2H, J=8 Hz), 7.78 (d, 2H, J=8 Hz);

B-25. $^1$H NMR (400 MHz, DMSO-d$_6$) δ ppm 0.77-1.5 (m, 40H), 1.7-2.3 (m, 15H) (including 2 unit of acetate salt), 2.4-2.8 (m, 9H), 3.08 (bs, 1H), 3.64 (bs, 2H), 3.72-3.86 (m, 4H), 4.09 (bs, 1H), 4.36-4.39 (m, 2H), 4.61-4.65 (m, 1H), 4.80-4.88 (m, 3H), 7.56-7.60 (m, 4H), 7.68 (d, 2H, J=8 Hz), 7.79 (d, 2H, J=8 Hz);

B-26. $^1$H NMR (400 MHz, DMSO-d6) δ ppm 0.76-1.19 (m, 32H) 1.27-1.48 (m, 7H) 1.62-1.81 (m, 2H) 1.86-1.95 (m, 6H) 2.00-2.07 (m, 1H) 2.12-2.19 (m, 1H) 2.35-2.39 (m, 3H) 2.56-2.70 (m, 9H) 2.79-2.84 (m, 1H) 3.06-3.13 (m, 1H) 3.30-3.32 (m, 3H) 3.41-3.51 (m, 2H) 3.61-3.73 (m, 1H) 3.78-3.89 (m, 1H) 4.07-4.14 (m, 1H) 4.36-4.45 (m, 2H) 4.77-4.90 (m, 3H) 7.28-7.41 (m, 2H) 7.59-7.76 (m, 2H);

B-27. $^1$H NMR (400 MHz, DMSO-d$_6$) δ ppm 0.77-1.5 (m, 38H), 1.7-2.3 (m, 18H) (including 3 unit of acetate salt), 2.4-2.8 (m, 6H), 3.13 (bs, 1H), 3.25-3.50 (m, 3H), 3.66 (s, 3H), 3.79 (bs, 1H), 3.85 (bs, 1H), 4.13 (bs, 1H), 4.37-4.47 (m, 3H), 4.83-4.86 (m, 2H), 4.97 (bs, 1H), 6.59 (d, 2H, J=8 Hz), 6.71 (d, 2H, J=8 Hz), 7.60 (d, 2H, J=8 Hz), 7.79 (d, 2H, J=8 Hz);

B-28. $^1$H NMR (400 MHz, DMSO-d$_6$) δ ppm 0.77-1.5 (m, 45H), 1.7-2.3 (m, 9H), 2.4-2.8 (m, 13H), 3.13 (bs, 1H), 3.20-3.47 (bs, 4H), 3.78-3.81 (bs, 3H), 4.06 (bs, 1H), 4.43-4.47 (m, 2H), 4.80-4.83 (m, 3H), 7.59 (d, 2H, J=8 Hz), 7.77 (d, 2H, J=8 Hz);

B-29. $^1$H NMR (400 MHz, DMSO-d$_6$) δ ppm 0.77-1.5 (m, 40H), 1.7-2.3 (m, 15H) (including 2 unit of acetate salt), 2.4-2.8 (m, 8H), 3.08 (bs, 1H), 3.28-3.31 (bs, 4H), 3.43 (bs, 2H), 3.64 (bs, 2H), 3.78 (bs, 1H), 4.08 (bs, 1H), 4.34-4.37 (m, 2H), 4.85 (bs, 3H), 7.24 (d, 2H, J=8 Hz), 7.60 (d, 2H, J=8 Hz), 7.78 (d, 2H, J=8 Hz), 8.43 (d, 2H, J=8 Hz);

B-30. $^1$H NMR (400 MHz, DMSO-d$_6$) δ ppm 0.77-1.5 (m, 38H), 1.7-2.3 (m, 12H) (including 1 unit of acetate salt), 2.4-2.8 (m, 6H), 3.13 (bs, 1H), 3.25-3.50 (m, 5H), 3.79 (bs, 1H), 3.85 (bs, 1H), 4.13 (bs, 1H), 4.33-4.49 (m, 2H), 4.61-4.65 (m, 1H), 4.79-4.86 (m, 2H), 4.97 (bs, 1H), 6.68 (d, 2H, J=8 Hz), 7.07 (d, 2H, J=8 Hz), 7.60 (d, 2H, J=8 Hz), 7.79 (d, 2H, J=8 Hz);

B-31. $^1$H NMR (400 MHz, DMSO-d$_6$) δ ppm 0.77-1.5 (m, 40H), 1.7-2.3 (m, 12H) (including 1 unit of acetate salt), 2.4-2.8 (m, 11H), 3.08 (bs, 1H), 3.64 (bs, 2H), 3.72-3.86 (m, 4H), 4.09 (bs, 1H), 4.36-4.39 (m, 2H), 4.61-4.65 (m, 1H), 4.83-4.85 (m, 3H), 7.44 (d, 2H, J=8 Hz), 7.58-7.63 (m, 4H), 7.79 (d, 2H, J=8 Hz);

B-32. $^1$H NMR (400 MHz, DMSO-d$_6$) δ ppm 0.77-1.5 (m, 38H), 1.7-2.3 (m, 18H) (including 2 unit of acetate salt), 2.4-2.8 (m, 6H), 3.13 (bs, 2H), 3.25-3.50 (m, 5H), 3.79 (bs, 1H), 3.85 (bs, 2H), 4.16 (bs, 1H), 4.37-4.49 (m, 2H), 4.83-4.85 (m, 3H), 4.97 (bs, 1H), 6.54 (t, 1H, J=8 Hz), 6.68 (d, 2H, J=8 Hz), 7.07 (d, 2H, J=8 Hz), 7.60 (d, 2H, J=8 Hz), 7.79 (d, 2H, J=8 Hz);

B-33. $^1$H NMR (400 MHz, DMSO-d$_6$) δ ppm 0.77-1.5 (m, 38H), 1.7-2.3 (m, 15H) (including 1 unit of acetate salt), 2.4-2.8 (m, 9H), 3.13 (bs, 1H), 3.25-3.50 (m, 5H), 3.79 (bs, 1H), 3.85 (bs, 2H), 4.10-4.23 (m, 4H), 4.39 (bs, 1H), 4.49 (d, 2H, J=8 Hz), 4.81-4.86 (m, 3H), 7.60 (d, 2H, J=8 Hz), 7.78 (d, 2H, J=8 Hz);

B-34. $^1$H NMR (400 MHz, DMSO-d$_6$) δ ppm 0.77-1.5 (m, 40H), 1.7-2.3 (m, 12H) (including 1 unit of acetate salt), 2.4-2.8 (m, 15H), 3.13 (bs, 1H), 3.25-3.70 (m, 7H), 3.75-3.82 (bs, 4H), 4.09 (bs, 1H), 4.38-4.40 (m, 2H), 4.81-4.86 (m, 3H), 7.60 (d, 2H, J=8 Hz), 7.77 (d, 2H, J=8 Hz);

B-35. $^1$H NMR (400 MHz, DMSO-d$_6$) δ ppm 0.77-1.5 (m, 42H), 1.7-2.3 (m, 18H) (including 3 unit of acetate salt), 2.4-2.8 (m, 15H), 3.13 (bs, 1H), 3.69 (bs, 2H), 3.72-3.79 (m, 4H), 3.85 (s, 1H), 4.11 (bs, 1H), 4.38 (d, 2H, J=8 Hz), 4.81-4.85 (m, 2H), 7.60 (d, 2H, J=8 Hz), 7.78 (d, 2H, J=8 Hz);

B-36. $^1$H NMR (400 MHz, DMSO-d$_6$) δ ppm 0.77-1.5 (m, 39H), 1.7-2.3 (m, 18H) (including 3 unit of acetate salt), 2.4-2.8 (m, 9H), 3.10 (bs, 1H), 3.25 (s, 3H), 3.69 (bs, 2H), 3.72-3.79 (m, 4H), 3.83 (s, 1H), 4.09 (bs, 1H), 4.38 (d, 2H, J=8 Hz), 4.81-4.85 (m, 2H), 7.60 (d, 2H, J=8 Hz), 7.78 (d, 2H, J=8 Hz);

B-37. $^1$H NMR (400 MHz, DMSO-d$_6$) δ ppm 0.77-1.5 (m, 35H), 1.7-2.3 (m, 15H) (including 2 unit of acetate salt), 2.4-2.8 (m, 12H), 3.13 (bs, 1H), 3.43 (bs, 2H), 3.64 (bs, 2H), 3.76-3.83 (m, 4H), 4.10 (bs, 1H), 4.35-4.37 (m, 3H), 4.81-4.86 (m, 2H), 7.49 (s, 1H), 7.60 (d, 2H, J=8 Hz), 7.78 (d, 2H, J=8 Hz), 9.05 (s, 1H);

B-38. $^1$H NMR (400 MHz, DMSO-d$_6$) δ ppm 0.77-1.5 (m, 38H), 1.7-2.3 (m, 15H) (including 2 unit of acetate salt), 2.4-2.8 (m, 8H), 3.13 (bs, 1H), 3.25-3.50 (m, 7H), 3.79 (bs, 1H), 3.85 (bs, 1H), 4.10 (bs, 1H), 4.39 (bs, 1H), 4.49 (d, 2H, J=8 Hz), 4.81-4.85 (m, 3H), 7.60 (d, 2H, J=8 Hz), 7.78 (d, 2H, J=8 Hz);

B-39. $^1$H NMR (400 MHz, DMSO-d$_6$) δ ppm 0.77-1.5 (m, 37H), 1.7-2.3 (m, 15H) (including 3 unit of acetate salt), 2.4-2.8 (m, 5H), 3.13 (bs, 2H), 3.25-3.50 (m, 4H), 3.85 (bs, 2H), 4.16 (bs, 1H), 4.37-4.61 (m, 5H), 4.83-4.85 (m, 3H), 4.97 (bs, 1H), 7.02 (bs, 1H), 7.60 (d, 2H, J=8 Hz), 7.79 (d, 2H, J=8 Hz), 8.45 (d, 2H, J=8 Hz);

B-40. $^1$H NMR (400 MHz, DMSO-d$_6$) δ ppm 0.5-1.5 (m, 39H), 1.7-2.3 (m, 18H) (including 3 units of acetate salt), 2.4-2.8 (m, 10H), 3.1-3.4 (m, 9H), 3.5-3.7 (m, 5H), 4.1 (s, 1H), 4.39-4.41 (m, 2H), 4.81-4.86 (m, 3H), 6.94 (brs, 1H), 7.15-7.26 (m, 5H);

B-41. $^1$H NMR (400 MHz, DMSO-d$_6$) δ ppm 0.5-1.5 (m, 39H), 1.7-2.3 (m, 12H) (including 1 unit of acetate salt), 2.4-2.8 (m, 10H), 3.1-3.4 (m, 8H), 3.5-3.7 (m, 5H), 4.1 (s, 1H), 4.24-4.25 (m, 2H), 4.40-4.44 (m, 2H), 4.81-4.87 (m, 2H), 7.34 (d, 2H, J=8 Hz), 7.41 (d, 2H, J=8 Hz);

B-42. $^1$H NMR (400 MHz, DMSO-d$_6$) δ ppm 0.5-1.5 (m, 40H), 1.7-2.3 (m, 10H), 2.4-2.8 (m, 10H), 3.1-3.4 (m, 9H), 3.5-3.7 (m, 5H), 4.1 (s, 1H), 4.32-4.41 (m, 4H), 4.79-4.84 (m, 2H), 5.13 (d, 1H, J=5 Hz), 7.10-7.14 (m, 4H);

B-43. $^1$H NMR (400 MHz, DMSO-d$_6$) δ ppm 0.5-1.5 (m, 40H), 1.7-2.3 (m, 16H) (including 2 units of acetate salt), 2.4-2.8 (m, 11H), 3.14-3.16 (m, 1H), 3.28-3.49 (m, 7H), 3.6-3.7 (m, 5H), 4.1 (s, 1H), 4.3-4.4 (m, 2H), 4.81-4.87 (m, 2H);

B-44. $^1$H NMR (400 MHz, DMSO-d$_6$) δ ppm 0.5-1.5 (m, 40H), 1.7-2.3 (m, 9H), 2.4-2.8 (m, 10H), 3.1-3.4 (m, 9H), 3.5-3.7 (m, 5H), 4.1 (s, 1H), 4.25-4.30 (m, 2H), 4.40-4.44 (m, 2H), 4.84-4.86 (m, 2H), 5.10 (d, 1H, J=5 Hz), 7.28-7.37 (m, 5H);

B-45. $^1$H NMR (400 MHz, DMSO-d$_6$) δ ppm 0.5-1.5 (m, 39H), 1.7-2.3 (m, 15H) (including 2 units of acetate salt), 2.4-2.8 (m, 10H), 3.1-3.4 (m, 8H), 3.5-3.7 (m, 4H), 4.1 (s, 1H), 4.39-4.42 (m, 2H), 4.56 (s, 4H), 4.81-4.83 (m, 2H), 5.10 (brs, 1H), 7.27 (s, 4H);
B-46. $^1$H NMR (400 MHz, DMSO-d$_6$) δ ppm 0.77-1.5 (m, 34H), 1.7-2.3 (m, 18H) (including 3 unit of acetate salt), 2.4-2.8 (m, 6H), 3.08 (bs, 1H), 3.29-3.40 (m, 5H), 3.79 (bs, 1H), 3.82-3.86 (m, 2H), 4.14 (bs, 1H), 4.28-4.32 (bs, 2H), 4.49-4.55 (m, 2H), 4.82-4.85 (m, 3H), 5.04 (bs, 1H), 6.83 (d, 2H, J=8 Hz), 7.59 (d, 2H, J=8 Hz), 7.77 (d, 2H, J=8 Hz), 8.18 (d, 2H, J=8 Hz);
B-47. $^1$H NMR (400 MHz, DMSO-d$_6$) δ ppm 0.5-1.5 (m, 44H), 1.7-2.3 (m, 9H), 2.4-2.8 (m, 12H), 3.1-3.4 (m, 9H), 3.5-3.7 (m, 5H), 4.1 (s, 1H), 4.2-4.4 (m, 3H), 4.81-4.97 (m, 3H);
B-48. $^1$H NMR (400 MHz, DMSO-d$_6$) δ ppm 0.5-1.5 (m, 40H), 1.7-2.3 (m, 16H) (including 2 units of acetate salt), 2.4-2.8 (m, 11H), 3.10-3.15 (m, 2H), 3.3-3.4 (m, 6H), 3.6-3.7 (m, 3H), 4.1 (s, 1H), 4.3-4.4 (m, 2H), 4.82-4.87 (m, 2H), 6.99 (t, 1H, J=7 Hz), 7.14-7.27 (m, 4H);
B-49. $^1$H NMR (400 MHz, DMSO-d$_6$) δ ppm 0.5-1.5 (m, 49H), 1.7-2.3 (m, 13H) (including 1 unit of acetate salt), 2.4-2.8 (m, 11H), 3.1-3.4 (m, 9H), 3.5-3.7 (m, 5H), 4.1 (s, 1H), 4.39-4.41 (m, 2H), 4.81-4.89 (m, 3H);
B-50. $^1$H NMR (400 MHz, DMSO-d$_6$) δ ppm 0.5-1.5 (m, 39H), 1.7-2.3 (m, 12H) (including 1 unit of acetate salt), 2.4-2.8 (m, 9H), 3.1-3.4 (m, 10H), 3.5-3.7 (m, 5H), 4.1 (s, 1H), 4.39-4.41 (m, 2H), 4.81-4.86 (m, 2H), 7.20 (d, 2H, J=8 Hz), 7.52 (d, 2H, J=8 Hz);
B-51. $^1$H NMR (400 MHz, DMSO-d$_6$) δ ppm 0.5-1.5 (m, 39H), 1.7-2.3 (m, 15H) (including 2 units of acetate salt), 2.4-2.8 (m, 14H), 3.1-3.4 (m, 9H), 3.5-3.7 (m, 5H), 4.1 (s, 1H), 4.39-4.41 (m, 2H), 4.81-4.84 (m, 2H), 5.07 (brs, 1H);
B-52. $^1$H NMR (400 MHz, DMSO-d$_6$) δ ppm 0.5-1.5 (m, 39H), 1.7-2.3 (m, 12H) (including 1 unit of acetate salt), 2.4-2.9 (m, 10H), 3.1-3.4 (m, 9H), 3.5-3.7 (m, 4H), 4.04-4.05 (m, 2H), 4.12 (s, 1H), 4.40-4.43 (m, 2H), 4.86-4.91 (m, 3H), 7.24-7.34 (m, 5H);
B-53. $^1$H NMR (400 MHz, DMSO-d$_6$) δ ppm 0.5-1.5 (m, 39H), 1.7-2.3 (m, 15H) (including 2 units of acetate salt), 2.4-2.8 (m, 10H), 3.1-3.4 (m, 9H), 3.5-3.7 (m, 5H), 4.1 (s, 1H), 4.39-4.42 (m, 2H), 4.81-4.85 (m, 2H), 7.03-7.07 (m, 4H);
B-54. $^1$H NMR (400 MHz, DMSO-d$_6$) δ ppm 0.5-1.5 (m, 39H), 1.7-2.3 (m, 15H) (including 2 units of acetate salt), 2.4-2.8 (m, 9H), 3.1-3.4 (m, 10H), 3.5-3.7 (m, 5H), 4.1 (s, 1H), 4.39-4.41 (m, 2H), 4.84-4.86 (m, 2H), 6.77 (d, 2H, J=4 Hz), 8.02 (brs, 2H);
B-55. $^1$H NMR (400 MHz, DMSO-d$_6$) δ ppm 0.5-1.5 (m, 39H), 1.7-2.3 (m, 18H) (including 3 units of acetate salt), 2.4-2.8 (m, 11H), 3.1-3.4 (m, 9H), 3.5-3.7 (m, 5H), 4.1 (s, 1H), 4.39-4.41 (m, 2H), 4.81-4.85 (m, 3H), 6.7 (brs, 1H);
B-56. $^1$H NMR (400 MHz, DMSO-d$_6$) δ ppm 0.5-1.5 (m, 49H), 1.7-2.3 (m, 13H) (including 1 unit of acetate salt), 2.4-2.8 (m, 8H), 3.1-3.4 (m, 9H), 3.5-3.7 (m, 5H), 4.1 (s, 1H), 4.38-4.40 (m, 2H), 4.81-4.89 (m, 3H), 6.74 (d, 1H, J=6 Hz);
B-57. $^1$H NMR (400 MHz, DMSO-d$_6$) δ ppm 0.5-1.5 (m, 39H), 1.7-2.3 (m, 18H) (including 3 units of acetate salt), 2.4-2.8 (m, 10H), 3.0-3.4 (m, 10H), 3.5-3.7 (m, 5H), 4.1 (s, 1H), 4.39-4.42 (m, 2H), 4.84-4.87 (m, 2H), 5.15 (brs, 1H), 7.23-7.25 (m, 1H), 7.31-7.39 (m, 4H);
B-58. $^1$H NMR (400 MHz, DMSO-d$_6$) δ ppm 0.77-1.5 (m, 47H), 1.7-2.3 (m, 18H) (including 3 unit of acetate salt), 2.4-2.8 (m, 17H), 3.13 (bs, 1H), 3.44 (bs, 1H), 3.70 (bs, 1H), 3.78 (bs, 1H), 3.85 (bs, 2H), 4.08 (bs, 1H), 4.41-4.44 (m, 2H), 4.81-4.84 (m, 3H), 7.60 (d, 2H, J=8 Hz), 7.78 (d, 2H, J=8 Hz);
B-59. $^1$H NMR (400 MHz, CHLOROFORM-d) δ 0.78-0.87 (m, 6H), 0.87-0.96 (m, 6H), 0.98-1.03 (m, 3H), 1.03-1.33 (m, 22H), 1.33-1.51 (m, 5H), 1.52-1.61 (m, 1H), 1.62-1.73 (m, 1H), 1.74-2.03 (m, 5H), 2.06-2.14 (m, 1H), 2.40-2.65 (m, 5H), 2.65-2.73 (m, 2H), 2.74-2.79 (m, 3H), 2.83-2.90 (m, 3H), 3.02-3.12 (m, 1H), 3.18-3.32 (m, 4H), 3.37-3.42 (m, 1H), 3.61-3.73 (m, 3H), 3.91-4.05 (m, 3H), 4.25-4.36 (m, 1H), 4.64 (s, 1H), 4.72-4.79 (m, 1H), 4.79-4.86 (m, 1H);
B-60. $^1$H NMR (400 MHz, DMSO-d6) δ ppm 0.8-1.5 (m, 48H), 1.6-2.3 (m, 6H), 2.6-2.8 (m, 8H), 3.0-3.4 (m, 5H), 3.44-3.46 (m, 1H), 3.6-3.9 (m, 2H), 4.08 (s, 1H), 4.39-4.41 (m, 2H), 4.82-4.86 (m, 3H), 7.60 (d, 2H, J=8.04 Hz), 7.78 (d, 2H, J=8 Hz);
B-61. $^1$H NMR (400 MHz, DMSO-d$_6$) δ ppm 0.5-1.5 (m, 39H), 1.7-2.3 (m, 15H) (including 2 units of acetate salt), 2.4-2.8 (m, 10H), 3.1-3.4 (m, 10H), 3.5-3.7 (m, 5H), 4.1 (s, 1H), 4.39-4.42 (m, 2H), 4.85-4.86 (m, 2H), 5.18 (d, 1H, 5 Hz), 7.15 (t, 2H, J=8.8 Hz), 7.41-7.45 (m, 2H);
B-62. $^1$H NMR (400 MHz, DMSO-d$_6$) δ ppm 0.5-1.5 (m, 39H), 1.7-2.3 (m, 18H) (including 3 units of acetate salt), 2.4-2.8 (m, 10H), 3.1-3.4 (m, 10H), 3.5-3.7 (m, 5H), 4.1 (s, 1H), 4.39-4.41 (m, 2H), 4.81-4.85 (m, 2H), 5.2 (brs, 1H), 7.54 (d, 2H, J=8 Hz), 7.77 (d, 2H, J=8 Hz);
B-63. $^1$H NMR (400 MHz, DMSO-d6) δ ppm 0.3-1.5 (m, 42H), 1.6-1.9 (m, 10H) (including 1 unit of acetate salt), 2.0-2.7 (m, 16H), 2.8-2.9 (m, 1H), 3.12 (bs, 2H), 3.4-3.5 (m, 5H), 3.6-3.9 (m, 3H), 4.09 (s, 1H), 4.3-4.4 (m, 2H), 4.8-4.9 (m, 2H), 5.07-5.08 (m, 1H), 6.43 (s, 1H), 6.6-6.7 (m, 1H), 7.11 (d, 1H, J=8.04 Hz), 7.4-7.5 (m, 1H), 7.58 (d, 1H, J=8 Hz);
B-64. $^1$H NMR (400 MHz, DMSO-d$_6$) δ ppm 0.77-1.5 (m, 35H), 1.6-2.5 (m, 16H) (including 2 unit of acetate salt), 2.6-2.8 (m, 9H), 3.1-3.28 (m, 4H), 3.47 (bs, 2H), 3.63 (bs, 2H), 3.79 (bs, 2H), 4.20 (bs, 1H), 4.36 (bs, 1H), 4.48 (bs, 1H), 4.82 (bs, 2H), 4.97 (bs, 1H) 6.54 (t, 1H, J=8 Hz), 6.62 (d, 2H, J=8 Hz), 6.81 (d, 2H, J=8 Hz), 7.06 (t, 2H, J=8 Hz), 7.24 (d, 2H, J=8 Hz);
B-65. $^1$H NMR (400 MHz, DMSO-d$_6$) δ ppm 0.77-1.5 (m, 35H), 1.6-2.1 (m, 12H) (including 1 unit of acetate salt), 2.4-2.9 (m, 13H), 3.1-3.25 (m, 6H), 3.43 (bs, 1H), 3.65 (bs, 2H), 3.75 (bs, 2H), 3.99 (bs, 1H), 4.37-4.42 (m, 3H), 4.83-4.88 (m, 2H), 7.30 (bs, 2H), 7.60 (bs, 2H);
B-66. $^1$H NMR (400 MHz, DMSO-d$_6$) δ ppm 0.77-1.5 (m, 45H), 1.6-2.4 (m, 13H) (including 1 unit of acetate salt), 2.6-2.8 (m, 17H), 3.05-3.19 (m, 2H), 3.42 (bs, 2H), 3.65 (bs, 1H), 3.80-3.84 (m, 2H), 4.02 (bs, 2H), 4.41 (bs, 2H), 4.88 (bs, 2H), 7.28 (bs, 2H), 7.60 (bs, 2H);
B-67. $^1$H NMR (400 MHz, DMSO-d$_6$) δ ppm 0.011 (bs, 2H), 0.36 (bs, 2H), 0.77-1.5 (m, 37H), 1.6-2.4 (m, 18H) (including 2 unit of acetate salt), 2.6-2.8 (m, 11H), 3.13 (bs, 2H), 3.2-3.35 (m, 2H), 3.45 (bs, 2H), 3.65 (bs, 2H), 3.75 (bs, 2H), 4.11 (bs, 1H), 4.38 (d, 2H, J=8 Hz), 4.84 (bs, 2H), 6.95 (bs, 2H), 7.33 (bs, 2H);
B-68. $^1$H NMR (400 MHz, DMSO-d$_6$) δ ppm 0.77-1.5 (m, 39H), 1.6-2.4 (m, 12H) (including 1 unit of acetate salt), 2.6-2.8 (m, 17H), 3.12 (bs, 1H), 3.13-3.47 (m, 5H), 3.32 (bs, 2H), 3.65 (bs, 1H), 3.79 (bs, 2H), 4.09 (bs, 1H), 4.39-4.41 (m, 3H), 4.81-4.84 (m, 2H), 7.16 (bs, 2H), 7.52 (bs, 2H);

B-69. ¹H NMR (400 MHz, DMSO-d₆) δ ppm 0.77-1.5 (m, 40H), 1.6-2.4 (m, 16H) (including 1 unit of acetate salt), 2.6-2.8 (m, 11H), 3.1-3.25 (m, 6H), 3.45 (bs, 1H), 3.65 (bs, 1H), 3.75 (bs, 2H), 4.09 (bs, 3H), 4.40 (d, 2H, J=8 Hz), 4.81-4.86 (m, 2H), 7.19 (bs, 2H), 7.50 (bs, 2H);

B-70. ¹H NMR (400 MHz, DMSO-d₆) δ ppm 0.19 (bs, 2H), 0.37 (bs, 2H), 0.77-1.5 (m, 35H), 1.6-2.4 (m, 12H) (including 1 unit of acetate salt), 2.6-2.8 (m, 9H), 3.13 (bs, 2H), 3.2-3.35 (m, 2H), 3.45 (bs, 2H), 3.63 (bs, 2H), 3.88 (bs, 3H), 4.08 (bs, 1H), 4.36-4.38 (m, 3H), 4.84 (bs, 3H), 7.21 (bs, 2H), 7.53 (bs, 2H);

B-71. ¹H NMR (400 MHz, DMSO-d₆) δ ppm 0.77-1.5 (m, 44H), 1.6-2.4 (m, 18H) (including 2 unit of acetate salt), 2.6-2.8 (m, 11H), 3.1-3.25 (m, 6H), 3.45 (bs, 2H), 3.65 (bs, 1H), 3.75 (bs, 2H), 4.09 (bs, 1H), 4.40 (d, 2H, J=8 Hz), 4.84 (bs, 2H), 7.16 (bs, 2H), 7.50 (bs, 2H);

B-72. ¹H NMR (400 MHz, DMSO-d₆) δ ppm 0.77-1.5 (m, 41H), 1.6-2.4 (m, 15H) (including 1 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 2H), 4.08 (bs, 1H), 4.40 (d, 2H, J=8 Hz), 4.86 (bs, 2H), 7.17 (bs, 2H), 7.51 (bs, 2H);

B-73. ¹H NMR (400 MHz, DMSO-d₆) δ ppm 0.77-1.5 (m, 43H), 1.6-2.4 (m, 15H) (including 1 unit of acetate salt), 2.6-2.8 (m, 11H), 3.13 (bt, 1H), 3.25-3.35 (m, 5H), 3.45 (bs, 1H), 3.65 (bs, 1H), 3.75 (bs, 2H), 4.08 (bs, 1H), 4.40 (d, 2H, J=8 Hz), 4.85 (bs, 2H), 7.19 (bs, 2H), 7.52 (bs, 2H);

B-74. ¹H NMR (400 MHz, DMSO-d₆) δ ppm 0.77-1.5 (m, 44H), 1.6-2.4 (m, 12H), 2.6-2.8 (m, 11H), 3.13 (bs, 1H), 3.2-3.35 (m, 5H), 3.45 (bs, 1H), 3.65 (bs, 1H), 3.78 (bs, 2H), 4.09 (bs, 1H), 4.38-4.40 (m, 2H), 4.81-4.86 (m, 2H), 7.20 (bs, 2H), 7.53 (bs, 2H);

B-75. ¹H NMR (400 MHz, DMSO-d₆) δ ppm 0.77-1.5 (m, 45H), 1.6-2.4 (m, 19H) (including 3 unit of acetate salt), 2.6-2.8 (m, 17H), 3.05-3.19 (m, 2H), 3.32 (bs, 2H), 3.52 (bs, 2H), 3.79 (bs, 2H), 4.25 (bs, 2H), 4.53 (bs, 2H), 4.81-4.90 (m, 2H), 6.87 (bs, 2H), 7.28 (bs, 2H);

B-76. ¹H NMR (400 MHz, DMSO-d₆) δ ppm 0.77-1.5 (m, 41H), 1.6-2.4 (m, 11H) (including 2 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 1H), 4.10 (bs, 1H), 4.40 (bs, 2H), 4.82-4.88 (m, 2H), 7.23 (d, 2H, J=8 Hz), 7.56 (d, 2H, J=8 Hz);

B-77. ¹H NMR (400 MHz, DMSO-d₆) δ ppm 0.77-1.5 (m, 41H), 1.6-2.4 (m, 15H) (including 2 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 1H), 4.10 (bs, 1H), 4.40 (bs, 2H), 4.82-4.86 (m, 2H), 7.17 (d, 2H, J=8 Hz), 7.51 (d, 2H, J=8 Hz);

B-78. ¹H NMR (400 MHz, DMSO-d₆) δ ppm 0.77-1.5 (m, 41H), 1.6-2.4 (m, 15H) (including 1 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 2H), 4.08 (bs, 1H), 4.40 (d, 2H, J=8 Hz), 4.86 (bs, 2H), 7.21 (bs, 2H), 7.54 (bs, 2H);

B-79. ¹H NMR (400 MHz, DMSO-d₆) δ ppm 0.77-1.5 (m, 35H), 1.6-2.1 (m, 12H) (including 1 unit of acetate salt), 2.4-2.8 (m, 15H), 3.1-3.25 (m, 6H), 3.45 (s, 1H), 3.65 (bs, 1H), 3.75 (bs, 2H), 4.09 (s, 1H), 4.33-4.38 (m, 2H), 4.83-4.85 (m, 2H), 7.19 (bs, 2H), 7.44 (d, 2H, J=8 Hz), 7.51 (bs, 2H), 7.62 (d, 2H, J=8 Hz);

B-80. ¹H NMR (400 MHz, DMSO-d₆) δ ppm 0.77-1.5 (m, 36H), 1.6-2.4 (m, 16H) (including 1 unit of acetate salt), 2.6-2.8 (m, 13H), 3.1-3.25 (m, 6H), 3.45 (bs, 1H), 3.65 (bs, 1H), 3.75 (bs, 2H), 4.09 (bs, 1H), 4.40 (bs, 2H), 4.83 (bs, 2H), 7.19 (bs, 2H), 7.50 (bs, 2H);

B-81. ¹H NMR (400 MHz, DMSO-d₆) δ ppm 0.77-1.5 (m, 40H), 1.6-2.4 (m, 19H) (including 2 unit of acetate salt), 2.6-2.8 (m, 17H), 3.13 (bs, 2H), 3.32 (bs, 2H), 3.52 (bs, 2H), 3.65 (bs, 1H), 3.79 (bs, 2H), 4.07 (bs, 1H), 4.40 (bs, 2H), 4.86-4.88 (bs, 2H), 7.20 (bs, 2H), 7.54 (bs, 2H);

B-82. ¹H NMR (400 MHz, DMSO-d₆) δ ppm 0.77-1.5 (m, 42H), 1.6-2.4 (m, 18H) (including 2 unit of acetate salt), 2.6-2.8 (m, 11H), 3.13 (bs, 1H), 3.2-3.35 (m, 5H), 3.45 (bs, 1H), 3.65 (bs, 1H), 3.78 (bs, 2H), 4.09 (bs, 1H), 4.39 (bs, 2H), 4.81-4.84 (m, 2H), 7.20 (bs, 2H), 7.53 (bs, 2H);

B-83. ¹H NMR (400 MHz, DMSO-d₆) δ ppm 0.77-1.5 (m, 41H), 1.6-2.4 (m, 15H) (including 1 unit of acetate salt), 2.6-2.8 (m, 11H), 3.13 (bs, 1H), 3.2-3.45 (m, 5H), 3.65 (bs, 1H), 3.75 (bs, 2H), 4.09 (bs, 1H), 4.37-4.41 (m, 2H), 4.81-4.86 (m, 2H), 7.20 (d, 2H, J=8 Hz), 7.53 (d, 2H, J=8 Hz);

B-84. ¹H NMR (400 MHz, DMSO-d₆) δ ppm 0.77-1.5 (m, 41H), 1.6-2.4 (m, 13H) (including 1 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 2H), 4.08 (bs, 1H), 4.37-4.40 (m, 2H), 4.84-4.86 (m, 2H), 7.21 (d, 2H, J=8 Hz), 7.54 (d, 2H, J=8 Hz);

B-85. ¹H NMR (400 MHz, DMSO-d₆) δ ppm 0.77-1.5 (m, 43H), 1.6-2.4 (m, 16H) (including 2 unit of acetate salt), 2.6-2.8 (m, 11H), 3.13 (bs, 1H), 3.25-3.35 (m, 5H), 3.45 (bs, 1H), 3.65 (bs, 1H), 3.75 (bs, 2H), 4.10 (bs, 1H), 4.40 (d, 2H, J=8 Hz), 4.85 (bs, 2H), 7.19 (bs, 2H), 7.50 (bs, 2H);

B-86. ¹H NMR (400 MHz, DMSO-d₆) δ ppm 0.77-1.5 (m, 35H), 1.7-2.3 (m, 15H) (including 2 unit of acetate salt), 2.4-2.8 (m, 10H), 3.0-3.5 (m, 6H), 3.69 (bs, 1H), 3.72-3.79 (m, 4H), 3.85 (s, 1H), 4.11 (s, 1H), 4.38 (d, 2H, J=8 Hz), 4.88-4.95 (m, 2H), 7.16 (bs, 3H), 7.34 (t, 1H, J=8 Hz), 7.41-7.47 (m, 5H), 7.61-7.67 (m, 4H);

B-87. ¹H NMR (400 MHz, DMSO-d₆) δ ppm 0.77-1.5 (m, 39H), 1.6-2.4 (m, 12H) (including 1 unit of acetate salt), 2.6-2.8 (m, 17H), 3.12 (bs, 1H), 3.13-3.47 (m, 5H), 3.32 (bs, 2H), 3.65 (bs, 1H), 3.77 (bs, 2H), 4.09 (bs, 1H), 4.39 (bs, 3H), 4.81-4.85 (m, 2H), 7.22 (bs, 2H), 7.53 (bs, 2H);

B-88. ¹H NMR (400 MHz, DMSO-d₆) δ ppm 0.77-1.5 (m, 44H), 1.6-2.4 (m, 19H) (including 2 unit of acetate salt), 2.6-2.8 (m, 17H), 3.13 (bs, 2H), 3.32 (bs, 2H), 3.52 (bs, 2H), 3.65 (bs, 1H), 3.79 (bs, 2H), 4.07 (bs, 1H), 4.40-4.41 (bs, 2H), 4.86-4.88 (bs, 2H), 7.25 (d, 2H, J=8 Hz), 7.57 (d, 2H, J=8 Hz);

B-89. ¹H NMR (400 MHz, DMSO-d₆) δ ppm 0.77-1.5 (m, 35H), 1.6-2.5 (m, 11H) (including 1 unit of acetate salt), 2.6-2.8 (m, 11H), 3.1-3.28 (m, 4H), 3.47 (bs, 2H), 3.63 (bs, 2H), 3.70-3.77 (m, 4H), 4.07 (bs, 1H), 4.37-4.39 (m, 2H), 4.81-4.89 (m, 2H), 7.24 (d, 2H, J=8 Hz), 7.34 (bs, 2H), 7.55 (d, 2H, J=8 Hz), 8.24 (s, 1H), 8.49 (bs, 1H);

B-90. ¹H NMR (400 MHz, DMSO-d₆) δ ppm 0.77-1.5 (m, 35H), 1.6-2.5 (m, 19H) (including 3 unit of acetate salt), 2.6-2.8 (m, 9H), 3.1-3.28 (m, 4H), 3.47 (bs, 2H), 3.63 (bs, 2H), 3.79 (bs, 2H), 4.20 (bs, 1H), 4.36 (bs, 1H), 4.48 (bs, 1H), 4.82 (bs, 2H), 4.97 (bs, 1H), 6.54 (t, 1H, J=8 Hz), 6.62 (d, 2H, J=8 Hz), 6.81 (d, 2H, J=8 Hz), 7.06 (t, 2H, J=8 Hz), 7.24 (d, 2H, J=8 Hz);

B-91. ¹H NMR (400 MHz, DMSO-d₆) δ ppm 0.77-1.5 (m, 36H), 1.6-2.4 (m, 18H) (including 2 unit of acetate salt), 2.6-2.8 (m, 11H), 3.13 (bs, 1H), 3.2-3.35 (m, 5H), 3.45 (bs, 1H), 3.65 (bs, 1H), 3.75 (bs, 2H), 4.08 (bs, 1H), 4.39-4.45 (m, 3H), 4.55 (bs, 1H), 4.86 (bs, 2H), 7.23 (d, 2H, J=8 Hz), 7.55 (d, 2H, J=8 Hz);

B-92. $^1$H NMR (400 MHz, DMSO-d$_6$) δ ppm 0.77-1.5 (m, 39H), 1.6-2.4 (m, 19H) (including 1 unit of acetate salt), 2.6-2.8 (m, 15H), 3.13 (bs, 2H), 3.32 (bs, 2H), 3.52 (bs, 2H), 3.65 (bs, 1H), 3.79 (bs, 2H), 4.10 (bs, 1H), 4.40 (bs, 2H), 4.81-4.87 (bs, 2H), 7.17 (bs, 2H), 7.50 (bs, 2H);

B-93. $^1$H NMR (400 MHz, CHLOROFORM-d) δ ppm 0.57-1.83 (m, 43H) 1.90-2.42 (m, 14H) 2.44-2.93 (m, 6H) 2.98-4.00 (m, 12H) 4.04-4.43 (m, 3H) 4.62-4.84 (m, 2H) 4.91-5.09 (m, 1H) 6.33-6.70 (m, 3H) 7.34-7.54 (m, 3H) 7.65-7.83 (m, 2H);

B-94. $^1$H NMR (400 MHz, CHLOROFORM-d) δ ppm 0.55-1.73 (m, 42H) 1.75-2.83 (m, 10H), 2.86-3.61 (m, 12H) 3.65-3.97 (m, 9H) 4.01-4.10 (m, 1H) 4.13-4.24 (m, 1H) 4.28-4.43 (m, 1H) 4.58-4.70 (m, 1H) 4.81-4.99 (m, 2H) 5.10-5.19 (m, 1H), 6.22-7.81 (m, 13H);

B-95. $^1$H NMR (400 MHz, CHLOROFORM-d) δ ppm 0.33-1.87 (m, 43H) 1.92-2.38 (m, 6H) 2.43-3.20 (m, 9H) 3.23-3.64 (m, 7H) 3.80-4.19 (m, 4H) 4.26-4.45 (m, 2H) 4.48-4.67 (m, 1H) 4.71-4.92 (m, 2H) 5.03-5.14 (m, 1H) 6.98-7.19 (m, 3H) 7.37-7.59 (m, 3H) 7.66-7.87 (m, 2H);

B-96. $^1$H NMR (400 MHz, CHLOROFORM-d) δ ppm 0.32-1.65 (m, 37H) 1.68-2.22 (m, 12H) 2.27-2.91 (m, 10H) 2.97-3.62 (m, 9H) 3.72-3.96 (m, 2H) 4.05-4.40 (m, 4H) 4.49-4.63 (m, 1H) 6.74-6.90 (m, 1H) 7.02-7.14 (m, 2H) 7.22 (br d, J=8.56 Hz, 1H) 7.54-7.72 (m, 1H) 7.75-7.84 (m, 1H);

B-97. $^1$H NMR (400 MHz, CHLOROFORM-d) δ ppm 0.38-1.82 (m, 33H) 1.87-2.35 (m, 8H) 2.36-3.27 (m, 11H), 3.31-3.60 (m, 6H) 3.66-3.96 (m, 14H) 4.01-4.30 (m, 2H) 4.32-4.47 (m, 1H) 4.52-5.15 (m, 3H) 6.68-6.96 (m, 4H) 7.46-7.86 (m, 4H);

B-98. $^1$H NMR (400 MHz, CHLOROFORM-d) δ ppm 0.29-1.56 (m, 39H) 1.57-2.20 (m, 8H) 2.89-3.24 (m, 12H), 3.29-3.49 (m, 5H) 3.50-3.62 (m, 1H) 3.76-3.93 (m, 2H) 4.05-4.19 (m, 1H) 4.20-4.44 (m, 2H) 4.53-4.65 (m, 1H) 4.65-4.82 (m, 2H) 4.87-4.98 (m, 1H) 5.00-5.12 (m, 1H) 6.88-7.11 (m, 2H) 7.11-7.18 (m, 1H) 7.18-7.29 (m, 1H) 7.54-7.73 (m, 1H) 7.77-7.91 (m, 1H);

B-99. $^1$H NMR (400 MHz, CHLOROFORM-d) δ ppm 0.31-1.82 (m, 43H) 1.85-2.30 (m, 4H) 2.33-2.90 (m, 7H) 2.95-3.95 (m, 13H) 3.99-4.17 (m, 1H) 4.18-4.44 (m, 2H) 4.63-4.87 (m, 2H) 4.92-5.17 (m, 1H) 6.78-7.15 (m, 3H) 7.36-7.53 (m, 3H) 7.56-7.81 (m, 2H);

B-100. $^1$H NMR (400 MHz, CHLOROFORM-d) δ ppm 0.28-1.50 (m, 41H) 1.52-2.26 (m, 18H) 2.32-3.35 (m, 1H) 2.34-3.45 (m, 1H) 3.25-3.44 (m, 2H) 3.47-3.57 (m, 1H) 3.61-3.89 (m, 4H) 4.12 (br d, J=4.89 Hz, 1H) 4.17-4.31 (m, 1H) 4.32-4.43 (m, 1H) 4.65-4.82 (m, 2H) 4.94-5.04 (m, 1H) 6.67-6.92 (m, 3H) 7.35-7.58 (m, 6H) 7.61-7.85 (m, 4H);

B-101. $^1$H NMR (400 MHz, CHLOROFORM-d) δ ppm 0.39-1.60 (m, 45H) 1.63-2.12 (m, 15H) 2.17-2.79 (m, 7H), 2.84-3.64 (m, 5H) 3.68-3.92 (m, 4H) 4.01-4.34 (m, 1H) 4.48-5.09 (m, 1H), 6.65-6.89 (m, 2H) 7.16-7.35 (m, 2H) 7.59-7.74 (m, 1H) 7.80-7.98 (m, 1H);

B-102. $^1$H NMR (400 MHz, CHLOROFORM-d) δ ppm 0.50-1.60 (m, 45H) 1.65-2.35 (m, 8H) 2.37-3.00 (m, 9H) 3.03-3.99 (m, 14H) 4.03-4.34 (m, 3H) 4.56-5.00 (m, 4H) 5.01-5.25 (m, 2H) 6.21-6.34 (m, 1H) 6.40-6.67 (m, 3H) 7.55-7.71 (m, 2H) 7.74-7.85 (m, 1H);

B-103. $^1$H NMR (400 MHz, CHLOROFORM-d) δ ppm 0.40-1.56 (m, 34H) 1.59-2.77 (m, 9H) 2.77-3.06 (m, 12H) 3.33-3.42 (m, 8H) 3.46-3.76 (m, 6H) 3.69-4.27 (m, 4H) 4.28-4.52 (m, 3H) 4.60-4.83 (m, 3H) 4.89-4.99 (m, 2H) 6.46-6.75 (m, 6H) 7.29-7.53 (m, 3H) 7.76-7.84 (m, 1H);

B-104. $^1$H NMR (400 MHz, DMSO-d6) δ ppm 0.69-1.53 (m, 30H) 1.69-2.22 (m, 9H) 2.60-3.41 (m, 10H) 3.51-3.63 (m, 3H) 3.64-3.82 (m, 4H) 3.86-4.12 (m, 7H) 4.25-4.53 (m, 7H) 4.71-4.95 (m, 5H) 4.96-5.13 (m, 3H) 7.13-7.39 (m, 4H) 7.52-7.69 (m, 4H);

B-105. $^1$H NMR (400 MHz, CHLOROFORM-d) δ ppm 0.45-1.56 (m, 34H) 1.64-2.57 (m, 19H) 2.68-3.00 (m, 2H) 3.09-3.79 (m, 21H) 3.87-4.13 (m, 1H) 4.16-4.55 (m, 3H) 4.56-4.76 (m, 1H) 4.80-5.12 (m, 3H) 5.12-5.30 (m, 1H) 6.59-6.79 (m, 2H) 6.75-7.00 (m, 2H) 7.27-7.60 (m, 2H) 8.51-8.78 (m, 1H) 9.23-9.51 (m, 1H);

B-106. $^1$H NMR (400 MHz, CHLOROFORM-d) δ ppm 0.44-1.55 (m, 42H) 1.59-1.89 (m, 5H) 2.06-2.54 (m, 8H) 2.87-3.25 (m, 6H) 3.31-3.88 (m, 7H) 3.94-4.11 (m, 1H) 4.16-4.47 (m, 2H) 4.58-4.87 (m, 3H) 4.95-5.07 (m, 1H) 6.59-6.89 (m, 4H) 6.99-7.15 (m, 2H) 7.65-7.83 (m, 2H);

B-107. $^1$H NMR (400 MHz, DMSO-d6) δ ppm 0.5-1.5 (m, 45H), 1.6-2.3 (m, 10H), 2.4-2.7 (m, 10H), 3.2-3.5 (m, 5H), 3.9-4.1 (m, 3H), 4.35-4.37 (m, 1H), 4.6-4.8 (m, 3H), 6.9-7.0 (m, 5H), 7.4 (s, 1H), 8.1 (bs, 1H);

B-108. $^1$H NMR (400 MHz, CHLOROFORM-d) δ ppm 0.39-1.47 (m, 28H) 1.58-1.96 (m, 12H) 2.10-3.22 (m, 12H) 3.30-3.64 (m, 7H) 3.72-3.90 (m, 2H) 3.96-4.37 (m, 4H) 4.46-4.97 (m, 4H) 4.98-5.19 (m, 2H) 5.31-5.52 (m, 1H) 6.45-6.84 (m, 4H) 7.30-7.55 (m, 2H) 7.56-7.79 (m, 2H) 8.67-8.92 (m, 1H) 9.32-9.56 (m, 1H);

B-109. $^1$H NMR (400 MHz, CHLOROFORM-d) δ ppm 0.52-1.26 (m, 29H) 1.30-2.53 (m, 18H) 2.83-3.93 (m, 13H) 4.03-4.46 (m, 6H) 4.67-4.88 (m, 3H) 4.99-5.15 (m, 2H) 5.42-5.58 (m, 2H) 6.61-6.91 (m, 5H) 7.37-7.77 (m, 4H) 8.76-9.04 (m, 1H) 9.32-9.56 (m, 1H);

B-110. $^1$H NMR (400 MHz, CHLOROFORM-d) δ ppm 0.28-1.84 (m, 48H) 1.95-2.43 (m, 10H) 2.46-2.97 (m, 8H) 3.23-3.98 (m, 8H) 4.38-4.76 (m, 3H) 5.02-5.37 (m, 2H) 6.57-7.10 (m, 5H);

B-111. $^1$H NMR (400 MHz, CHLOROFORM-d) δ ppm 0.50-1.83 (m, 40H) 1.96-2.64 (m, 9H) 2.79-3.56 (m, 12H) 3.61-3.97 (m, 5H) 4.02-4.43 (m, 3H) 4.56-4.72 (m, 2H) 4.75-4.92 (m, 1H) 4.94-5.29 (m, 3H) 5.35-5.57 (m, 1H) 6.45-6.96 (m, 5H) 7.26-7.45 (m, 1H) 8.18-8.41 (m, 1H) 8.42-8.58 (m, 1H) 8.83-8.96 (m, 1H) 9.27-9.49 (m, 1H);

B-112. $^1$H NMR (400 MHz, DMSO-d$_6$) δ ppm 0.5-1.5 (m, 39H), 1.7-2.3 (m, 12H) (including 1 unit of acetate salt), 2.4-2.8 (m, 12H), 3.1-3.4 (m, 10H), 3.5-3.7 (m, 5H), 4.1 (s, 1H), 4.39-4.41 (m, 2H), 4.81-4.85 (m, 2H), 5.15 (brs, 1H);

B-113. $^1$H NMR (400 MHz, DMSO-d$_6$) δ ppm 0.5-1.5 (m, 39H), 1.7-2.3 (m, 12H) (including 1 unit of acetate salt), 2.4-2.8 (m, 10H), 3.0-3.4 (m, 10H), 3.5-3.7 (m, 5H), 4.1 (s, 1H), 4.35-4.47 (m, 2H), 4.82-4.86 (m, 2H), 5.23 (brs, 1H), 7.59 (d, 2H, J=8 Hz), 7.67 (d, 2H, J=8 Hz);

B-114. $^1$H NMR (400 MHz, DMSO-d6) δ ppm 0.53 (br d, 3H), 0.75-1.21 (m, 33H), 1.29-1.49 (m, 6H), 1.54-1.82 (m, 8H), 1.90 (s, 2H, AcOH), 2.01 (br dd, 1H), 2.15 (br d, 1H), 2.39-2.48 (m, 2H), 2.56 (s, 3H), 2.62 (s, 3H), 2.69 (br d, 2H), 2.80 (br d, 1H), 3.24 (br s, 1H), 3.38 (s, 3H), 3.48 (br d, 1H), 3.62-3.67 (m, 1H), 3.87-3.93 (m, 1H), 4.03-4.16 (m, 4H), 4.40 (br d, 1H), 4.65 (br d, 1H), 4.79 (br d, 1H), 4.84 (br d, 1H), 6.65 (br dd, 2H), 6.92 (br t, 2H), 9.24 (s, 1H);

B-115. ¹H NMR (400 MHz, DMSO-d6) δ ppm 0.50 (br d, 3H), 0.77-1.19 (m, 32H), 1.27-1.50 (m, 6H), 1.56-1.84 (m, 8H), 1.90 (s, 2H, AcOH), 2.01 (br dd, 1H), 2.14 (br d, 1H), 2.40-2.47 (m, 2H), 2.60 (br d, 2H), 2.66 (s, 3H), 2.67-2.72 (m, 2H), 2.80 (br d, 1H), 3.24 (br s, 1H), 3.37 (s, 3H), 3.48 (br d, 1H), 3.62-3.71 (m, 1H), 3.87 (br d, 1H), 4.03 (br s, 1H), 4.08-4.20 (m, 2H), 4.37-4.44 (m, 1H), 4.64 (br d, 1H), 4.78 (br d, 1H), 4.84 (br d, 1H), 6.61 (br dd, 2H), 6.90 (br t, 2H), 7.78 (d, 1H), 7.87 (d, 1H), 8.13 (t, 1H);

B-116. ¹H NMR (400 MHz, CHLOROFORM-d) δ ppm 0.38-2.24 (m, 51H) 2.40-3.10 (m, 11H) 3.15-3.60 (m, 8H) 3.63-4.00 (m, 6H) 4.01-4.23 (m, 2H) 4.25-4.38 (m, 1H) 4.57-4.67 (m, 1H) 4.74-4.84 (m, 1H) 4.93-5.04 (m, 1H) 6.32-6.51 (m, 2H) 6.51-6.66 (m, 2H) 8.08-8.18 (m, 1H) 8.55-8.68 (m, 1H);

B-117. ¹H NMR (400 MHz, CHLOROFORM-d) δ ppm 0.49-1.98 (m, 45H) 2.02-2.76 (m, 13H) 3.06-3.91 (m, 14H) 3.99-4.29 (m, 3H) 4.58-4.80 (m, 2H) 4.90-5.10 (m, 2H) 6.45-6.91 (m, 4H) 7.32-7.72 (m, 2H) 8.20-8.40 (m, 1H) 8.42-8.59 (m, 1H);

B-118. ¹H NMR (400 MHz, DMSO-d6) δ ppm 0.43 (br d, 3H), 0.68-1.52 (m, 42H), 1.60-1.84 (m, 6H), 1.90 (s, 3H, AcOH), 1.98-2.05 (m, 1H), 2.14-2.19 (m, 1H), 2.43-2.49 (m, 1H), 2.52-2.57 (m, 1H), 2.63 (s, 3H), 2.69-2.75 (m, 1H), 2.80 (br d, 1H), 3.23 (br s, 1H), 3.39 (s, 3H), 3.44 (br d, 1H), 3.61 (s, 3H), 3.65-3.67 (m, 1H), 3.68 (s, 1H), 3.70 (d, 1H), 3.86-3.94 (m, 1H), 4.00-4.12 (m, 2H), 4.40 (q, 1H), 4.60 (br d, 1H), 4.78 (br dd, 1H), 4.84 (br d, 1H), 6.26 (br d, 1H), 6.48-6.51 (m, 1H), 6.70-6.75 (m, 1H), 6.76-6.81 (m, 1H), 7.09-7.15 (m, 1H), 7.55-7.61 (m, 1H), 7.86 (d, 1H), 8.08 (s, 1H), 8.50 (br dd, 1H);

B-119. ¹H NMR (400 MHz, CHLOROFORM-d) δ ppm 0.45-1.56 (m, 45H) 1.61-2.29 (m, 10H) 2.32-2.96 (m, 8H) 3.03-3.64 (m, 2H) 3.67-3.89 (m, 2H) 3.74-4.96 (m, 2H) 3.93-4.09 (m, 1H) 4.14-4.28 (m, 1H) 4.35-4.41 (m, 1H) 4.42-4.92 (m, 3H) 4.94-5.13 (m, 1H) 4.99-5.11 (m, 1H) 6.31-6.92 (m, 4H) 7.07-7.23 (m, 2H) 7.22-7.31 (m, 1H) 7.24-7.30 (m, 1H) 7.36-7.51 (m, 1H) 7.71-7.95 (m, 1H);

B-120. ¹H NMR (400 MHz, CHLOROFORM-d) δ ppm 0.35-1.89 (m, 42H) 2.03-2.66 (m, 18H) 2.81-3.14 (m, 4H) 3.17-3.81 (m, 3H) 3.74-4.91 (m, 3H) 4.96-5.17 (m, 1H) 6.28-6.69 (m, 3H) 6.83-7.13 (m, 2H) 7.25-7.43 (m, 1H) 7.54-7.76 (m, 2H) 7.88-8.07 (m, 1H) 8.35-8.49 (m, 1H);

B-121. ¹H NMR (400 MHz, CHLOROFORM-d) δ ppm 0.43-1.82 (m, 53H) 1.86-2.32 (m, 9H) 2.40-3.00 (m, 5H) 3.09-3.52 (m, 5H) 3.56-4.09 (m, 2H) 4.19-4.49 (m, 2H) 4.54-4.73 (m, 1H) 4.75-4.90 (m, 1H) 4.94-5.06 (m, 1H) 5.36-5.51 (m, 1H) 6.55-7.13 (m, 5H) 8.64-8.85 (m, 1H) 9.01-9.24 (m, 1H);

B-122. ¹H NMR (400 MHz, CHLOROFORM-d) δ ppm 0.27-1.62 (m, 40H) 1.65-2.42 (m, 10H) 2.46-3.03 (m, 13H) 3.04-4.07 (m, 9H) 4.21-4.48 (m, 4H) 4.66-5.14 (m, 2H) 6.86-7.08 (m, 2H) 7.22-7.34 (m, 3H);

B-123. ¹H NMR (400 MHz, CHLOROFORM-d) δ ppm 0.53-1.53 (m, 46H) 1.56-2.18 (m, 13H) 2.42-2.85 (m, 5H) 2.91-3.16 (m, 5H) 3.20-3.47 (m, 2H) 3.47-3.94 (m, 2H) 3.96-4.46 (m, 2H) 4.66-4.88 (m, 2H) 4.92-5.02 (m, 1H) 6.58-6.72 (m, 3H) 6.83-7.06 (m, 6H);

B-124. ¹H NMR (400 MHz, CHLOROFORM-d) δ ppm 0.46-1.55 (m, 40H) 1.59-2.32 (m, 15H) 2.43-3.43 (m, 9H) 3.67-3.92 (m, 3H) 3.97-4.13 (m, 2H) 4.13-4.52 (m, 3H) 4.63-4.83 (m, 3H) 4.90-5.10 (m, 1H) 6.35-6.56 (m, 2H) 6.59-6.73 (m, 2H) 7.75-7.91 (m, 1H) 7.99-8.17 (m, 2H) 8.56-8.72 (m, 1H) 8.78-8.90 (m, 1H);

B-125. ¹H NMR (600 MHz, DMSO-d6) δ ppm 0.79-1.22 (m, 32H), 1.30-1.51 (m, 5H), 1.61-1.88 (m, 5H), 1.90 (s, 1H, AcOH), 1.91-1.97 (m, 2H), 2.21 (br d, 1H), 2.56 (br d, 1H), 2.62-2.65 (m, 3H), 2.65-2.69 (m, 1H), 2.83 (br d, 1H), 3.03 (br dd, 1H), 3.14-3.19 (m, 1H), 3.24 (br dd, 1H), 3.32 (s, 3H), 3.49 (d, 1H), 3.63-3.65 (m, 3H), 3.67 (td, 1H), 3.71-3.78 (m, 3H), 4.15-4.18 (m, 1H), 4.40 (d, 1H), 4.44-4.47 (m, 1H), 4.49 (br dd, 1H), 4.84 (dd, 1H), 4.88 (br d, 1H), 4.98 (d, 1H), 6.39 (s, 2H), 6.58-6.62 (m, 2H), 6.70-6.74 (m, 2H);

B-126. ¹H NMR (400 MHz, DMSO-d₆) δ ppm 0.77-1.5 (m, 42H), 1.6-2.4 (m, 12H) (including 1 unit of acetate salt), 2.6-2.8 (m, 11H), 3.13 (bs, 1H), 3.2-3.35 (m, 5H), 3.45 (bs, 1H), 3.65 (bs, 1H), 3.78 (bs, 2H), 4.09 (bs, 1H), 4.37-4.39 (m, 3H), 4.81-4.84 (m, 2H), 7.20 (bs, 2H), 7.53 (bs, 2H);

B-127. ¹H NMR (400 MHz, DMSO-d₆) δ ppm 0.77-1.5 (m, 45H), 1.6-2.4 (m, 19H) (including 3 unit of acetate salt), 2.6-2.8 (m, 13H), 3.13 (bs, 3H), 3.32 (bs, 3H), 3.65 (bs, 2H), 3.79 (bs, 2H), 4.09 (bs, 1H), 4.37-4.40 (bs, 2H), 4.81-4.86 (m, 2H), 7.20 (bs, 2H), 7.53 (bs, 2H);

B-128. ¹H NMR (400 MHz, DMSO-d₆) δ ppm 0.77-1.5 (m, 35H), 1.6-2.1 (m, 12H) (including 1 unit of acetate salt), 2.4-2.8 (m, 15H), 3.1-3.25 (m, 4H), 3.45 (bs, 3H), 3.65 (bs, 1H), 3.75 (bs, 2H), 4.09 (s, 1H), 4.32-4.37 (m, 2H), 4.80 (bs, 2H), 7.19 (bs, 2H), 7.44 (bs, 2H), 7.63-7.71 (m, 2H), 7.73-7.89 (m, 1H), 7.89 (d, 2H, J=8 Hz);

B-129. ¹H NMR (400 MHz, DMSO-d₆) δ ppm 0.77-1.5 (m, 35H), 1.6-2.1 (m, 9H), 2.4-2.8 (m, 13H), 3.1-3.25 (m, 6H), 3.45 (s, 1H), 3.65 (bs, 1H), 3.75 (bs, 3H), 4.09 (bs, 3H), 4.33-4.38 (m, 3H), 4.81-4.86 (m, 2H), 7.19 (bs, 2H), 7.50 (bs, 2H);

B-130. ¹H NMR (400 MHz, DMSO-d6) δ ppm 0.48-1.86 (m, 50H), 1.90 (s, 3H, AcOH), 2.03 (br dd, 1H), 2.18 (br d, 1H), 2.42-2.48 (m, 1H), 2.52-2.62 (m, 3H), 2.64 (s, 3H), 2.74 (br dd, 2H), 3.22 (br s, 1H), 3.39 (br s, 1H), 3.41 (s, 3H), 3.74 (br dd, 1H), 3.79-3.90 (m, 1H), 3.99 (br s, 1H), 4.16 (td, 1H), 4.37-4.46 (m, 1H), 4.67 (d, 1H), 4.79 (dd, 1H), 4.84 (br d, 1H), 5.26 (dd, 1H), 6.20 (d, 1H), 6.83 (dd, 1H), 7.45-7.55 (m, 3H), 7.58 (d, 1H), 7.61-7.67 (m, 2H), 7.97 (dd, 1H);

B-131. ¹H NMR (400 MHz, DMSO-d6) δ ppm 0.52-1.84 (m, 49H), 1.90 (s, 2H, AcOH), 1.99 (br dd, 1H), 2.16 (br d, 1H), 2.40-2.48 (m, 2H), 2.54-2.62 (m, 2H), 2.66-2.71 (m, 1H), 2.73-2.80 (m, 4H), 3.22 (br s, 1H), 3.37 (s, 3H), 3.42 (br d, 1H), 3.67 (br d, 1H), 3.72 (s, 3H), 3.78-3.88 (m, 1H), 4.01 (br d, 1H), 4.06-4.16 (m, 1H), 4.22 (br d, 1H), 4.41 (q, 1H), 4.71 (d, 1H), 4.79 (dd, 1H), 4.83 (br d, 1H), 5.30 (dd, 1H), 6.48 (d, 1H), 6.89 (dd, 1H), 6.96 (d, 1H), 7.38 (s, 1H), 7.62 (ddd, 1H), 8.04 (dd, 1H);

B-132. ¹H NMR (600 MHz, DMSO-d6) δ ppm 0.51-1.84 (m, 48H), 1.89 (s, 2H, AcOH), 1.98 (br dd, 1H), 2.13 (br d, 1H), 2.41-2.48 (m, 2H), 2.53-2.59 (m, 2H), 2.66-2.71 (m, 3H), 2.81 (br d, 1H), 3.24 (br d, 1H), 3.31 (br s, 3H), 3.46-3.50 (m, 2H), 3.66 (br d, 1H), 3.79 (s, 3H), 3.81-3.88 (m, 1H), 3.94-4.00 (m, 1H), 4.02-4.09 (m, 2H), 4.23 (br s, 1H), 4.36-4.42 (m, 1H), 4.55-4.62 (m, 1H), 4.65 (br d, 1H), 4.79 (br dd, 1H), 4.82 (br d, 1H), 6.51-6.57 (m, 2H), 7.01 (s, 1H), 7.27 (dd, 1H), 7.44 (s, 1H);

B-133. ¹H NMR (400 MHz, DMSO-d6) δ ppm 0.34-1.88 (m, 49H), 1.91 (s, 2H, AcOH), 2.03 (s, 2H), 2.07-2.13

(m, 1H), 2.14-2.19 (m, 1H), 2.44 (s, 3H), 2.82 (br d, 1H), 3.20-3.27 (m, 2H), 3.41 (s, 3H), 3.43 (br s, 1H), 3.54 (ddd, 1H), 3.72-3.87 (m, 2H), 4.00-4.13 (m, 2H), 4.25 (br s, 2H), 4.33-4.42 (m, 1H), 4.46 (q, 1H), 4.55 (s, 1H), 4.62-4.72 (m, 2H), 4.79 (br dd, 1H), 4.85 (br t, 1H), 4.90 (br d, 1H), 6.86 (t, 1H), 6.98-7.04 (m, 1H), 7.04-7.09 (m, 1H), 7.35 (br d, 1H), 7.53-7.61 (m, 2H), 7.63-7.69 (m, 1H), 7.72-7.79 (m, 2H);

B-134. $^1$H NMR (400 MHz, DMSO-d6) δ ppm 0.38-1.86 (m, 47H), 1.90 (s, 3H, AcOH), 1.96 (br s, 1H), 2.11-2.18 (m, 1H), 2.40-2.48 (m, 2H), 2.53-2.58 (m, 2H), 2.62 (s, 3H), 2.70 (br d, 1H), 2.82 (br d, 1H), 3.24 (br s, 1H), 3.37 (s, 3H), 3.45 (br d, 1H), 3.61-3.71 (m, 1H), 3.84 (s, 3H), 3.86-3.93 (m, 1H), 3.99 (br d, 1H), 4.14-4.31 (m, 3H), 4.37-4.46 (m, 2H), 4.68-4.83 (m, 4H), 4.86-4.94 (m, 1H), 5.76 (s, 2H), 6.87 (t, 1H), 6.99-7.06 (m, 2H), 7.08-7.13 (m, 1H), 7.35 (br d, 1H), 7.42 (s, 1H);

B-135. $^1$H NMR (600 MHz, DMSO-d6) δ ppm 0.38-1.92 (m, 52H), 2.03 (br dd, 1H), 2.16 (br d, 1H), 2.41-2.47 (m, 2H), 2.53-2.61 (m, 2H), 2.62-2.65 (m, 2H), 2.66-2.76 (m, 2H), 3.21 (br s, 1H), 3.39-3.41 (m, 3H), 3.60 (br s, 1H), 3.85 (br dd, 1H), 3.97-4.01 (m, 1H), 4.16 (td, 1H), 4.36-4.42 (m, 1H), 4.65 (br d, 1H), 4.79 (br dd, 1H), 4.83 (br d, 1H), 5.15 (br dd, 1H), 6.22 (br d, 1H), 7.28-7.34 (m, 1H), 7.47-7.53 (m, 2H), 7.57-7.61 (m, 1H), 7.64 (ddd, 2H), 8.02 (d, 1H);

B-136. $^1$H NMR (400 MHz, DMSO-d6) δ ppm 0.50-1.86 (m, 50H), 1.90 (br s, 2H, AcOH), 1.97 (br dd, 1H), 2.14 (br d, 1H), 2.39-2.48 (m, 2H), 2.53-2.60 (m, 3H), 2.62 (s, 3H), 2.66-2.71 (m, 1H), 2.82 (br d, 1H), 3.25 (br s, 2H), 3.49 (br d, 1H), 3.66 (br d, 1H), 3.81 (s, 3H), 3.87 (br dd, 1H), 4.03 (br s, 1H), 4.06-4.16 (m, 2H), 4.18-4.28 (m, 1H), 4.40 (q, 1H), 4.70 (br d, 1H), 4.79 (dd, 1H), 4.82 (br d, 1H), 6.93 (d, 2H), 7.02 (s, 1H), 7.20 (d, 2H), 7.44 (s, 1H);

B-137. $^1$H NMR (600 MHz, DMSO-d6) δ ppm 0.49-1.85 (m, 48H), 1.89 (s, 2H, AcOH), 1.99 (br dd, 1H), 2.07-2.09 (m, 1H), 2.13-2.17 (m, 1H), 2.40-2.48 (m, 3H), 2.55-2.61 (m, 2H), 2.66-2.70 (m, 1H), 2.73-2.79 (m, 3H), 3.22 (br d, 1H), 3.36 (br s, 3H), 3.41 (br d, 1H), 3.62 (br d, 1H), 3.71-3.78 (m, 3H), 3.81-3.88 (m, 1H), 4.00 (br dd, 1H), 4.12 (ddd, 2H), 4.22 (br s, 1H), 4.37-4.43 (m, 1H), 4.71 (br d, 1H), 4.79 (br dd, 1H), 4.82 (br d, 1H), 5.21 (br dd, 1H), 6.54 (d, 1H), 6.96 (d, 1H), 7.36-7.41 (m, 1H), 7.70-7.76 (m, 1H), 8.10 (d, 1H);

B-138. $^1$H NMR (400 MHz, DMSO-d6) δ ppm 0.34-1.87 (m, 47H), 1.90 (s, 1H, AcOH), 2.10 (br dd, 1H), 2.18-2.25 (m, 1H), 2.55 (br dd, 2H), 2.67 (s, 3H), 2.79 (br t, 1H), 3.10-3.25 (m, 4H), 3.41 (s, 3H), 3.44 (br d, 1H), 3.63-3.84 (m, 3H), 3.95 (br d, 1H), 4.06 (br s, 1H), 4.15-4.32 (m, 3H), 4.43-4.51 (m, 1H), 4.63-4.69 (m, 1H), 4.81 (br d, 1H), 4.97 (br d, 1H), 6.57-6.79 (m, 1H), 7.02 (br s, 1H), 7.14 (t, 1H), 7.28 (td, 1H), 7.52-7.53 (m, 1H), 7.58 (br d, 1H), 7.66 (d, 2H), 7.73 (br dd, 2H), 7.82 (br d, 2H);

B-139. $^1$H NMR (400 MHz, DMSO-d6) δ ppm 0.46-1.86 (m, 48H), 1.89 (s, 3H, AcOH), 1.97 (br dd, 1H), 2.08 (s, 1H), 2.13 (br s, 1H), 2.40-2.48 (m, 2H), 2.53-2.60 (m, 2H), 2.62 (d, 3H), 2.67-2.75 (m, 4H), 2.78-2.85 (m, 1H), 3.23 (br s, 1H), 3.35 (d, 3H), 3.50 (br d, 1H), 3.71 (br d, 1H), 3.81 (d, 3H), 3.86-3.93 (m, 1H), 4.03 (br s, 1H), 4.10-4.20 (m, 2H), 4.23-4.32 (m, 1H), 4.41 (q, 1H), 4.69-4.88 (m, 3H), 6.93-7.06 (m, 2H), 7.16-7.28 (m, 2H), 7.38 (td, 1H), 7.43 (d, 1H);

B-140. $^1$H NMR (600 MHz, DMSO-d6) δ ppm 0.77-1.20 (m, 37H), 1.27-1.50 (m, 7H), 1.61-1.82 (m, 4H), 1.86 (br t, 1H), 1.90 (s, 3H, AcOH), 1.90-1.94 (m, 1H), 2.02-2.07 (m, 1H), 2.12-2.16 (m, 1H), 2.43 (dt, 2H), 2.55-2.59 (m, 1H), 2.62 (s, 3H), 2.63-2.68 (m, 2H), 2.83 (br d, 1H), 3.12-3.17 (m, 2H), 3.28 (s, 3H), 3.29 (br d, 2H), 3.48 (br d, 1H), 3.63-3.76 (m, 3H), 4.11 (dd, 1H), 4.37-4.42 (m, 2H), 4.82 (dd, 1H), 4.86 (d, 1H), 6.39 (s, 2H);

B-141. $^1$H NMR (400 MHz, DMSO-d6) δ ppm 0.8-1.5 (m, 41H), 1.6-1.9 (m, 5H), 2.1-2.4 (m, 3H), 2.6-2.8 (m, 5H), 3.1-3.5 (m, 5H), 3.6-4.0 (m, 5H), 4.1-4.5 (m, 5H), 4.6-4.8 (m, 3H), 6.9-7.2 (m, 5H), 7.23-7.26 (m, 1H), 7.30-7.33 (m, 4H), 7.43 (s, 1H), 8.1 (bs, 1H);

B-142. $^1$H NMR (400 MHz, DMSO-d6) δ ppm 0.68-1.20 (m, 38H), 1.21-1.87 (m, 15H), 1.89 (s, 3H, AcOH), 1.91-1.94 (m, 1H), 2.03 (br dd, 1H), 2.11-2.18 (m, 1H), 2.40-2.48 (m, 2H), 2.52-2.73 (m, 5H), 2.78-2.85 (m, 1H), 3.05 (br t, 2H), 3.13-3.22 (m, 2H), 3.26 (s, 3H), 3.46 (br d, 1H), 3.60-3.75 (m, 3H), 4.09 (br s, 1H), 4.34-4.42 (m, 2H), 4.79-4.87 (m, 2H), 7.59 (d, 2H), 7.83 (d, 2H);

B-143. $^1$H NMR (400 MHz, CHLOROFORM-d) δ ppm 0.76-1.44 (m, 37H) 1.48-2.26 (m, 23H) 2.54-3.13 (m, 8H) 3.28-3.37 (m, 2H) 3.39-3.49 (m, 2H) 3.50-3.63 (m, 1H) 3.78-3.97 (m, 1H) 4.12-4.21 (m, 1H) 4.30-4.47 (m, 1H) 4.49-4.61 (m, 1H) 4.62-4.90 (m, 1H) 4.95-5.06 (m, 1H) 6.74-6.97 (m, 1H) 6.83-6.87 (m, 1H) 6.93 (s, 1H) 7) 7.21-7.30 (m, 2H) 7.34-7.42 (m, 2H);

B-144. $^1$H NMR (400 MHz, CHLOROFORM-d) δ ppm 0.73-1.55 (m, 34H) 1.69-2.24 (m, 16H) 2.37-3.64 (m, 16H) 3.69-3.89 (m, 3H) 4.00-4.14 (m, 1H) 4.19-4.46 (m, 2H) 4.41-4.54 (m, 1H) 4.52-4.74 (m, 1H) 4.85-5.00 (m, 1H) 5.04-5.11 (m, 1H) 6.71-7.01 (m, 1H) 6.73-6.99 (m, 1H) 7.12-7.20 (m, 5H) 7.56-7.78 (m, 2H) 8.89-9.10 (m, 1H) 9.27-9.54 (m, 1H);

B-145. $^1$H NMR (400 MHz, CHLOROFORM-d) δ ppm 0.75-1.52 (m, 36H) 1.60-2.00 (m, 10H) 2.12-3.34 (m, 17H) 3.35-3.46 (m, 10H) 3.52-3.71 (m, 2H) 3.78-3.99 (m, 1H) 4.04-4.17 (m, 1H) 4.23-4.51 (m, 2H) 4.59-4.71 (m, 1H) 4.77-4.97 (m, 1H) 5.00-5.11 (m, 1H) 7.08-7.21 (m, 3H) 7.12-7.16 (m, 2H) 7.32-7.58 (m, 3H) 7.64-7.82 (m, 2H);

B-146. $^1$H NMR (400 MHz, CHLOROFORM-d) δ ppm 0.67-1.50 (m, 41H) 1.56-2.15 (m, 9H) 2.50-2.76 (m, 5H) 2.99-3.57 (m, 12H) 3.67-3.89 (m, 7H) 4.04-4.49 (m, 6H) 4.61-4.77 (m, 1H) 4.90-5.00 (m, 1H) 6.75-6.95 (m, 4H) 7.24-7.35 (m, 2H);

B-147. $^1$H NMR (400 MHz, CHLOROFORM-d) δ ppm 0.77-1.58 (m, 42H) 1.68-2.21 (m, 11H) 2.29-3.16 (m, 10H) 3.18-3.33 (m, 5H) 3.34-3.57 (m, 3H) 3.62-3.91 (m, 3H) 4.00-4.13 (m, 1H) 4.13-4.35 (m, 3H) 4.37-4.48 (m, 1H) 4.67-4.80 (m, 1H) 4.86-4.93 (m, 1H) 6.59-6.75 (m, 2H) 6.77-6.86 (m, 2H) 7.06-7.26 (m, 2H) 7.53-7.75 (m, 2H);

B-148. $^1$H NMR (400 MHz, CHLOROFORM-d) δ ppm 0.75-1.56 (m, 30H) 1.71-2.24 (m, 17H) 2.27-3.13 (m, 12H) 3.17-3.32 (m, 4H) 3.37-3.44 (m, 1H) 3.46-3.73 (m, 5H) 3.77-3.99 (m, 2H) 4.01-4.10 (m, 1H) 4.19-4.39 (m, 3H) 4.44 (br d, J=7.09 Hz, 1H) 4.75 (br d, J=8.80 Hz, 1H) 4.90 (br s, 1H) 6.65-6.77 (m, 4H) 7.30-7.39 (m, 2H) 7.40-7.52 (m, 1H) 7.67-7.81 (m, 2H);

B-149. $^1$H NMR (400 MHz, DMSO-d6) δ ppm 0.57-1.27 (m, 44H), 1.29-1.88 (m, 13H), 1.91 (s, 3H, AcOH), 1.93-2.04 (m, 1H), 2.16 (br d, 1H), 2.53-2.58 (m, 2H), 2.60-2.71 (m, 3H), 2.72-2.78 (m, 1H), 2.84-3.01 (m, 4H), 3.22 (br s, 1H), 3.27 (s, 3H), 3.42 (br d, 1H), 3.57-3.66 (m, 2H), 3.82 (s, 3H), 4.03 (br s, 1H), 4.33-4.42 (m, 2H), 4.72 (br s, 1H), 4.80-4.90 (m, 2H), 7.03 (d, 2H), 7.74 (d, 2H);

B-150. $^1$H NMR (400 MHz, DMSO-d6) δ ppm 0.58-1.27 (m, 45H), 1.28-1.89 (m, 14H), 1.91 (s, 3H, AcOH), 2.00 (br d, 1H), 2.15 (br d, 1H), 2.53 (br d, 1H), 2.67 (br d, 2H), 2.71-2.79 (m, 1H), 2.87 (br d, 1H), 2.91-3.04 (m, 3H), 3.15-3.22 (m, 1H), 3.25 (s, 3H), 3.40-3.44 (m, 1H), 3.52-3.59 (m, 1H), 3.61-3.68 (m, 1H), 4.03 (br s, 1H), 4.33 (br d, 1H), 4.36-4.42 (m, 1H), 4.80-4.89 (m, 3H), 7.58-7.60 (m, 2H), 7.80 (d, 2H);

B-151. $^1$H NMR (400 MHz, DMSO-d6) δ ppm 0.74-1.25 (m, 41H) 1.30-1.54 (m, 8H) 1.72-1.81 (m, 1H) 1.84-2.24 (m, 11H) 2.33-2.48 (m, 2H) 2.53-2.82 (m, 8H) 3.04-3.14 (m, 1H) 3.23-3.33 (m, 4H) 3.45-3.55 (m, 2H) 3.65-3.87 (m, 3H) 3.89-4.05 (m, 2H) 4.24-4.49 (m, 3H) 4.75-4.91 (m, 3H) 7.57-7.63 (m, 2H) 7.74-7.83 (m, 2H);

B-152. $^1$H NMR (400 MHz, DMSO-d6) δ ppm 0.77-1.22 (m, 39H) 1.35-1.49 (m, H) 1.71-1.81 (m, 1H) 1.86-1.93 (m, 6H) 1.95-2.09 (m, 3H) 2.10-2.20 (m, 1H) 2.40-2.48 (m, 2H) 2.53-2.63 (m, 3H) 2.64-2.74 (m, 6H) 2.87-2.96 (m, 1H) 3.04-3.13 (m, 1H) 3.28-3.31 (m, 4H) 3.46-3.54 (m, 2H) 3.66-3.74 (m, 1H) 3.76-3.89 (m, 2H) 3.95-4.02 (m, 1H) 4.34-4.47 (m, 2H) 4.75-4.81 (m, 1H) 4.82-4.89 (m, 2H) 7.57-7.64 (m, 2H) 7.74-7.82 (m, 2H);

B-153. $^1$H NMR (400 MHz, DMSO-d6) δ ppm 0.76-1.20 (m, 36H) 1.22-1.54 (m, 8H) 1.72-1.81 (m, 1H) 1.88-1.92 (m, 6H) 1.99-2.18 (m, 4H) 2.17-2.22 (m, 3H) 2.32-2.38 (m, 1H) 2.43-2.49 (m, 1H) 2.58-2.73 (m, 7H) 3.06-3.13 (m, 1H) 3.25-3.29 (m, 1H) 3.30-3.33 (m, 3H) 3.41-3.49 (m, 2H) 3.65-3.75 (m, 1H) 3.76-3.86 (m, 1H) 4.12-4.16 (m, 1H) 4.37-4.43 (m, 2H) 4.70-4.76 (m, 1H) 4.81-4.86 (m, 2H) 7.58-7.62 (m, 2H) 7.77-7.81 (m, 2H);

B-154. $^1$H NMR (400 MHz, DMSO-d6) δ ppm 0.75-1.21 (m, 35H) 1.31-1.54 (m, 9H) 1.72-1.82 (m, 1H) 1.87-1.93 (m, 4H) 1.93-2.24 (m, 5H) 2.34-2.48 (m, 5H) 2.53-2.81 (m, 9H) 3.06-3.17 (m, 1H) 3.22-3.34 (m, 5H) 3.46-3.54 (m, 2H) 3.64-3.74 (m, 1H) 3.79-3.89 (m, 1H) 3.90-4.01 (m, 2H) 4.33-4.41 (m, 1H) 4.42-4.51 (m, 1H) 4.75-4.82 (m, 2H) 4.84-4.91 (m, 1H) 7.31-7.37 (m, 2H) 7.64-7.72 (m, 2H);

B-155. $^1$H NMR (400 MHz, DMSO-d6) δ ppm 0.77-1.21 (m, 35H) 1.33-1.48 (m, 7H) 1.73-1.81 (m, 1H) 1.87-1.92 (m, 6H) 1.94-2.08 (m, 3H) 2.12-2.19 (m, 1H) 2.35-2.39 (m, 3H) 2.42-2.49 (m, 1H) 2.54-2.74 (m, 9H) 2.87-2.95 (m, 1H) 3.06-3.13 (m, 1H) 3.27-3.32 (m, 4H) 3.47-3.53 (m, 2H) 3.64-3.72 (m, 1H) 3.79-3.90 (m, 2H) 3.97-4.01 (m, 1H) 4.35-4.42 (m, 1H) 4.42-4.47 (m, 1H) 4.76-4.83 (m, 2H) 4.84-4.89 (m, 1H) 7.32-7.36 (m, 2H) 7.66-7.70 (m, 2H);

B-156. $^1$H NMR (400 MHz, DMSO-d6) δ ppm 0.81-1.20 (m, 32H) 1.22-1.55 (m, 7H) 1.73-1.82 (m, 1H) 1.87-1.93 (m, 6H) 2.00-2.24 (m, 6H) 2.32-2.39 (m, 4H) 2.41-2.48 (m, 2H) 2.58-2.72 (m, 7H) 3.06-3.14 (m, 1H) 3.29-3.33 (m, 4H) 3.42-3.50 (m, 2H) 3.63-3.72 (m, 1H) 3.77-3.87 (m, 1H) 4.12-4.16 (m, 1H) 4.24-4.31 (m, 1H) 4.37-4.44 (m, 2H) 4.70-4.77 (m, 1H) 4.78-4.86 (m, 2H) 7.31-7.37 (m, 2H) 7.64-7.71 (m, 2H);

B-157. $^1$H NMR (400 MHz, DMSO-d6) δ ppm 0.73-1.25 (m, 33H), 1.28-1.60 (m, 7H), 1.67-1.81 (m, 2H), 1.91 (s, 2H, AcOH), 1.92-2.12 (m, 4H), 2.20 (br d, 1H), 2.35-2.45 (m, 1H), 2.59 (br d, 1H), 2.63 (s, 3H), 2.69-2.81 (m, 3H), 3.01 (br dd, 1H), 3.14-3.26 (m, 3H), 3.31 (br s, 3H), 3.49-3.53 (m, 2H), 3.64 (s, 3H), 3.66-3.80 (m, 2H), 3.83 (s, 1H), 3.96 (br d, 1H), 4.04 (br d, 1H), 4.31 (s, 1H), 4.43 (br d, 2H), 4.47-4.52 (m, 1H), 4.86-4.91 (m, 3H), 6.41 (s, 2H), 6.60 (d, 2H), 6.69-6.75 (m, 2H);

B-158. $^1$H NMR (400 MHz, DMSO-d6) δ ppm 0.74-1.23 (m, 36H), 1.23-1.85 (m, 12H), 1.91 (s, 3H, AcOH), 1.93-2.18 (m, 5H), 2.35-2.48 (m, 3H), 2.53-2.61 (m, 1H), 2.62 (s, 3H), 2.64-2.83 (m, 4H), 3.11-3.20 (m, 2H), 3.27 (s, 3H), 3.50 (br d, 2H), 3.64-3.78 (m, 2H), 3.92 (br d, 1H), 3.99 (br d, 1H), 4.31 (br s, 1H), 4.37 (q, 1H), 4.44 (br d, 1H), 4.78 (br d, 1H), 4.83-4.90 (m, 2H), 6.40 (s, 2H);

B-159. $^1$H NMR (400 MHz, DMSO-d6) δ ppm 0.8-1.5 (m, 44H), 1.6-1.9 (m, 4H), 2.1-2.4 (m, 6H), 2.5-2.8 (m, 7H), 3.1-3.5 (m, 7H), 3.6-4.0 (m, 4H), 4.1-4.5 (m, 5H), 4.7-4.8 (m, 2H), 7.26 (bs, 2H), 7.56-7.57 (m, 2H);

B-160. No NMR

B-161. $^1$H NMR (600 MHz, DMSO-d6) δ ppm 0.43-1.88 (m, 54H), 1.91 (s, 1H, AcOH), 1.97-2.06 (m, 2H), 2.08-2.16 (m, 1H), 2.52-2.54 (m, 1H), 2.59-2.65 (m, 1H), 2.66-2.77 (m, 2H), 2.81-2.95 (m, 1H), 3.09-3.20 (m, 1H), 3.22-3.27 (m, 1H), 3.35-3.39 (m, 3H), 3.39-3.43 (m, 1H), 3.45-3.55 (m, 2H), 3.83-3.97 (m, 2H), 3.97-4.05 (m, 1H), 4.09-4.17 (m, 1H), 4.34-4.43 (m, 1H), 4.57-4.88 (m, 4H), 6.58-6.68 (m, 2H), 6.88 (td, 2H), 7.55-7.61 (m, 2H), 7.65-7.69 (m, 1H), 7.73 (br d, 2H);

B-162. $^1$H NMR (400 MHz, DMSO-d6) δ ppm 0.8-1.5 (m, 44H), 1.6-1.9 (m, 5H), 2.1-2.4 (m, 6H), 2.5-2.8 (m, 7H), 3.1-3.5 (m, 5H), 3.6-4.0 (m, 6H), 4.1-4.5 (m, 4H), 4.7-4.8 (m, 3H), 6.9-7.1 (m, 5H), 7.43 (s, 1H);

C-1. $^1$H NMR (400 MHz, DMSO-$d_6$) δ ppm 0.77-1.5 (m, 37H), 1.7-2.3 (m, 12H) (including 1 unit of acetate salt), 2.4-2.8 (m, 13H), 3.13 (bs, 1H), 3.25-3.70 (m, 6H), 3.79 (bs, 2H), 3.85 (bs, 2H), 4.07 (bs, 1H), 4.40-4.44 (m, 2H), 4.81-4.85 (m, 3H), 7.60 (d, 2H, J=8 Hz), 7.78 (d, 2H, J=8 Hz);

C-2. $^1$H NMR (400 MHz, DMSO-$d_6$) δ ppm 0.77-1.5 (m, 39H), 1.7-2.3 (m, 18H) (including 3 unit of acetate salt), 2.4-2.8 (m, 6H), 3.13 (bs, 1H), 3.25-3.50 (m, 8H), 3.79 (bs, 1H), 3.80 (bs, 1H), 4.06 (bs, 1H), 4.34-4.41 (m, 2H), 4.79-4.81 (bs, 3H), 7.60 (d, 2H, J=8 Hz), 7.78 (d, 2H, J=8 Hz);

C-3. $^1$H NMR (400 MHz, DMSO-$d_6$) δ ppm 0.77-1.5 (m, 41H), 1.7-2.3 (m, 12H) (including 1 unit of acetate salt), 2.4-2.8 (m, 7H), 3.13 (bs, 1H), 3.25-3.50 (m, 8H), 3.74-3.81 (m, 3H), 4.04 (bs, 1H), 4.31-4.50 (m, 3H), 4.81-4.84 (bs, 3H), 7.60 (d, 2H, J=8 Hz), 7.78 (d, 2H, J=8 Hz);

C-4. $^1$H NMR (400 MHz, DMSO-$d_6$) δ ppm 0.77-1.5 (m, 39H), 1.7-2.3 (m, 12H) (including 1 unit of acetate salt), 2.4-2.8 (m, 13H), 3.13 (bs, 1H), 3.25-3.70 (m, 6H), 3.75-3.82 (bs, 4H), 4.07 (bs, 1H), 4.42-4.46 (m, 2H), 4.81-4.84 (m, 3H), 7.60 (d, 2H, J=8 Hz), 7.77 (d, 2H, J=8 Hz);

C-5. $^1$H NMR (400 MHz, DMSO-$d_6$) δ ppm 0.77-1.5 (m, 35H), 1.7-2.3 (m, 12H) (including 1 unit of acetate salt), 2.4-2.8 (m, 6H), 3.13 (bs, 1H), 3.25-3.50 (m, 5H), 3.79 (bs, 1H), 3.85 (bs, 1H), 4.10-4.23 (m, 4H), 4.35 (d, 2H, J=8 Hz), 4.49 (d, 2H, J=8 Hz), 4.85 (bs, 2H), 5.02 (s, 1H), 7.23 (s, 1H), 7.60 (d, 2H, J=8 Hz), 7.68 (s, 1H), 7.78 (d, 2H, J=8 Hz);

C-6. $^1$H NMR (400 MHz, DMSO-$d_6$) δ ppm 0.77-1.5 (m, 37H), 1.7-2.3 (m, 18H) (including 3 unit of acetate salt), 2.4-2.8 (m, 13H), 3.13 (bs, 1H), 3.25-3.70 (m, 6H), 3.78 (bs, 2H), 3.85 (bs, 2H), 4.07 (bs, 1H), 4.40-4.44 (m, 2H), 4.81-4.83 (m, 3H), 7.60 (d, 2H, J=8 Hz), 7.77 (d, 2H, J=8 Hz);

C-7. ¹H NMR (400 MHz, DMSO-d₆) δ ppm 0.77-1.5 (m, 40H), 1.7-2.3 (m, 15H) (including 2 unit of acetate salt), 2.4-2.8 (m, 13H), 3.13 (bs, 1H), 3.25-3.70 (m, 6H), 3.78 (bs, 2H), 3.85 (bs, 2H), 4.07 (bs, 1H), 4.41-4.44 (m, 2H), 4.81-4.84 (m, 3H), 7.60 (d, 2H, J=8 Hz), 7.77 (d, 2H, J=8 Hz);

C-8. ¹H NMR (400 MHz, DMSO-d₆) δ ppm 0.77-1.5 (m, 35H), 1.7-2.3 (m, 15H) (including 2 unit of acetate salt), 2.4-2.8 (m, 6H), 3.13 (bs, 1H), 3.25-3.50 (m, 5H), 3.79 (bs, 1H), 3.81 (bs, 1H), 4.11 (bs, 1H), 4.34-4.39 (m, 4H), 4.49 (bs, 1H), 4.83 (bs, 2H), 4.92 (bs, 2H), 6.25 (s, 1H), 7.42 (s, 1H), 7.59 (d, 2H, J=8 Hz), 7.76-7.79 (m, 3H);

C-9. ¹H NMR (400 MHz, DMSO-d₆) δ ppm 0.77-1.5 (m, 38H), 1.7-2.3 (m, 15H) (including 2 unit of acetate salt), 2.4-2.8 (m, 6H), 3.13 (bs, 1H), 3.25-3.50 (m, 5H), 3.79 (bs, 1H), 3.85 (bs, 1H), 4.13 (bs, 1H), 4.33-4.49 (m, 2H), 4.61-4.65 (m, 1H), 4.79-4.86 (m, 2H), 4.97 (bs, 1H), 7.59 (d, 2H, J=8 Hz), 7.77 (d, 2H, J=8 Hz), 9.22 (s, 1H);

C-10. ¹H NMR (400 MHz, DMSO-d₆) δ ppm 0.77-1.5 (m, 34H), 1.7-2.3 (m, 9H), 2.4-2.8 (m, 8H), 3.08 (bs, 1H), 3.29-3.40 (m, 4H), 3.71-3.85 (m, 6H), 4.09 (bs, 1H), 4.28-4.32 (bs, 2H), 4.41-4.47 (m, 3H), 4.82-4.87 (m, 3H), 5.04 (bs, 1H), 7.03-7.18 (m, 4H), 7.59 (d, 2H, J=8 Hz), 7.77 (d, 2H, J=8 Hz), 8.18 (d, 2H, J=8 Hz);

C-11. ¹H NMR (400 MHz, DMSO-d₆) δ ppm 0.77-1.5 (m, 40H), 1.6-2.4 (m, 12H) (including 1 unit of acetate salt), 2.6-2.8 (m, 17H), 3.05-3.19 (m, 2H), 3.32 (bs, 2H), 3.52 (bs, 2H), 3.79 (bs, 2H), 4.06 (bs, 2H), 4.44-4.47 (m, 3H), 4.81-4.84 (m, 2H), 7.20 (bs, 2H), 7.52 (bs, 2H);

C-12. ¹H NMR (400 MHz, DMSO-d₆) δ ppm 0.77-1.5 (m, 39H), 1.6-2.2 (m, 15H) (including 1 unit of acetate salt), 2.4-2.8 (m, 16H), 3.13 (bs, 1H), 3.25-3.35 (m, 5H), 3.45 (bs, 1H), 3.65 (bs, 1H), 3.75 (bs, 2H), 4.08 (bs, 1H), 4.44 (d, 2H, J=8 Hz), 4.85 (bs, 2H), 7.26 (d, 2H, J=8 Hz), 7.58 (d, 2H, J=8 Hz);

C-13. ¹H NMR (400 MHz, DMSO-d₆) δ ppm 0.77-1.5 (m, 39H), 1.6-2.4 (m, 16H) (including 1 unit of acetate salt), 2.6-2.8 (m, 11H), 3.1-3.25 (m, 6H), 3.45 (bs, 1H), 3.65 (bs, 2H), 3.79 (bs, 2H), 4.09 (bs, 3H), 4.40 (d, 2H, J=8 Hz), 4.81-4.87 (m, 2H), 7.17 (bs, 2H), 7.50 (bs, 2H);

C-14. ¹H NMR (400 MHz, DMSO-d₆) δ ppm 0.77-1.5 (m, 41H), 1.6-2.2 (m, 18H) (including 2 unit of acetate salt), 2.4-2.8 (m, 16H), 3.13 (bs, 1H), 3.25-3.35 (m, 5H), 3.45 (bs, 1H), 3.65 (bs, 1H), 3.75 (bs, 2H), 4.08 (bs, 1H), 4.40 (d, 2H, J=8 Hz), 4.86 (bs, 2H), 7.14 (bs, 2H), 7.48 (bs, 2H);

C-15. ¹H NMR (400 MHz, DMSO-d₆) δ ppm 0.77-1.5 (m, 41H), 1.6-2.2 (m, 15H) (including 1 unit of acetate salt), 2.4-2.8 (m, 16H), 3.13 (bs, 1H), 3.25-3.35 (m, 5H), 3.45 (bs, 1H), 3.65 (bs, 1H), 3.75 (bs, 2H), 4.06 (bs, 1H), 4.41 (d, 2H, J=8 Hz), 4.82-4.86 (m, 2H), 7.25 (bs, 2H), 7.56 (bs, 2H);

C-16. ¹H NMR (400 MHz, DMSO-d6) δ ppm 0.68-1.55 (m, 48H), 1.56-1.88 (m, 6H), 1.89 (s, 3H, AcOH), 1.91-1.96 (m, 1H), 2.12 (br d, 1H), 2.32 (br d, 1H), 2.52 (br s, 1H), 2.54-2.60 (m, 3H), 2.64-2.69 (m, 1H), 2.83 (br d, 1H), 3.11-3.18 (m, 1H), 3.27 (s, 3H), 3.32 (s, 1H), 3.48 (br d, 1H), 3.67-3.83 (m, 3H), 4.08 (br s, 1H), 4.41-4.50 (m, 2H), 4.80-4.93 (m, 2H), 6.39 (br s, 2H);

C-17. ¹H NMR (400 MHz, DMSO-d6) δ ppm 0.74-1.23 (m, 28H), 1.29-1.61 (m, 16H), 1.63-1.82 (m, 5H), 1.91 (s, 3H, AcOH), 1.93-2.16 (m, 3H), 2.28-2.46 (m, 3H), 2.56 (br d, 3H), 2.62 (s, 2H), 2.65-2.83 (m, 3H), 2.92 (br t, 4H), 3.15 (br t, 1H), 3.26 (s, 3H), 3.49 (br d, 2H), 3.69-3.81 (m, 2H), 3.87-4.00 (m, 2H), 4.30 (br s, 1H), 4.39-4.52 (m, 2H), 4.76 (br d, 1H), 4.85 (br s, 2H), 6.39 (s, 2H), 6.65 (s, 2H);

C-18. ¹H NMR (400 MHz, CHLOROFORM-d) δ 0.78-0.86 (m, 3H), 0.88-0.92 (m, 5H), 1.01 (s, 3H), 1.04-1.15 (m, 12H), 1.17-1.28 (m, 7H), 1.30-1.60 (m, 12H), 1.74-1.97 (m, 5H), 2.04-2.30 (m, 4H), 2.37-2.50 (m, 2H), 2.51-2.72 (m, 9H), 3.03-3.11 (m, 2H), 3.16-3.25 (m, 2H), 3.30-3.35 (m, 3H), 3.39-3.44 (m, 1H), 3.50-3.57 (m, 1H), 3.78-3.89 (m, 1H), 3.98-4.12 (m, 2H), 4.43-4.51 (m, 1H), 4.51-4.57 (m, 1H), 4.69-4.79 (m, 1H), 4.83-4.91 (m, 1H), 7.60-7.69 (m, 2H), 7.89-7.96 (m, 2H);

C-19. ¹H NMR (400 MHz, CHLOROFORM-d) δ 0.77-0.85 (m, 3H), 0.89-0.97 (m, 6H), 0.99-1.04 (m, 3H), 1.05-1.17 (m, 12H), 1.18-1.64 (m, 18H), 1.69-1.89 (m, 2H), 1.90-1.95 (m, 3H), 1.95-2.20 (m, 5H), 2.21-2.71 (m, 10H), 2.75-2.84 (m, 1H), 3.10-3.24 (m, 2H), 3.29-3.35 (m, 3H), 3.45-3.50 (m, 1H), 3.52-3.58 (m, 1H), 3.74-3.84 (m, 1H), 3.95-4.08 (m, 2H), 4.42-4.50 (m, 1H), 4.52-4.57 (m, 1H), 4.79-4.88 (m, 3H), 7.07 (t, J=8.56 Hz, 2H), 7.77-7.85 (m, 2H);

C-20. ¹H NMR (400 MHz, DMSO-d6) δ ppm 0.8-1.5 (m, 48H), 1.6-1.9 (m, 16H) (including 3 units of acetate salt), 2.1-2.4 (m, 6H), 2.5-2.8 (m, 8H), 3.1-3.5 (m, 7H), 3.6-4.0 (m, 6H), 4.43-4.48 (m, 2H), 4.7-4.9 (m, 2H), 7.0-7.3 (m, 5H);

C-21. ¹H NMR (400 MHz, DMSO-d6) δ ppm 0.8-1.5 (m, 51H), 1.6-1.9 (m, 15H) (including 3 units of acetate salt), 2.1-2.4 (m, 7H), 2.6-2.8 (m, 8H), 3.1-3.5 (m, 6H), 3.6-4.0 (m, 5H), 4.3-4.5 (m, 3H), 4.8-4.9 (m, 2H), 6.9-7.0 (m, 1H), 7.09 (d, 2H, J=7.84 Hz), 7.22 (t, 2H, J=7.44 Hz);

C-22. ¹H NMR (400 MHz, DMSO-d6) δ ppm 0.8-1.5 (m, 55H), 1.6-1.9 (m, 10H) (including 1 unit of acetate salt), 2.1-2.4 (m, 5H), 2.6-2.8 (m, 8H), 3.0-3.1 (m, 1H), 3.28 (s, 3H), 3.40-3.42 (m, 1H), 3.6-3.8 (m, 4H), 4.08 (s, 1H), 4.4-4.5 (m, 2H), 4.81-4.84 (m, 2H), 7.08 (d, 2H, J=8.52 Hz), 7.26 (d, 2H, J=8.6 Hz);

C-23. ¹H NMR (400 MHz, DMSO-d6) δ ppm 0.8-1.5 (m, 47H), 1.6-1.9 (m, 12H) (including 2 units of acetate salt), 2.1-2.4 (m, 6H), 2.6-2.8 (m, 6H), 3.1-3.5 (m, 6H), 3.6-3.8 (m, 4H), 4.08 (s, 1H), 4.44-4.47 (m, 3H), 4.81-4.84 (m, 2H), 6.88-7.18 (m, 4H);

C-24. ¹H NMR (400 MHz, DMSO-d6) δ ppm 0.8-1.5 (m, 46H), 1.6-1.9 (m, 15H) (including 3 units of acetate salt), 2.1-2.4 (m, 5H), 2.5-2.8 (m, 6H), 3.1-3.5 (m, 10H), 3.6-3.8 (m, 4H), 4.09 (s, 1H), 4.4-4.5 (m, 2H), 4.82-4.85 (m, 2H), 6.39-6.41 (m, 1H), 6.61-6.65 (m, 2H), 7.02-7.04 (m, 1H);

C-25. ¹H NMR (400 MHz, DMSO-d6) δ ppm 0.8-1.5 (m, 46H), 1.6-1.9 (m, 18H) (including 3 units of acetate salt), 2.1-2.5 (m, 5H), 2.6-2.9 (m, 15H), 3.1-3.4 (m, 7H), 3.6-3.7 (m, 2H), 4.39-4.41 (m, 2H), 4.78-4.80 (m, 2H), 6.37-6.40 (m, 2H), 6.47 (s, 1H), 7.00-7.03 (m, 1H);

C-26. ¹H NMR (400 MHz, DMSO-d6) δ ppm 0.8-1.5 (m, 47H), 1.6-1.9 (m, 14H) (including 2 units of acetate salt), 2.1-2.4 (m, 7H), 2.6-2.8 (m, 7H), 3.1-3.5 (m, 7H), 3.6-3.8 (m, 4H), 4.09 (s, 1H), 4.44-4.46 (m, 2H), 6.46-6.48 (m, 1H), 6.87-6.97 (m, 2H), 7.11 (t, 1H, J=7.66 Hz), 7.63 (s, 1H);

C-27. ¹H NMR (400 MHz, DMSO-d6) δ ppm 0.8-1.5 (m, 46H), 1.6-1.9 (m, 7H), 2.1-2.4 (m, 7H), 2.5-2.8 (m, 6H), 3.0-3.5 (m, 7H), 3.6-3.8 (m, 4H), 4.11 (s, 1H), 4.4-4.5 (m, 2H), 4.81-4.84 (m, 2H), 6.56 (d, 2H, J=8.36 Hz), 6.6-6.7 (m, 2H);

C-28. $^1$H NMR (400 MHz, DMSO-d6) δ ppm 0.8-1.5 (m, 46H), 1.6-1.9 (m, 7H), 2.1-2.4 (m, 6H), 2.6-2.8 (m, 5H), 3.1-3.5 (m, 5H), 3.6-4.0 (m, 4H), 4.10 (s, 1H), 4.4-4.5 (m, 2H), 4.82-4.83 (m, 2H), 6.37 (s, 1H), 6.58 (dd, 1H, J=8.8 Hz, J=2.4 Hz), 6.87 (d, 1H, J=2.4 Hz), 7.08 (d, 1H, J=8.8 Hz);

C-29. $^1$H NMR (400 MHz, DMSO-d6) δ ppm 0.8-1.5 (m, 46H), 1.6-1.9 (m, 11H) (including 2 units of acetate salt), 2.1-2.4 (m, 5H), 2.5-2.8 (m, 9H), 3.0-3.5 (m, 8H), 3.6-3.8 (m, 3H), 4.08 (s, 1H), 4.43-4.47 (m, 2H), 4.81-4.83 (m, 2H), 7.07 (d, 2H, J=8.6 Hz), 7.42 (d, 2H, J=8.64 Hz);

C-30. $^1$H NMR (400 MHz, DMSO-d6) δ ppm 0.8-1.5 (m, 46H), 1.6-1.9 (m, 11H) (including 2 units of acetate salt), 2.1-2.4 (m, 5H), 2.5-2.8 (m, 9H), 3.1-3.5 (m, 8H), 3.6-3.8 (m, 3H), 4.09 (s, 1H), 4.41-4.47 (m, 2H), 4.82-4.84 (m, 2H), 6.81 (d, 2H, J=8.4 Hz), 7.43 (d, 2H, J=8.44 Hz);

C-31. $^1$H NMR (400 MHz, DMSO-d6) δ ppm 0.8-1.5 (m, 47H), 1.6-1.9 (m, 14H) (including 2 units of acetate salt), 2.1-2.4 (m, 5H), 2.6-2.8 (m, 6H), 3.1-3.5 (m, 7H), 3.6-3.8 (m, 3H), 4.08 (s, 1H), 4.41-4.47 (m, 2H), 4.82-4.83 (m, 2H), 7.07-7.33 (m, 3H);

C-32. $^1$H NMR (400 MHz, DMSO-d6) δ ppm 0.8-1.5 (m, 48H), 1.6-1.9 (m, 11H) (including 1 unit of acetate salt), 2.1-2.4 (m, 8H), 2.6-2.9 (m, 8H), 3.0-3.4 (m, 6H), 4.02 (s, 1H), 4.39-4.41 (m, 2H), 4.77-4.81 (m, 2H), 7.04-7.05 (m, 4H);

C-33. $^1$H NMR (400 MHz, DMSO-d6) δ ppm 0.8-1.5 (m, 47H), 1.6-1.9 (m, 12H) (including 2 units of acetate salt), 2.1-2.4 (m, 12H), 2.5-2.8 (m, 8H), 3.0-3.5 (m, 6H), 3.6-3.8 (m, 3H), 4.08 (s, 1H), 4.43-4.45 (m, 2H), 4.82-4.84 (m, 2H), 6.86-6.88 (m, 1H), 6.96 (s, 1H), 7.00 (d, 1H, J=8.08 Hz);

C-34. $^1$H NMR (400 MHz, DMSO-d6) δ ppm 0.5-1.5 (m, 48H), 1.6-1.9 (m, 8H), 2.1-2.4 (m, 6H), 2.5-2.8 (m, 4H), 3.2-3.5 (m, 7H), 3.7-3.9 (m, 3H), 4.1-4.4 (m, 4H), 4.8-4.9 (m, 2H), 6.66 (d, 1H, J=2.08 Hz), 6.86 (d, 1H, J=2.08 Hz);

C-35. $^1$H NMR (400 MHz, DMSO-d6) δ ppm 0.8-1.5 (m, 45H), 1.6-1.9 (m, 9H), 2.1-2.4 (m, 5H), 2.5-2.8 (m, 8H), 3.0-3.5 (m, 10H), 3.6-3.8 (m, 3H), 3.9-4.1 (m, 2H), 4.4-4.5 (m, 3H), 4.83-4.88 (m, 3H);

C-36. $^1$H NMR (400 MHz, DMSO-d6) δ ppm 0.8-1.5 (m, 48H), 1.6-1.9 (m, 15H) (including 3 units of acetate salt), 2.1-2.4 (m, 7H), 2.5-2.8 (m, 8H), 3.1-3.5 (m, 8H), 3.7-4.0 (m, 5H), 4.44-4.46 (m, 2H), 4.7-4.9 (m, 2H), 6.84 (d, 2H, J=8.4 Hz), 7.26 (d, 2H, J=8.48 Hz);

C-37. $^1$H NMR (400 MHz, CHLOROFORM-d) δ 0.71-0.86 (m, 3H), 0.88-0.98 (m, 5H), 0.98-1.06 (m, 3H), 1.06-1.18 (m, 11H), 1.18-1.28 (m, 4H), 1.28-1.55 (m, 11H), 1.56-1.67 (m, 1H), 1.69-1.89 (m, 3H), 1.93-1.97 (m, 3H), 2.05-2.19 (m, 2H), 2.37-2.49 (m, 2H), 2.53-2.78 (m, 6H), 2.85-2.91 (m, 3H), 3.08-3.38 (m, 12H), 3.40-3.46;

C-38. $^1$H NMR (400 MHz, DMSO-d6) δ ppm 0.8-1.5 (m, 46H), 1.6-1.9 (m, 5H), 2.1-2.4 (m, 9H), 2.5-2.8 (m, 5H), 3.1-3.5 (m, 7H), 3.6-4.0 (m, 3H), 4.1-4.5 (m, 3H), 4.7-4.8 (m, 2H), 7.58 (d, 2H, J=8.36 Hz), 7.77 (d, 2H, J=8.32 Hz);

C-39. $^1$H NMR (400 MHz, DMSO-d6) δ ppm 0.73-1.23 (m, 38H), 1.30-1.85 (m, 18H), 1.91 (s, 3H, AcOH), 1.92-1.98 (m, 1H), 2.11 (br d, 1H), 2.32 (br d, 1H), 2.53-2.57 (m, 2H), 2.64-2.70 (m, 2H), 2.88 (br d, 1H), 3.17 (s, 3H), 3.43 (br d, 1H), 3.60-3.74 (m, 2H), 4.02 (br s, 1H), 4.26-4.52 (m, 6H), 4.79-4.88 (m, 2H), 7.10-7.26 (m, 3H), 7.44-7.57 (m, 2H), 7.65-7.72 (m, 1H), 8.36 (dd, 1H), 8.47 (s, 1H);

C-40. $^1$H NMR (400 MHz, DMSO-d6) δ ppm 0.71-1.29 (m, 39H), 1.30-1.85 (m, 20H), 1.91 (s, 2H, AcOH), 1.94 (br d, 1H), 2.13 (br d, 1H), 2.31-2.37 (m, 1H), 2.55 (br d, 2H), 2.66-2.72 (m, 1H), 2.90-2.97 (m, 1H), 3.06 (br t, 2H), 3.15-3.21 (m, 1H), 3.25 (s, 3H), 3.34-3.38 (m, 1H), 3.42 (br d, 1H), 3.61-3.79 (m, 3H), 3.99 (br s, 1H), 4.39-4.46 (m, 1H), 4.84 (br dd, 3H), 7.34-7.40 (m, 2H), 7.83 (d, 2H);

C-41. $^1$H NMR (400 MHz, DMSO-d6) δ ppm 0.68-1.29 (m, 38H), 1.50 (br d, 20H), 1.91 (s, 2H, AcOH), 1.92-1.98 (m, 1H), 2.13 (br d, 1H), 2.31-2.37 (m, 1H), 2.55 (br d, 2H), 2.66-2.73 (m, 1H), 2.89-2.97 (m, 1H), 2.98-3.04 (m, 2H), 3.16-3.22 (m, 1H), 3.27 (s, 3H), 3.29-3.31 (m, 1H), 3.37 (br s, 1H), 3.43 (br d, 1H), 3.61-3.74 (m, 2H), 3.82 (s, 3H), 4.00 (br s, 1H), 4.44 (br dd, 2H), 4.74 (br d, 1H), 4.80-4.89 (m, 2H), 7.00-7.07 (m, 2H), 7.76 (d, 2H);

C-42. $^1$H NMR (400 MHz, DMSO-d6) δ ppm 0.69-1.28 (m, 42H), 1.29-1.90 (m, 19H), 1.91 (s, 2H, AcOH), 2.12 (br d, 1H), 2.33 (br d, 1H), 2.52-2.57 (m, 2H), 2.65-2.71 (m, 1H), 2.89-3.07 (m, 4H), 3.19 (br s, 1H), 3.23 (s, 3H), 3.35 (br s, 1H), 3.41 (br d, 1H), 3.52-3.63 (m, 1H), 3.71 (br dd, 1H), 3.99 (br s, 1H), 4.38 (br d, 1H), 4.44 (br d, 1H), 4.77-4.88 (m, 3H), 7.59 (d, 3H), 7.80 (d, 2H);

C-43. $^1$H NMR (400 MHz, DMSO-d6) δ ppm 0.70-1.27 (m, 42H), 1.32-1.87 (m, 18H), 1.91 (s, 3H, AcOH), 1.92-1.95 (m, 1H), 2.12 (br d, 1H), 2.30-2.36 (m, 1H), 2.52-2.57 (m, 3H), 2.62-2.69 (m, 2H), 2.83-3.02 (m, 4H), 3.17-3.24 (m, 1H), 3.25 (s, 3H), 3.44 (br d, 1H), 3.53-3.61 (m, 1H), 3.66-3.73 (m, 1H), 3.82 (s, 3H), 4.03 (br s, 1H), 4.39 (br d, 1H), 4.45 (q, 2H), 4.69 (br d, 1H), 4.80-4.87 (m, 2H), 7.03 (d, 2H), 7.73 (d, 2H);

C-44. $^1$H NMR (400 MHz, DMSO-d6) δ ppm 0.62-1.27 (m, 43H), 1.27-1.81 (m, 17H), 1.83-1.89 (m, 1H), 1.91 (s, 2H, AcOH), 1.93 (br d, 1H), 2.12 (br d, 1H), 2.27-2.37 (m, 2H), 2.55 (br d, 2H), 2.62-2.71 (m, 2H), 2.81-3.01 (m, 4H), 3.15-3.24 (m, 1H), 3.26 (s, 3H), 3.45 (br d, 1H), 3.63-3.71 (m, 1H), 4.05 (br s, 1H), 4.36-4.50 (m, 3H), 4.79-4.87 (m, 2H), 7.18-7.32 (m, 2H), 7.51-7.66 (m, 2H);

C-45.

C-46. $^1$H NMR (400 MHz, DMSO-d6) δ ppm 0.66-1.27 (m, 38H), 1.28-1.85 (m, 17H), 1.91 (s, 3H, AcOH), 1.93 (br d, 1H), 2.29-2.37 (m, 2H), 2.51-2.57 (m, 3H), 2.63-2.73 (m, 2H), 2.86-2.94 (m, 1H), 3.16-3.23 (m, 1H), 3.23-3.27 (m, 3H), 3.43 (br d, 1H), 3.61-3.71 (m, 1H), 3.74-3.84 (m, 1H), 4.02 (br s, 1H), 4.46 (br dd, 2H), 4.56-4.67 (m, 1H), 4.70-4.77 (m, 1H), 4.80-4.87 (m, 2H), 7.15 (br s, 2H), 7.43-7.56 (m, 2H), 7.62 (br d, 1H), 7.66 (d, 1H);

C-47. $^1$H NMR (400 MHz, CHLOROFORM-d) δ 0.86-0.94 (m, 3H), 0.97-1.04 (m, 5H), 1.08-1.14 (m, 3H), 1.15-1.26 (m, 10H), 1.26-1.36 (m, 4H), 1.37-1.40 (m, 3H), 1.41-1.72 (m, 10H), 1.85-2.07 (m, 7H), 1.86-2.08 (m, 6H), 2.20-2.28 (m, 2H), 2.68-2.82 (m, 7H), 3.17-3.23 (m, 3H), 3.27-3.34 (m, 3H), 3.40-3.46 (m, 3H), 3.49-3.53 (m, 1H), 3.64-3.70 (m, 1H), 3.87-4.00 (m, 1H), 4.08-4.21 (m, 2H), 4.51-4.61 (m, 1H), 4.61-4.67 (m, 1H), 4.85-4.91 (m, 1H), 4.91-4.98 (m, 1H), 7.89 (s, 2H), 7.95-8.08 (m, 1H);

C-48. $^1$H NMR (400 MHz, DMSO-d6) δ ppm 0.30-1.87 (m, 44H), 1.91 (s, 1H), 2.08 (s, 1H), 2.13-2.21 (m, 1H), 2.32-2.40 (m, 1H), 2.53-2.59 (m, 2H), 2.63 (s, 3H), 2.67 (br s, 1H), 2.87-2.99 (m, 1H), 3.00-3.13 (m, 1H), 3.18 (br d, 1H), 3.26-3.31 (m, 2H), 3.41 (br s, 3H), 3.84-3.98 (m, 2H), 4.14-4.25 (m, 1H), 4.29 (br d, 1H), 4.44 (br d, 1H), 4.68-4.74 (m, 1H), 4.78-4.85 (m, 2H), 5.17 (br dd, 1H), 6.07 (br s, 1H), 6.18 (d, 1H), 7.28-7.32 (m, 3H), 7.47-7.54 (m, 2H), 7.57-7.61 (m, 3H), 7.62-7.68 (m, 3H), 8.01 (d, 1H), 8.04-8.12 (m, 1H);

C-49. $^1$H NMR (400 MHz, DMSO-d6) δ ppm 0.44-1.89 (m, 54H), 1.91 (s, 3H), 2.08-2.15 (m, 1H), 2.31 (br d, 1H), 2.52-2.62 (m, 5H), 2.73 (s, 3H), 2.83 (br d, 1H), 3.22-3.27 (m, 1H), 3.47 (br d, 1H), 3.70-3.78 (m, 1H), 3.80 (s, 3H), 3.91-4.02 (m, 2H), 4.12-4.20 (m, 1H), 4.26 (td, 1H), 4.44 (q, 1H), 4.48-4.55 (m, 1H), 4.73-4.83 (m, 3H), 6.73 (d, 2H), 7.02 (d, 1H), 7.45 (s, 1H), 7.90-7.97 (m, 1H);

C-50. $^1$H NMR (400 MHz, DMSO-d6) δ ppm 0.8-1.5 (m, 45H), 1.6-1.9 (m, 7H) (including 1 unit of acetate salt), 2.1-2.4 (m, 5H), 2.5-2.8 (m, 7H), 3.0-3.5 (m, 5H), 3.6-3.8 (m, 6H), 4.0-4.4 (m, 4H), 4.6-4.8 (m, 5H), 6.66 (d, 2H, J=8.96 Hz), 6.81 (d, 2H, J=8.8 Hz), 7.02 (t, 1H, J=7.24 Hz), 7.13 (d, 2H, J=7.92 Hz), 7.27 (t, 2H, J=7.7 Hz), 9.80 (s, 1H);

C-51. $^1$H NMR (400 MHz, DMSO-d6) δ ppm 0.5-1.5 (m, 46H), 1.6-2.3 (m, 16H) (including 2 units of acetate salt), 2.4-2.8 (m, 9H), 2.9-3.5 (m, 8H), 3.8-4.1 (m, 4H), 4.4-4.8 (m, 3H), 6.84-7.03 (m, 5H), 7.11 (d, 2H, J=7.84 Hz), 7.25-7.29 (m, 2H);

C-52. $^1$H NMR (400 MHz, DMSO-d6) δ ppm 0.5-1.5 (m, 40H), 1.6-2.3 (m, 13H) (including 1 unit of acetate salt), 2.4-2.6 (m, 6H), 2.8-3.3 (m, 8H), 3.4-3.8 (m, 3H), 3.9-4.8 (m, 11H), 6.83-6.87 (m, 3H), 7.01-7.26 (m, 7H), 9.82 (s, 1H);

C-53. $^1$H NMR (400 MHz, DMSO-d6) δ ppm 0.40-1.84 (m, 53H), 1.91 (s, 1H), 2.15 (br d, 1H), 2.33-2.39 (m, 1H), 2.56 (br d, 3H), 2.85-2.94 (m, 1H), 3.27 (br d, 2H), 3.39 (s, 3H), 3.45 (br d, 1H), 3.90-4.00 (m, 2H), 4.04-4.18 (m, 3H), 4.43-4.51 (m, 1H), 4.71 (br d, 1H), 4.76-4.90 (m, 2H), 6.59 (br d, 2H), 6.80 (br t, 1H), 7.02-7.11 (m, 2H), 7.26-7.35 (m, 2H), 7.55-7.62 (m, 3H), 7.66-7.75 (m, 3H);

C-54. $^1$H NMR (400 MHz, DMSO-d6) δ ppm 0.40-1.86 (m, 50H), 1.91 (br s, 2H), 2.11-2.19 (m, 1H), 2.31-2.40 (m, 1H), 2.55-2.70 (m, 5H), 2.76-2.84 (m, 1H), 2.92-3.02 (m, 1H), 3.29 (br s, 1H), 3.37 (br s, 1H), 3.39 (s, 3H), 3.41-3.44 (m, 1H), 3.86-4.19 (m, 5H), 4.21-4.33 (m, 1H), 4.41-4.50 (m, 1H), 4.71 (br d, 1H), 4.78-4.85 (m, 2H), 6.58 (br dd, 2H), 6.83-6.92 (m, 2H), 7.28-7.32 (m, 2H), 7.56-7.61 (m, 3H), 7.70-7.75 (m, 2H);

C-55. $^1$H NMR (400 MHz, DMSO-d6) δ ppm 0.34-1.88 (m, 46H), 1.91 (s, 1H, AcOH), 2.14 (br d, 1H), 2.36 (br d, 1H), 2.55 (br d, 2H), 2.60 (s, 3H), 2.61-2.70 (m, 2H), 2.91-3.01 (m, 1H), 3.16-3.25 (m, 1H), 3.25-3.31 (m, 2H), 3.38 (s, 3H), 3.41 (br s, 1H), 3.85-4.03 (m, 2H), 4.12-4.32 (m, 2H), 4.39-4.50 (m, 2H), 4.70-4.85 (m, 3H), 6.35 (br d, 1H), 6.47 (s, 1H), 7.28-7.35 (m, 3H), 7.55-7.63 (m, 4H), 7.66-7.75 (m, 3H), 7.84 (d, 1H);

C-56. $^1$H NMR (400 MHz, DMSO-d6) δ ppm 0.45-2.04 (m, 53H), 2.12 (br d, 1H), 2.31 (br d, 1H), 2.52-2.58 (m, 3H), 2.60 (s, 4H), 2.85 (br d, 1H), 3.27 (br s, 1H), 3.33 (br s, 3H), 3.50 (br d, 1H), 3.82 (s, 3H), 3.92 (br dd, 1H), 3.98-4.07 (m, 2H), 4.09-4.18 (m, 1H), 4.29 (br s, 1H), 4.47 (q, 1H), 4.75 (br d, 1H), 4.77-4.83 (m, 2H), 6.88-7.05 (m, 5H), 7.44 (s, 1H);

C-57. $^1$H NMR (400 MHz, DMSO-d6) δ ppm 0.8-1.5 (m, 48H), 1.6-1.9 (m, 12H) (including 2 units of acetate salt), 2.1-2.4 (m, 7H), 2.5-2.7 (m, 7H), 3.1-3.4 (m, 6H), 3.7-3.8 (m, 3H), 4.13 (s, 1H), 4.2-4.5 (m, 3H), 4.7-4.8 (m, 2H), 7.0 (bs, 2H), 7.4 (bs, 2H);

C-58. $^1$H NMR (400 MHz, DMSO-d6) δ ppm 0.8-1.5 (m, 50H), 1.6-1.9 (m, 12H) (including 2 units of acetate salt), 2.1-2.4 (m, 6H), 2.6-2.8 (m, 8H), 3.1-3.5 (m, 6H), 3.6-4.0 (m, 6H), 4.3-4.5 (m, 3H), 4.8-4.9 (m, 2H), 7.05 (bs, 2H), 7.42 (bs, 2H);

D-1. $^1$H NMR (400 MHz, DMSO-d6) δ ppm 0.75-1.22 (m, 36H), 1.26-1.84 (m, 10H), 1.91 (s, 3H, AcOH), 1.93-1.98 (m, 1H), 2.03-2.10 (m, 2H), 2.14-2.20 (m, 1H), 2.40-2.48 (m, 2H), 2.52-2.56 (m, 1H), 2.57-2.65 (m, 2H), 2.67 (s, 3H), 2.68-2.74 (m, 2H), 2.87 (br d, 1H), 3.25 (s, 3H), 3.37-3.44 (m, 2H), 3.75 (br d, 1H), 3.91-3.96 (m, 1H), 3.98 (br d, 1H), 4.11 (dd, 1H), 4.27-4.37 (m, 2H), 4.81-4.87 (m, 2H), 4.94 (d, 1H);

D-2. $^1$H NMR (400 MHz, DMSO-d6) δ ppm 0.68-1.25 (m, 40H), 1.26-1.85 (m, 11H), 1.91 (s, 3H, AcOH), 2.02-2.08 (m, 2H), 2.14-2.20 (m, 1H), 2.32-2.41 (m, 1H), 2.42-2.48 (m, 1H), 2.52-2.56 (m, 1H), 2.61 (br d, 2H), 2.67 (s, 3H), 2.69-2.78 (m, 3H), 3.23 (s, 3H), 3.40 (br dd, 1H), 3.46 (br d, 2H), 3.87 (br d, 1H), 3.93-3.99 (m, 1H), 3.99-4.03 (m, 1H), 4.11 (dd, 1H), 4.27-4.34 (m, 2H), 4.77 (br d, 1H), 4.90 (dd, 1H), 4.99 (br d, 1H), 6.52-6.89 (m, 1H);

D-3. $^1$H NMR (400 MHz, DMSO-d6) δ ppm 0.74-1.24 (m, 37H), 1.25-1.58 (m, 9H), 1.71-1.89 (m, 2H), 1.91 (s, 1H, AcOH), 1.92-2.22 (m, 6H), 2.34-2.48 (m, 3H), 2.55-2.82 (m, 6H), 3.24 (s, 3H), 3.43-3.49 (m, 2H), 3.59 (td, 1H), 3.75 (s, 3H), 3.86 (br d, 1H), 3.92 (br s, 1H), 4.01 (br d, 1H), 4.07-4.24 (m, 3H), 4.26-4.35 (m, 2H), 4.77 (br d, 1H), 4.90 (dd, 1H), 5.00 (br d, 1H), 6.91 (d, 2H), 7.30 (d, 2H);

D-4. $^1$H NMR (600 MHz, DMSO-d6) δ ppm 0.74-1.88 (m, 52H), 1.91 (s, 1H, AcOH), 1.95 (br s, 1H), 2.13 (br d, 1H), 2.86 (br s, 2H), 2.94 (br d, 1H), 3.06 (br s, 1H), 3.25 (s, 3H), 3.47 (br s, 1H), 3.70-3.72 (m, 3H), 3.86 (br d, 1H), 3.94 (br dd, 3H), 4.40 (br dd, 1H), 4.54 (br d, 1H), 4.69-4.78 (m, 1H), 4.82 (br dd, 1H), 4.99 (br s, 1H), 5.31-5.39 (m, 1H), 6.77-6.82 (m, 2H), 7.27 (d, 2H), 7.81-7.98 (m, 2H);

D-5. $^1$H NMR (400 MHz, DMSO-d6) δ ppm 0.63-1.87 (m, 49H), 1.91 (s, 2H, AcOH), 1.98-2.04 (m, 1H), 2.09 (br d, 1H), 2.17 (br d, 1H), 2.31-2.43 (m, 2H), 2.52-2.58 (m, 2H), 2.67 (s, 3H), 2.70-2.81 (m, 5H), 2.98-3.04 (m, 1H), 3.24 (s, 3H), 3.37 (br d, 1H), 3.43 (m, 1H), 3.90 (br d, 1H), 4.01 (br s, 1H), 4.11 (br dd, 1H), 4.37 (q, 1H), 4.83-4.89 (m, 2H), 4.99 (br d, 1H);

D-6. $^1$H NMR (400 MHz, DMSO-d6) δ ppm 0.62-1.59 (m, 47H), 1.66-2.24 (m, 8H), 2.31-2.43 (m, 2H), 2.47 (br s, 1H), 2.53-2.64 (m, 2H), 2.67 (s, 3H), 2.69-2.84 (m, 3H), 3.23 (s, 3H), 3.28-3.32 (m, 1H), 3.35-3.41 (m, 1H), 3.43-3.49 (m, 2H), 3.84 (br d, 1H), 4.03 (br d, 2H), 4.11 (dd, 1H), 4.25 (br s, 1H), 4.30 (s, 1H), 4.36 (q, 1H), 4.75 (br d, 1H), 4.90 (br dd, 1H), 5.03 (br d, 1H);

D-7. $^1$H NMR (600 MHz, DMSO-d6) δ ppm 0.70-1.89 (m, 44H), 1.91 (s, 1H, AcOH), 1.93 (br s, 1H), 1.99-2.07 (m, 2H), 2.15-2.26 (m, 1H), 2.67-2.83 (m, 3H), 2.99-3.13 (m, 3H), 3.23-3.32 (m, 3H), 3.39-3.51 (m, 2H), 3.52-3.64 (m, 1H), 3.68-3.73 (m, 1H), 3.75 (s, 3H), 3.76-3.84 (m, 1H), 3.85-4.02 (m, 2H), 4.08-4.25 (m, 4H), 4.33-4.41 (m, 2H), 4.84-4.93 (m, 3H), 5.00 (br d, 1H), 5.13 (s, 1H), 6.25 (br s, 1H), 6.89-6.94 (m, 2H), 7.30 (d, 2H);

A3-1. $^1$H NMR (400 MHz, DMSO-d$_6$) δ ppm 0.77-1.5 (m, 38H), 1.7-2.3 (m, 9H), 2.4-2.8 (m, 6H), 3.13 (bs, 2H), 3.25-3.50 (m, 5H), 3.79 (bs, 1H), 3.85 (bs, 2H), 4.16 (bs, 1H), 4.37-4.49 (m, 2H), 4.83-4.85 (m, 3H), 4.97 (bs, 1H), 7.16 (t, 1H, J=8 Hz), 7.30 (t, 2H, J=8 Hz), 7.36 (d, 2H, J=8 Hz), 7.60 (d, 2H, J=8 Hz), 7.79 (d, 2H, J=8 Hz);

A4-1. $^1$H NMR (400 MHz, DMSO-d$_6$) δ ppm 0.77-1.5 (m, 35H), 1.7-2.3 (m, 9H), 2.4-2.8 (m, 7H), 3.13 (bs, 1H), 3.25-3.50 (m, 5H), 3.62-3.85 (m, 4H), 4.10 (bs, 2H), 4.36-4.46 (m, 2H), 4.82-4.89 (m, 3H), 7.60 (d, 2H, J=8 Hz), 7.78 (d, 2H, J=8 Hz); and A6-1. $^1$H NMR (400 MHz, DMSO-d$_6$) δ ppm 0.77-1.5 (m, 35H), 1.7-2.3 (m, 12H), (including 1 unit of acetate salt), 2.4-2.8 (m, 8H), 3.13 (bs, 1H), 3.25-3.50 (m, 8H), 3.82 (bs, 1H), 4.02 (bs, 2H), 4.35-4.46 (m, 2H), 4.54 (bs, 2H), 7.59 (d, 2H, J=8 Hz), 7.80 (d, 2H, J=8 Hz).

Biological

BRD pathogens include, for example, *Pasteurella multocida; Mannheimia haemolytica; Histophilus somni*; and *Mycoplasma bovis*. There is some debate as to whether *M. bovis* is a primary pathogen, secondary invader or predisposing factor for other BRD agents. The polymicrobial nature of BRD makes it difficult to ascribe a specific pathogen(s) to an individual case of BRD, since affected animals typically present non-specific clinical signs. The epidemiology of BRD is well known, with cases occurring within 6-10 day of entry into the feedlot (FIG. 1). Therefore, antimicrobial metaphylaxis is routine for on-arrival cattle that are deemed high risk of developing BRD. Low risk cattle may also be administered a parenteral metaphylaxis. Macrolides tend to be the primary antimicrobials that are administered to high risk cattle.

Primary screening of the compounds of the invention included the evaluation of antibacterial activity of analogs through determination of microbial inhibition concentration (MIC) as per CLSI guidelines. The screening panel included the relevant BRD pathogens: 1) *M. haemolytica* (e.g., 12726, 46571 and 49023, all AHDRCC; and 33396 (ATCC)); and 2) *P. multocida* (e.g., 34135 and 46572 (both AHDRCC) and 43137 (ATCC)). In some instances, *H. somni* (A700025K) pathogens were also included in the screening panel. The AHDRCC strains originated from the Zoetis BRD/SRD surveillance program and refer to the Animal Health Development and Research Culture Collection. In addition, the screen assessed *S. aureus* (29213 ATCC) as a representative Gram-positive isolate, *E. faecalis* (19433 ATCC) as a commensal gram-positive gastrointestinal bacterium and *E. coli* (100, 3110 and 25922 (ATCC)) for the evaluation of efflux potential. The screening panel BRD pathogens were assessed in determining antibacterial activity of the Formula (1) compounds.

All relevant BRD pathogens were initially screened at a top concentration of 64 μg/mL of a Formula (1) compound in an eleven-point dilution series. The analogs were then characterized based on their minimum inhibitory concentration (MIC) values to the BRD pathogens with the goal to be >64 μg/mL for progression, and to be considered a non-antibiotic compound. Formula (1) compounds were considered to be non-antibacterial if the pathogen MIC was >64 μg/mL for *M. haemolytica* and *P. multocida* strains. In addition, if Formula (1) compounds were also tested against the *H. somni* strain, to be considered non-antibacterial, the MIC was also >64 μg/mL. Generally, if the analogs had an MIC >64 μg/mL for the BRD pathogens, then the MIC's reported for *S. aureus, E. faecalis* and *E. coli* were also >64 μg/mL. In most instances, compounds of the invention with an initial screening BRD pathogen MIC result >64 μg/mL were not tested beyond this top concentration since this MIC value was determinant for lack of antibacterial activity. In addition, it should be noted that some Examples described in the Tables that are flagged as antibacterial (i.e., MIC ≤64 μg/mL) may actually be non-antibacterial but for potential residual (minor impurity(s)) antibacterial starting material (i.e., tulathromycin epoxide, M9 epoxide, M8 epoxide or azithromycin) that was used in its preparation. If an Example was purified further, the MICs moved up essentially two dilutions across all strains tested in the screening panel.

In-Vitro MIC Model

Compounds were analyzed for antibacterial activity against a panel of animal health specific gram-positive and gram-negative clinical strains by diluting compounds in DMSO to an appropriate stock concentration to determine the Minimal Inhibitory Concentration (MIC) via a semi-automated broth micro-dilution method (CLSI reference method) with QC strains and anti-microbial agent(s). Specifically, bacteria were grown overnight on TSA w/5% sheep blood agar plates and diluted in saline buffer to a McFarland Standard 0.5, then further diluted in cation-ion adjusted Mueller Hinton Broth to a final concentration of approximately 5×10$^5$ CFU/mL. 100 μL of inoculated media was added to 96-well plate(s) with 3 μL of serially diluted compound in each row. Depending on strain (see CLSI reference method), bacteria were incubated 18-22 hours at 35-37° C. in ambient air, with 5% $CO_2$ or anaerobically (up to 48 hours).

In-Vitro Immunological Assay(s)

Whole Blood Assay—Fresh whole bovine blood samples were collected into heparinized vacutainer tubes. Assay plates were prepared with 25 μL of drug diluted in PBS at varying concentration in 96 round bottom wells, then 225 μL of blood was added and plates incubated at 37° C. for 4 hours. Cells were stimulated with LPS (or PBS for controls) by adding 25 μL to the plates at a final concentration of 1 μg/mL and incubated at 37° C. for 18 hours. To collect plasma, plates were centrifuged at 2,000×g for 10 minutes and 100 μL of supernatant was transferred to a 96 well polypropylene plate that was sealed and stored at −80° C. Samples were assayed for cytokines using the Meso Scale Discovery (MSD) platform (described below). This same MSD platform was used to assess cytokines in the plasma collected directly from drug treated animals.

Cytokine Detection—An MSD U-Plex cytokine assay was developed following the MSD U-Plex protocol guide and included biotinylated capture antibodies against: bovine Interleukin (IL)-1β (Biorad), bovine IL-6 (R&D Systems) and bovine tumor necrosis factor (TNF)-α (R&D Systems). The anti-IL-1β antibody was biotinylated using EZ-Link Sulfo-NHS-Biotin (Thermo Scientific) at a challenge ratio of 1:20 according to manufacturer instructions. Assay calibrators (Kingfisher) were diluted to a concentration of 40,000 μg/mL in control lithium heparin plasma, followed by 4-fold serial dilutions into plasma. The detection antibodies were sulfo-tagged following the MSD quick guide conjugation protocol using a challenge ratio of 1:20. Antibodies were used at the following concentrations: anti-IL-1β at 1 μg/mL, anti-IL-6 at 1 μg/mL and anti-TNF-α at 0.5 μg/mL. Cytokines were quantified according to manufacturer's instructions using a chemiluminescent readout. In brief, 0.5 mL of all biotinylated antibodies were diluted to 10 μg/mL with Diluent 100 and paired to their respective linkers by adding 750 μL of supplied Linker solution and incubated for 30 minutes followed by addition of Stop solution for another 30 minutes. The linked antibodies were then diluted 10-fold into Stop solution. Plates were coated by adding 50 μL of antibody solutions per well and incubated covered and shaking for 1 hour at room temperature. Plates were washed three times with PBS/Tween20 prior to samples or standards being added at 30 µL per well and incubated as above. Plates were washed three times before detection antibodies were added along with 2% goat and rabbit serum to block and incubated same as above. Plates were washed a further three times before addition of 150 µL 2× Read buffer and read immediately on the S16000 instrument (MSD). For soluble protein levels, a BCA protein kit (Thermofisher) was used. The cytokine concentrations (µg/mL) were normalized to the total protein levels for each sample. [Bassel et. al., BMC Veterinary Research (2020) 16:168]

CD163 Expression by Flow Cytometry—Fresh whole bovine blood samples were collected into EDTA vacutainer tubes, placed on ice and processed within two hours of collection. Blood was placed in 96 well round bottom plates at 30 µL per well, 5 µL of goat serum was added as a blocking reagent and the plate was rocked at 4° C. for approximately 15 minutes. To label cells, 10 µL of a master mix panel of antibodies including anti-CD14 (BioLegend #301854), anti-CD172a (BioRad #MCA2041C), anti-CD163 (Kingfisher #WSC0832B-100) and anti-CD16 (BioRad #MCA5665F), was added to the samples and returned to 4° C. (protected from light) for 30 minutes. Single stain controls were included for use in fluorescence compensation matrices. Red blood cells were removed by adding 200 µL of lysis buffer and incubating for 10 minutes at room temperature while rocking. The plate was then centrifuged at 270×g for three minutes and supernatant removed. This step was repeated until supernatant was clear. 200 µL of FACS buffer was added to each well to wash cells, centrifuged as above, resuspended in 80 µL of FACS buffer and read immediately on a digital FACS Canto II HTS (BD Bioscience) flow cytometer. Data was analyzed using FlowJo software (BD Bioscience). Macrophage subpopulations were determined using CD172, CD14, CD16 markers and assessed for expression of CD163.

In Vivo Mouse Lung Infection Challenge Model (Murine)

The challenge organism was *P. multocida* 46572. Target challenge concentration was $5 \times 10^2$ CFU/mouse. Isolated colonies from overnight growth (37° C. with 5% $CO_2$) on trypticase soy agar (TSA II) blood plates were transferred to room temperature Brain Heart Infusion Broth (BHIB). The broth culture was incubated 3.5-4 hours to approximately mid-log phase of growth, as measured by forward light scatter at 600 nm (OD600, 0.200). The culture was centrifuged to collect the bacterial pellet. The pellet was re-suspended in BHIB and adjusted to provide an approximate concentration of 2.7 $\log^{10}$ colony forming units (CFU) in 0.04 mL at the highest concentration. The challenge inoculum concentration was confirmed by serial dilutions of the inoculum for CFU enumeration. On Day −5, CD-1 female mice were received. Mice were given standard rodent diet and water ad libitum. On Day 0, bacterial inoculum (0.04 mL) was administered to each mouse (n=36) intranasally. Compounds of the invention were dosed at 20 mg/kg (0.1 mL) in a buffered (~pH 5.4) propylene glycol, monothioglycerol and water solution by subcutaneous injection. Animals were observed from Days 1-10. The study was terminated on Day 10. In addition, some treatment groups were sampled at 6, 24, and 48 hours post bacterial challenge for RNA sequence analysis of lung tissue.

In Vivo Temporal Study

A clinical and genomics temporal study was conducted to mimic typical management cattle practices that result in the development of BRD. The design included extensive longitudinal genomics sampling, including the airway, as well as comprehensive clinical evaluation, with the goal of linking mechanism of disease to clinical phenotype. The study resulted in a 20% incidence of classic BRD as assessed by standard clinical scoring criteria. To allow data analysis, animals were assigned to phenotypic groups based on clinical signs, lung lesions, and treatment qualification as per feedlot standards. The study served as the framework to interpret the biological processes that resulted in healthy, subclinical, and diseased animals at the typical intervention point of arrival at the feedlot. For example, comparison of whole transcriptome RNA sequencing data of naso-pharyngeal swabs collected at the time analogous to arrival at the feedlot (when drug administration often occurs, yet prior to presentation of full BRD) could be aligned with a known clinical outcome from the study results.

The study demonstrated that contrary to the dogma, there is an upregulation of innate inflammatory pathways associated with stress experienced by BRD at-risk cattle at shipment and at the post-shipping feedlot arrival timepoint. This heightened inflammatory state is seen in virtually all animals despite the final clinical outcome. Further analysis of the comprehensive data revealed that animals that progressed to develop BRD continued to have elevated innate inflammatory pathway signatures expressed in the airway while the healthy and subclinical animals (healthy cohort) showed self-moderated decrease of the inflammatory signals within a couple of days as shown in FIG. 2. After weaning, cattle are transported to the sale barns and then to the feed lot. Prior to arrival at the feed lot, animals are stressed, some of which may recover while others progress to disease.

Of significance, is the presence of the unresolved exacerbated inflammation state at Days 4-6 in the BRD cohort of animals which results in differential bacterial involvement of *H. somni* and *M. haemolytica* and the transition to the full BRD disease complex. Both healthy and diseased cohorts were confirmed by RNA sequence analysis to have similar viral and bacterial exposures from Day −1 through Day 4. The healthy cohort (no disease and subclinical) were able to resolve the inflammation state early, Day 0 or Day 1. The BRD (diseased) cohort did not resolve the pathologic inflammation and progressed to the full BRD complex. A significant increase of typical BRD-associated microorganisms (*M. bovis, H. somni*, and *M. haemolytica*) was not detectable until after the innate inflammatory pathways failed to resolve at Day 4-6. It is believed that it is the unresolved, converting to chronic inflammatory process that enables progression to the full BRD complex.

From this temporal study, pathways for intervention were identified. These include Pattern Recognition Receptor (PRR) TLR-4 activation, inflammasome signaling, NF-κB and STAT transcription, which were targeted to reduce the pathologic innate inflammatory cascade prior to disease onset. Some key inflammatory cytokines included IL-1β, IL-6, IL-8, IL-17, IL-36, IFN-γ and TNF-α many of which were further confirmed through in vitro cell-based assays and ex vivo bovine infection models. The study also served to identify biomarkers correlating with disease severity (CD163, IL-6 and haptoglobin).

Plasma samples were collected from at-risk calves upon arrival at a feedlot, assessed for cytokine levels. The data was correlated with final disease (BRD) as assessed by clinical scoring for seven days. Of the cohort, 14 animals were healthy and 24 were diagnosed with BRD. As predicted for BRD etiology and pathogenesis, NF-κB mediated cytokines, including IL-6, were highest in animals that would develop clinical BRD. Interestingly, there was a correlation between higher levels of IFN-γ in animals at arrival associated with animals that did not progress to clinical BRD (FIG. 3). This data further supports that calves with heightened levels of some pro-inflammatory cytokines (IL-6 and IL-8) on arrival to the feedlot are associated with poor clinical outcome whereas calves that have increased IFN-γ, a cytokine associated with pathogen clearance, are associated with remaining healthy and not progressing to BRD.

In-Vitro Studies

The compounds of the invention had MIC values for multiple BRD pathogenic bacterial strains of *M. haemolytica* and *P. multocida* and from other pathogenic bacterial strains including *E. coli*, *S. aureus*, and *E. faecalis* that were considered to be non-antibacterial (i.e., MIC >64 µg/mL). Bacterial strains included the following: *E. coli* (A25922K/T, W3110WT, AG100T, AG100AT); *E. faecalis* (A19433K/T); *M. haemolytica* (12726K, 46571K/T, A33396K/T, 49023T, and others); *P. multocida* (46572K, 43137K, 34135T, and others), and *S. aureus* (A29213K/T). The K and T represent a specific strain at two different study site locations. Except for a few compounds of the invention, most had MIC values >64 µg/mL for the BRD pathogenic strains (i.e., non-antibacterial), and for the non-BRD strains as well.

Comparatively, gamithromycin had MIC values ranging from about 0.5-1 µg/mL and 1-2 µg/mL for the same *M. haemolytica* and *P. multocida* strains respectively; and about 0.25-8 µg/mL for the *H. somni* strains. For the same *H. somni* strains, florfenicol and enrofloxacin had MIC's ranging from 0.12-2 µg/mL and <0.06-1 µg/mL, respectively; clearly showing their antibacterial potential against these bacterial strains. In addition, the MIC's (µg/mL) for tulathromycin (Tula) and M9 for the following bacterial isolates is shown in Table 1.

TABLE 1

Comparative MIC's (µg/mL) for Bacterial Isolates

| Bacterial Isolate | Tula | M9 | A-9 | B-26 | B-50 | C-4 | C-11 |
|---|---|---|---|---|---|---|---|
| *S. aureus* 29213 | 8 | 64 | >64 | >64 | >64 | >128 | >64 |
| *E. coli* 25922 | 2 | >64 | >64 | >64 | >64 | >128 | >64 |
| *E. coli* W3110 | 8 | 64 | >64 | >64 | >64 | >128 | >64 |
| *M. haemolytica* 33396 | 1 | 32 | >64 | >64 | >64 | >128 | >64 |
| *M. haemolytica* 12726 | 2 | 22 | >64 | >64 | >64 | >128 | >64 |
| *M. haemolytica* 46571* | 1 | 32 | >64 | >64 | >64 | >128 | >64 |
| *P. multocida* 43137 | 1 | 16 | >64 | >64 | >64 | >128 | >64 |
| *P. multocida* 46572** | 1 | 8 | >64 | >64 | >64 | >128 | >64 |

*Indicates bovine efficacy challenge strain
**Indicates murine efficacy challenge strain.

In summary, non-antibacterial compounds in Tables A-D demonstrated a lack of in vitro activity vs. clinically relevant pathogenic strains for BRD (*M. haemolytica* and *P. multocida*) and a lack of clinically relevant MICs against other zoonotic bacterial strains.

The compounds of the invention share the most commonly described immune-effects with the parent macrolide class including modulation of pro-inflammatory cytokine production and the trafficking/fate of granulocytes. Reductions in IL-1β, IL-6 and TNFα with the compounds of the invention have been observed and have been associated with a positive clinical outcome (mouse murine). Therefore, underlying mechanism of the compounds of the invention are likely the broad-spectrum modulation of innate inflammatory response.

Early in vitro systems utilizing single cell types had marginal success in their ability to demonstrate the immune modulating effect of the compounds. This suggested that a more complex multi-cell system was required to recapitulate the immunological pathways affected. Therefore, a fresh whole bovine blood assay was developed with LPS as a stimulant (TLR-4 agonist) and with IL-1β and TNF-α as the read-out. Compounds of the invention were evaluated against a positive control for their ability to inhibit LPS-induced IL-1β and TNF-α as an overall evaluation of relative potency and modulation of target pathways.

The second immunomodulation in vitro assay evaluated the potential for phospholipidosis with the compounds (250 µM or 500 µM^) of the invention in bovine alveolar macrophages. The phospholipidosis assay is being used as a convenient method for the evaluation of cellular uptake. This assay utilized Invitrogen's commercially available HCS LipidTox detection kit with an Incucyte real time fluorescence reader to observe variations in $EC_{50}$ and phospholipidosis profiles based on compound concentrations (Table 2). Murine intraperitoneal macrophages were also used in the same assay to evaluate species variability for potential correlation with mouse efficacy results. The combination of the bovine whole blood assay and phospholipidosis assays enabled rank ordering for progression into in vivo testing in the murine challenge model.

TABLE 2

Immunomodulation Whole Blood Assay Results

| Ex# | TNF-α $IC_{50}$ | IL-1β OS of LPS | IL-6 $IC_{50}$ | Ex# | TNF-α $IC_{50}$ | IL-1β OS of LPS | IL-6 $IC_{50}$ |
|---|---|---|---|---|---|---|---|
| M9 | 250 | n/a | >250 | B-110 | 154 | 18 | 75 |
| A-1 | 22 | 16 | | B-111 | >250 | 17 | 141 |
| A-2 | 28 | 40 | | B-112 | 39 | 40 | 45 |
| A-3 | 23 | 14 | 43 | B-113 | 7 | | |
| A-4 | 10 | 4 | | B-117 | | 16 | 142 |
| A-8 | 40 | 100 | | B-118 | 45 | | 10 |
| A-9 | 4 | 16 | 21 | B-119 | | 6 | |
| A-21 | 16 | 16 | 16 | B-120 | | | 6 |
| A-22 | 30 | 16 | 22 | B-121 | | | 5 |
| A-23 | 36 | 16 | 22 | B-123 | | 6 | 4 |
| A-24 | 30 | 19 | 26 | B-124 | | 6 | 4 |
| A-25 | 75 | 16 | 28 | B-125 | 34 | 16 | 88 |
| A-26 | 130 | 16 | 49 | B-126 | 68 | 11 | |
| A-27 | 141 | 100 | 66 | B-128 | 11 | | 23 |
| A-28 | >250 | 81 | 120 | B-129 | 10 | 2 | |
| A-32 | | 100 | 167 | B-130 | 3 | 6 | 3 |
| A-34 | 205 | 40 | 59 | B-131 | 28 | 6 | 17 |
| A-36 | 10 | 4 | | B-133 | 12 | 16 | 24 |
| A-37 | 19 | | 46 | B-134 | 17 | 40 | 83 |
| B-2 | 37 | | 46 | B-135 | 3 | 6 | 3 |
| B-4 | 12 | 40 | | B-136 | 8 | 6 | 9 |
| B-5 | >250 | >250 | | B-138 | 26 | 40 | 70 |
| B-6 | 24 | 16 | | B-139 | 40 | 40 | 73 |
| B-7 | 25 | 40 | | B-140 | | >250 | |
| B-9 | 55 | 40 | | B-141 | 7 | | 4 |
| B-10 | 33 | 15 | | B-142 | 8 | | 9 |
| B-11 | | >250 | | B-143 | 7 | 2 | 8 |
| B-12 | | >250 | | B-144 | 9 | 2 | 10 |
| B-13 | >250 | 100 | | B-145 | 8 | 2 | 6 |
| B-15 | | >250 | | B-146 | 10 | 2 | 10 |
| B-16 | >250 | >250 | | B-147 | 7 | 1 | 5 |
| B-17 | | 100 | | B-148 | 2 | 2 | 4 |
| B-18^ | 15 | 32 | | B-149 | 7 | | 8 |
| B-19 | 30 | 16 | | B-150 | 4 | | 5 |
| B-21 | 5 | | 6 | B-151 | 8 | | 10 |
| B-22 | 9 | | 11 | B-152 | 11 | | 11 |
| B-23 | 3 | | 13 | B-153 | 7 | | 10 |
| B-24 | 10 | | | B-154 | 7 | | 15 |
| B-25 | 5 | | 17 | B-157 | 22 | | 31 |
| B-26 | 20 | 16 | | B-158 | 102 | >250 | |

TABLE 2-continued

Immunomodulation Whole Blood Assay Results

| Ex# | TNF-α $IC_{50}$ | IL-1β OS of LPS | IL-6 $IC_{50}$ | Ex# | TNF-α $IC_{50}$ | IL-1β OS of LPS | IL-6 $IC_{50}$ |
|---|---|---|---|---|---|---|---|
| B-27 | 17 | | 33 | B-159 | 4 | | 3 |
| B-29 | 18 | 12 | 54 | B-162 | 8 | | 9 |
| B-31 | 4 | | 7 | C-2 | | 6 | 13 |
| B-32 | 23 | | | C-3 | 5 | 16 | 9 |
| B-34 | | 6 | 20 | C-4 | 5 | 16 | |
| B-35 | >250 | 16 | 54 | C-5 | | 16 | 31 |
| B-36 | 29 | 16 | 18 | C-6 | 6 | 16 | 32 |
| B-37 | 8 | | 13 | C-7 | 66 | 6 | 50 |
| B-38 | 32 | 5 | 22 | C-9 | 23 | 8 | 23 |
| B-41 | | 6 | 12 | C-10 | 23 | | |
| B-42 | 13 | 2 | 8 | C-11 | 17 | | 13 |
| B-43 | 43 | 100 | 148 | C-12 | 13 | 100 | 140 |
| B-44 | 13 | 3 | 9 | C-13 | >250 | 6 | >250 |
| B-45 | 16 | 3 | 8 | C-14 | >250 | >250 | >250 |
| B-46 | 159 | 19 | | C-15 | 10 | 16 | 48 |
| B-47 | 13 | 40 | 24 | C-17 | 23 | 250 | |
| B-48^ | 25 | 32 | | C-18 | 6 | | 5 |
| B-49 | 37 | 6 | 16 | C-19 | 5 | | 7 |
| B-50 | | 6 | 49 | C-20 | 12 | 10 | 24 |
| B-51 | 38 | 97 | 62 | C-22 | 4 | | 6 |
| B-53 | 85 | 16 | 26 | C-23 | 9 | | 10 |
| B-55 | >250 | 26 | >32 | C-24 | 16 | 3 | 25 |
| B-56 | 86 | 16 | 26 | C-25 | 37 | | |
| B-57 | 5 | 16 | 8 | C-26 | 16 | | 25 |
| B-58 | 29 | 40 | 75 | C-27 | 73 | | 72 |
| B-59 | 150 | 57 | | C-28 | 25 | | 25 |
| B-60^ | 5 | 13 | | C-29 | 14 | | |
| B-61 | 37 | | 71 | C-30 | 9 | | |
| B-62 | 11 | 3 | | C-31 | 8 | | 11 |
| B-63 | 9 | | 10 | C-32 | 5 | | 8 |
| B-64 | 8 | | | C-33 | 7 | | 7 |
| B-65 | 9 | 6 | 15 | C-35 | 33 | 11 | 23 |
| B-66 | 30 | | | C-36 | 6 | | 9 |
| B-68 | 5 | 16 | 25 | C-38 | 9 | 28 | 4 |
| B-69 | 18 | | 16 | C-39 | 15 | 6 | |
| B-70 | 4 | | 13 | C-40 | 5 | | 4 |
| B-74 | 33 | 16 | | C-41 | 3 | >250 | 4 |
| B-75 | 31 | >250 | | C-42 | 6 | | 6 |
| B-76 | >250 | >250 | >250 | C-43 | 3 | | 4 |
| B-78 | 21 | | | C-44 | 4 | 6 | 4 |
| B-79 | 7 | | 7 | C-47 | 3 | | 4 |
| B-81 | 22 | 15 | | C-48 | 4 | 6 | 6 |
| B-82 | 71 | >250 | >250 | C-49 | 6 | 6 | 9 |
| B-83 | 30 | | | C-51 | 9 | | 11 |
| B-84 | 51 | | | C-52 | 15 | | |
| B-85 | 9 | | 26 | C-53 | 2 | 6 | 2 |
| B-87 | 17 | 9 | | C-54 | 2 | 6 | 4 |
| B-88 | 22 | 14 | 40 | C-55 | 6 | 6 | 9 |
| B-89 | 9 | | 23 | C-56 | 5 | | 4 |
| B-90 | 8 | | 26 | C-57 | 6 | 16 | 9 |
| B-91 | 34 | 2 | 101 | C-58 | 9 | 12 | 13 |
| B-103 | 11 | 1 | 4 | D-1 | 5 | 16 | 27 |
| B-104 | 15 | 3 | 7 | D-3 | 3 | >250 | 3 |
| B-105 | 12 | 3 | 7 | D-5 | 4 | >250 | 11 |
| B-106 | 7 | 3 | 9 | D-6 | 4 | >250 | 9 |
| B-107 | 22 | 2 | 9 | D-7 | 5 | | 4 |
| B-108 | 5 | 6 | 10 | A3-1 | 27 | | 31 |
| B-109 | 9 | 3 | 10 | A4-1 | 44 | 12 | 26 |

^dose of 500 µM

The results presented in Table 2 demonstrate a significant increase in inhibition of TNFα for the compounds tested compared to M9 at concentrations of drug at 250 µM. For M9, the top dose of 500 µM was not high enough to determine an overstimulation of IL-1β which was recorded as not applicable (n/a). The enhanced response indicates increased concentration of IL-1β cytokine at the drug concentration indicated. This is generally observed when compounds are out of range (high concentration) and stimulate a cellular toxicity signal. Further data supporting this hypothesis includes murine studies using a *P. multocida* infection in mice. For example, M9 was clinically efficacious when airway tissues were collected longitudinally and evaluated for transcriptomic analysis. Using these results, specific transcriptional expression demonstrated regulators consistent with some key BRD pathways (PRRs, cytokines, STAT) and cellular cross-talk activity were assessed.

TNFα is a cell signaling protein, cytokine, that plays a key role in both acute and chronic inflammation. In the bovine whole blood in vitro screening assay the inhibition of TNFα as induced by stimulation by lipopolysaccharide (LPS) and as measured by half the maximal inhibitory concentration ($IC_{50}$) is recognized as the primary biomarker of immunomodulation potency upon pretreatment with the compounds of the invention. IL-1β is a mediator of the inflammation response and is involved in a number of cellular activities including proliferation, differentiation and apoptosis. IL-1β is also released upon cellular stress or cytotoxicity or upon TLR stimulation. In the bovine whole blood assay the stimulation of IL-1β release upon increasing concentration of test compound is seen as a potential cellular toxicity signal as induced by the test compound. In order to estimate a therapeutic index from the in vitro assay a differential between the TNFα $IC_{50}$ (immunomodulation potency) versus the perceived cellular toxicity concentration (IL-1β release or overstimulation) was utilized. A lower TNFα $IC_{50}$ would indicate a lower overall mg/kg dose in vivo, assuming a sufficient therapeutic index of >2. As the in vitro assay index approaches 1 it is proposed that the balance between immunomodulation and cytotoxicity would be too narrow in order to achieve an efficacious dose in vivo.

The screening assays used to identify the compounds are utilized due to their ability to recapitulate key components of BRD. Activation of pathways including the TLRs and the downstream transcription factor NFKB are associated with the disease state in BRD. The regulation or mitigation of these pathways is associated with protection from disease and therefore the inhibition of markers of pathway activation is used to identify compounds of interest. Lipopolysaccharide (LPS) is a component of bacterial membrane (including *M. haemolytica* and *P. multocida*, where it associated with virulence) which binds to and signals through CD14 and Toll-like receptor 4 (TLR4). These receptors are expressed on macrophages which are a cell type that express CD163 (a BRD disease marker), and are relevant to the pathobiology BRD. After LPS binding occurs, signaling through NFκB results in upregulation of cytokines including IL-1β, IL-6 and TNF-α which is associated with many diverse diseases, including BRD. Reduction of NFκB-regulated cytokines is an approach often taken in diseases with an inflammation component of pathobiology. The new understanding is that inflammation, and specifically IL-1β, IL-6 and TNFα, is a component of BRD etiology.

Mouse Murine Study

Compounds of the invention were selected for progression into murine efficacy and beyond based on a significant MIC increase (target >64 μg/mL) for all bacterial strains in the screening panel. This assessment was combined with an in vitro immunomodulation potency equal to or better than M9, TNF-α and IL-1β $IC_{50}$ of ~250 μM for both cytokines and an $EC_{50}$ for phospholipidosis of 53.74 mM.

The murine efficacy model (*P. multocida* challenge) was optimized, and the treatment group size was powered to be able to observe statistically significant improvement of survival to expected ranges for immunomodulatory compounds. The experimental design was a randomized complete block design. Mice were individually identified and treatment groups comingled within a cage, with every treatment group equally represented across cages. Mortality was the primary variable. Mortality data was analyzed using a generalized mixed model with fixed effect of treatment and random effect of block. Survival time was also analyzed using the SAS PHREG (survival analysis) procedure to examine whether there were significant differences between treatment groups and the control group. Numerous compounds of the invention and M9 (positive control) were tested in this model at a dose of 20 mg/kg (Table 3). Typical percent survival for no treatment control is in the range of 0-20% based on study to study variation in challenge inoculum and rate of infection. The analogs tested had an MIC vs. challenge strain at ≥64 µg/ml compared to M9 at (8 µg/mL). Mouse survival for M9 was about 90-100%, further supporting its residual antibacterial properties against the bacterial strain. Harmonized (accounts for % survival relative to vehicle ("−" control) and M9 ("+" control) survival data. The "*" represents an MIC ≤64 µg/mL for P. multocida challenge strain (46572K); and survival may have also been attributed partially to the antibacterial activity.

TABLE 3

Mouse Murine Percent Survival

| Ex.# | % Survival |
|---|---|
| A-3 | 24 |
| A-8 | 20 |
| A-9 | 41 |
| B-14 | 16 |
| B-26 | 37 |
| B-41 | 52 |
| B-48 | 33 |
| B-49 | 53 |
| B-50 | 88 |
| B-58 | 32 |
| B-60 | 37 |
| B-107 | 82 |
| B-113 | 59 |
| B-130 | 42 |
| B-148 | 68 |
| C-4 | 76 |
| C-11 | 56 |
| C-59 | 71 |
| C-64 | 44 |

In one murine P. multocida intranasal challenge study, mice were administered tulathromycin (16 mg/kg; T02), M9 (32 mg/kg; T03), or ceftiofur (9 mg/kg; T04) by subcutaneous injection 18 hours after bacterial challenge ($5 \times 10^3$ CFU/mouse) for lung tissue RNA sequence analysis. Survival at Day 7 was about 80%, 50%, and 90% for T02, T03, and T04, respectively, compared to placebo at 0%. Differential gene expression from total lung tissue RNA sequence analysis indicated at least 226 unique genes were up or down regulated (with significance) for T03. Output from ingenuity pathway analysis of these unique genes predicted major upstream regulators of the involved pathways. Data was analyzed based on the number of genes being modulated in the same direction that were associated with a given upstream regulator. An activation z-score of 2 or greater is considered significant and the direction change is indicated by + (activated) or − (inhibited). The top 5 pathways included: IL-9 signaling, glucocorticoid receptor signaling, prolactin signaling, JAK STAT signaling, and IL-17 signaling. The top 6 upstream regulators (activation z-score) included: lipopolysaccharide (−6.725), TNF (−4.669), IFNγ (−5.759), IL-1β (−5.947), STAT1 (−2.787), and poly rI:rC-RNA (−5.289). Even though this study was run in the murine model, the top upstream regulators identified as being modulated by M9 include an almost ubiquitous overlap with the pathways identified in the natural disease study as being key mediators in BRD, and therefore is modulating highly relevant pathways in BRD pathobiology.

Single cell RNA sequencing was employed using the whole blood assay described above demonstrating drug-induced changes in protein cytokine expression to further substantiate cell type and pathway modulation by the compounds of the invention. Whole blood contains a variety of types of immune cells including both myeloid (e.g., neutrophils and macrophages) and lymphoid (e.g., T and B cells) derived cells as well as further differentiated cell-type specific subsets. Cells with transcriptional similarities were clustered together and identities were projected based on marker reference lists which were cross-checked with top differentially expressed genes against our established bovine antibody-based marker panels. Samples were sequenced at 30 minutes, 4 hours, and 20 hours stimulation (LPS, as described above) with the relatively largest changes seen at 20-hours. Among the genes with the largest differentially expression values included but were not limited to cytokines such as IL-1β, chemokines such as CXCL2 and CXCL8, and interferon-stimulated gene (ISG) family members (data not shown).

Focusing on the clusters of cells identified in the drug influence correlation, lists of significantly modulated genes (adjusted $p<0.05$ and absolute log(Fold Change)>0.25) were used to identify the predicted upstream regulators of the associated pathways. These regulators include (but are not limited to) components central to hypothesized pathological pathways in BRD such as TNFα, LPS (TLR4 agonist), NFκB, IL-1β and IL-6. As described previously, the mitigation of these inflammatory pathways that are increased in BRD correlates with positive clinical outcome. In this experimental system, LPS was administered to activate the inflammatory pathways seen in calves at-risk for BRD and full transcriptome sequencing was used to determine drug effect on these key pathways. Within the myeloid cell populations, the neutrophil/activated macrophage cluster and monocyte cluster, the drug mitigated the activation of the majority of the inflammatory pathways described above. Within the B lymphocyte populations, the drug mitigated the LPS-induced activation within nearly all the top pathways regulators identified. This result makes sense as the PRR associated pathways described here are consistently expressed between the myeloid cell populations and B cells (both can serve as professional antigen-presenting cells). T cells express the family of PRRs to a much less extent so it follows that the pathways targeted by the drug are less affected in this cell type. Interestingly, the group of pathway regulators that were increased by drug in the context of stimulation (within myeloid and T cell clusters) represent pathways often associated with immunity against viral-type pathogens, interferons and STAT (which is a signaling molecule for the interferon family). This result expands on the mechanism of action description above where drug mitigates exacerbates innate proinflammatory pathways related to bacterial process pathobiology to may also upregulate immune defenses to viral pathogens known to be a major component in BRD.

The des-methyl tulathromycin metabolite, M9, with reduced antimicrobial activity was utilized in a natural bovine respiratory disease study. The primary clinical endpoint for efficacy was treatment failure/success over a 14-day observation period. Clinically normal beef calves (150-200 kg) at moderate risk for BRD were dosed on arrival to the feedlot. Animals (N=114/group) received saline (T01), 5 mg/kg M9 (T02) or 10 mg/kg M9 (T03); or Zactran (T04). Percent failure was 43%, 19.3%, 8.8%, and 29.8% for the T01, T02, T03, and T04 groups, respectively. Bacterial isolates were collected at necropsy and MICs were evaluated (Table 4). In a separate PK study, the maximum plasma concentration following a 10 mg/kg dose was 5 µg/mL. Based on the MICs observed (Table 4) and the maximum plasma concentration it was postulated that the residual MIC activity of M9 was not responsible for the significant overall outcome and the efficacy was primarily due to the immunomodulatory effects of M9. M9 demonstrated efficacy in a natural BRD infection study with statistical superiority demonstrated over untreated control groups in the reduction of lung lesions and treatment failure (attitude, rectal temperature, and respiratory rate/effort and nasal/ocular discharge). However, as can be seen for some of the BRD bacterial isolates, M9 has antibacterial (i.e., MIC <64 µg/mL) properties.

TABLE 4

MIC of Recovered Isolates: Natural Bovine Respiratory Disease Study Lung Bacteria Isolated at Necropsy

| | M9 | | | gamithromycin (Zactran) | | |
|---|---|---|---|---|---|---|
| Bacteria (n) | MIC50 (µg/mL) | MIC90 (µg/mL) | Range (µg/mL) | MIC50 (µg/mL) | MIC90 (µg/mL) | Range (µg/mL) |
| M. haemolytica (116) | >64 | >64 | 32->64 | 1 | >64 | 0.5->64 |
| P. multocida (33) | 16 | >64 | 8->64 | 1 | >64 | 0.5->64 |
| H. somni (25) | 32 | 32 | 8-64 | 0.25 | 2 | 0.12-2 |

To evaluate immunomodulation effects and potential biomarkers, a bovine M. haemolytica (strain: OSU-012103-BHI) intratracheal lung challenge model study was completed utilizing M9 treatment in the presence and absence of bacterial challenge and a Draxxin® comparator. It is important to note that the MIC for M9 to the challenge strain is >64 µg/mL indicating the effects observed were primarily through immunomodulation and not reduction of the bacterial challenge. Animals were administered 0.05 mL/kg saline (T01), 10 mg/kg M9 (T02); Draxxin 2.5 mg/kg (T03) and 10 mg/kg M9 (T04) by subcutaneous injection on Day −1. Dose was based on body weight. Animals were challenge on Day 0 with the exception of T04. Blood was collected longitudinally throughout the study for biomarker evaluation panel (e.g., IL-6 and CD163) including two baseline samples prior to treatment. Study results are presented in Table 5 and in FIG. 4. FIG. 4A depicts the area under the curve concentrations for IL-6 protein for individual animals against percent lung lesion scores and FIG. 4B depicts the CD163 fold change area under the curve for individual animals against percent lung lesion scores. Data is represented as percent lung lesion scores against the area under the curve (AUC) for IL-6 protein (immunoassay expressed in µg/mL) and CD163 (flow cytometric mean fluorescent intensity (MFI) in fold change from baseline). In both assays, a 2-fold change is typically considered to be relevant.

TABLE 5

M9 Intratracheal Lung Challenge Study

| Treatment Group | Challenge | No. Animals | Mortality |
|---|---|---|---|
| T01 | M. haemolytica | 6 | 4/6 |
| T02 | | 6 | 1/6 |
| T03 | | 6 | 0/6 |
| T04 | No challenge | 6 | 0/6 |

IL-6 was elevated and was correlated with higher rectal temperature (data not presented) and mortality. M9 and Draxxin® significantly reduced IL-6 levels which also correlated with overall animal survival or disease progression. CD163 receptor expression followed the initial innate inflammatory cascade signaling in animals that showed clinical signs of BRD within a few days. The increased expression of CD163 on monocytes/macrophages correlates to clinical disease progression in longitudinal sampling of whole blood. M9 mitigates the pathologic increase in CD163 expression.

In summary, M9 demonstrated statistically significant efficacy in both a natural BRD infection as compared to saline (T01) in the M. haemolytica challenge model. In a separate study, 10 mg/kg of M9 demonstrated statistical superiority versus saline control in reduction of lung lesions (20% vs. 31%, p=0.023) and mortality (13% vs. 38.9%, p=0.025). Additionally, reduction of biomarkers consistent with the proposed mechanism were observed. However, the residual antibacterial activity of M9 (MIC's ≤64 µg/mL) against target pathogens was not in line with the non-antibiotic immunomodulator profile (>64 µg/mL).

Drug Binding Partners as Potential Biological Targets

The data provided herein relative to the immunological mechanistic activity of the compounds of the invention is consistent with the pathways presented herein that have been discovered to be important in the pathobiology of BRD. Key pathways associated with the onset of naturally occurring disease include NFκB, TLR4 (often represented by its agonist such as LPS), JAK-STAT, TNFα and IL-1β. Downstream signaling of these pathways lead to induction of pro-inflammatory cytokines such as TNFα and IL-1β, and IL-6 and chemokines such as CXCL8. These same pathways and their respective components are modulated both in vitro and in vivo by these compounds. Additionally, the types of cells known to be involved in these pathways including macrophages, neutrophils and lymphocytes have been used via a whole blood LPS stimulation format (both in vitro and ex vivo) to demonstrate drug-induced changes in gene expression, cytokine expression, and cell surface receptor activation. In addition to classical immune cells, tissue-resident epithelial and endothelial cells can express innate immune receptors and activate the canonical pathway.

We claim:
1. A Formula (1) compound;

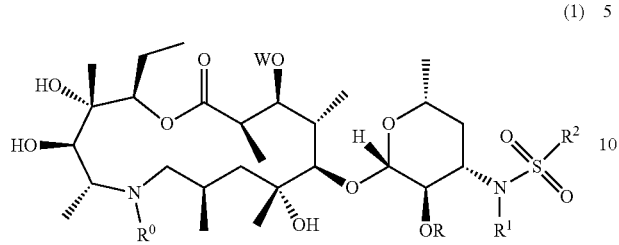

wherein W is a Formula (A) compound

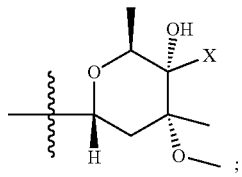

wherein X is —(CH$_2$)$_m$NR$^5$R$^6$;

R is H, phenyl, naphthyl, a 5- or 6-member monocyclic heteroaryl ring or a 9- or 11-membered fused heteroaryl ring, wherein each of the heteroaryl rings contains at least one heteroatom selected from N, O and S; wherein each of the heteroaryl rings contains at least one heteroatom selected from N, O and S; and wherein the phenyl, naphthyl and heteroaryl rings are each substituted with (R$^9$)$_n$;

R$^a$, R$^0$ and R$^1$ are each independently H or C$_1$-C$_6$alkyl; or R$^1$ is benzyl optionally substituted with (R$^9$)$_n$;

or R$^1$ is —CH$_2$Het, wherein Het is a 5- or 6-membered heteroaryl ring containing at least one heteroatom selected from N, O and S; and wherein the heteroaryl ring is optionally substituted with (R$^9$)$_n$;

or R$^1$ is C$_3$-C$_6$cycloalkyl optionally substituted with (R$^9$)$_n$;

R$^b$ is H, C$_1$-C$_4$alkyl, C$_1$-C$_4$haloalkyl, C$_0$-C$_3$alkylphenyl, C$_0$-C$_3$alkylC$_3$-C$_6$cycloalkyl, C$_0$-C$_3$alkylheterocycle or C$_0$-C$_3$alkylheteroaryl; wherein the heterocycle is a 5- or 6-membered saturated or partially saturated monocyclic ring; the heteroaryl is a 5- or 6-membered monocyclic ring; wherein the heterocycle and heteroaryl rings each contain at least one heteroatom selected from N, O and S; and wherein the cycloalkyl, phenyl, heterocycle and heteroaryl rings are each substituted with (R$^9$)$_n$;

R$^c$ is C$_1$-C$_4$alkyl;

R$^2$ is H, C$_1$-C$_6$alkyl, —R$^c$OR$^b$, C$_1$-C$_6$haloalkyl, C$_0$-C$_3$alkylC$_5$-C$_6$cycloalkyl, —R$^c$NR$^a$R$^b$, —NR$^a$R$^c$S(O)$_p$R$^8$, —NR$^a$R$^c$C(O)NR$^a$R$^c$, R$^c$CN, —R$^c$S(O)$_p$R$^8$, —NR$^a$R$^b$, —NR$^b$R$^b$, C$_0$-C$_3$alkylaryl, C$_0$-C$_3$alkylheterocycle that is a 5- or 6-membered saturated or partially saturated heterocycle ring or C$_0$-C$_3$alkylheteroaryl, wherein the heteroaryl is a 5- or 6-membered heteroaryl ring; wherein the heterocycle and heteroaryl rings each contain at least one heteroatom selected from N, O and S; wherein the cycloalkyl, aryl, heterocyclic and heteroaryl rings are each substituted with (R$^9$)$_n$ and wherein each ring is optionally fused with Y;

R$^5$ and R$^6$ taken together with the nitrogen atom to which they are attached form Ring B, wherein Ring B is a 4- to 8-membered heterocyclic ring or a 5-membered heteroaryl ring, each optionally containing at least one additional heteroatom selected from N, O and S; and wherein each ring is optionally substituted with (R$^9$)$_n$; and wherein each ring is optionally fused with Y;

R$^8$ is C$_1$-C$_6$alkyl, C$_1$-C$_6$haloalkyl, C$_0$-C$_4$alkylC$_5$-C$_6$cycloalkyl, —NR$^a$R$^b$, phenyl, a 5- or 6-membered heterocyclic ring or heteroaryl ring each containing at least one heteroatom selected from N, O and S; and wherein the cycloalkyl, phenyl, heterocycle and heteroaryl rings are each substituted with (R$^9$)$_n$ independently selected from the group consisting of methyl, ethyl, isopropyl, methoxy, F, Cl, Br, I, oxo, cyano, —NH$_2$, —N(CH$_3$)$_2$, —CF$_3$, —CHF$_2$ and —OCHF$_2$;

R$^9$ is independently selected from the group consisting of C$_1$-C$_6$alkyl optionally substituted with hydroxy; C$_1$-C$_6$alkoxy, C$_0$-C$_4$alkylC$_5$-C$_6$cycloalkyl, halo, oxo, nitro, hydroxy, —R$^c$OR$^b$, cyano, —NR$^a$R$^b$, C$_1$-C$_6$haloalkyl, C$_1$-C$_6$haloalkoxy, —S(O)$_p$R$^8$, —SF$_5$, phenyl; a 5- or 6-membered heterocyclic or heteroaryl ring each containing at least one heteroatom selected from the group consisting of N, O and S; and wherein the phenyl, heterocyclic and heteroaryl rings are further optionally substituted with F, Cl, cyano or —CF$_3$;

Y is cyclopentyl, cyclohexyl, phenyl, pyridinyl, pyrimidyl, pyrazolyl, thiophenyl, thiazolyl, triazolyl, isothiazolyl, pyrrolyl, oxazolyl, oxadiazolyl, imidazolyl, furanyl or tetrahydrothiophenyl, each substituted with methyl, F, Cl, cyano, oxo or —CF$_3$;

m is the integer 1, 2, or 3;

n is the integer 0, 1, 2 or 3; and p is the integer 0, 1, or 2;

or a stereoisomer, or a pharmaceutically acceptable salt thereof.

2. A compound of Formula (1) of claim 1, wherein W is Formula (A) that is Formula (A1)

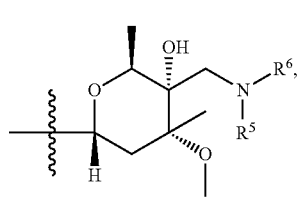

and wherein R$^0$ is H, methyl, ethyl or propyl; or a stereoisomer, or a pharmaceutically acceptable salt thereof.

3. The Formula (1) compound of claim 2 that is a Formula (1-A1) compound

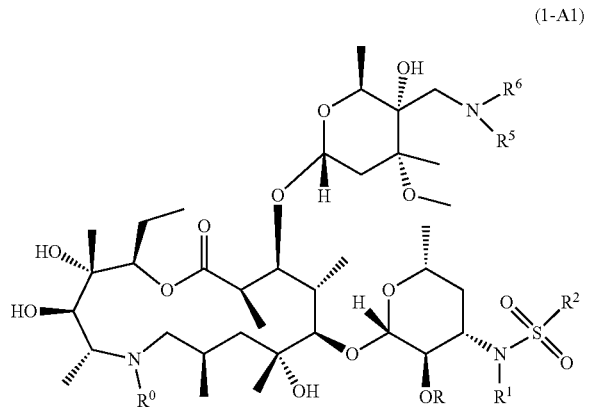

(1-A1)

or a stereoisomer, or a pharmaceutically acceptable salt thereof.

4. A compound of claim 3, that is a Formula (1-A1a) compound, wherein

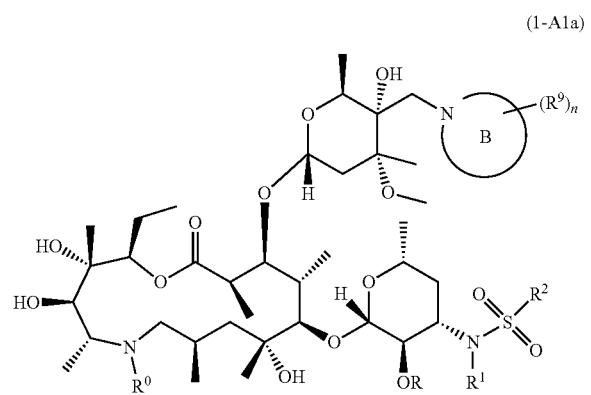

(1-A1a)

$R^0$ is H;
R is H; or
R is phenyl, pyridinyl or thiophenyl, each substituted with $(R^9)_n$;
$R^1$ is methyl;
$R^2$ is H, methyl, ethyl, propyl, isopropyl, butyl, isobutyl, n-butyl, —CH$_2$OCH$_3$, —(CH$_2$)$_2$OCH$_3$, —CH$_2$CF$_3$, —CF$_3$, —NHR$^b$ or —NCH$_2$R$^b$, wherein R$^b$ is methyl, cyclohexyl, phenyl or pyridinyl, and wherein the phenyl and pyridinyl rings are optionally substituted with F, Cl, cyano or —CF$_3$;
or $R^2$ is cyclopropyl, —CH$_2$cyclopropyl, cyclohexyl, piperidinyl, piperazinyl, morpholinyl, phenyl, thiophenyl, pyrazolyl, imidazolyl, isoxazolyl, thiazolyl, pyridinyl or pyrimidinyl, each substituted with $(R^9)_n$;
or $R^2$ is phenyl or pyridinyl each substituted with morpholine;
Ring B is azetidinyl, pyrazolyl, pyrrolidinyl, piperidinyl, piperazinyl, morpholinyl, imidazolyl, azathianyl or tetrazolyl, each substituted with $(R^9)_n$; and n is the integer 0, 1 or 2; or a stereoisomer, or a pharmaceutically acceptable salt thereof.

5. The Formula (1-A1a) compound of claim 4, that is a non-antibacterial compound selected from the group consisting of:
4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(morpholinomethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;
N-((2S,3R,4S,6R)-2-(((2R,3S,4R,5R,8R,10R,11R,12S,13S,14R)-13-(((2R,4R,5S,6S)-5-(azetidin-1-ylmethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzene-sulfonamide;
4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(pyrrolidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;
4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;
N-((2S,3R,4S,6R)-2-(((2R,3S,4R,5R,8R,10R,11R,12S,13S,14R)-13-(((2R,4R,5S,6S)-5-((1H-imidazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;
4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(thiomorpholinomethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;
4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide;
N-((2S,3R,4S,6R)-2-(((2R,3S,4R,5R,8R,10R,11R,12S,13S,14R)-13-(((2R,4R,5S,6S)-5-((1H-pyrazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-4-chloro-N-methylbenzenesulfonamide;
N-((2S,3R,4S,6R)-2-(((2R,3S,4R,5R,8R,10R,11R,12S,13S,14R)-13-(((2R,4R,5S,6S)-5-((1H-tetrazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6- azacyclopentadecan-11-yl)oxy)-3-hydroxy-6-
methyltetrahydro-2H-pyran-4-yl)-4-chloro-N-
methylbenzenesulfonamide;
4-chloro-N-((2S,3R,4S,6R)-2-(((2R,3S,4R,5R,8R,10R,
11R,12S,13S,14R)-13-(((2R,4R,5S,6S)-5-((3,4-dihy-
droisoquinolin-2(1H)-yl)methyl)-5-hydroxy-4-
methoxy-4,6-dimethyltetrahydro-2H-pyran-2-yl)oxy)-
2-ethyl-3,4,10-trihydroxy-3,5,8,10,12,14-hexamethyl-
15-oxo-1-oxa-6-azacyclopentadecan-11-yl)oxy)-3-
hydroxy-6-methyltetrahydro-2H-pyran-4-yl)-N-
methylbenzenesulfonamide;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-11-[(2S,3R,4S,6R)-3-hydroxy-6-methyl-4-
[methyl-[[4-(trifluoromethyl)phenyl]sulfamoyl]-
amino]oxan-2-yl]oxy-3,5,8,10,12,14-hexamethyl-15-
oxo-1-oxa-6-azacyclopentadecane;
(2R,3S,4R,5R,8R,10R,11R,12S,13S,14R)-2-ethyl-13-
[(2R,4R,5S,6S)-5-[(4-ethylpiperazin-1-yl)methyl]-5-
hydroxy-4-methoxy-4,6-dimethyloxan-2-yl]oxy-3,4,
10-trihydroxy-11-[(2S,3R,4S,6R)-3-hydroxy-6-
methyl-4-[methyl-[[4-(trifluoromethyl)phenyl]-
sulfamoyl]amino]oxan-2-yl]oxy-3,5,8,10,12,14-
hexamethyl-15-oxo-1-oxa-6-azacyclopentadecane;
(2R,3S,4R,5R,8R,10R,11R,12S,13S,14R)-13-[(2R,4R,
5S,6S)-5-[(1,1-dioxo-1,4-thiazinan-4-yl)methyl]-5-hy-
droxy-4-methoxy-4,6-dimethyloxan-2-yl]oxy-2-ethyl-
3,4,10-trihydroxy-11-[(2S,3R,4S,6R)-3-hydroxy-6-
methyl-4-[methyl-[[4-(trifluoromethyl)phenyl]-
sulfamoyl]amino]oxan-2-yl]oxy-3,5,8,10,12,14-
hexamethyl-15-oxo-1-oxa-6-azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-[(4-propan-2-ylpiperazin-1-
yl)methyl]oxan-2-yl]oxy-11-[(2S,3R,4S,6R)-3-
hydroxy-6-methyl-4-[methyl-[[4-(trifluoromethyl)
phenyl]sulfamoyl]-amino]oxan-2-yl]oxy-3,5,8,10,12,
14-hexamethyl-15-oxo-1-oxa-6-azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-[(4-methylsulfonylpiperazin-
1-yl)methyl]oxan-2-yl]oxy-11-[(2S,3R,4S,6R)-3-
hydroxy-6-methyl-4-[methyl-[[4-(trifluoromethyl)
phenyl]-sulfamoyl]amino]oxan-2-yl]oxy-3,5,8,10,12,
14-hexamethyl-15-oxo-1-oxa-6-azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-11-[(2S,3R,4S,6R)-3-hydroxy-6-methyl-4-
[methyl(sulfamoyl)amino]oxan-2-yl]-oxy-3,5,8,10,12,
14-hexamethyl-15-oxo-1-oxa-6-azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-11-[(2S,3R,4S,6R)-3-hydroxy-6-methyl-4-
[methyl(sulfamoyl)amino]oxan-2-yl]oxy-3,5,8,10,12,
14-hexamethyl-15-oxo-6-propyl-1-oxa-6-
azacyclopentadecane;
N-[(2S,3R,4S,6R)-2-[[(2R,3S,4R,5R,8R,10R,11R,12S,
13S,14R)-2-ethyl-3,4,10-trihydroxy-13-[(2R,4R,5S,
6S)-5-hydroxy-4-methoxy-4,6-dimethyl-5-(piperidin-
1-ylmethyl)oxan-2-yl]oxy-3,5,8,10,12,14-hexamethyl-
15-oxo-1-oxa-6-azacyclopentadec-11-yl]oxy]-3-
hydroxy-6-methyloxan-4-yl]-N-methyl-4-
(trifluoromethyl)benzene-sulfonamide;
N-[(2S,3R,4S,6R)-2-[[(2R,3S,4R,5R,8R,10R,11R,12S,
13S,14R)-2-ethyl-3,4,10-trihydroxy-13-[(2R,4R,5S,
6S)-5-hydroxy-4-methoxy-4,6-dimethyl-5-(piperidin-
1-ylmethyl)oxan-2-yl]oxy-3,5,8,10,12,14-hexamethyl-
15-oxo-1-oxa-6-azacyclopentadec-11-yl]oxy]-3-
hydroxy-6-methyloxan-4-yl]-4-fluoro-N-
methylbenzenesulfonamide;
(2R,3S,4R,5R,8R,10R,11R,12S,13S,14R)-2,6-diethyl-3,
4,10-trihydroxy-13-[(2R,4R,5S,6S)-5-hydroxy-4-
methoxy-4,6-dimethyl-5-(piperidin-1-ylmethyl)oxan-
2-yl]oxy-11-[(2S,3R,4S,6R)-3-hydroxy-6-methyl-4-
[methyl(phenylsulfamoyl)amino]-oxan-2-yl]oxy-3,5,8,
10,12,14-hexamethyl-15-oxo-1-oxa-6-
azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-11-[(2S,3R,4S,6R)-3-hydroxy-6-methyl-4-
[methyl(phenylsulfamoyl)amino]-oxan-2-yl]oxy-3,5,8,
10,12,14-hexamethyl-15-oxo-6-propyl-1-oxa-6-
azacyclopentadecane;
(2R,3S,4R,5R,8R,10R,11R,12S,13S,14R)-11-[(2R,3S,
4R,6S)-4-[(4-tert-butylphenyl)sulfamoyl-methyl-
amino]-3-hydroxy-6-methyloxan-2-yl]oxy-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-3,5,8,10,12,14-hexamethyl-15-oxo-1-oxa-6-
azacyclopentadecane;
(2R,3S,4R,5R,8R,10R,11R,12S,13S,14R)-11-[(2R,3S,
4R,6S)-4-[(3-chlorophenyl)sulfamoyl-methylamino]-
3-hydroxy-6-methyloxan-2-yl]oxy-2-ethyl-3,4,10-tri-
hydroxy-13-[(2R,4R,5S,6S)-5-hydroxy-4-methoxy-4,
6-dimethyl-5-(piperidin-1-ylmethyl)-oxan-2-yl]oxy-3,
5,8,10,12,14-hexamethyl-15-oxo-1-oxa-6-
azacyclopentadecane;
(2R,3S,4R,5R,8R,10R,11R,12S,13S,14R)-11-[(2R,3S,
4R,6S)-4-[(3,4-dichlorophenyl)sulfamoyl-methyl-
amino]-3-hydroxy-6-methyloxan-2-yl]oxy-2-ethyl-3,4,
10-trihydroxy-13-[(2R,4R,5S,6S)-5-hydroxy-4-
methoxy-4,6-dimethyl-5-(piperidin-1-ylmethyl)-oxan-
2-yl]oxy-3,5,8,10,12,14-hexamethyl-15-oxo-1-oxa-6-
azacyclopentadecane;
(2R,3S,4R,5R,8R,10R,11R,12S,13S,14R)-11-[(2R,3S,
4R,6S)-4-[(4-bromophenyl)sulfamoyl-methylamino]-
3-hydroxy-6-methyloxan-2-yl]oxy-2-ethyl-3,4,10-tri-
hydroxy-13-[(2R,4R,5S,6S)-5-hydroxy-4-methoxy-4,
6-dimethyl-5-(piperidin-1-ylmethyl)-oxan-2-yl]oxy-3,
5,8,10,12,14-hexamethyl-15-oxo-1-oxa-6-
azacyclopentadecane;
(2R,3S,4R,5R,8R,10R,11R,12S,13S,14R)-2-ethyl-3,4,
10-trihydroxy-11-[(2R,3S,4R,6S)-3-hydroxy-4-[(4-io-
dophenyl)sulfamoyl-methylamino]-6-methyloxan-2-
yl]oxy-13-[(2R,4R,5S,6S)-5-hydroxy-4-methoxy-4,6-
dimethyl-5-(piperidin-1-ylmethyl)-oxan-2-yl]oxy-3,5,
8,10,12,14-hexamethyl-15-oxo-1-oxa-6-
azacyclopentadecane;
(2R,3S,4R,5R,8R,10R,11R,12S,13S,14R)-11-[(2R,3S,
4R,6S)-4-[[4-chloro-3-(trifluoromethyl)phenyl]sulfa-
moyl-methylamino]-3-hydroxy-6-methyloxan-2-yl]
oxy-2-ethyl-3,4,10-trihydroxy-13-[(2R,4R,5S,6S)-5-
hydroxy-4-methoxy-4,6-dimethyl-5-(piperidin-1-
ylmethyl)oxan-2-yl]oxy-3,5,8,10,12,14-hexamethyl-
15-oxo-1-oxa-6-azacyclopentadecane;
(2R,3S,4R,5R,8R,10R,11R,12S,13S,14R)-2-ethyl-3,4,
10-trihydroxy-13-[(2R,4R,5S,6S)-5-hydroxy-4-
methoxy-4,6-dimethyl-5-(piperidin-1-ylmethyl)oxan-
2-yl]oxy-11-[(2R,3S,4R,6S)-3-hydroxy-6-methyl-4-

[methyl-[(4-methylphenyl)sulfamoyl]amino]oxan-2-yl]oxy-3,5,8,10,12,14-hexamethyl-15-oxo-1-oxa-6-azacyclopentadecane;

(2R,3S,4R,5R,8R,10R,11R,12S,13S,14R)-11-[(2R,3S,4R,6S)-4-[(3,4-dimethylphenyl)sulfamoyl-methyl-amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-hydroxy-6-methyl-4-[methyl-[(1-methylimidazol-2-yl)sulfamoyl]amino]oxan-2-yl]oxy-3,5,8,10,12,14-hexamethyl-15-oxo-1-oxa-6-azacyclopentadecane;

(2R,3S,4R,5R,8R,10R,11R,12S,13S,14R)-11-[(2S,3R,4S,6R)-4-[diethylsulfamoyl(methyl)amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-1-oxa-6-azacyclopentadecan-15-one;

(2R,3S,4R,5R,8R,10R,11R,12S,13S,14R)-2,6-diethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]-sulfamoyl]amino]oxan-2-yl]oxy-3,5,8,10,12,14-hexamethyl-15-oxo-1-oxa-6-azacyclopentadecane;

N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-N-methyl-1-methylsulfonylmethanesulfonamide;

(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[pyridin-3-ylmethyl-[[4-(trifluoromethyl)phenyl]sulfamoyl]amino]oxan-2-yl]oxy-3,5,8,10,12,14-hexamethyl-15-oxo-1-oxa-6-azacyclopentadecane;

4-chloro-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclo-pentadec-11-yl]oxy]-3-hydroxy-6-methyloxan-4-yl]-N-propylbenzenesulfonamide;

N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-4-methoxy-N-propylbenzenesulfonamide;

4-chloro-N-cyclohexyl-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]benzenesulfonamide;

N-cyclohexyl-N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(propylaminomethyl)oxan-2-yl]oxy-3,5,8,10,12,14-hexamethyl-15-oxo-1-oxa-6-azacyclopentadec-11-yl]oxy]-3-hydroxy-6-methyloxan-4-yl]-4-methoxybenzene-sulfonamide;

(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[2-methylpropyl-[[4-(trifluoromethyl)phenyl]-sulfamoyl]amino]oxan-2-yl]oxy-3,5,8,10,12,14-hexamethyl-15-oxo-1-oxa-6-azacyclopentadecane;

(2R,3S,4R,5R,8R,10R,11R,12S,13S,14R)-11-[(2S,3R,4S,6R)-4-[cyclohexyl-[[4-(trifluoromethyl)phenyl]sulfamoyl]amino]-3-hydroxy-6-methyloxan-2-yl]oxy-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadecane;

(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[[1,3-thiazol-2-ylmethyl-[4-(trifluoromethyl)phenyl]-sulfamoyl]amino]oxan-2-yl]oxy-3,5,8,10,12,14-hexamethyl-15-oxo-1-oxa-6-azacyclopentadecane, acetic acid;

N-((2S,3R,4S,6R)-2-(((2R,3S,4R,5R,8R,10R,11R,12S,13S,14R)-2-ethyl-3,4,10-trihydroxy-13-(((6R)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methyl-4-(pentafluoro-16-sulfanyl)benzenesulfonamide;

N-[(2S,3R,4S,6R)-3-(5-chloropyridin-2-yl)oxy-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-6-methyloxan-4-yl]-N-methylbenzenesulfonamide;

N-[(2S,3R,4S,6R)-2-[[(2R,3S,4R,5R,8R,10R,11R,12S,13S,14R)-2-ethyl-3,4,10-trihydroxy-13-[(4R,5S,6S)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(2-fluoropyridin-4-yl)oxy-6-methyloxan-4-yl]-N,1-dimethylimidazole-2-sulfonamide;

(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2R,3S,4R,6S)-3-(4-methoxyphenoxy)-6-methyl-4-[methyl(phenylsulfamoyl)amino]oxan-2-yl]oxy-3,5,8,10,12,14-hexamethyl-15-oxo-1-oxa-6-azacyclopentadecane;

(2R,3S,4R,5R,8R,10R,11R,12S,13S,14R)-2-ethyl-11-[(2R,3S,4R,6S)-3-(4-fluorophenoxy)-6-methyl-4-[methyl(phenylsulfamoyl)amino]oxan-2-yl]oxy-3,4,10-trihydroxy-13-[(2R,4R,5S,6S)-5-hydroxy-4-methoxy-4,6-di methyl-5-(piperidin-1-ylmethyl)oxan-2-yl]oxy-3,5,8,10,12,14-hexamethyl-15-oxo-1-oxa-6-azacyclopentadecane;

(2R,3S,4R,5R,8R,10R,11R,12S,13S,14R)-2-ethyl-3,4,10-trihydroxy-13-[(2R,4R,5S,6S)-5-hydroxy-4- methoxy-4,6-dimethyl-5-(piperidin-1-ylmethyl)oxan-2-yl]oxy-3,5,8,10,12,14-hexamethyl-11-[(2R,3S,4R,6S)-6-methyl-4-[methyl(phenylsulfamoyl)amino]-3-phenoxyoxan-2-yl]oxy-15-oxo-1-oxa-6-azacyclopentadecane;

N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-6-methyl-3-phenoxyoxan-4-yl]-N-methylbenzenesulfonamide;

N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N-methylbenzenesulfonamide;

N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(2-fluoropyridin-4-yl)oxy-6-methyloxan-4-yl]-N-methylbenzenesulfonamide; and N-[(2S,3R,4S,6R)-2-[[(2R,3S,4R,5R,8R,10R,11R,12S,13S,14R)-2-ethyl-3,4,10-trihydroxy-13-[(6R)-5-hydroxy-4-methoxy-4,6-dimethyl-5-(piperidin-1-ylmethyl)oxan-2-yl]oxy-3,5,8,10,12,14-hexamethyl-15-oxo-1-oxa-6-azacyclopentadec-11-yl]oxy]-3-(4-fluorophenoxy)-6-methyloxan-4-yl]-N,1-dimethylimidazole-2-sulfonamide;

or a stereoisomer, or a pharmaceutically acceptable salt thereof.

6. A compound of claim 5, that is 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide or (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-5-(piperidin-1-ylmethyl)oxan-2-yl]oxy-11-[(2S,3R,4S,6R)-3-hydroxy-6-methyl-4-[methyl-[[4-(trifluoromethyl)phenyl]sulfamoyl]amino]oxan-2-yl]oxy-3,5,8,10,12,14-hexamethyl-15-oxo-1-oxa-6-azacyclopentadecane, or a stereoisomer, or a pharmaceutically acceptable salt thereof.

7. A compound of claim 6 that is 4-chloro-N-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylbenzenesulfonamide, or a stereoisomer, or a pharmaceutically acceptable salt thereof.

8. A composition comprising a Formula (1) compound of claim 1, or a stereoisomer, or a pharmaceutically acceptable salt thereof, and wherein said composition further comprises a pharmaceutically acceptable carrier.

9. A composition comprising a Formula (1) compound of claim 5, or a stereoisomer, or a pharmaceutically acceptable salt thereof, and wherein said composition further comprises a pharmaceutically acceptable carrier.

10. A method for treating a respiratory disease mediated by TNF-α, IL-1β or IL-6 in an animal in need thereof by administering to said animal a therapeutically effective amount of a Formula (1) compound of claim 1, or a stereoisomer, or a pharmaceutically acceptable salt thereof.

11. A method for treating a respiratory disease mediated by TNFα, IL-1β, or IL-6 in an animal in need thereof by administering to said animal a therapeutically effective amount of a Formula (1) compound of claim 5, or a stereoisomer, or a pharmaceutically acceptable salt thereof.

* * * * *